US007792249B2

(12) United States Patent
Gertner et al.

(10) Patent No.: US 7,792,249 B2
(45) Date of Patent: Sep. 7, 2010

(54) METHODS AND DEVICES FOR DETECTING, CONTROLLING, AND PREDICTING RADIATION DELIVERY

(75) Inventors: Michael Gertner, Menlo Park, CA (US); Mark Arnoldussen, San Carlos, CA (US); Erik Chell, Oakland, CA (US); Steven D. Hansen, Concord, CA (US); Matt Herron, Redwood City, CA (US); Igor Koruga, Pacifica, CA (US); Junzhong Liang, Fremont, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 113 days.

(21) Appl. No.: 12/338,634

(22) Filed: Dec. 18, 2008

(65) Prior Publication Data

US 2009/0161827 A1 Jun. 25, 2009

Related U.S. Application Data

(63) Continuation-in-part of application No. 12/262,031, filed on Oct. 30, 2008, and a continuation-in-part of application No. 12/103,534, filed on Apr. 15, 2008, said application No. 12/262,031 is a continuation-in-part of application No. 12/100,398, filed on Apr. 9, 2008, now Pat. No. 7,693,260, said application No. 12/103,534 is a continuation-in-part of application No. 12/027,083, filed on Feb. 6, 2008, and a continuation-in-part of application No. 12/027,094, filed on Feb. 6, 2008, and a continuation-in-part of application No. 12/027,069, filed on Feb. 6, 2008.

(60) Provisional application No. 61/101,013, filed on Sep. 29, 2008, provisional application No. 61/093,092, filed on Aug. 29, 2008, provisional application No. 61/076,128, filed on Jun. 26, 2008, provisional application No. 61/016,472, filed on Dec. 23, 2007, provisional application No. 61/020,655, filed on Jan. 11, 2008.

(51) Int. Cl.
*A61N 5/10* (2006.01)

(52) U.S. Cl. ........................................... 378/65; 606/4

(58) Field of Classification Search .................. 378/65; 606/4

See application file for complete search history.

(56) References Cited

U.S. PATENT DOCUMENTS 3,073,960 A 1/1963 Guentner et al.

(Continued)

FOREIGN PATENT DOCUMENTS

WO WO-0126591 A1 4/2001

(Continued)

OTHER PUBLICATIONS

International Search Report and Written Opinion for PCT/US2008/012341, search report dated Feb. 5, 2009, 21 pages (2009).

(Continued)

*Primary Examiner*—Chih-Cheng G Kao
(74) *Attorney, Agent, or Firm*—McDermott Will & Emery LLP; James W. Hill; M. Todd Hales

(57) ABSTRACT

Embodiments provide method and systems for determining alignment of a patient's body part, such as an eye, in an external coordinate system of a treatment or diagnostic device, such as a radiotherapy device, so as to define a reference axis for guiding device operation. Additional embodiments provide image-based methods and systems for aligning, tracking and monitoring motion of a body part and a treatment target in relation to a radiation beam axis. Particular ophthalmic embodiments provide method and systems including an eye-contact guide device and imaging system for aligning and tracking motion of an eye and ocular treatment target in relation to an orthovoltage X-ray beam axis, so as to monitor application of radiation to a lesion, such as a macular lesion of the retina. Particular methods for controlling radiation in response to motion of the target during treatment are described, such as algorithms for gating or interrupting radiation emission, both to ensure treatment goals and to avoid exposure to sensitive structures.

46 Claims, 62 Drawing Sheets

U.S. PATENT DOCUMENTS 4,521,905 A 6/1985 Hosokawa
4,710,193 A 12/1987 Volk
4,718,418 A 1/1988 L'Esperance, Jr.
4,817,432 A 4/1989 Wallace et al.
5,008,907 A 4/1991 Norman et al.
5,027,818 A 7/1991 Bova et al.
5,139,494 A 8/1992 Freiberg
5,171,254 A 12/1992 Sher
5,189,687 A 2/1993 Bova et al.
5,207,223 A 5/1993 Adler
5,216,255 A 6/1993 Weidlich
5,304,167 A 4/1994 Freiberg
5,336,215 A 8/1994 Hsueh et al.
5,339,347 A 8/1994 Slatkin et al.
5,354,323 A 10/1994 Whitebook
5,373,844 A 12/1994 Smith et al.
5,411,026 A 5/1995 Carol
5,427,097 A 6/1995 Depp
5,430,308 A 7/1995 Feichtner et al.
5,468,238 A 11/1995 Mersch
5,528,652 A 6/1996 Smith et al.
5,556,417 A 9/1996 Sher
5,635,721 A 6/1997 Bardi et al.
5,644,616 A 7/1997 Landi et al.
5,651,043 A 7/1997 Tsuyuki et al.
5,668,847 A 9/1997 Hernandez
5,708,696 A 1/1998 Kantor
5,724,400 A 3/1998 Swerdloff et al.
5,727,042 A 3/1998 Brenneisen
5,737,384 A 4/1998 Fenn
5,744,919 A 4/1998 Mishin et al.
5,745,545 A 4/1998 Hughes
5,771,270 A 6/1998 Archer et al.
5,778,043 A 7/1998 Cosman
5,820,553 A 10/1998 Hughes
5,870,697 A 2/1999 Chandler et al.
5,901,199 A 5/1999 Murphy et al.
6,001,054 A 12/1999 Regulla et al.
6,104,778 A 8/2000 Murad
6,126,668 A 10/2000 Bair et al.
6,134,294 A 10/2000 Gibbs
6,135,996 A 10/2000 Kolesa et al.
6,144,875 A 11/2000 Schweikard et al.
6,245,059 B1 6/2001 Clapham
6,257,722 B1 7/2001 Toh
6,260,005 B1 7/2001 Yang et al.
6,278,764 B1 8/2001 Barbee, Jr. et al.
6,287,299 B1 9/2001 Sasnett et al.
6,299,054 B1 10/2001 Gibbs, Jr.
6,299,307 B1 10/2001 Oltean et al.
6,301,328 B1 10/2001 Sliski et al.
6,359,963 B1 3/2002 Cash
6,385,286 B1 5/2002 Fitchard et al.
6,436,113 B1 8/2002 Burba et al.
6,459,762 B1 10/2002 Wong et al.
6,494,878 B1 12/2002 Pawlowski et al.
6,501,981 B1 12/2002 Schweikard et al.
6,512,813 B1 1/2003 Krispel et al.
6,535,574 B1 3/2003 Collins et al.
6,560,312 B2 5/2003 Cash
6,690,965 B1 2/2004 Riaziat et al.
6,714,620 B2 3/2004 Caflisch et al.
6,728,335 B1 4/2004 Thomson et al.
6,744,846 B2 6/2004 Popescu et al.
6,778,850 B1 8/2004 Adler et al.
6,789,900 B2 9/2004 Van de Velde
6,792,073 B2 9/2004 Deasy et al.
6,810,107 B2 10/2004 Steinberg
6,837,862 B2 1/2005 Driver, Jr.
6,863,667 B2 3/2005 Webb et al.
6,865,253 B2 3/2005 Blumhofer et al.
6,865,254 B2 3/2005 Nafstadius
6,888,919 B2 5/2005 Graf et al.
6,937,696 B1 8/2005 Mostafavi
6,942,656 B2 9/2005 Pawlowski et al.
6,965,847 B2 11/2005 Wessol et al.
6,977,987 B2 12/2005 Yamashita et al.
6,990,175 B2 1/2006 Nakashima et al.
7,018,376 B2 3/2006 Webb et al.
7,027,557 B2 4/2006 Llacer
7,044,602 B2 5/2006 Chernyak
7,046,762 B2 5/2006 Lee
7,046,765 B2 5/2006 Wong et al.
7,070,327 B2 7/2006 Collins
7,103,144 B2 9/2006 Wong et al.
7,103,145 B2 9/2006 Wong et al.
7,115,120 B2 10/2006 Lin
7,139,601 B2 11/2006 Bucholz et al.
7,154,991 B2 12/2006 Earnst et al.
7,158,607 B2 1/2007 Dimanian et al.
7,158,610 B2 1/2007 Mostafavi
7,166,852 B2 1/2007 Saracen et al.
7,171,257 B2 1/2007 Thomson
7,178,666 B2 2/2007 Huang
7,179,254 B2 2/2007 Pendekanti et al.
7,187,792 B2 3/2007 Fu et al.
7,194,063 B2 3/2007 Dilmanian et al.
7,204,640 B2 4/2007 Fu et al.
7,221,733 B1 5/2007 Takai et al.
7,225,012 B1 5/2007 Susil et al.
7,227,925 B1 6/2007 Mansfield et al.
7,231,076 B2 6/2007 Fu et al.
7,239,684 B2 7/2007 Hara et al.
7,260,426 B2 8/2007 Schweikard et al.
7,266,176 B2 9/2007 Allison et al.
7,278,787 B2 10/2007 Hack et al.
7,280,865 B2 10/2007 Adler et al.
7,283,610 B2 10/2007 Low et al.
7,346,144 B2 3/2008 Hughes et al.
2002/0051513 A1 5/2002 Pugachev et al.
2002/0065461 A1 5/2002 Cosman
2002/0099363 A1 7/2002 Woodward et al.
2002/0106054 A1 8/2002 Caflisch et al.
2002/0106055 A1 8/2002 Cash
2002/0115902 A1 8/2002 Dejuan et al.
2002/0161356 A1 10/2002 Bille et al.
2002/0198453 A1 12/2002 Herrick, II
2002/0198553 A1 12/2002 Schumer et al.
2003/0112922 A1 6/2003 Burdette et al.
2003/0120141 A1 6/2003 Adler
2003/0125622 A1 7/2003 Schweikard et al.
2003/0189689 A1 10/2003 Rathjen
2003/0211075 A1 11/2003 Thorpe et al.
2003/0219098 A1 11/2003 McNutt et al.
2004/0019274 A1 1/2004 Galloway, Jr. et al.
2004/0054359 A1 3/2004 Ruiz et al.
2004/0071261 A1 4/2004 Earl et al.
2004/0131150 A1 7/2004 Pankratov et al.
2004/0267294 A1 12/2004 Will
2005/0010109 A1 1/2005 Faul
2005/0049478 A1 3/2005 Kuduvalli et al.
2005/0058245 A1 3/2005 Ein-Gal
2005/0111621 A1 5/2005 Riker et al.
2005/0175218 A1 8/2005 Vertegaal et al.
2005/0180544 A1 8/2005 Sauer et al.
2005/0192562 A1 9/2005 Loesel et al.
2005/0203499 A1 9/2005 Pendekanti et al.
2005/0226482 A1 10/2005 Kuduvalli
2005/0228255 A1 10/2005 Saracen et al.
2005/0234327 A1 10/2005 Saracen et al.
2005/0270486 A1 12/2005 Teiwes et al.
2005/0271590 A1 12/2005 Schwartz et al.
2006/0002601 A1 1/2006 Fu et al.
2006/0002615 A1 1/2006 Fu et al.

| | | | |
|---|---|---|---|
| 2006/0002630 A1 | 1/2006 | Fu et al. | |
| 2006/0002631 A1 | 1/2006 | Fu et al. | |
| 2006/0002632 A1 | 1/2006 | Fu et al. | |
| 2006/0004281 A1 | 1/2006 | Saracen | |
| 2006/0033044 A1 | 2/2006 | Gentry et al. | |
| 2006/0067469 A1 | 3/2006 | Dooley et al. | |
| 2006/0072821 A1 | 4/2006 | Wang | |
| 2006/0074292 A1 | 4/2006 | Thomson et al. | |
| 2006/0074299 A1 | 4/2006 | Sayeh | |
| 2006/0074304 A1 | 4/2006 | Sayeh | |
| 2006/0078087 A1 | 4/2006 | Forman et al. | |
| 2006/0084952 A1 | 4/2006 | Pallikaris et al. | |
| 2006/0093089 A1 | 5/2006 | Vertatschitsch et al. | |
| 2006/0170679 A1 | 8/2006 | Wang et al. | |
| 2006/0170865 A1 | 8/2006 | Hirohara et al. | |
| 2006/0176997 A1 | 8/2006 | Dilmanian et al. | |
| 2006/0182326 A1 | 8/2006 | Schildkraut et al. | |
| 2006/0192921 A1 | 8/2006 | Loesel et al. | |
| 2006/0193441 A1 | 8/2006 | Cadman | |
| 2006/0199991 A1 | 9/2006 | Lewis et al. | |
| 2006/0203964 A1 | 9/2006 | Nyholm et al. | |
| 2006/0271025 A1 | 11/2006 | Jones et al. | |
| 2006/0274061 A1 | 12/2006 | Wang et al. | |
| 2006/0274885 A1 | 12/2006 | Wang et al. | |
| 2006/0274924 A1 | 12/2006 | West et al. | |
| 2006/0274925 A1 | 12/2006 | West et al. | |
| 2006/0285641 A1 | 12/2006 | Scherch | |
| 2006/0291621 A1 | 12/2006 | Yan et al. | |
| 2006/0291710 A1 | 12/2006 | Wang et al. | |
| 2006/0293583 A1 | 12/2006 | Saracen et al. | |
| 2007/0003007 A1 | 1/2007 | Carrano et al. | |
| 2007/0003123 A1 | 1/2007 | Fu et al. | |
| 2007/0015991 A1 | 1/2007 | Fu et al. | |
| 2007/0038058 A1 | 2/2007 | West et al. | |
| 2007/0053490 A1 | 3/2007 | Wang et al. | |
| 2007/0053491 A1 | 3/2007 | Schildkraut et al. | |
| 2007/0071168 A1 | 3/2007 | Allison et al. | |
| 2007/0071176 A1 | 3/2007 | Main et al. | |
| 2007/0078306 A1 | 4/2007 | Allison et al. | |
| 2007/0083087 A1 | 4/2007 | Carda | |
| 2007/0093795 A1 | 4/2007 | Melcher et al. | |
| 2007/0118010 A1 | 5/2007 | Hillstead et al. | |
| 2007/0127622 A1 | 6/2007 | Main et al. | |
| 2007/0127845 A1 | 6/2007 | Fu et al. | |
| 2007/0140413 A1 | 6/2007 | Saracen | |
| 2007/0169265 A1 | 7/2007 | Saracen et al. | |
| 2007/0225691 A1 | 9/2007 | Silvestrini et al. | |
| 2007/0225693 A1 | 9/2007 | Muehlhoff et al. | |
| 2007/0249911 A1 | 10/2007 | Simon | |
| 2008/0056434 A1 | 3/2008 | Grozinger et al. | |
| 2008/0159478 A1* | 7/2008 | Keall et al. | 378/65 |
| 2008/0187099 A1 | 8/2008 | Gertner | |
| 2008/0187101 A1 | 8/2008 | Gertner | |
| 2008/0192892 A1 | 8/2008 | Dilmanian et al. | |
| 2008/0212737 A1* | 9/2008 | D'Souza et al. | 378/65 |
| 2008/0212738 A1 | 9/2008 | Gertner | |
| 2008/0317312 A1 | 12/2008 | Carl et al. | |

FOREIGN PATENT DOCUMENTS

| | | | |
|---|---|---|---|
| WO | WO-0235996 A1 | 5/2002 | |
| WO | WO-03/039370 A1 | 5/2003 | |
| WO | WO-2006086631 A2 | 8/2006 | |
| WO | WO-2007/027164 | 3/2007 | |

OTHER PUBLICATIONS

International Search Report and Written Opinion for PCT/US2008/013886, search report dated May 22, 2009, 19 pages (2009).

U.S. application and Preliminary Amendment for U.S. Appl. No. 12/027,069, filed Feb. 6, 2008, 94 pages (2008).

U.S. application and Preliminary Amendment U.S. Appl. No. 12/027,083, filed Feb. 6, 2008, 105 pages (2008).

U.S. application and Preliminary Amendment U.S. Appl. No. 12/027,094, filed Feb. 6, 2008, 111 pages (2008).

U.S. Appl. No. 12/103,534, filed Apr. 15, 2008, 99 pages (2008).

U.S. application and Preliminary Amendment U.S. Appl. No. 12/262,031, filed Oct. 30, 2008, 163 pages (2008).

Dieckmann et al., "A Linac-Based Stereotactic Irradiation Technique of Uveal Melanoma," Radiotherapy and Oncology, 61:49-56 (2001).

Gao et al., "Orthovoltage radiation therapy treatment planning using Monte Carlo Simulation: treatment of neuroendocrine carcinoma of the maxillary sinus," ISSN: 0031-9155; vol. 42, No. 12., pp. 2421-2433 (1997).

Kim et al., "Combination hyperthermia and radiation therapy for malignant melanoma," Cancer, 50:478-482 (1982).

Kobayashi et al., Radiotherapy for subfoveal neovascularisation associated with pathological myopia: a pilot study., J. Ophth. 87:761-766 (2000).

Bangerter, A. and Jager, T., "Forty Years' Experience with a Special, Non-Tumorous Application of Radiotherapy for the Eye", *European Journal of Medical Research*, 1:582-588 (1996).

California Department of Health and Human Services, Bailey Edgar D., C.H.P., Chief Radiologic Health Branch, Syllabus on Radiography, Radiation Protection, Filtration Regulatory Requirements, pp. 11-12 (2004).

International Search Report and Written Opinion for PCT/US2008/004999, search report dated Sep. 2, 2008, 9 pages (2008).

International Search Report and Written Opinion for PCT/US2008/005101, search report dated Sep. 2, 2008, 11 pages (2008).

Cornsweet, T.N. and Crane, H.D., "Accurate Two-Dimensional Eye Tracker Using First and Fourth Purkinje", *Journal of the Optical Society of America*, 63(8):921-928 (1973).

Das et al., "Small Fields: Nonequilibrium Radiation Dosimetry", *Medical Physics*, 35(1):206-215 (2008).

Esquivel, Carlos Jr. et al., Novel low-kVp beamlet system for choroidal melanoma, *Radiation Oncology*, I:36, 12 pages (2006).

Fakiris, Achilles J. et al., Gamma-Knife-Based Stereotactic Radiosurgery for Uveal Melanoma, *Stereotactic and Functional. Neurosurgery.*, 85:106-112 (2007).

Francescon et al., "Total Scatter Factors of Small Beans: A Multidetector and Monte Carlo Study", *Medical Physics*, 35(2):504-513 (2008).

Georgopoulos, Michael et al., Tumour Regression of Uveal Melanoma after Ruthenium-106 Brachytherapy or Stereotactic Radiotherapy with Gamma Knife or Linear Accelerator, *Ophthalmologica*, 217:315-319 (2003).

Jaywant, S.E. et al., "Stereotactic Radiotherapy in the Treatment if Ocular Melanoma: A Noninvasive Eye Fixation Aid and Tracking System", Journal of Applied Clinical Medical Physics, 4(2):156-161 (2003).

Kirwan, James F. et al., Effect of β radiation on success of glaucoma drainage surgery in South Africa: randomized controlled trial, *BMJ online*, BMJ doi:10.1136/bmj.38971.395301.7C (Oct. 5, 2006).

Kishi, Kazushi et al., Lead Contact Lens for Crystalline Lens Shielding in Electron Therapy for Eyelid Tumors, *Radiation Medicine*, 14(2):107-109 (1996).

Marcus et al., "External Beam Irradiation of Subfoveal Choroidal Neovascularization Complicating Age-Related Macular Degeneration", *Arch Ophthalmology*, 119:171-180 (2001).

Marcus, D.M. and the Amdrt Research Group, "The Age-Related Macular Degeneration Radiotherapy Trial (AMDRT): On e Year Results From a Pilot Study", *American Journal of Ophthalmology*, 138:818-828 (2004).

Sagerman, R.H. and Alberti, W.E., Radiotherapy of Intraocular and Orbital Tumors, 2nd Revised Edition, Springer, Chapter 24, Radiation Techniques for the Treatment of Retinoblastoma and Orbital Tumors, pp. 233-237 (2003).

Schilling et al., "Long Term Results After Low Dose Ocular Irradiation for Choroidal Haemangiomas", *British Journal of Ophthalmology*, 81:267-273 (1997).

Schipper, J. and Tan, K.E., "Management of Retinoblastoma by Precision Megavoltage Irradiation" Department of Radiation Therapy of the University Hospital and the Royal Dutch Eye Hospital, Utrecht, The Netherlands, 534-540 (1983).
Senan, S. and Smit, E.F., "Design of Clinical Trials of Radiation Combined with Antiangiogenic Therapy", *The Oncologist*, 12:465-477 (2007).
Toma et al., "External Bean Radiotherapy for Retinoblastoma:II Lens Sparing Technique", *British Journal of Ophthalmology*, 79:112-117 (1995).

* cited by examiner

FIG. 19
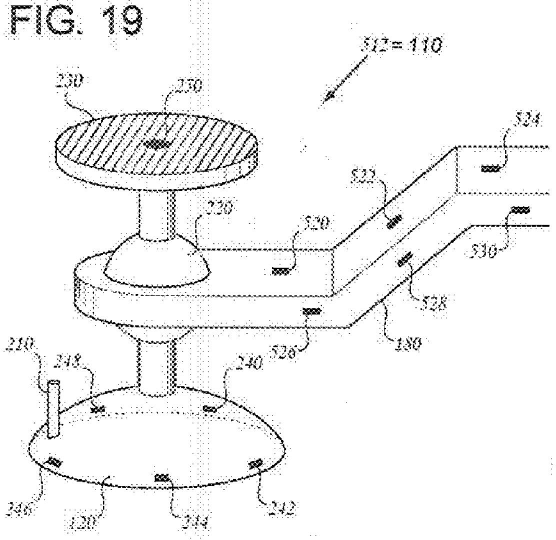
FIG. 20H
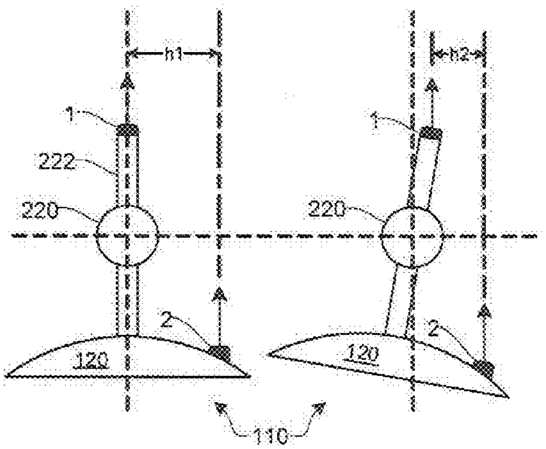
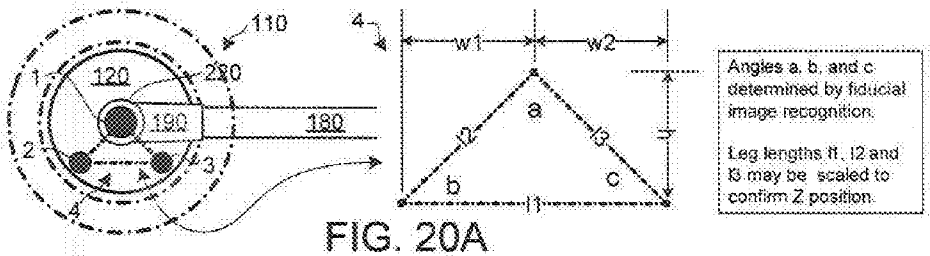
FIG. 20A
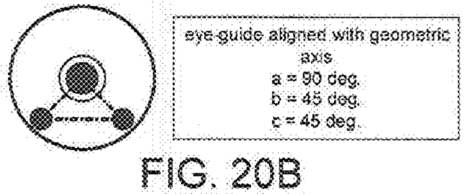
FIG. 20B
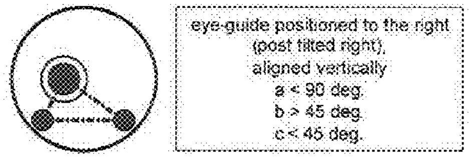
FIG. 20E
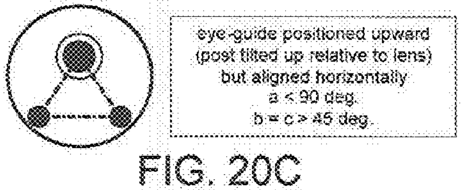
FIG. 20C
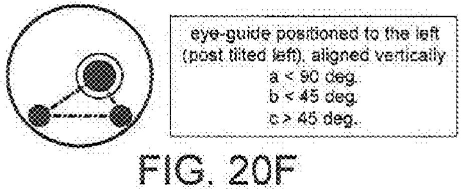
FIG. 20F
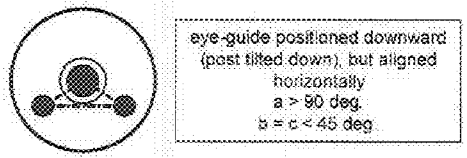
FIG. 20D
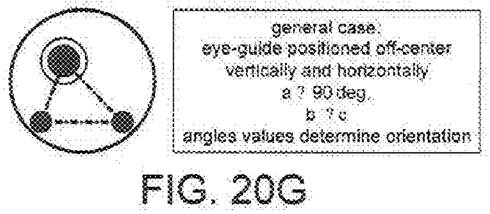
FIG. 20G FIG. 21B
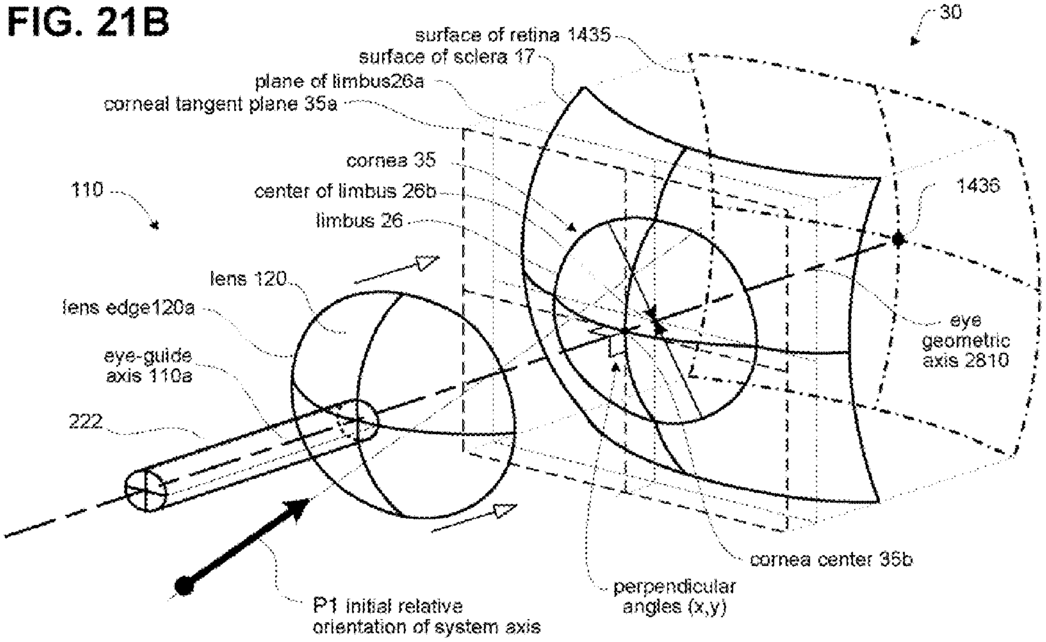
FIG. 21C(1)
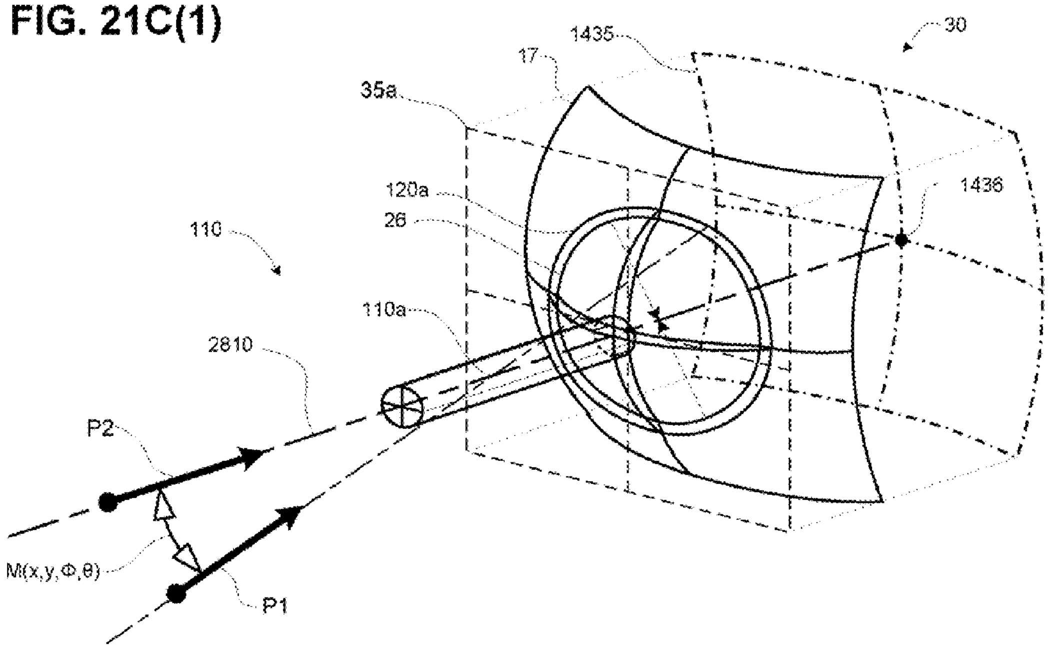

FIG. 21C(2)
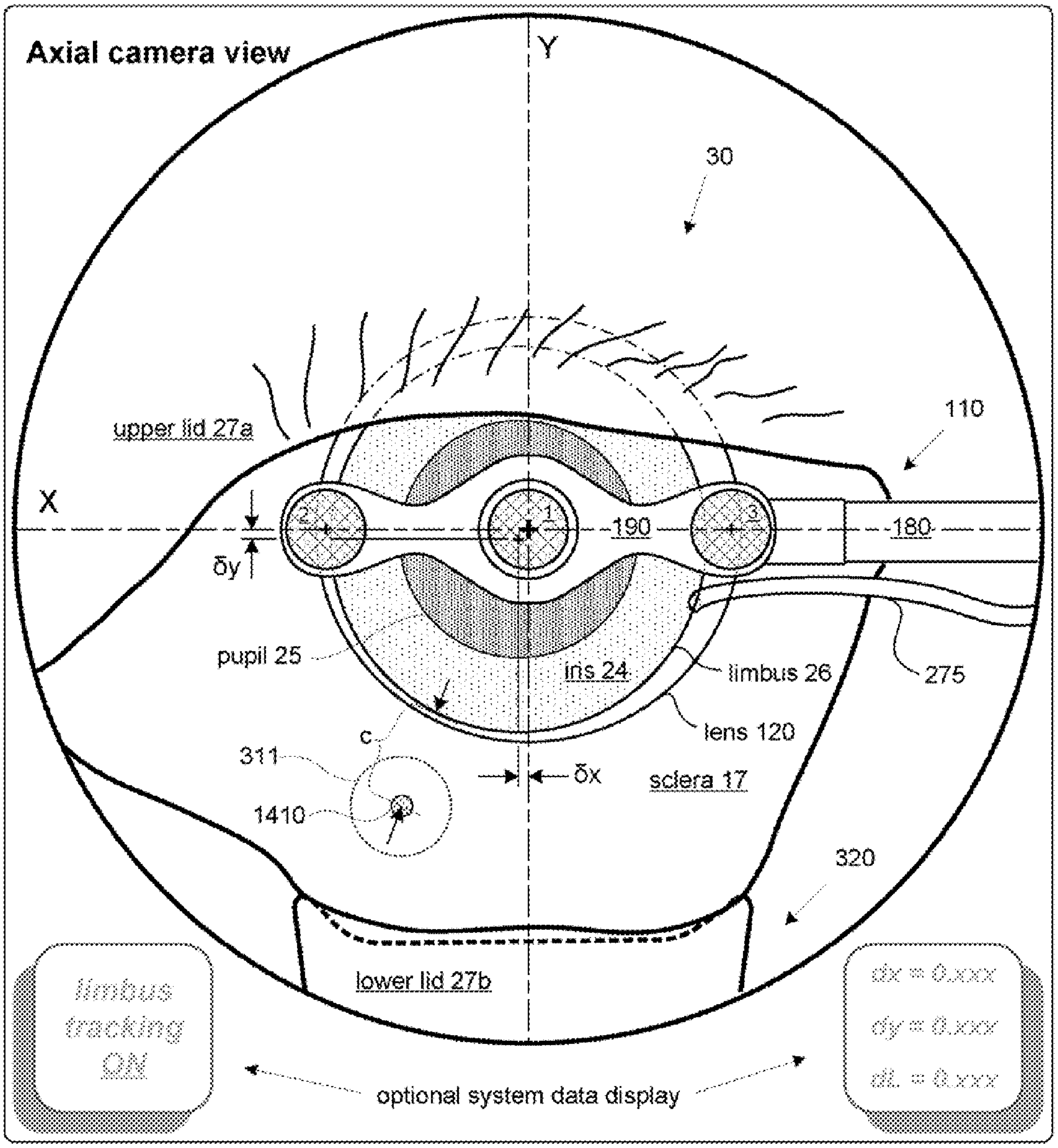

FIG. 24A
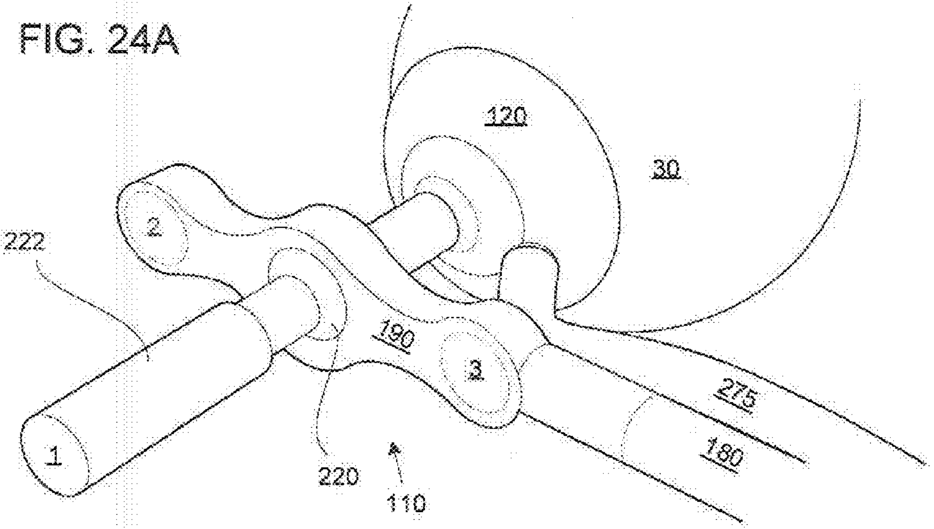
FIG. 24B
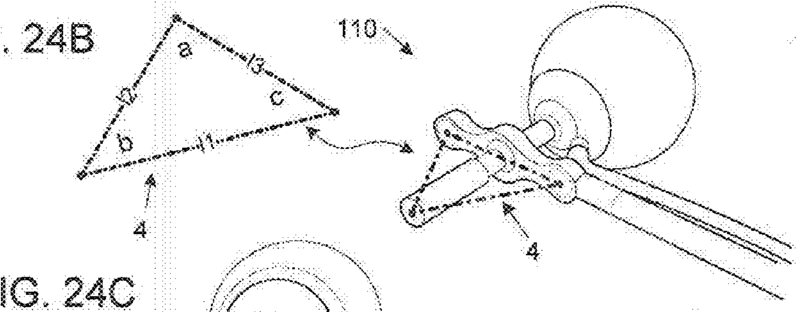
FIG. 24C
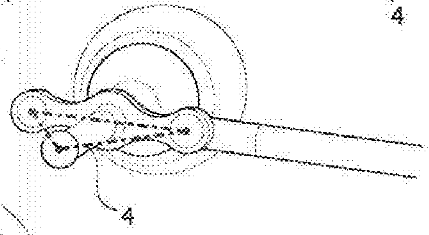
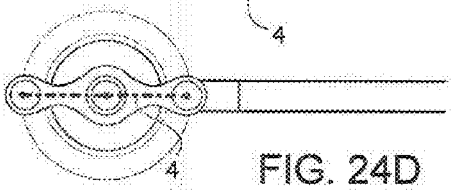
FIG. 24D
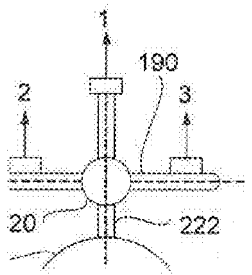
FIG. 25A
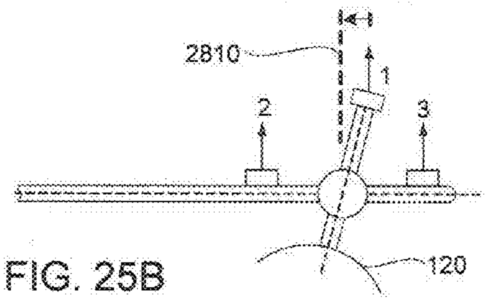
FIG. 25B Flowchart (continued next sheet)

Flowchart

FIG. 34 - Eye rotation (1) Eye-guide pivot tilt:
horizontal: $x_0 = (D + L) \tan \theta_x$, where D is eye axial length)
vertical: (similar method)

(2a) Limbus-to-lens motion model (rotation about eye center):
horizontal: $\delta x \approx 1^*(x_3 - x_4)$, where $D \approx 2R_e$ (radius of eye globe)
vertical: (similar method)

(2b) Alternative model (rotation along corneal surface):
horizontal: $\delta x \approx (k_c - 1)^*(x_3 - x_4)$, where $D \approx k_c^*R_c$ (radius of cornea), and $k_c \approx$ about 3 to about 4
vertical: (similar method)

(2c) Alternative combined model:
horizontal:
$\delta x \approx (k_e - 1)^*(x_3 - x_4)$,
where $D \approx k_e^*R_e$ (effective rotation radius),
and $\sim 2 < k_e < \sim 4$
(e.g., $k_e \approx 2.25$)
vertical: (similar method)

(3) Combined rotation effect:
horizontal: $\Delta x = x_0 + \delta x$ ;
vertical: $\Delta y = y_0 + \delta y$

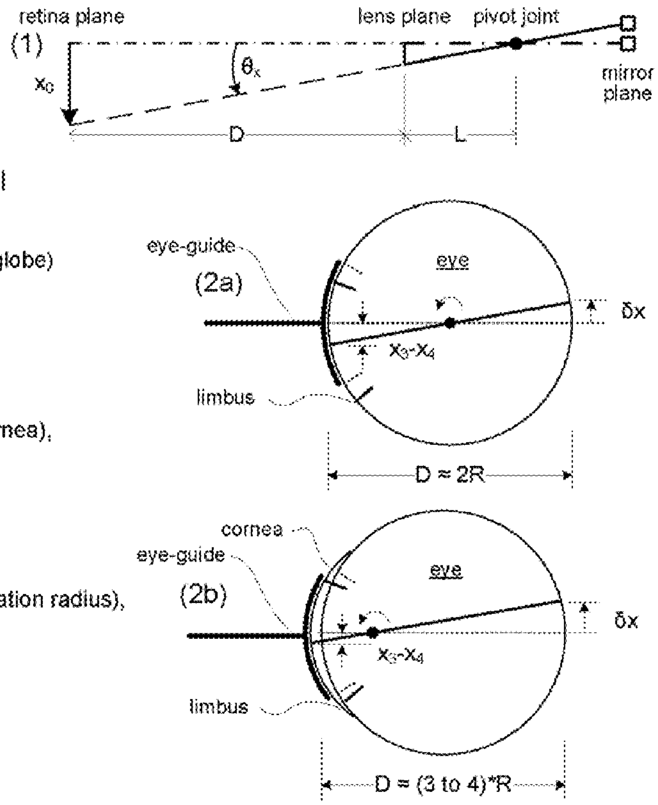

FIG. 35

Retinal motion related to Z displacement $$\delta y = \delta z * \tan \beta$$

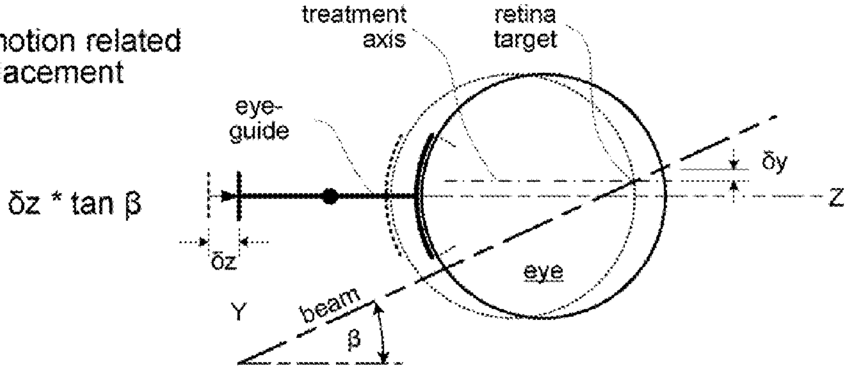

FIG. 36A

Transformation Formula

Horizontal Coordinate

| | |
|---|---|
| X = X0 | Initial coordinate |
| + L /(L+l) *X1 + l/(L+l) * X3 | Pivot x displacement; X1:IGM, X3:IGL |
| - (L+D) * θy | I-guide mirror y-tilt, solid Eye[2] |
| - x4* (D-R)/R | Limbus to I-guide decoupling, X4:Limbus to IGL |
| + $X_{567}$ | Z-displacement/angled beam related |

$X_{567}$ = { 0 — 6 clock beam; - 2* Z* sin(15) — 7 clock beam; 2 * Z * sin(15) — 5 clock beam }

Vertical Coordinate

| | |
|---|---|
| Y= Y0 | Initial coordinate |
| + L /(L+l) *Y1 + l/(L+l) * Y3 | Pivot displacement; Y1:IGM, Y3:IGL |
| - (L+D) * θx | I-guide mirror x-tilt, solid Eye |
| - y4* (D-R)/R | Limbus to I-guide decoupling, Y4:Limbus to IGL |
| - Z * tan (28) | Z-displacement /angled beam related (5,6,7) |

L: distance between the pivot and the IGL, D: Length of an eyeball l: distance between the pivot and the ILM R: Corneal radius of curvature

FIG. 36B

Z-displacement/angled beam related motions

1. Initial target position $x_{50}$, $y_{50}$

2 Real-time position 6 o'clock beam $x_{51} = x_{50}$ $y_{51} = y_{50} - Z * \tan(28)$ 5 o'clock beam $x_{51} = x_{50} + 2* Z* \sin(15)$ $y_{51} = y_{50} - Z * \tan(28)$ 7o'clock beam $x_{51} = x_{50} - 2* Z* \sin(15)$ $y_{51} = y_{50} - Z * \tan(28)$ where z is the distance of IGL from its initial z position

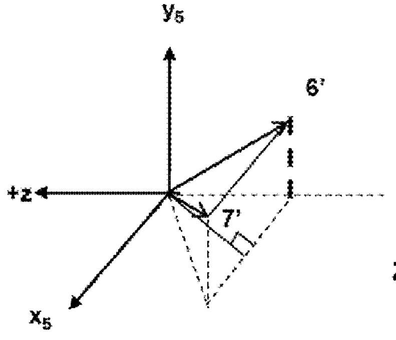

XYZ Coordinate System

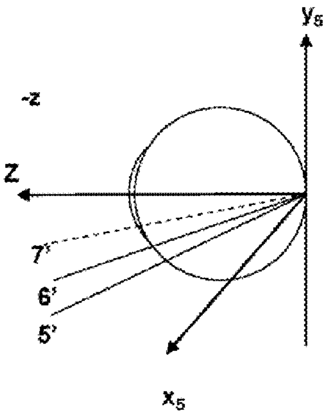

Monte Carlo simulation with CT scan anatomy model
(cross-section along central beam plane, with 3-beam overlap)

X drift beyond thresholds x drift, no gating control x drift with gating and realigning comparison case: acceptable motion (within threshold)

X drift beyond thresholds without gating and realigning with gating and realigning Alternative gating blinking, upward transients (+y)

Blinking, upward transients (+y )

FIG. 43D
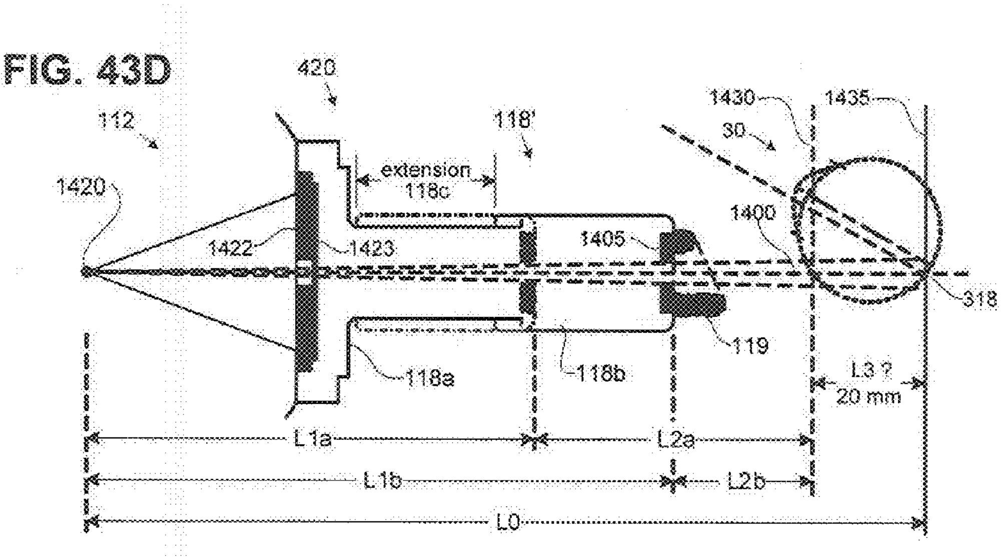
Example of collimator length variation
(constant anode distance, horizontal scale exaggerated)
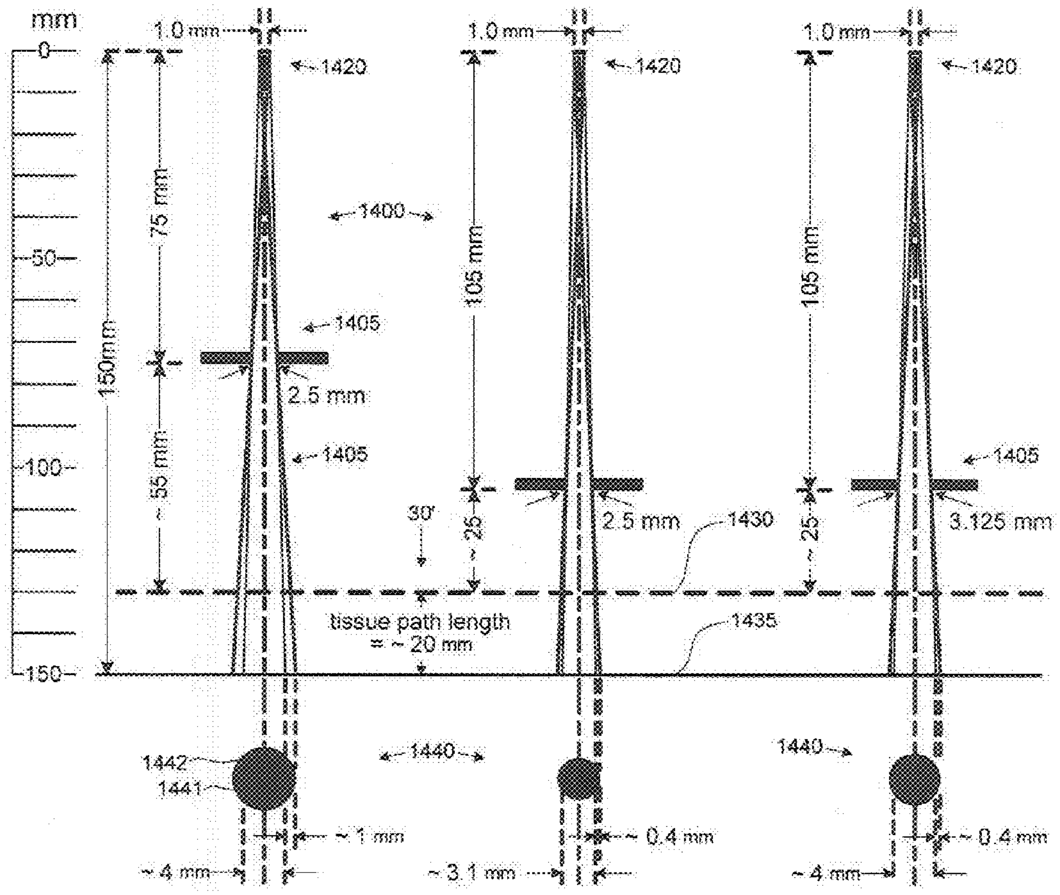
FIG. 43E FIG. 43F FIG. 43G (1)
118b
1405a
1405a
1405'
3.125 mm
1405b
1405b
0.3125 mm
(2)
119c
119a
118b
1405a
1405b
3.125 mm
1400
119a
collimator
outer portion
118b (1)
118b
1405
2.5 mm
1405b
1405b
(2)
119c
119a
118b
1405a
2.5 mm
1400
119a (1)
(2)
1400
1405a
1405b
119c
119a
118b
2.5 mm
3.125 mm 1405
118b
2.5 mm
3.125 mm

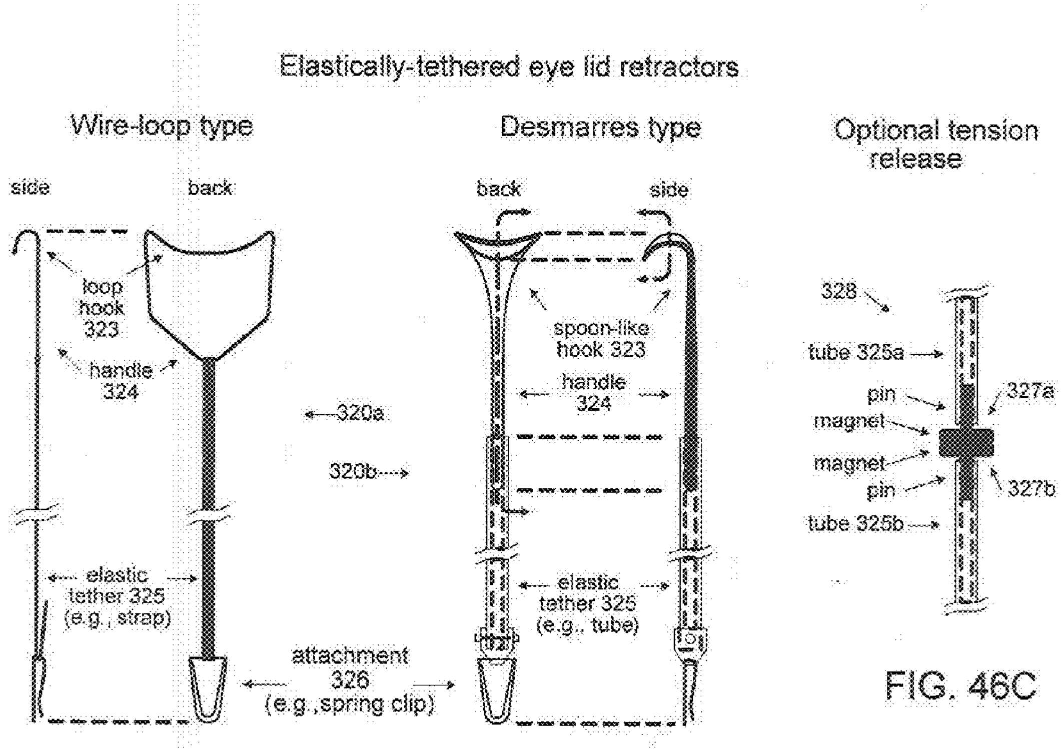
FIG. 46A
FIG. 46B
FIG. 46C
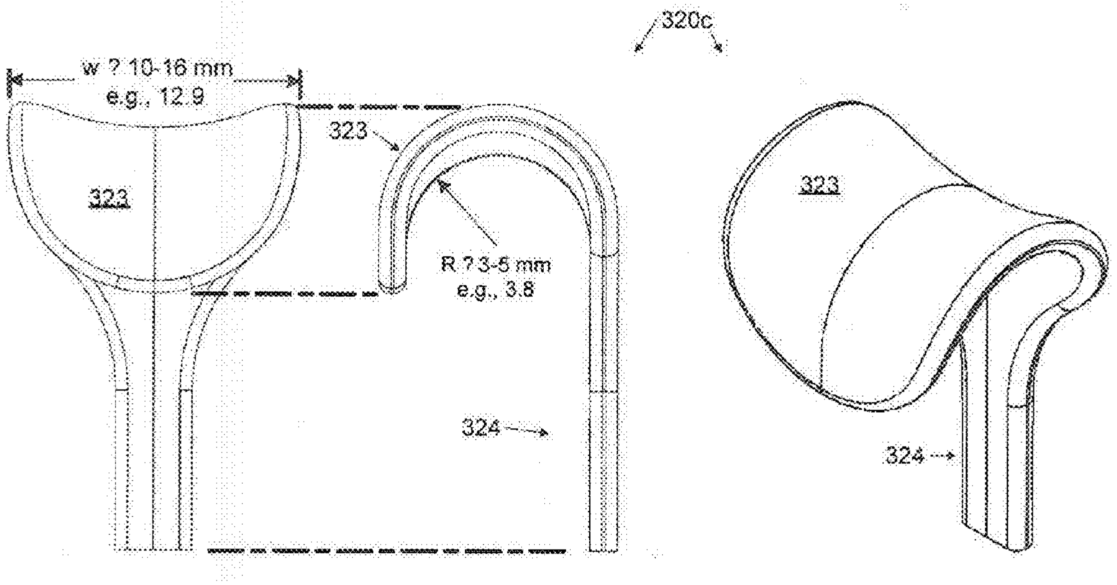
FIG. 47A
FIG. 47B
FIG. 47C (from US Pat. 6,758,564)

(from US Pat. 6,758,564)

[from Hammer, et al.; J. Biomedical Optics (2006) 114, 041126]

LSLO optical path
SM: source module
S: source
L: lens
CL: cylindrical lens
SL: scan lens
OL: ophthalmoscopic lens
O: detector objective
G: galvanometer
BC: beam combining optic
PS: pupil stop
BD: beam displacement optic
LA: linear array sensor (2)
P: pupil splitting optic

METHODS AND DEVICES FOR DETECTING, CONTROLLING, AND PREDICTING RADIATION DELIVERY

RELATED APPLICATIONS

This application is a continuation-in-part of U.S. application Ser. No. 12/262,031 filed Oct. 30, 2008, now pending, which claims the benefit of priority to U.S. Application Nos. 61/101,013 filed Sep. 29, 2008, 61/093,092 filed Aug. 29, 2008, and 61/076,128 filed Jun. 26, 2008. U.S. application Ser. No. 12/262,031 is also a continuation-in-part of U.S. application Ser. No. 12/103,534 filed Apr. 15, 2008, now pending, which claims benefit of priority to U.S. Application Nos. 61/016,472 filed Dec. 23, 2007, and 61/020,655 filed Jan. 11, 2008. U.S. application Ser. No. 12/262,031 is also a continuation-in-part of U.S. application Ser. No. 12/100,398 filed Apr. 9, 2008, now U.S. Pat. No. 7,693,260. U.S. application Ser. No. 12/103,534 is also a continuation-in-part of U.S. application Ser. No. 12/027,083 filed Feb. 6, 2008, now pending. U.S. application Ser. No. 12/103,534 is also a continuation-in-part of U.S. application Ser. No. 12/027,094 filed Feb. 6, 2008, now pending. U.S. application Ser. No. 12/103,534 is also a continuation-in-part of U.S. application Ser. No. 12/027,069 filed Feb. 6, 2008, now pending. All of these patent applications are incorporated herein in their entirety by reference.

TECHNICAL FIELD

The present disclosure pertain to a system and method for performing an image-guided low-energy X-ray therapy procedure on a patient's eye, to systems for planning and controlling such treatments, and to eye alignment-stabilization systems useful in opthalmologic procedures.

BACKGROUND

Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused by or results in an inflammatory process that ultimately causes destruction of the retina. The inflammatory process can result in direct destruction of the retina or destruction via formation of neovascular membranes which leak fluid and blood into the retina, quickly leading to scarring.

Many treatments for macular degeneration are aimed at stopping the neovascular (or "wet") form of macular degeneration rather than geographic atrophy, or the "dry" form of Age-related Macular Degeneration (AMD). All wet AMD begins as dry AMD. Indeed, the current trend in advanced ophthalmic imaging is that wet AMD is being identified prior to loss of visual acuity. Treatments for macular degeneration include the use of medication injected directly into the eye (Anti-VEGF therapy) and laser therapy in combination with a targeting drug (photodynamic therapy); other treatments include brachytherapy (i.e., the local application of a material which generates beta-radiation).

Accurate alignment of a subject's eye is important in a number of situations. For example, when taking certain types of eye measurements, it is critical to know that the eye is in a particular reference position. When measuring the cornea of a patient's eye before therapeutic treatment, it can be important to repeat those measurements after the treatment to determine how much, if any, the treatment has affected the measurements. In order to accomplish this, one must ensure that the eye alignment is in the same position each time the particular measurements are made. Otherwise, the difference in data from before and after the treatment might be due to a change in eye alignment rather than the treatment.

A number of treatment and surgery procedures, typically involving irradiating one or more selected targets in the eye, require a patient's eye to be stabilized or positioned prior to and/or during treatment. For example, refractive laser surgery involves ablating corneal tissue of the eye with an ultra-fast, ultra-short pulse duration laser beam, to correct refractive errors in a patient's eye. As such, the patient's eye must be stabilized, and either the laser system must be properly and precisely aligned with the patient's eye, or the patient's eye must be properly and precisely aligned with the laser system. The eye is predisposed to saccades, which are fast, involuntary movements of small magnitude. A patient may voluntarily shift their gaze during surgery, and furthermore, eye position stability is affected by the patient's heartbeat and other physiological factors.

In order to achieve the goal of maximizing results while minimizing risks to the patient during such eye treatment, it is important to eliminate, or at least significantly reduce, as many system errors as possible. This includes the improper alignment of the patient's eye relative to the treatment system. Alignment errors may result from either a misconfiguration of the system, or from the patient's interaction with the system. Insofar as patient/system interaction is concerned, any voluntary or involuntary movement of the patient's eye during treatment can significantly alter the alignment of the eye relative to the treatment system. It is necessary, therefore, to hold the eye of the patient stationary during these procedures.

In addition, there is a need to control the distribution of radiation absorption by ocular structures during treatment, such as to assure an adequate dosage to a lesion being treated, and to avoid damaging collateral structures by stray radiation.

SUMMARY

Further description may be found in priority U.S. application Ser. Nos. 12/103,534 filed Apr. 15, 2008, 12/027,069 filed Feb. 6, 2008, and 12/100,398 filed Apr. 9, 2008, each of which is incorporated herein by reference.

A. Radiotherapy Methods:

In one embodiment, a Method of Treating a lesion on or adjacent the retina of an eye of a patient with an external-beam radiation device, comprises (a) placing the patient's eye in alignment with a known system axis in an external three-dimensional coordinate system, and measuring the eye's axial length; (b) from the known position of the system axis and from the measured axial length, determining the coordinates of the lesion to be treated in the external coordinate system; (c) directing a collimated radiation beam along a known beam axis in the external coordinate system at the lesion to be treated; (d) during said directing, tracking the position of the patient's eye with respect to the known system axis, thus to track the position of the lesion to be treated in the external coordinate system; and (e) based on the known beam axis of the collimated beam in the external coordinate system, and the instantaneous position of the lesion to be treated in the external coordinate system, as determined at least in part by the tracked position of the eye, calculating a total radiation equivalent received at the lesion to be treated during the treatment.

Such method may further provide that step (b) includes determining the coordinates of at least one radiation-sensitive structure in the external coordinate system; step (d) includes tracking the position of the at least one radiation-sensitive structure in the external coordinate system; and step (e) includes, based on the instantaneous position of the at least one radiation-sensitive structure in the external coordinate system, calculating a total radiation equivalent received at the at least one radiation-sensitive structure during the treatment; the method further comprising the step of (f) based on the calculated radiation equivalent from step (e), controlling the radiation beam to insure that the at least one radiation-sensitive structure does not receive more than a preselected radiation equivalent during the treatment.

The method may further provide that step (a) include measuring the axial length of the patient's eye by ultrasound imaging, and step (b) include scaling the measured axial length from step (a) to a standard human-eye model, and determining the coordinates of the lesion to be treated and the at least one radiation-sensitive structure from the eye model. Step (a) may include determining a patient-eye geometric axis that extends through the center of the limbus and contains a corneal reflection of the patient's eye, and aligning the geometric axis with the known system axis; and step (d) may include tracking the angular deviation of the geometric axis of the eye with the known system axis. The method may include attaching on eye guide to the patient's eye, centered thereon so that the geometric axis of the eye corresponds approximately to the axis of the eye guide, and aligning the axis of the eye guide with the known system axis.

The method may further provide that step (b) include using the measured optical length of the patient's eye to place the patient's in registry with the eye model, and using the coordinates of the lesion to be treated and the at least one radiation-sensitive structure in the model to determine the coordinates thereof in the external coordinate system. Step (d) may include tracking the position of the eye guide axis with respect to the system axis, thus to track the positions of the lesion and radiation-sensitive structures in the external coordinate system. The eye model may include a virtual medium by which the attenuation of a radiation beam along a known path through the model can be determined; and step (e) may include determining the spatial accumulation of radiation received at the macular region of the eye based the known intensity of the collimated beam, the instantaneous positions of the of the patient's eye, and the attenuation of the beam through the virtual medium along known pathways within the eye.

The method may further provide that step (e) includes mapping a spatial quantity indicative of a distribution of total radiation onto the eye model, based on the tracked position of the patient's eye during a period of directing a radiation beam at the retinal region of the patient's eye. The lesion to be treated may be the macula, the at least one radiation-sensitive structure may include at least a portion of the optic nerve or optic disk of the eye, and step (e) may include calculating the total radiation equivalent received at the macula and at the optic disk during the treatment. Step (f) of controlling the radiation beam may include controlling the radiation beam to do one or more of: (i) achieve a desired dose of radiation at the lesion; (ii) avoid exceeding a selected level of radiation dose at the radiation-sensitive structure; and (iii) avoid exceeding a selected threshold based on the spatial quantity, the threshold indicative of eye-motion-based departure of the beam axis from the selected target.

The method may further provide that step (e) of calculating total radiation equivalent received at the lesion to be treated and the at least one radiation-sensitive structure during the treatment, may include determining a time-increment vector summation of a parameter indicative of an eye-motion-based departure of the beam axis from the selected target lesion to be treated. Step (e) of calculating total radiation equivalent received at the lesion to be treated and the at least one radiation-sensitive structure during the treatment may include modulating a pre-determined radiation distribution model representing predicted radiation dose distribution to be received by tissue of the patient from the collimated radiation beam in the absence of eye motion, the modulation based tracked eye motion during treatment, so as to determine a radiation dose distribution accounting for actual eye motion during treatment.

The method may further provide that step (e) of calculating total radiation equivalent received at the lesion to be treated and the at least one radiation-sensitive structure during the treatment, may further include sequentially performing the modulating a pre-determined radiation distribution model for a plurality of successive time increments during radiation treatment so as to determine a cumulative dose distribution during the course of treatment; and step (f) may include (i) comparing the cumulative dose received by a selected non-target anatomical structure with a pre-determined dose threshold quantity to determine if the threshold has been exceeded and (ii) in the event that the threshold has been exceeded, controlling the controlling the radiation beam or beam axis to reduce or eliminate further radiation dose to the selected non-target anatomical structure.

The method may further provide that step (e) of calculating total radiation equivalent received at the lesion to be treated and the at least one radiation-sensitive structure during the treatment; further includes sequentially performing the modulating a pre-determined radiation distribution model for a plurality of successive time increments during radiation treatment so as to determine a cumulative dose distribution during the course of treatment; and wherein step (f) includes (i) comparing the cumulative dose received by a selected anatomical target region with a pre-determined dose threshold quantity to determine if the threshold has been reached, and (ii) in the event that the threshold has been reached, controlling the radiation beam or beam axis to reduce or eliminate further radiation dose to the selected anatomical target region.

The method may further provide that the lesion may be a macular lesion, wherein the radiation beam is an collimated X-ray beam, and step (c) may include determining the position of the patient's macula in the treatment coordinate system from the known position of the eye and the coordinates of the macula in the external coordinate system, and determining a treatment axis in the external coordinate that intersects the patient macula. Step (c) may include directing a collimated X-ray beam along each of at least two different known treatment axes in the treatment coordinate system at a region of the macular region of the patient's retina. Step (f) may include controlling the X-ray beam to deliver approximately equal doses of radiation at the patient's macula along each of the different known treatment axes.

The method may further provide that step (f) includes turning off the beam being directed onto the patient's eye when the position of the patient's macula, as tracked in step (c), relative to the axis of the beam, is greater than a predetermined threshold distance. Step (f) may include directing the beam against the patient's macular region until the spatial accumulation of radiation mapped at the macula of the eye model reaches a predetermined dose level.

B. Radiotherapy Systems:

In one embodiment, a Radiotherapy System for treating a target area in a patient with an irradiation beam, comprises: (a) a tracking assembly for tracking the position of a patient body region containing the target area and at least one radiation-sensitive area with respect to a known reference axis in an external coordinate system; (b) a beam source for directing an irradiation beam at the patient target area along a known treatment axis in the external coordinate system; and (c) a processor operatively connected to the tracking device and beam source; the processor operable to: (i) determine, from the known position of body region in the external coordinate system, the coordinates of the target area to be treated and the coordinates of the at least one radiation-sensitive patient structure; (ii) during a period when the irradiation beam is being directed along the treatment axis at the target area, and based on information received from the tracking device, track the positions of the target area to be treated and the at least one radiation-sensitive structure; (iii) based on the known beam axis of the collimated beam in the external coordinate system, and the instantaneous positions of the target area to be treated and the at least one radiation-sensitive structure, calculate a total radiation equivalent received at the target area and at least one radiation-sensitive structure; and (iv) based on the calculated radiation equivalents from step (iii), control the irradiation beam to insure that the at least one radiation-sensitive structure does not receive more than a preselected radiation equivalent during the treatment.

The system may comprise a tracking assembly which includes (i) an imaging device for recording an image of a region of the patient's body that contains natural or fiducial landmarks that define a geometric axis of the imaged region and (ii) an image detector operably connected to the imaging device for converting the recorded image to a digital image made up of known-coordinate pixels, and the processor may be operably connected to the detector for determining pixel coordinates of the geometric axis of the body region and step (ii) of the processor operation includes using the pixel coordinates of the geometric axis, relative to known pixel coordinates of the reference axis, to track the position of the patient body region relative to the reference axis.

Ocular systems. The system may be configured for treating an ocular lesion, wherein the body region includes the patient eye, the target area includes the ocular lesion, the at least one radiation-sensitive structure includes the optic disc of the eye, the natural landmarks of the eye that define its geometric axis are the center of the limbus and a first corneal reflection, and the beam source produces a collimated x-ray beam. The system may alternatively include an eye guide adapted to be placed on the patient's eye, centered thereon so that the geometric axis of the eye corresponds approximately to the axis of the eye guide, and a detector for determining the coordinates of the axis of the eye guide in the external coordinate system, and the processor may be operably connected to the detector for determining the coordinates of the eye guide axis and step (ii) of the processor operation includes using the coordinates of the eye-guide axis, relative to the known coordinates of the reference axis, to track the position of the patient's eye relative to the reference axis.

The system may be configured so that the tracking system is operable to capture a plurality of time-sequenced images of the body region and its landmarks during the treatment method, and the processor is operable to determine the coordinates of the body region geometric axis for each of the plurality of images, and in step (ii) to determine a time-dependent change in the coordinates of the target area to be treated and the at least one radiation-sensitive structure. The system may be configured so that the processor is operable to carry out, in step (iii) generating a map of total equivalent radiation covering the target area and the at least one radiation-sensitive area in the patient body region, and in step (iii), to determine from the total equivalent radiation map, the radiation equivalent received at any time during treatment by the target area and at least one radiation-sensitive area.

The system may be configured so that the body region includes the patient eye, the target area includes the ocular lesion, the at least one radiation-sensitive structure includes the optic disc of the eye, and the processor is operable, to carry out in step (iii) generating a map of total equivalent radiation covering the target area and the at least one radiation-sensitive area in the patient body region, and in step (iii), determining from the total equivalent radiation map, the radiation equivalent received at any time during treatment by ocular lesion and at least one radiation-sensitive area.

The system may be configured so that the target area includes the ocular lesion, the at least one radiation-sensitive structure includes the optic disc of the eye, and the processor includes a model of the human eye by which the coordinates of the lesion to be treated and the at least one radiation-sensitive structure can be determined, when the patient's eye is superimposed on the eye model. The eye model in the processor may include a virtual medium by which the attenuation of a radiation beam along a known path through the model can be determined, and the processor is operable to determine from the known intensity of the beam and the length of the radiation path through the virtual medium within the eye model, the amount of radiation that is received by the retina in the eye model.

The system may be configured so that the body region includes the patient eye, the target area includes the ocular lesion, the at least one radiation-sensitive structure includes the optic disc of the eye, wherein the processor is operable, by determining the position of the ocular lesion in the external coordinate system, to determine a treatment axis in the treatment coordinate system that intersects the lesion. The processor may be operable to determine at least two different treatment axes in the treatment coordinate system, and to control the radiation beam to deliver approximately equal doses of radiation at the lesion along each of the different known axes. The processor is operable to turn off the beam being directed onto the patient's eye when the distance between the position of the patient's lesion, as determined in operation (d)(ii), and the intersection of the axis of the beam on the retina, is greater than a predetermined threshold distance. The processor may be operable to direct the beam against the patient's retinal region until the spatial accumulation of radiation mapped at the lesion of the eye model reaches a predetermined dose level.

C. Machine-Readable Code for System Operation:

Monitoring. One embodiment includes Machine-Readable Code operable on an electronic computer included in a Radiotherapy System which is operable for monitoring the total radiation dose received at a target site during the course of treatment in which the target site is irradiated with a collimated x-radiation. The code may be operable to perform the steps comprising: (a) defining, in an external coordinate system, coordinates for (i) a reference axis, (ii) a radiation-beam axis, and (iii) the target site which, when a body axis having a known relationship to the target site is aligned with the reference axis, places the radiation beam at the center of the target area, (b) receiving from a body tracking device, ongoing information during the course of radiation treatment on the position of the body axis with respect to the reference axis, (c) from the information received in step (b), and from the known intensity of the beam at the radiation beam, calculating the spatial distribution of radiation received in the region of the target site over the course of the treatment, and (d) using the spatial distribution of radiation calculated in step (c) to monitor the total radiation dose at the target site over the course of the treatment.

The machine-readable code may be configured to carry out steps wherein the target area includes the ocular lesion, the body axis is the geometric axis of the eye, and information received from a body tracking device is in the form of ocular images from which the geometric axis of the eye can be determined. The eye may be irradiated during the course of treatment by an a collimated x-radiation beam directed at the target site along at least two different beam axes. The machine-readable code may be configured to carry out steps wherein an eye guide is centered on the eye such that an eye guide axis corresponds approximately to the geometric axis of the eye, and the information received from a body tracking device is in the form of information on the position of the eye guide. The machine-readable code may be further operable, in step (a) to determine the coordinates, in the external coordinate system, of the optic disc of the patient's eye, based on a known spatial relationship between the lesion of the optic disc, and further operable in step (d) to use the spatial distribution of radiation calculated in step (c) to monitor the total radiation dose at the optic disc during the course of treatment.

Controlling. One embodiment includes Machine-Readable Code operable on an electronic computer included in a Radiotherapy System which is operable for controlling the treatment of an ocular lesion by exposing the lesion to a collimated x-radiation beam. The code may be operable to perform the steps comprising: (a) using information received from a eye-tracking system to determine a geometric axis of the eye in an external coordinate system, (b) with the geometric axis of the eye placed in alignment with a reference axis, determining the coordinates of the lesion in an external coordinate system, (c) from the coordinates of the ocular lesion determined in step (b), determining a beam axis that intersects the lesion with the patient eye in an defined position with respect to the reference axis, and (d) controlling the position of an x-ray beam source to position the beam along the beam axis determined in step (d).

The machine-readable code may be configured to carry out steps wherein the information received from the eye tracking system is an ocular image from which the geometric axis can be determined by determining the center of the sclera and a corneal reflection from the ocular image. The machine-readable code may be configured to carry out steps wherein an eye guide is centered on the eye such that an eye guide axis corresponds approximately to the geometric axis of the eye, and the information received from a body tracking device is in the form of information on the position of the eye guide.

The machine-readable code may be configured wherein step (c) may further include determining two or more beam axes that intersect the lesion with the patient eye in an defined position with respect to the reference axis. The computer may be operably connected to a beam-source robotic device for position the beam along a selected beam axis, and step (d) may include acting on the robotic device to shift the beam axis during the course of treatment, from one beam axis to another determined in step (c).

Tracking. One embodiment includes Machine-Readable Code operable on an electronic computer in a treatment system for treating a lesion of a patient's eye by directing a collimated radiation beam along a beam path to the lesion and including, operably connected to an eye-tracking device which includes an eye-contact member configured to engage the eye and having visible fiducials, and a camera configured to capture an electronic image of the eye. The code may be operable to execute instructions effective to perform the steps comprising: (a) aligning the camera to a known position and/or orientation with respect to a treatment system coordinate system (system coordinates) wherein the camera is directed to the eye as engaged with the contact member; (b) capturing an image of the eye as engaged with the contact member; (c) identifying one or more pixels of the image representing the location of an axis of the contact member; (d) determining from image data that the eye-guide axis is aligned to a known position and/or orientation with respect to the system coordinates; (e) determining from image data the location of the center of limbus in the system coordinates; and (f) determining a deviation of the location of the center of limbus to a known position and/or orientation of the eye-guide.

The machine-readable code may be configured so that the step (e) of determining the location of the center of limbus includes: (i) determine a portion of the image including all or a portion of the exposed portion of the limbus boundary, and identifying the locations in the image corresponding to the limbus boundary image; (ii) determining a mathematical representation of a "best fit" shape corresponding to the limbus boundary locations; and (iii) calculate a center of "best fit" shape so as to determine the location of the limbus center. The code may further include the steps of: (g) registering the positions and/or orientations determined in steps (a-d) of one or both of contact member and limbus in a virtual computer eye model; (h) calculating the position of an anatomical eye structure in the system coordinates based on the registered eye model; and (i) controlling the at least one operational aspect of the collimated radiation beam in response to the calculated the position of the anatomical eye structure.

D. Computer-Executed Method for Non-Ocular and Ocular Target Tracking:

One embodiment includes a Computer-Executed Method for use in a radiation treatment device including a computer processor and a body-part motion tracking device operably connected to the computer processor, the tracking device including an body-contact member configured to engage the surface of a body part of the patient which includes a radiation treatment target, and a camera configured to capture an electronic image of the body part The processor may be effective to execute instructions to perform the steps comprising: (a) determining an initial position and orientation of the body part, based on: (i) determining the alignment of the contact member as engaged with the body so as to have a known orientation relative to an anatomical axis of the body part and a known position relative to the contacted body surface; and (ii) determining the alignment of the contact member as engaged with the body with the radiation treatment device so as to have a known initial position and orientation in a coordinate system of radiation treatment device; (b) determining an initial position of the treatment target in the coordinate system of radiation treatment device, based on determining the relative position of the treatment target to the contact member; (c) electronically capturing a plurality of time-sequenced images including the contact member while engaged with the body during the administration of radiation treatment; (d) processing the images in the computer processor so as to determine one or both of an orientation and a position of the contact member in a coordinate system of the radiation treatment device at the time of capture of each image; and (e) determining for each image, from the orientation and/or position of the contact member at the time of capture of the image, the change from the initial orientation and/or position of the contact member in the coordinate system of radiation treatment device; and (f) determining for each image, the change from the initial position of the treatment target in the coordinate system of radiation treatment device, so as to track the sequential motion of the treatment target; and (g) controlling at least one aspect of the radiation treatment based on the tracking of the sequential motion of the treatment target.

In certain embodiments the computer-executed method provides the body part includes a treatment target is selected from the group consisting essentially of a portion of the brain, spine, a breast, musculoskeletal tissue, vasculature, abdominal and gastrointestinal lesions. In alternative embodiments the computer-executed method provides that the body part is an eye, wherein the treatment target includes a portion of the retina, and wherein the contact member includes a lens element contacting the surface of the eye.

E. Additional or Alternative Method and Apparatus Embodiments:

Several embodiments having aspects of the invention are part of the written description and drawings of this application; and may be pursued this application or in one or more continuations or divisional applications.

Virtual of phantom model. In one embodiment, a method of treating a patient with radiation emitted from a radiation source, comprises in any operative order the steps of: a) providing a phantom model including a representation of patient anatomy; b) registering the phantom model with virtually projected radiation beams from a virtual radiation source and simulating dose deposition in the phantom model; c) simulating movement of the phantom model while keeping the registration between the phantom model and the virtually projected radiation beams; d) registering the phantom model with a subject receiving radiation, and registering the virtually projected radiation beams with a radiation source treating the subject; e) registering movement of the patient with movement of the phantom model in the simulation; f) determining, from the model as registered with the patient, at least a dose of radiation absorbed by the treated tissue during the treatment time.

The phantom model may include an anatomic representation of one or more structures of an eye, such as a treatment target regions (areas or volumes planned to receive radiation dosage), e.g., a portion of a retina. The model may also include representation of non-target anatomical structures (areas or volumes planned to have radiation dosage minimized or avoided), e.g., an optic disk, an optic nerve and a lens of the eye; and adjacent anatomical structures, e.g., volumes through which the radiation beam propagates and is attenuated, both before reaching a target region, and beyond a target region.

A phantom model may be modified based on one or more measured patient anatomic features, such as by scaling a phantom eye model relative to a measured eye dimension, e.g., an A-scan eye axial length. In alternatives, medical imagery may be registered, superimposed and/or scaled to the model and included to provide patient-specific content. For example, a fundus image of a patient's retina (optionally scaled) may be superimposed on a retinal representation in the model so as to permit imaged features to be superimposed on model features, such as treatment plan target region data in relation to a visible lesion, the optic disk, and the like.

A phantom model may be registered or correlated with measured movement of a patient so as to determine a corresponding virtual movement of the model. In addition, a real radiation source may be registered or correlated with the model so as to correlate the radiation emission configuration of the radiation source with the virtual movement of the model. Thus a real radiation dose to anatomy may be determined by reference to the model, where the model includes representations of anatomy and radiation source, by determining a virtual movement of the model correlated with real or detected patient movement. Embodiments having aspects of the invention may further including modifying the radiation treatment in response to the determined radiation dose, such as by automatically or manually reducing or stopping radiation emission; or by automatically or manually reorienting the radiation source.

In exemplary embodiments of methods and devices having aspects of the invention, an algorithm for determining motion of a point on a retina comprises: from an image of a fiducial on an eye, correlating position of the fiducial to a structure on the retina. The correlation may be performed via a mathematical transformation, such as a trigonometric transformation. The mathematical transformation may be performed in a software program. The algorithm may further comprise detecting a subsequent image after a period of time and correlating the new position of the fiducial relative to the first position, and a corresponding error function may be created or generated. The algorithm may further comprise detecting more than one fiducial and correlating with greater than one coordinate of the retina. The fiducial position may be placed or registered in an external coordinate frame, such as the system reference frame of a radiotherapy treatment device.

Eye-stabilization system. An embodiment having aspects of the invention comprises of an eye-contact device (eye-guide) for securing a patient eye at a selected position, such as may be used cooperatively with an ocular stabilization and alignment device, as described in the co-invented priority applications, particularly No. 12/103,534 filed Apr. 15, 2008 and No. 12/027,083 filed Feb. 1, 2008; each of which is incorporated herein by reference. In one embodiment, the eye-contact device or eye-guide comprises, in operative condition, (a) a lens body having an internal concave contact surface adapted to be placed against the front surface of a patient's eye so as to cover at least a portion of the cornea, an external surface including one or more mounting locations, and a transparent window portion arranged to permit, when in operative position, visualization of an interior portion of the eye via the cornea; (b) a support member mountable to a base; and (c) two or more linkages pivotally mounted to the support member and connecting to a mounting location of the lens body, the links configured form a assembly supporting the lens body against the eye. In certain embodiments, the eye-guide further comprising an adjustment mechanism engaging at least one linkage and configured to provide adjustment of the range and/or resistance of at least one pivotal degree of freedom of the lens body with respect to the support member.

The window portion may have at least one optical property selected from the group consisting of a selected transparency, a selected refraction, a selected magnification, a selected filtration, a selected polarity, and a selected pattern of markings. The eye-guide may further comprise a port in fluid communication with the contact surface by which a negative pressure can be applied between a patient's eye and the contact surface, to stabilize the position of the eye with respect to the contact device. The eye-guide may further comprise a biasing mechanism operatively connected to the contact device connector for biasing the eye-contact device against the eye with a force sufficient to the hold the contact device against the eye.

Eye alignment. In exemplary embodiments of methods and devices having aspects of the invention, a patient's eye may be aligned and stabilized for diagnostic or therapeutic purposes, such as radiotherapy treatment. In exemplary embodiments of a method of aligning an axial anatomic axis of a patient's eye with a coordinate system of a medical device, the method may comprise: (a) engaging the anterior surface of the eye with a contact lens member, the contact lens member having a defined axis; (b) aligning the lens with the eye so that the lens axis intersects the center of the limbus of the eye and so that the lens axis has a known orientation to the corneal surface at the center of the cornea so as to define an axial anatomic axis of the eye; and (c) aligning the lens axis with a coordinate axis of the medical device, so that the coordinate axis of the medical device has a known orientation to the axial anatomic axis of the eye.

The step (b) of aligning the lens with the eye may include: (i) electronically capturing one or more images including the eye and the lens member; (ii) processing the image in a computer processor so as to determine the location of the lens member axis relative to the location of the limbus; and (iii) adjusting the position of the lens member relative to the eye until the lens axis substantially intersects the center of the limbus of the eye. The sub-step (ii) of processing the image to determine the location of the lens member may include: A. processing the image so as to determine the location of the center of the contact lens in a coordinate system; B. processing the image so as to determine the location of the center limbus in the coordinate system; and C. comparing the location of the center of the contact lens of the center limbus in the coordinate system so as to determine the difference in location, if any.

In an embodiment wherein the lens member includes one or more reflective fiducials having a known location relative to an eye contact surface of the lens member, the sub-step (a) of determining the location of the center of the contact lens may include: (i) electronically detecting a contrasting image of each fiducial to define a respective fiducial data set; (ii) mathematically determining the center of each fiducial data set; (iii) from the known location of the fiducials relative to an eye contact surface computing the location of the center of the eye contact surface in the coordinate system. In an embodiment, the sub-step (b) of determining the location of the center limbus may include 1. electronically detecting a contrasting boundary between sclera and iris to define a boundary data set; 2. mathematically fitting geometric shape to represent the boundary data set; and 3. computing the center of the geometric shape in the coordinate system.

In an embodiment, step (c) of aligning the lens axis with a coordinate axis of the medical device may include: (i) electronically capturing one or more images including the lens member as engaged and aligned with the eye; (ii) processing the image in a computer processor so as to determine the one or both of an orientation and a position of the lens member in the coordinate system of the medical device; (iii) adjusting one or both of the orientation and the position of the lens member relative to the coordinate axis of the medical device until the coordinate axis of the medical device has a known orientation to the axial anatomic axis of the eye. The method may further include: (d) determining a distance coordinate axis of the medical device to the contact lens member as engaged and aligned with the eye; in the wherein the determination of the distance includes (i) electronically capturing one or more images including the contact lens member as engaged and aligned with the eye; and (ii) processing the image in a computer processor so as to determine the distance.

Eye motion. In exemplary embodiments of methods and devices having aspects of the invention, motion of a patient's eye may be measured or tracked for a diagnostic or therapeutic purpose, such as radiotherapy treatment. In exemplary embodiments of a method of tracking motion of a patient's eye in the a coordinate system of medical device, the method may comprise: (a) determining an initial position and orientation of the eye, including: (i) engaging the anterior surface of the eye with a contact lens member; (ii) aligning the contact lens member with the eye so as to have a known orientation relative to an anatomical axis of the eye and a known position relative to the contacted eye surface; and (iii) aligning the contact lens member with the medical device so as to have a known initial position and orientation in the coordinate system of medical device;

The method may further comprise: (b) electronically capturing a plurality of time-sequenced images including the contact lens member while maintaining the engagement and alignment of the contact lens member with the eye; (c) processing the images in a computer processor so as to determine one or both of an orientation and a position of the contact lens member in the coordinate system of the medical device at the time of capture of each image; and (d) determining for each image, from the orientation and/or position of the contact lens member at the time of capture of the image, the change from the initial orientation and/or position of the contact lens in the coordinate system of medical device, so as to track the sequential motion of the eye in the coordinate system of medical device.

Target motion: In exemplary embodiments of methods and devices having aspects of the invention, motion of a patient's eye may be used to infer motion of a target tissue or other region within the eye, for a diagnostic or therapeutic purpose, such as radiotherapy treatment. In exemplary embodiments of a method of tracking motion of a patient's eye, the method may further comprise: (e) determining the position of the target tissue relative to the anatomical axis and contacted eye surface; and (f) following step (a) of determining an initial position and orientation of the eye, determining an initial position of the target tissue in the coordinate system of medical device; (g) determining for each image, from the change from the initial orientation and/or position of the contact lens, the change from the initial position of the target tissue in the coordinate system of medical device, so as to track the sequential motion of the target tissue in the coordinate system of medical device.

The method may further comprise: the step of changing at least one operational parameter of the medical device in response to a change from the initial position of the target tissue. For example, where the medical device is an external radiation beam treatment device configured to treat the patient by emitting a collimated radiation beam directed to the target tissue; the change in operational parameter may include one of (i) re-directing the collimated radiation beam to follow target tissue motion and (ii) interrupting the emission of the beam upon a threshold of motion of the target tissue.

Tissue propagation: Exemplary methods and devices having aspects of the invention may embody a radiotherapy treatment plan providing for propagation of an external radiation beam to target tissue, where passage through tissue effects beam characteristics. In exemplary embodiments of a method of treating a patient with external radiation beam from a radiation source, the radiation beam emitted so as to propagate along an tissue path to reach a target tissue region within the patient's body, the treatment carried out according to a radiotherapy treatment plan anatomically specifying the tissue path, the may method comprises (a) selecting one or more input parameters (P1, P2 . . . Pi,), the input parameters selected from human anatomical measurements, other human measurements, and other person-specific characteristics; (b) characterizing variation with respect to the selected parameters in a human population which includes the patient, the variation correlated with the tissue path length (PL) for the radiotherapy treatment plan; (d) determining a mathematical function and/or calculation algorithm effectively expressing a relationship between the selected parameters and the tissue path length (PL=f (P1, P2 . . . Pi); (e) determining values of the selected parameters (P1, P2 . . . Pi,) for the patient; (f) using the mathematical function and/or calculation algorithm, determining PL for the patient (PL0); (g) modifying or adjusting one or more aspects of the radiotherapy treatment plan based on the determined value PL0; and (h) treating the patient according to the modified or adjusted treatment plan.

Radiation dose mapping: In exemplary embodiments of methods and devices having aspects of the invention, motion of a region including target tissue within the eye may be used to track the deposition of radiation dose to anatomical structures. In exemplary embodiments of a method of tracking motion of a target tissue or other region in a patient's eye, the method may further comprise: (h) providing a virtual radiation dose distribution model representing a treatment radiation dose distribution to a region of tissue including the target tissue; and (i) determining, from the dose distribution model and from the determined motion of the target tissue, a modified dose distribution model accounting for eye motion.

A dose distribution accounting for eye motion may be used to trigger radiotherapy operation changes. For example, the method may further comprise: (j) defining a geometric parameter in a coordinate system of the region of tissue including the target tissue, the geometric parameter characterizing a reference location of an time-increment of radiation dose of the model provided in step (h); (k) defining an accumulation vector providing a vector summation of the geometric parameter in a coordinate system of the region of tissue including the target tissue; (l) performing steps (h) and (i) for a time-sequenced image captured per step (c) to determine a modified time-increment dose distribution and a respective value of the geometric parameter for the time increment; (m) adding the time-increment geometric parameter to the accumulation vector; (n) comparing the value of the accumulation vector in one or both of magnitude and direction to one or more predetermined threshold values to determine if the value exceeds the threshold; (o) in the event that the value in step (n) exceeds a threshold, interrupting the emission of the radiation beam. (p) repeating steps (l) through (o) for a plurality of time-sequenced images. The geometric parameter may have linear relationship or a non-linear (e.g., quadratic) relationship to a change from the initial position of the target tissue.

Where the target tissue includes a portion of the retina of a patient's eye, and the geometric parameter the difference in the location for each time sequence of a centroid of the dose distribution in a plane of the retinal surface relative to an initial location of the centroid of the dose distribution.

Imaging method of alignment: In exemplary embodiments of a method having aspects of the invention, an algorithm for aligning a patient body part with a radiation device comprises: (a) defining a normal axis to the body part (e.g., by locating fiducials on the body part); (b) aligning the normal axis to a pixel on a camera image visualizing the body part; and (c) linking the pixel on the camera image to a coordinate frame of a robotic positioning system thereby linking the normal axis of the body part to an axis of the robotic positioning system.

The algorithm may further comprise determining the distance between the body part and the robotic positioning system wherein the distance is measure along the normal axis. Where the body part is an eye, normal axis may be defined by detecting fiducials on a device that contacts the eye, such as adjacent the limbus of the eye. A treatment target on the retina, such as the macula, may be located with respect to the normal axis by an eye axial length measurement.

In exemplary embodiments of a method having aspects of the invention for aligning a patient's eye with a medical device coordinate system, the device may be provided to include an eye-guide device configured to engage the eye and a camera configured to capture an electronic image of the eye, the eye-guide having visible fiducials and the camera linked to a computer processor. The method may include: (a) aligning the camera to a known position and/or orientation with respect to the medical device coordinate system wherein the camera is directed to the eye as engaged with eye-guide; (b) capturing an image of the eye as engaged with eye-guide; (c) identifying one or more pixels of the image representing the location of the eye-guide central axis; (d) determining from image data that the eye-guide central axis is aligned to a known position and/or orientation with respect to the medical device coordinate system; (e) determining from image data the location of the center of limbus in the system coordinates; and (f) determining any deviation of the location of the center of limbus to a known position and/or orientation of the eye-guide.

The method may further include (i) that the camera is aligned co-axially with a principle axis of the medical device coordinate system ("Z axis"); (ii) that the processor is programmed with software code acting on camera image data in computer memory, so as to carry out calculations and algorithms based on image data, and so as to determine pixel-scale distances between locations within an image ("distance within the image"); and (iii) that the eye-guide includes at least three fiducials in known position with respect to an eye-guide central axis. The method may further provide that step (c) of identifying a pixel includes: (i) determining a the portion of the image including a first fiducial ("fiducial 1"); (ii) determining a geometric center of the fiducial image area; (iii) select a pixel representing the fiducial center; and (iv) determining a pixel of the image representing the eye-guide central axis based on the known position of the first fiducial.

The method may further provide that: (i) the step, of determining that the eye-guide central axis is aligned, is repeated with respect to one or both of a second fiducial ("fiducial 2") and third fiducial ("fiducial 3") so as to select a pixel representing the center of the respective fiducial; and further include:

(ii) calculating a horizontal ("X") center-to-center distance within the image between fiducial 1 and each of fiducials 2 and 3;

(iii) predicting, from the known position of the fiducials on the eye-guide, the relative distance within the image from fiducial 1 to one or both of fiducials 2 and 3 corresponding to horizontal alignment of the central axis of the eye-guide with the Z axis ("no horizontal tilt");

(iv) comparing the distances calculated in (ii) with the distances predicted in (iii) so as to determine whether the eye-guide has no horizontal tilt;

(v) calculating a vertical ("Y") displacement within the image between fiducial 1 and one or both of fiducials 2 and 3;

(vi) predicting, from the known position of the fiducials on the eye-guide, the relative Y displacement from fiducial 1 within the image of one or both of fiducials 2 and 3 corresponding to vertical alignment of the central axis of the eye-guide with the Z axis ("no vertical tilt");

(vii) comparing the displacements calculated in (v) with the displacements predicted in (vi) so as to determine whether the eye-guide has no vertical tilt;

(viii) determine if the pixel representing the eye-guide central axis is located at the center of the camera image; and (ix) determining if (iv), (vii) and (viii) are true, that eye-guide is aligned with the device Z axis.

The method may further provide that the step (e) of determining the location of the center of limbus includes: (i) determine a portion of the image including all or a portion of the exposed portion of the limbus boundary, and identifying the pixel locations corresponding to the limbus boundary image; (ii) determining a mathematical representation of a "best fit" shape corresponding to the limbus boundary pixel data; and (iii) calculate the center of "best fit" shape so as to determine the location of the limbus center.

The method may further include the steps: (g) registering the positions and/or orientations determined in steps (a-d) of one or both of eye-guide and limbus in a virtual computer eye model. (h) calculating the position of an anatomical eye structure in the device coordinate system based on the registered eye model.

Eye contact device and lid retractor: In an exemplary embodiment of eye contact device having aspects of the invention for use in a system for securing a patient eye at a selected position, the device comprises: (a) a lens body having an internal concave contact surface adapted to be placed against the front surface of a patient's eye so as to cover at least a portion of the cornea, an external surface including one or more mounting locations, and a transparent window portion arranged to permit, when in operative position, visualization of an interior portion of the eye via the cornea; (b) a support member mountable to a base; and (c) two or more linkages pivotally mounted to the support member and connecting to a mounting location of the lens body, the links configured form a assembly supporting the lens body against the eye.

The device may further include an adjustment mechanism engaging at least one linkage and configured to provide adjustment of the range and/or resistance of at least one pivotal degree of freedom of the lens body with respect to the support member. The window portion may have at least one optical property selected from the group consisting of a selected transparency, a selected optical refraction, a selected magnification, a selected optical filtration, a selected optical polarity, and a selected pattern of markings.

In an exemplary embodiment of eye lid retractor device having aspects of the invention, the device comprises: (a) a lid-engaging spoon-like hook mounted configured to hold an eyelid without injury; (b) an elastic tension member (e.g., an elastic strap or tube) linked to the spoon-like hook and linked to a securing base member (e.g. a clip or other attachment), the tension member being adjustable in both tension and direction of application of tension relative to the eye. The tension adjustment may include altering the length of the tension member (e.g., a conventional strap adjustment, Velcro adjustment, or the like) or may include altering the location of the securing base member (such as attaching a clip to a different location). The tension member may include a tension release mechanism (such as a magnetic release). The securing base member may be configured to attach to clothing of a subject or to the subjects body.

X-ray collimator with moveable elements: In an exemplary embodiment of collimator having aspects of the invention for producing a collimated treatment X-ray beam, the collimator comprises: (a) a collimator body configured to be supported in operative association with an X-ray source assembly having an X-ray source; (b) a collimator axis defining the X-ray beam direction of propagation; (c) a collimator exit aperture supported relative to the collimator body so as to determine one or more cross-sectional characteristics of the X-ray beam; (d) either or both of the collimator body and the collimator exit aperture include one or more beam-effecting elements configured to produce a collimated X-ray beam directable to intersect a treatment target of a subject's body, such that least one of the beam-effecting elements is moveable to adjust a physical parameter of the X-ray beam.

In one embodiment, the beam effecting element may include one or more of the following: (i) a extendable body portion configured to alter the distance of the aperture from the X-ray source; (ii) a movable portion configured to alter the position of the aperture relative to the X-ray source, so as to alter the direction of the beam axis; (iii) a movable portion configured to alter the rotational position of the aperture with respect to the collimator axis; and (iv) a movable aperture element configured to be adjusted to change one of a beam diameter and a beam cross-sectional shape.

In one embodiment, one or more movable elements are mounted to one or more actuators configured to move the elements during the course of X-ray treatment, the actuators controlled by a tracking controller effective to detect a motion of the treatment target during treatment; the controller effective to control the actuators so as to adjust a physical parameter of the X-ray beam so as to substantially maintain intersection of the beam with the treatment target in the event that the target moves during treatment.

It should be understood that in general, where a method of treatment having aspects of the invention is described herein, the concept of the invention includes embodiments of a device for performing the method, and embodiments of software or machine-readable code effective to carry out the method be means of a computer processor operatively connected to such a device embodiment.

These and other objects and features of the invention will be more fully appreciated when the following detailed description of the invention is read in conjunction with the accompanying figures.

BRIEF DESCRIPTION OF THE FIGURES

The FIGURES and the associated descriptions are provided to illustrate embodiments of the disclosure and not to limit the scope of the disclosure. Throughout the figures, reference numbers are reused to indicate correspondence between referenced elements. The FIGURES are in simplified form and are not necessarily to scale. In reference to the disclosure herein, for purposes of convenience and clarity only, directional terms, such as top, bottom, left, right, up, down, over, above, below, beneath, rear, and front are used with respect to the accompanying figures. Such directional terms are not to be construed as limiting the scope of the invention in any manner.

The drawings generally illustrate embodiments of methods and devices having aspects of the invention, except where particular features of the drawings are specifically identified as being prior art. Thus the drawings are an integral part of the written description of the inventions herein. The figures may be summarized as follows:

FIG. 19 schematically illustrates an eye-guide device for use in an eye stabilizing system having aspects of the invention having fiducials.

FIGS. 20A-H schematically illustrate an eye-guide device for use in an eye stabilizing system having aspects of the invention, and having patterned fiducials, and a method of determining orientation by image recognition.

FIGS. 21B-E are schematic illustrations of an patient's eye associated with a treatment system embodiment, showing particular steps described in FIG. 21A.

FIGS. 24A-D illustrate an eye-guide shown in FIG. 23, the device having a pattern of fiducials, the guide for use in a eye stabilizing system having aspects of the invention, shown in contact with an eye and depicting the method of determining alignment.

FIGS. 25A-B illustrates the effect of tilt on the position of fiducials of the eye-guide of FIG. 24.

FIGS. 31A-B are views illustrating from a frontal perspective the motion shown in FIGS. 30A-B.

FIGS. 32-36A-B are diagrams depicting transformation procedures having aspects of the invention for converting detected input signals related to eye movements (see FIGS. 29-31) into corresponding movements of a beamspot relative to the retina.

FIGS. 43D-G illustrate an embodiment of a collimator assembly having aspects of the invention, having a variable collimator length.

FIGS. 46A-C illustrate two exemplary embodiments of elastically-tethered eyelid retractors having aspects of the invention, and a magnetic tension release.

FIGS. 47A-C illustrate an alternative embodiment of an eye-lid retractor.

DETAILED DESCRIPTION

Figure 1A:
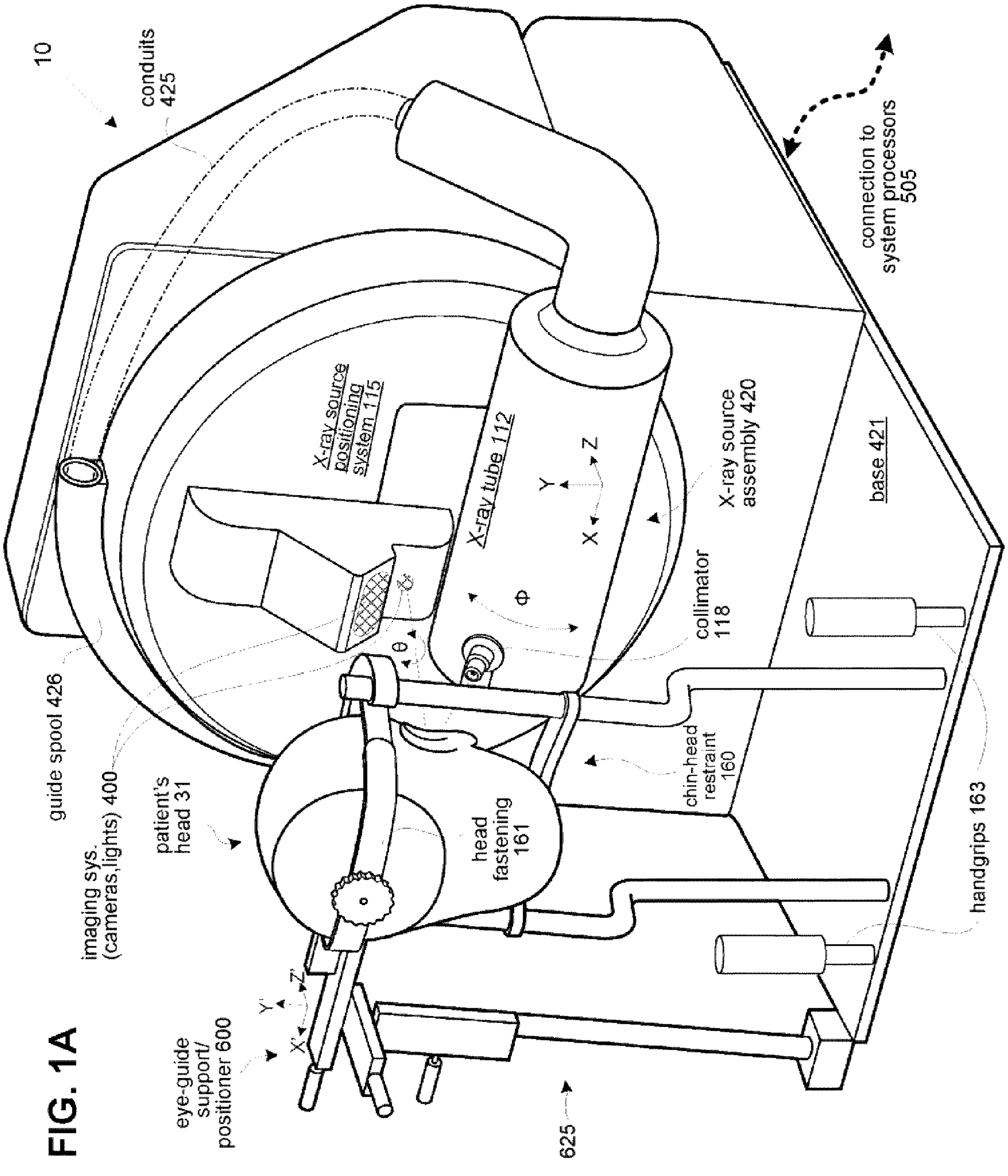
FIG. 1A is a perspective view of an embodiment of an X-ray treatment system having aspects of the invention.

The following disclosure is related to the subject matter with is found in the priority applications, in particular U.S. application Ser. No. 12/103,534 filed Apr. 15, 2008; Ser. No. 12/027,069 filed Feb. 1, 2008; and Ser. No. 12/100,398 filed Apr. 9, 2008; each of which is incorporated by reference, to which the reader is directed for further description and examples. In particular, these applications describe eye alignment and stabilization devices having aspects of the invention, and methods of their use. In addition, these applications describe devices methods of ocular radiotherapy, and methods of planning treatments which are relevant to the disclosure below.

I. DEFINITIONS

The terms below have the following definitions herein, unless indicated otherwise.

A "lesion" refers to a localized area of diseased or disordered tissue. An "ocular lesion" may refer to a retinal or non-retinal lesion, and a retinal lesion may refer to any localized pathology associated with the retina, including macular degeneration, such as wet and age-related macular degeneration where the lesion is associated with the macula, lesions associated with tumors or with vascular abnormalities, drusen, including optic-disc drusen, diseases of the optic disc, lesions associated with inflammation, such as Behcet's Syndrome, lesions associated with heritable diseases, such as Watanabe Heritable HyperLipidemia, and lesions associated with viral, bacterial, or parasitic infection, such as lesions associated infection, such as lesions associated with Trypanosoma infection.

A "radiation-sensitive structure" refers to a normally healthy tissue area or structure that is in the vicinity of a lesion, and which is at risk of loss of function by overexposure to radiation, e.g., by a collimated x-ray beam. An example is the optic disc, which is in the vicinity of the macula in the retina of a patient eye.

An "external coordinate system" or "treatment coordinate system" refers to the coordinate system in which the coordinate positions of various components of a treatment system, such as an eye guide, a tracking system, and a radiation beam axis can be determined and their positions with respect to one another known.

A "patient axis" refers to an internal axis defined by natural or fiducial landmarks on the patient, and which can therefore be used in tracking patient position by a suitable tracking system in the external coordinate system. One exemplary patient axis is an ocular "geometric axis" defined as a line extending through the center of the limbus and through the center of a corneal reflection, e.g., the first reflection produced from the cornea when illuminated by a light source.

An "eye guide axis" refers to an axis defined by an eye guide in the external coordinate system. Ideally, an eye guide is centered on the patient eye so that the geometric axis of the eye in the patient coordinate system is aligned with the eye guide axis in the external coordinate system. This can be done, for example, by centering the eye guide on the eye, e.g., with respect to the limbus of the eye.

A "reference axis" or "system axis" refers to an axis having known, and defined coordinates in the external coordinate system. As will be seen below, the reference axis may be defined by a given patient axis at a known body position, so that the body position can be tracked by movement of the body axis with respect to the reference axis. For example, if the patient region to be treated is a retinal structure, such as the macula, the patient eye is initially placed in a preferably immobilized position with the patient looking straight ahead. The geometric axis of the eye is determined in this position, and the coordinates of the geometric axis in the external coordinate system then defines the reference axis. The reference axis can be thought of as the axis which forms the frame of reference for transforming internal body coordinates to the external coordinate system, by matrix transformation, where this transformation is determined according to a measured variation of the body axis with respect to the reference axis. Alternatively, where eye position is tracked by tracking the position of an eye guide on the eye, the reference axis may be defined by the eye guide axis when the patient is initially placed in a preferably immobilized position with the patient looking straight ahead. The eye guide axis then becomes the frame of reference for determining the position of the eye with respect to the reference axis.

The "axial length" of the eye is the distance along the geometric axis of the eye between the front of the cornea and the back of the retina. This distance can be measured by the ultrasound according to known methods.

A "standard model of the eye" or "human-eye model" refers to a geometric model of the eye as constructed from a large population of human eyes. This model will have its own coordinate system in which the coordinates of ocular structures of interest, including the macula and optic disc, are known.

A patient eye is "scaled to human-eye model" by aligning a known axis of the patient eye, e.g., the geometric axis, with the same axis in the model, and scaling the model so that axial length of the model matches the measured axial length of the patient, in effect, superimposing the model on the patient eye. Once the model has been superimposed on the patient eye, the coordinates of internal ocular structures from the model can be assigned to the patient eye, to define internal ocular coordinates of the patient-eye structures. These internal coordinates, in turn, can be transformed to the external coordinates from the known transformation between the geometric axis of the patient eye with the reference axis. Thus, by tracking the geometric axis of the eye with respect to the reference axis, the coordinates of the geometric axis in the external coordinate system are known, and from these known coordinates, the coordinates of internal ocular structures in the external coordinate system can be determined. The eye model may contain a "virtual medium" which simulates the radiation-attenuation characteristics of the medium, e.g., vitreous human, within the actual eye.

A "time increment vector summation of a parameter indicative of an eye-motion-based departure of a beam axis from the selected target to be treated" is determined by the steps of (i) at successive points in time, e.g., intervals of tenths or hundredths of a second during the course of radiation treatment, using the tracked position of the eye to determine the instantaneous coordinates of the target in the external coordinate system, (ii) from the known position of the radiation beam axis in the external coordinate system, determining the position of the radiation beam with respect to the target position, (iii) using the positions determined in (ii) to calculate a vector representing the magnitude and direction of the beam position with respect to the target position, and (iv) summing these vectors over time.

A "collimated radiation beam" refers to an x-radiation beam that has been collimated, e.g., by passage through a narrow-bore filter, such as described in co-owned U.S. patent application . . . .

"Radiation equivalent" refers to a radiation dose received at a position on or near a lesion, and determined by integrating the instantaneous radiation dose that position over total exposure time. Alternatively, "Radiation equivalent" may refer to a integral parameter based on radiation beam geometry and time history, in which the integral parameter may be correlated with an equivalent radiation dose based on known radiation beam properties. For example, where a beam has a constant dose rate (e.g., Gy/sec), the relation between beam duration and radiation dose at a point intersected by the beam may be a simple linear relationship, allowing a integral time-position parameter (sometimes referred to as "Accumulation Factor" herein) to be used as an equivalent to a cumulative radiation dose at a geometric location (e.g., in monitoring and controlling or "gating" the beam).

A "tracking assembly" refers to various imaging and/or coordinate tracking devices in the external coordinate system that can be used to track the position of a body region, e.g., patient eye. Where the body region is being tracked by natural body features, e.g., where a patient eye and the eye is being tracked by determining the position of a geometric axis of the eye, the tracking system may include (i) a camera for imaging the body region being tracked, (ii) a light source from illuminated the imaged region, and (iii) a detector on which the camera image can be represented as a digital image. Where the body region is being tracked by applied fiducials that can either emit or reflect position-related signals, such as an eye-guide fiducial consisting or more or more reflectors for reflecting an external beam or beams, such as electromagnetic or ultrasound beams, the tracking system includes the fiducial(s) applied to the body, and external signal-responsive element(s) for detecting the emitted or reflected signals and determining from the signals, the position(s) of the fiducial(s) in the external coordinate system. A tracking system may include both imaging and signal responsive elements. For example, in the case of tracking eye position by means of an eye guide attached to the eye, the tracking system may include an imaging system to image the eye and attached fudicials, such as eye guide fiducial and a fiducial tracking device.

"Machine-readable code operable on an electronic computer" refers to software or hard-wired instructions used to control the logic operations of the computer. The term computer or processor refers to an electronic computer or its specific logic-processing hardware. The machine-readable code is embodied in a tangible medium, such as a hard disc or hard-wired instructions.

II. RADIOTHERAPY SYSTEM

In one general aspect, the invention includes system for treating a target area in a patient with an irradiation beam. The system includes a tracking assembly for tracking the position of a patient body region containing the target area and at least one radiation-sensitive area with respect to a known reference axis in an external coordinate system. A tracking system for tracking patient eye movement, based only of natural features of the eye, is detailed in Sections VIIC and with respect to FIGS. 54-56. A tracking system for tracking the position of the eye, by tracking an eye guide centered on the eye, is detailed in Sections IV and V. Also included in the system is a beam source for directing an irradiation beam at the patient target area along a known treatment axis in the external coordinate system, as detailed in Section IIC below. A processor in the system (described below with reference to Section IID) is operatively connected to the tracking device and to the beam source is operable to carry out operations operation for:

(i) determining the coordinates of the target area and radiation-sensitive patient structure(s) during the course of treatment;

(ii) calculating the coordinates of the target area and the radiation-sensitive structure(s) during the course of treatment;

(iii) based on the known beam axis of the collimated beam in the external coordinate system, and the instantaneous positions of the target area to be treated and the at least one radiation-sensitive structure, calculate a total radiation equivalent received at the target area and at least one radiation-sensitive structure; and (iv) based on the calculated radiation equivalents from step (iii), control the irradiation beam to insure that the at least one radiation-sensitive structure does not receive more than a preselected radiation equivalent during the treatment.

Figure 1B:
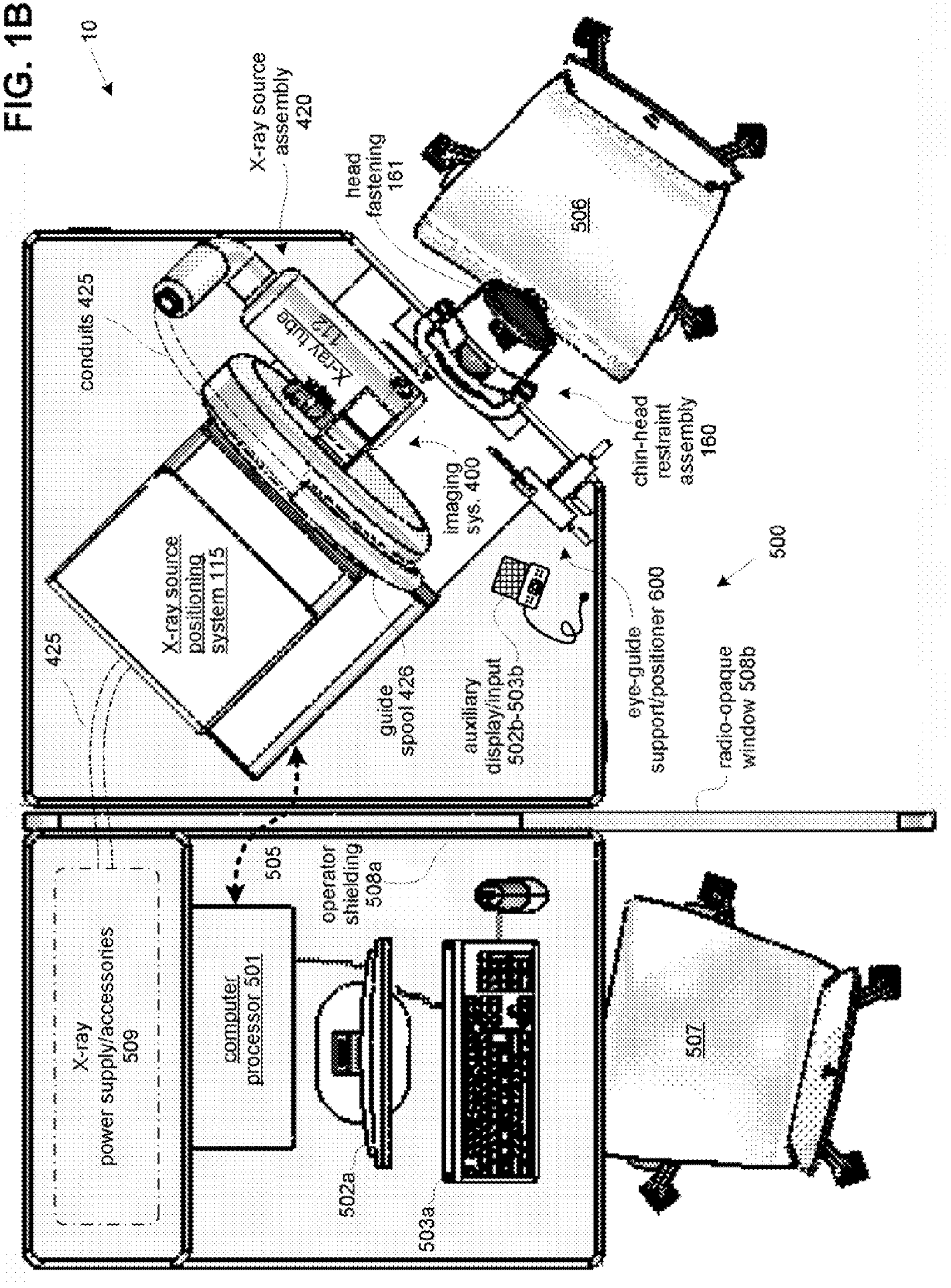
FIG. 1B is a plan view of the treatment system embodiment of FIG. 1A, further shown system processors and operator devices, depicted as installed in an exemplary console.

FIG. 1A is a perspective view of an exemplary embodiment having aspects of the invention of an X-ray treatment system 10 for treating ocular diseases. FIG. 1B is a plan view of the treatment system embodiment of FIG. 1A, further showing associated system processors 501 and operator input/output devices 502-503, depicted as installed in an exemplary operating console 500. FIGS. 2-6 illustrate alternative or additional aspects of system 10.

With reference to FIG. 1A, the system is shown with a phantom of a patient's head 31 engaged with head-chin restraint device 160 and head fastening 161, the head aligned in treatment position. System 10 includes a radiotherapy generation module or X-ray source assembly 420, for example comprising one or more X-ray tubes 112, each having a collimator for producing a tightly collimated X-ray treatment beam. The system 10 includes a radiotherapy control module which preferably includes an interface display 502, processing module 501, operator input devices 503 and a power supply (not shown). The system includes an imaging module 400, which can include one or more cameras and associated light sources, such as LEDs or low-powered lasers. The processing module, and machine-readable code used to control various operations of the module, will be described below in Section IID. The module is also referred to herein as a processor and an electronic computer.

Figure 16:
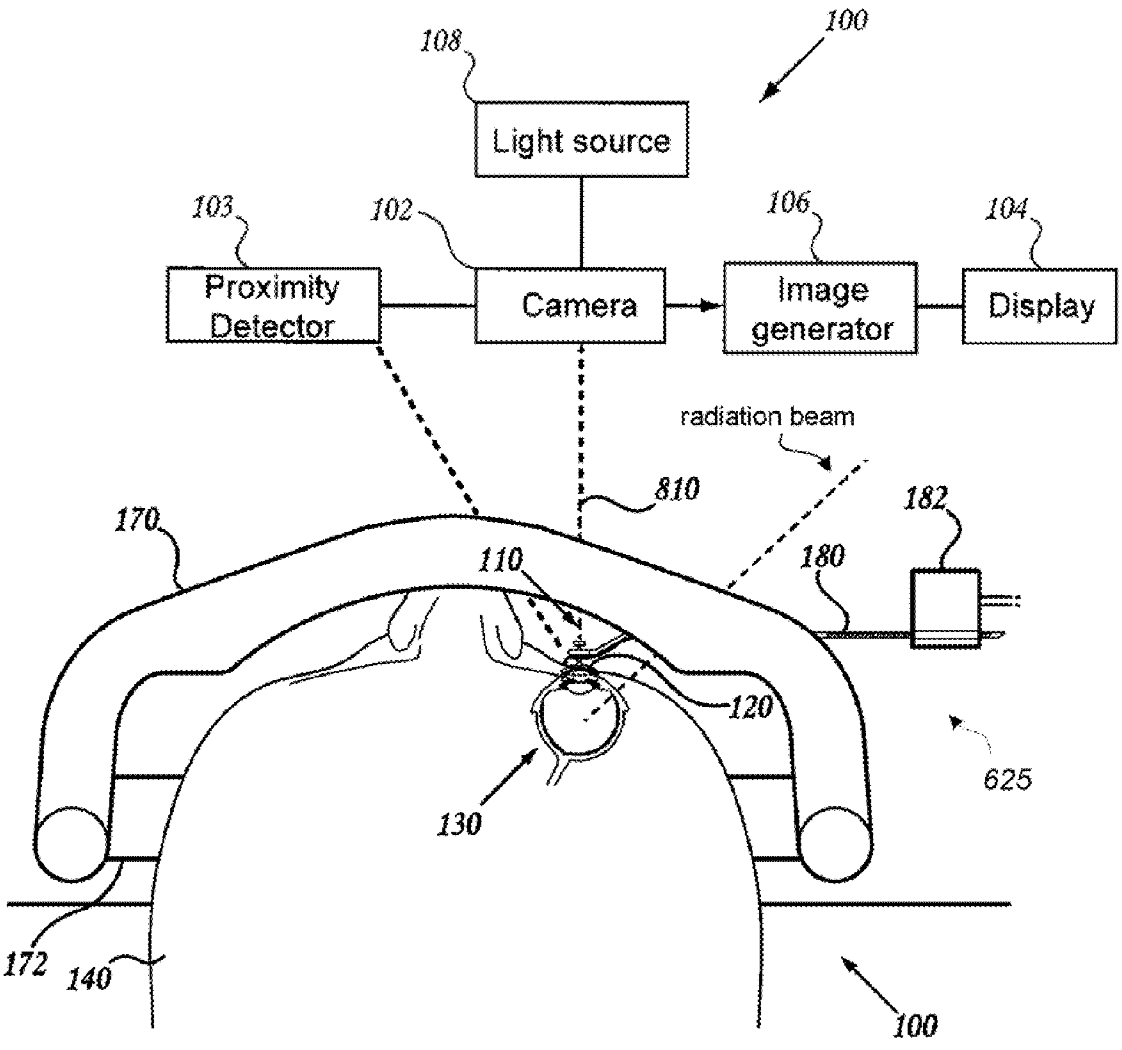
FIG. 16 illustrates a top view of one embodiment of a system for controllably positioning and/or stabilizing the eye of a subject for therapeutic treatment.

System 10 comprises an eye alignment and/or stabilizing module including an eye contact device or eye-guide device 625 having aspects of the invention, which is describe further with respect to FIGS. 2 and 16, among other places. In the example shown, the eye alignment and/or stabilizing module is configured for use with system 10, although it additionally may be usefully employed independent of system 10. The eye stabilization device may further comprise sensors or motion detection aids or cameras to assist with delivery of radiation to a patient.

In the embodiment shown, system 10 includes an automated positioning system (APS) 115 for moving and aiming the X-ray source assembly 420 (including X-ray tube 112 and collimator 118) to direct a treatment beam to a target from one or more selected directions. Further description of system 10 follows below.

FIG. 1B illustrates one particular embodiment of an operating console 500 having aspects of the invention, suited to house the components of system 10 and to provide for its effective and safe operation in patient treatment. It should be understood that the intercommunicating components of system 10 can be mounted in a variety of different architectural configurations, and the components may be distributed remotely and/or integrated with other devices without departing from spirit of the invention. For example, components shown in FIG. 1B in a "desktop" type mounting (e.g., X-ray source positioning system 115) may alternatively be supported in a ceiling or wall-mount configuration, or may be mounted on wheeled carts, or the like. Similarly, alternative embodiments of system 10 having aspects of the invention may be optimized to reduce size, weight and volume to permit integration of components into one (or a few) physical modules, for integration into other medical systems, and/or to provide portability.

The exemplary operating console 500 provides seating 506, 507 for patient and one or more operators, and may also include supplemental radiation shielding 508*a,b* between the operator and X-ray source assembly 420. Cameras of imaging system 410 (e.g., one or more CCD or other electronic image capture devices) communicate with computer processors 501 of system 10. Processors 501 communicate with operator displays 502 and operator input devices, such as keyboard 503. The console also houses one or more computer processors 501, operator input/output/display devices 502*a*-503*a*, and interconnections 505 to various system components, such as imaging system 420, positioning system 115 and X-ray source assembly 420.

In should be understood that computer processor elements, and associated input, output, display, memory and/or control components can be distributed, embedded and/or linked in a number of alternative arrangements by means known in the electronic arts, and the arrangement shown in FIG. 1B is exemplary. Likewise, intercommunication of electronic elements of system 10 may be wireless, and alternatively certain processor, memory and/or I/O functions may be performed remotely or over a network.

For example, supplemental displays and control devices communicating with processor 501 can be positioned to assist or interact with an operator or physician while working close to the patient (e.g., prior to X-ray beam emission). An auxiliary display/input device 402*b*-403*b* is shown to adjacent to eye-guide positioner 600, e.g., to assist an operator in engaging and aligning an eye-guide (110 in FIG. 2) on a patient's eye, and/or in adjusting the positioner 115 and X-ray source 420 to an initial treatment position.

In addition, a number of sensor elements may be embedded in the components of system 10 in communication with processor 501 of provide feedback, monitoring and safety functions. For example, chin-head restraint assembly 160 may include a right-left pair of hand grips 163 for the patient to hold, helping to maintain the patient's torso and shoulders in perpendicular alignment to eye-guide 110. The hand grips may include force or contact sensor to monitor that the patient is in position. Similar sensors may be included in head-fastening 161, e.g., to monitor head position and/or motion. Such safety/monitoring sensors may produce trigger signals to alert an operator and/or may be employed to gate or interrupt X-ray emission during treatment. In another example, light intensity and/or spectral sensors (not shown) may be positioned on system 10, and configured to automatically control the lighting elements of imaging system 400 (e.g., lights 405,406) so as to maximize image recognition performance as well as other operating parameters.

The console 500 comprises a power/accessories assembly 509 which may include power supply, power regulators, high voltage source and/or other accessories needed for operation of X-ray tube 112. It should be noted that a number of alternative commercially-available types of X-ray tubes or sources (as well as dedicated tube designs) may be included in X-ray source assembly 420 without departing from the spirit of the invention. An X-ray power supply/high voltage source may be a relatively large unit which is most conveniently housed separately from movable X-ray source assembly 420. In the example shown, conduits 425 lead from X-ray power/accessories assembly 509 in console 500 via guide spool 426 to connect to X-ray tube 112. The guide spool 426 is configured to support conduits 425 as X-ray source assembly 420 moves during system operation, as is described further herein.

Additionally, many commercially-available X-ray tubes are designed to use liquid cooling to increase output capacity. Power supply/accessories assembly 509 and conduits 425 may optionally include connections to coolant and/or an integrated coolant supply/chiller, so as to supply coolant to X-ray tube 112. Optionally, assembly 509 may include batteries or an uninterruptible power supply (UPS) of sufficient capacity to permit system 10 to complete a radiotherapy treatment independently of line power.

The exemplary operating console 500 provides seating 506, 507 for patient and one or more operators. System 10 may be configured to minimize stray X-ray radiation. However, as a radiation safety practice, console 500 may include supplemental radiation shielding 508*a* between the operator seating position 507 and the X-ray source assembly 420. The shielding may optionally include a radio-opaque window 508*b* (e.g., comprising a transparent silicate glass including heavy nuclei such as lead) to permit direct observation of (and reassurance to) the patient during X-ray emission. Such an operator station configuration allows close monitoring of the patient during irradiation treatment, and promotes easy access for direct assistance to the patient when radiation is not being emitted. Alternatively or additionally, observation cameras (not shown) may be mounted so as to allow an operator and/or physician to monitor the patient during treatment via electronic displays.

IIA. Eye Alignment and Stabilizing Module

Figure 2B:
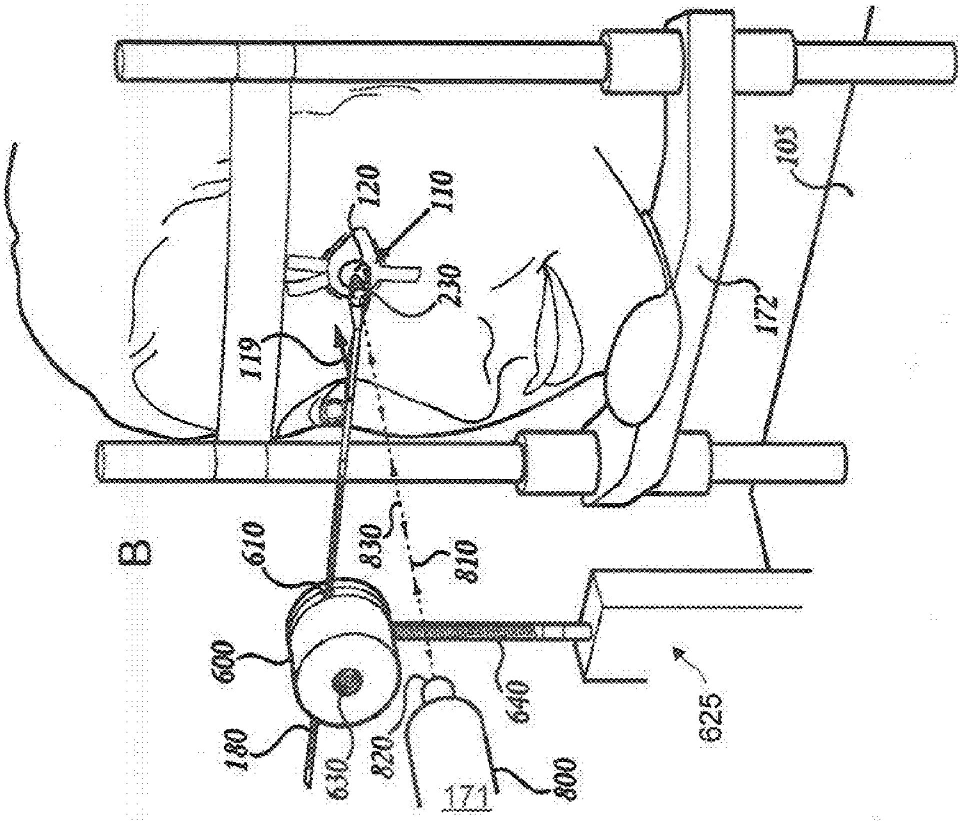
FIGS. 2A-B illustrate perspective views of the contact device or eye guide having aspects of the invention in various cases of alignment with a system axis.
Figure 2A:
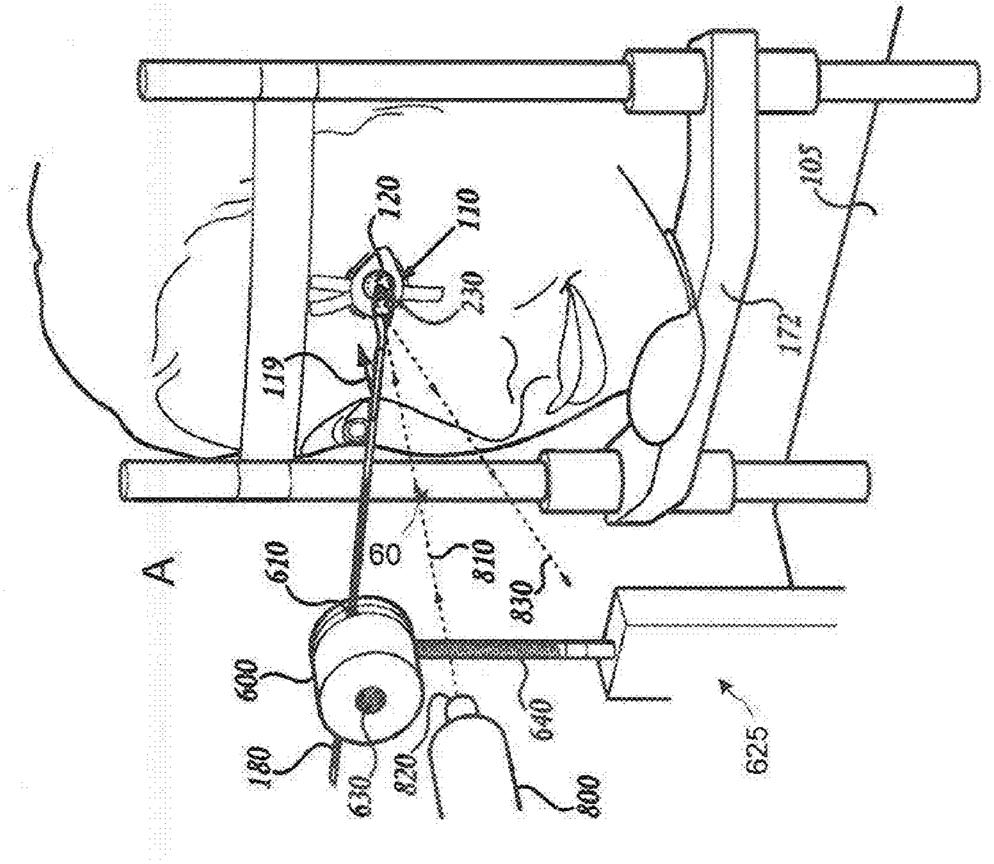

FIGS. 2A-2B illustrate perspective views of an exemplary embodiment 625 having aspects of the invention of a contact device or eye-guide and eye alignment and stabilizing module configured for use with system 10 (it additionally may be usefully employed independent of system 10). This may be used together with head-chin restraint device 160, which includes a head support or support 170 for stabilizing the head of subject, and includes a chin rest 172.

Figure 3A:
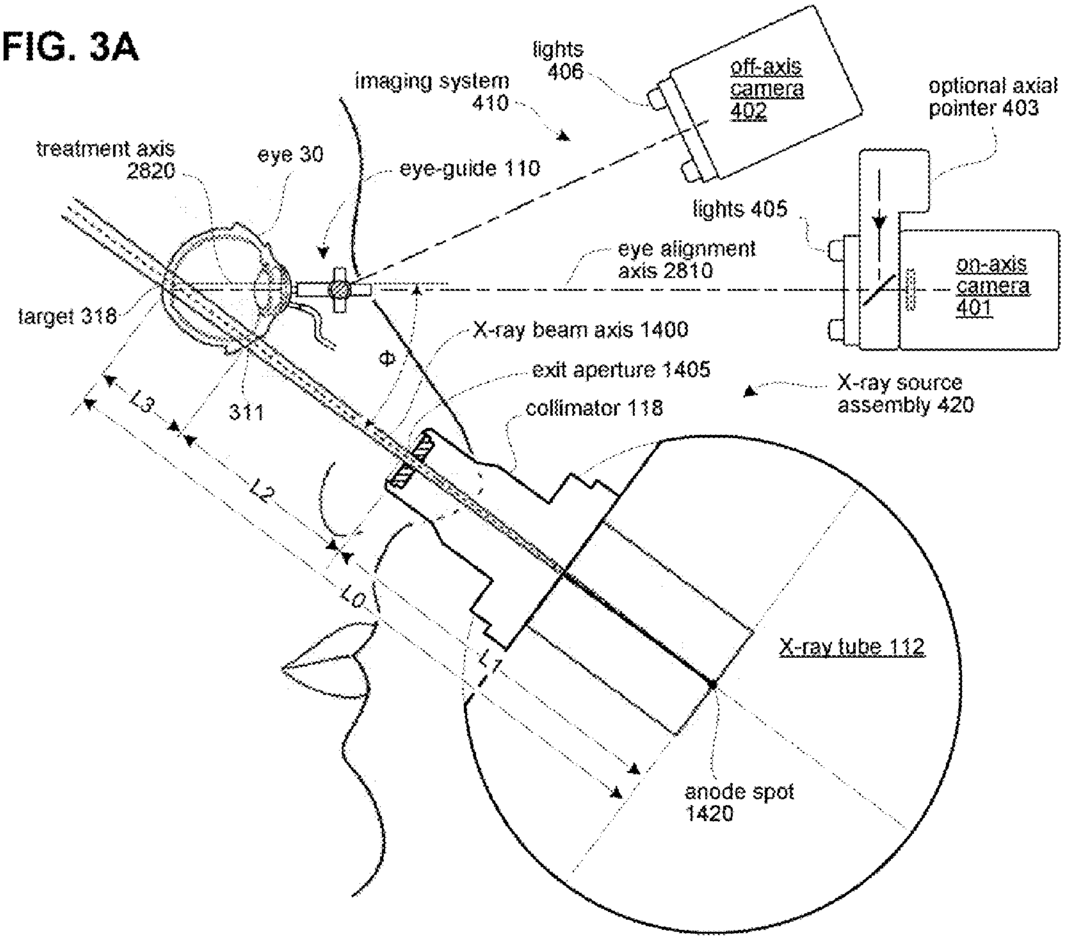
FIGS. 3A-B and 4 depict portions of an exemplary radiotherapy system including of an eye alignment and stabilization subsystem and X-ray source-collimator having aspects of the invention.

FIGS. 2A-2B and 3A-3B depict one example embodiment of an image-based method of aligning a patients eye 30 and engaged eye-guide 110 with the coordinate s of radiotherapy system 10, using a laser beacon 150 to align the eye with laser alignment system 800. Optionally, the alignment mechanism also directly aligns a treatment system, such as a radiotherapy system (not shown) in which the radiotherapy system directs its energy toward the eye in relation to the alignment system. Laser pointer beam 810 (which is collinear with the therapeutic beam in some embodiments) is emitted from laser system 800 through a collimator opening 820 and reflects off the surface of beam-directing mirror 230 of the contact device 110. In the non-alignment case depicted in FIG. 2A, the laser pointer beam 810 will not reflect off the surface of mirror 230 collinearly with the collimator opening 820, but will be off-axis, as shown by reflection beam 830. The orientation of the laser system 800 and/or the contact device 600 can be manually or automatically adjusted by direct visualization of the location of the reflection beam 830 or by sensors that detect the location of the reflection beam 830 and adjust the laser system 800 to bring the laser reflection beam 830 into alignment. FIG. 2B shows a case where the laser pointer is in fact aligned, the laser pointer beam 810 is reflected, and the laser reflection beam 830 is substantially collinear with the laser pointer beam 830. See description regarding FIGS. 3A-3B regarding geometry of mirror 230 and angular alignment of eye-guide 110. FIGS. 2 and 3A depicts a laser beacon 403 mounted to project coaxially with a system image detection camera 401.

Alternatively or additionally, alignment of eye-guide 110 with a system coordinate axis may be determined by image capture and recognition methods. See device and method embodiments described herein with respect to FIGS. 3A-3B and the sections captioned “Imaging subsystem” and “Example of image-based eye and eye-guide measurements”. In addition, the image processing and recognition methodology description herein are applicable to detecting the deflection of laser beacon 150 (403 in FIG. 3A) from mirror 230, and measuring any alignment error thereby. For further description of laser-beacon alignment, reference is made to application Ser. No. 12/027,083 filed Feb. 1, 2008; Ser. No. 12/027,094 filed Feb. 1, 2008; Ser. No. 12/027,069 filed Feb. 1, 2008, each of which is incorporated by reference.

The eye-positioning assembly 600 used to position the eye-contact or eye-guide device at a selected orientation. Contact device 110 may be attached to a control arm 180 in the positioning assembly 625, which is being fed into slot 610 of drive mechanism 600. In some embodiments, the contact device 110 of the system can be attached to a coupling component to hold the eye in place.

Eye-guide device 110 is preferably disposable such that a separate (e.g. disposable) contact device 110 is employed for each subject and/or use. Alternatively, contact device 110 may be non-disposable and be treated, e.g., with anti-infective agents, prior to being utilized in multiple subjects’ eyes. Drive mechanism 600 is fixed to base 620 through connector 640, which may robotically controlled or manually controlled, and has a known coordinate system. In one embodiment, drive mechanism 600 is fixed in a known, or predetermined, location with respect to the head positioning system (not shown) and/or the eye of the subject (not shown) and/or the positioning system of the radiotherapy device. Push button 630 allows free manual positioning of contact device 110 into and/or out of slot 610. The control arm 180 is fully engaged with the drive mechanism 600 and is fixed in a known, or predetermined location, which allows the eye of the subject to be fixed in a known, or predetermined location, when contact device 110 engages the eye. Although not shown, the eye-positioning device may include internal position sensors operable to detect the position of the end of arm 110 in the external coordinate system, in accordance with movement of the arm in a y direction.

Note that the eye-guide support arm 180 is illustrated in the examples shown as extending primarily in the “X” direction of the system ordinates. It should be understood that alternative embodiments of module 625 may have the eye-guide 110 supporting from below or above in the Y direction, or from the Z direction, or combinations of these. Eye-guide and eye alignment and stabilizing module 625 is described further with respect to FIG. 16 et seq.

IIB. X-Ray Source and Positioning System

Figure 4:
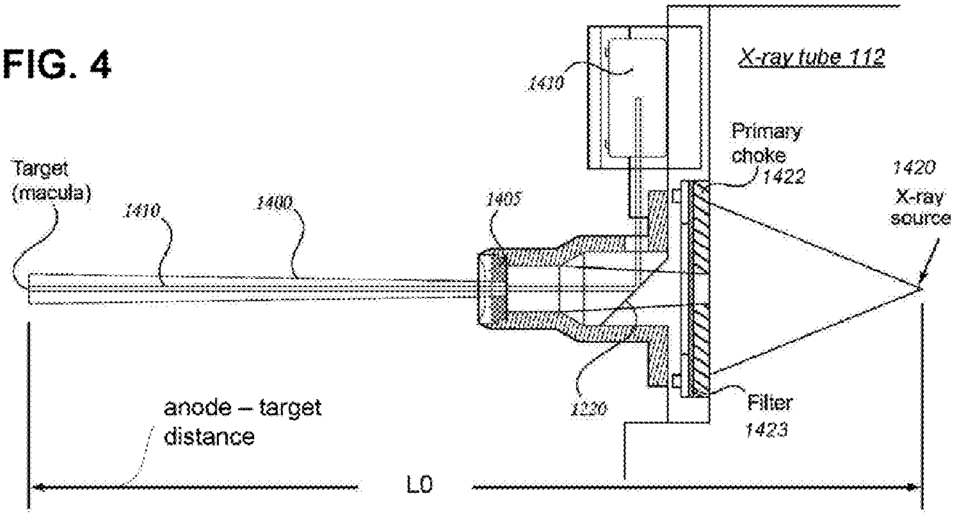
Figure 3B:
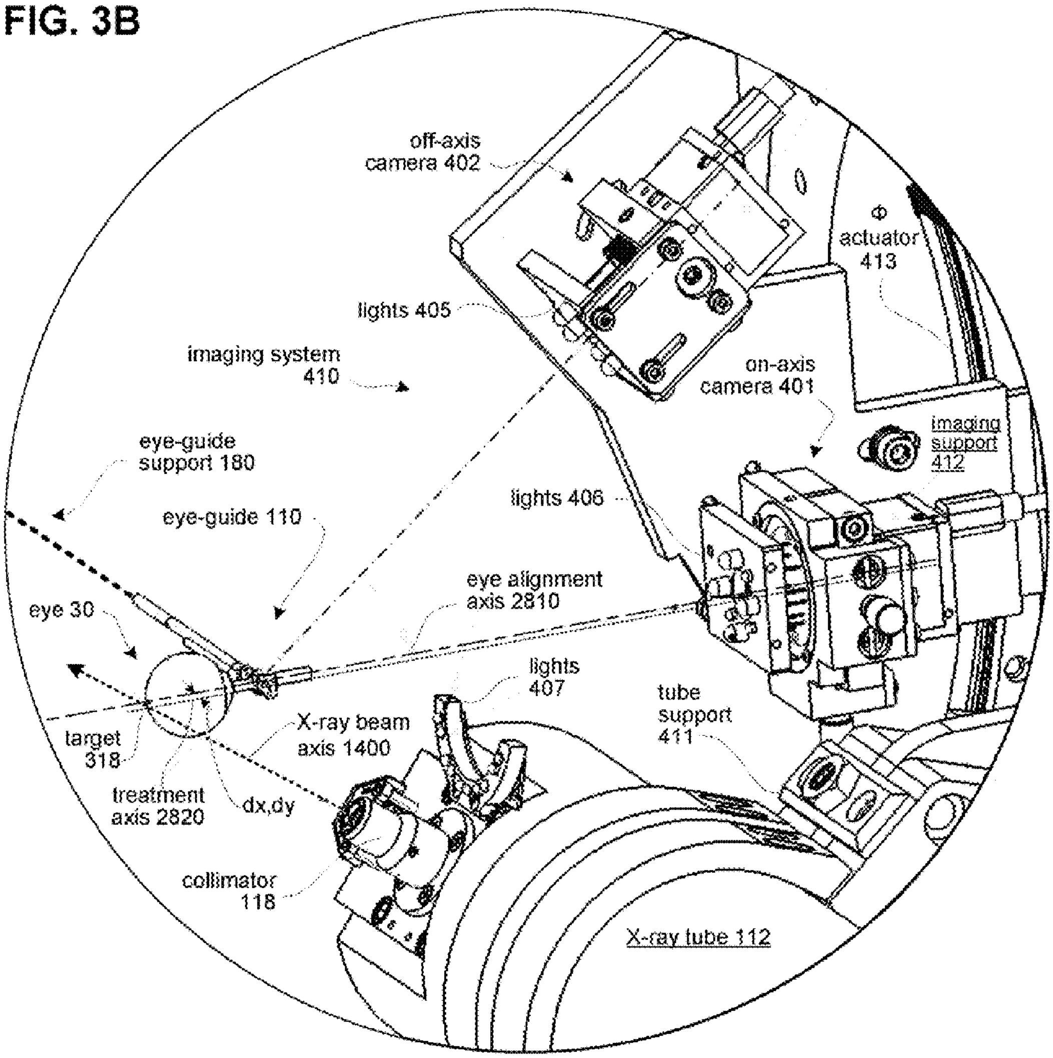
Figure 5:
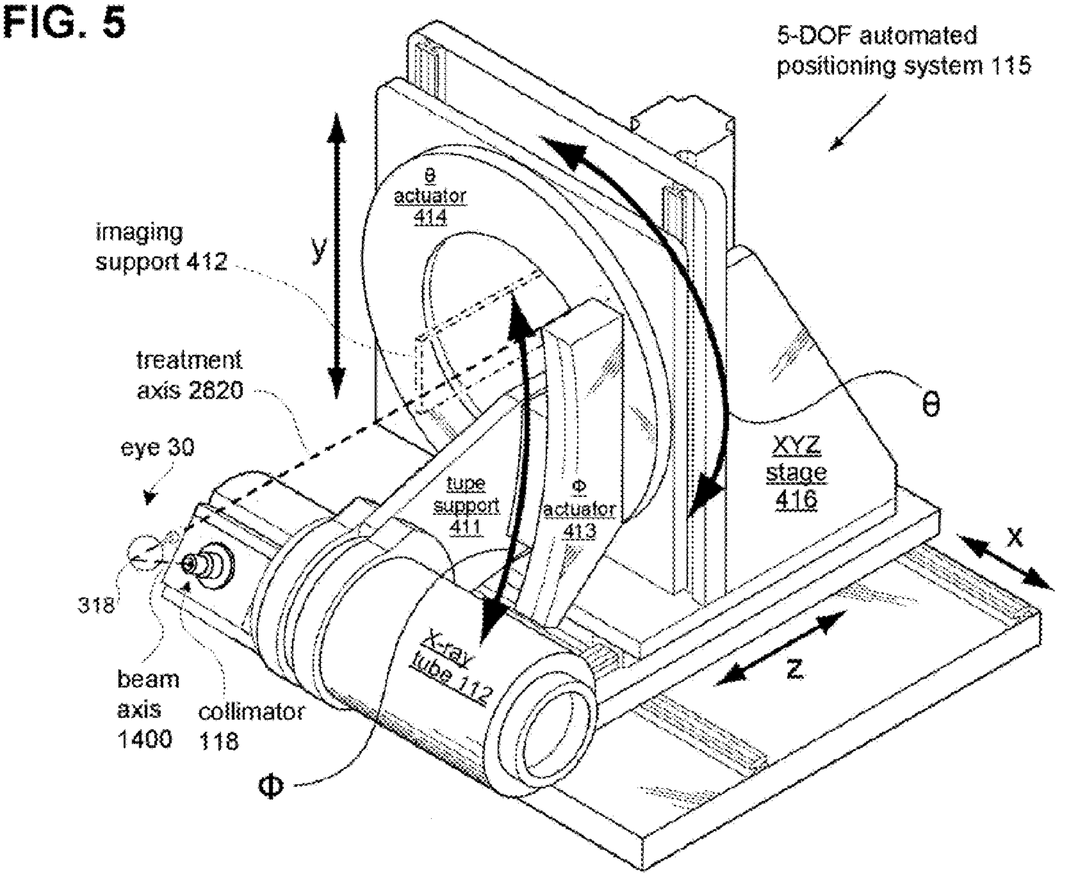
FIGS. 5 and 6 depicts embodiments of a constrained X-ray positioning system to treat the eye.
Figure 6:
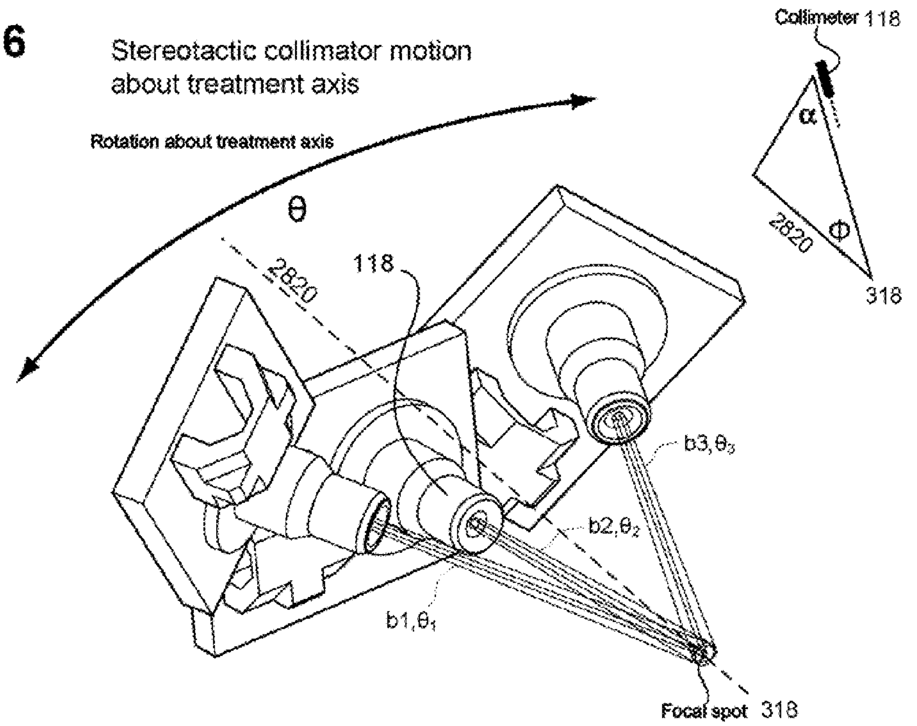

FIGS. 3A-3B and 4 depict the X-ray source and collimator (112 and 118 in FIG. 1) having aspects of the invention, shown in FIG. 3A as aligned in position for treatment of the retina of an eye. FIG. 3A shows a patient’s head including cross-section of an eye in the vertical plane of symmetry of the eye, shown in association with imaging system 410, and an X-ray source assembly comprising X-ray tube 112 and collimator 118. FIG. 3B is a perspective detail view of the system components shown in FIG. 3A together with portions of the positioning system 115 (see FIG. 5), illustrated in association with a phantom patient eye 30 coupled to eye-guide 110. FIG. 4 is a longitudinal cross-sectional view of collimator 118 and a portion of X-ray tube 112. FIG. 5 is a perspective illustration of an embodiment of a positioning system 115 having aspects of the invention, in this example a 5-degree of freedom automated positioning assembly, shown supporting X-ray tube 112 and collimator 118 in association with a phantom eye 30. FIG. 6 depicts embodiments of a motion control system in which the collimator 118.

Figure 9:
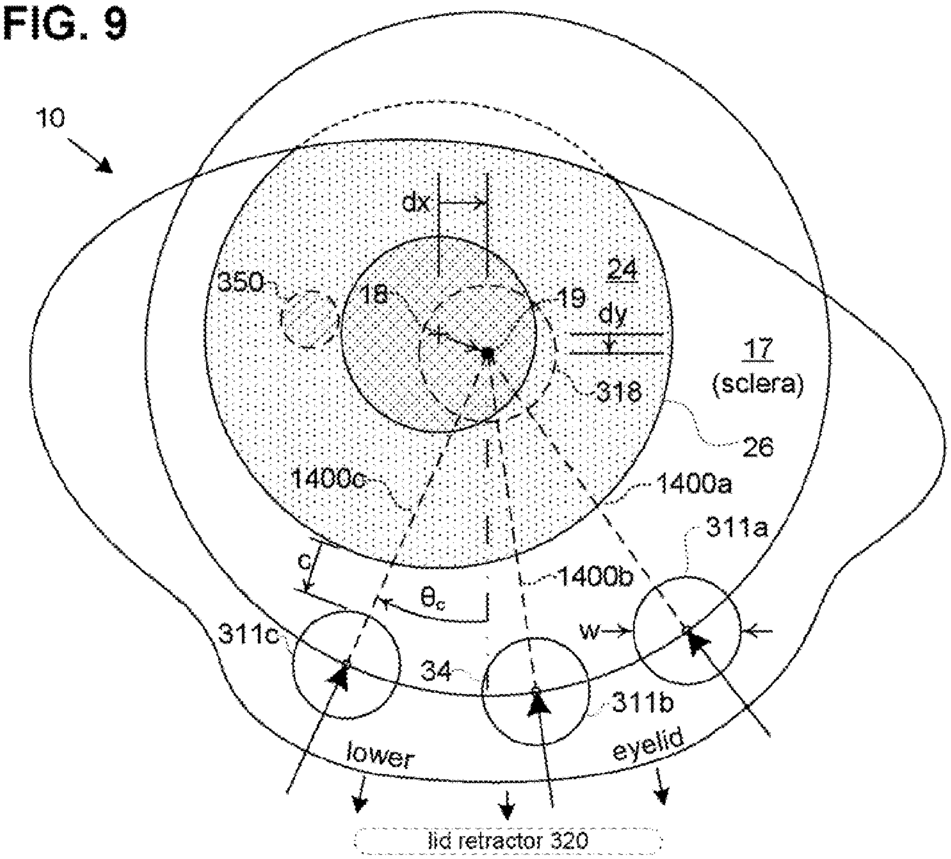
FIG. 9 is a frontal view of an eye as seen aligned with a system reference axis and depicting stereotactic X-ray treatment beam geometry.

As shown in FIGS. 3A and 3B, the X-ray source assembly 420 is aligned in position for treatment of the retina target 318 of an eye 30. For clarity and simplicity of illustration, the example of FIGS. 3A and 3B, shows the assembly 420 aligned in the vertical plane including treatment axis 2820 with an upwardly directed X-ray beam axis 1400. This corresponds approximately to example beam 1400*b* as shown in FIG. 9, such that the value of azimuth angle θ is 180 degrees. The polar angle (angle between treatment axis 2820 and beam axis 1400) is shown as approximately 30 degrees. It should be understood that orientation of beam 1400 may be selected and adjusted to suit a particular treatment plan method having aspects of the invention, and need not be restricted to any of the orientations shown in these examples.

FIG. 3A shows components of imaging/data acquisition system 410 including data acquisition devices functioning to track and/or identify the position of the eye 30, its anatomical structures (e.g., the limbus of the eye), and/or an eye-guide 110. In the example shown, the data acquisition devices comprise one or more cameras (e.g., camera 401 located aligned with the eye geometric axis 2810, camera 402 aligned off axis, or both). The cameras may be sensitive to visible and/or non-visible wave lengths (e.g., IR) and may include filters configured to tune sensitivity to certain ranges of wavelength. Alternatively or additionally, the data acquisition devices may comprise non-light emitters and detectors, such as ultrasound transducers/generators, radio-frequency devices and the like. A number of types of fiducials, transponders and/or mirrors may be included as system components to enhance the function of the data acquisition system. Likewise, radiation emitters may be included, such as lights, lasers, LEDs and the like.

In certain exemplary embodiments, the imaging system 410 comprises an off-axis camera configured to measure the eye-guide 110 and eye position relative to the Z axis (distance from the system), optionally assisted by one or more lights 406 (e.g., visible or IR LEDs). An on-axis camera 401 is included, configured to determine the alignment or offset of the eye 30 and/or eye-guide 110 with axis 2810. Similarly, one or more lights 405 (e.g., LEDs) may be included to assist camera 401.

In certain embodiments, eye-guide 110 includes an axially perpendicular mirror, and imaging system 410 includes a axial collimated light pointer 403 (e.g., including a diode laser, beam splitter, and camera filter) aligned to reflect off the mirror to be received by camera 401, permitting determination of the axial alignment (or alignment difference) of eye-guide 110 with respect to axis 2810.

In alternative embodiments described in detail herein, eye-guide 110 includes a geometric pattern of highly-reflective fiducials, and camera 401 is configured to image the pattern, the camera in communication with a system processor unit programmed to determine the alignment (or alignment difference of eye-guide 110 with respect to axis 2810.

IIC. Imaging System

FIGS. 3A and 3B illustrate a particular example of an imaging system 410 having aspects of the invention. In operation, the imaging system 410 may be configured for several functions, most of which may be performed automatically using image processing and pattern recognition, including:

1. Alignment of eye 30 to eye-guide 110.

Monitor and assist in initial placement of the eye-guide lens 120 by physician (display and guidance).

Confirm alignment of eye-guide 110 (may be automatic).

Monitor and measure the relation of eye-guide lens 120 to the patient's limbus 26, may be performed automatically using image processing and pattern recognition (may be automatic).

Measurement and verification to identify the center of the lens and the limbus in x-y (may be automatic).

Locate and measure the I-Guide in depth z (may be automatic).

Measure orientation of eye-Guide in angular space (may be automatic).

2. Verification of entry position 311 of X-ray beam 1400.

Identify and calculate the position of the laser spot 1410 indicating scleral entry of the X-ray beam and relation to limbus 26 (may be automatically performed, and may also be operator-verified prior to X-ray emission).

The algorithm used may be based on imaging analysis of the border of the limbus 26 as compared to the center of the limbus. In one treatment plan example, the center of the X-ray beam is placed about 4 mm from the limbus border, the beam diameter being about 3.5 mm, so that the beam edge is about 2.25 mm beyond the limbus (the beam 1400 traverses the pars plana region to reach the target 318 at or near the fovea, and so minimizes dosage to the lens.

3. Treatment monitoring (gating)

Continuous x-y-z-θ spatial monitoring of the eye-guide 110.

Continuous measurement of x-y limbus position (may be automatic).

In the example shown in FIGS. 3A and 3B, imaging system 410 comprises two cameras. The cameras may interface to computer processors (not shown) of system 10, e.g. via USB connectors. Illumination (e.g., LED lights) may be controlled by signals from computer processors. The cameras include:

1 Main System X-Y camera 401 (on-axis)

Located along the center axis of the Automated Positioning System (APS).

Will display live images to the physician at video rate (30 Hz).

2 Range Z camera (off-axis)

Mounted above the system axis.

Angled downward to obtain a perspective view of the fiducials 1-3 of eye-guide 110.

The lights 405, 406 and 407 provide safe, regulated light levels coordinated with imaging procedures, such that imaging applications are insensitive to room light conditions. These functions include:

Lighting the field of view for the Main System x-y Camera to see the patient's eye.

Directing light along each camera path onto the retro-reflecting fiducial targets for I-Guide monitoring Lighting the lower limbus boundary 26 for enhancing the contract for limbus detection.

Marking the X-ray entrance point with a laser spot that has been aligned with the x-ray source.

Please see description below with respect to FIGS. 21A-21E and the example captioned "Example of image-based eye and eye-guide measurements" for further description of the methods of use of imaging system 410.

The collimator 118 is positioned close to the eye of the patient, so as to allow for an acceptable penumbra as well as a tightly collimated radiation beam as described in the above noted U.S. application Ser. No. 12/103,534 filed Apr. 15, 2008; Ser. No. 12/027,069 filed Feb. 1, 2008; each of which is incorporated by reference. In certain embodiments, the collimator exit aperture diameter is between about 1 mm and about 4 mm so that the spot size on the back of the retina is approximately about 2 mm to about 7 mm.

FIG. 4 depicts a cross-section schematic view of a portion of a X-ray source assembly 420 of system 10. Laser pointer 1410 travels through a beam splitter 1220 and exits the collimator with its center aligned with the radiation beam. In the example shown, the x-ray anode 1420 has a greatest dimension between about 0.1 mm and about 5 mm and can be placed at a distance L from the retina of about 50 mm to about 250 mm, and preferably from about 100-200 mm, and more preferably about 150 mm. Maintaining the anode 1420 at such a distance from the retina in one embodiment allows maintaining a low penumbra. The radiation beam 1400 is delivered through the collimator 118, and its diverging path enters the eye approximately in the pars plana region, missing the important structures of the anterior chamber such as the lens and the cornea. In the example shown, eye-guide 110 lens contacts the sclera and/or the cornea of the eye.

As shown in FIGS. 3A and 4, the collimator 1405 is preferably collinear with the collimated light beam, 1410, which can act as a pointer to indicate the point on the eye through which the radiation enters the eye 1300. In some embodiments, the light pointer position is used to track the radiotherapy source vis-à-vis an image recognition system which identifies the position of the pointer relative to an ocular structure (e.g., the limbus) and the radiotherapy device is then moved based on the image (e.g., to a region further away from or closer to the limbus of the eye). In some embodiments, the physician visualizes the position of the laser pointer relative to the limbus and manually adjusts the x-ray source into position.

Light pointer 1410 (e.g., a laser beam emitted from a source, such as a diode laser, fiber-coupled gas laser, or the like) is coupled to a collimator 1405, or behind the collimator 1405, so that the light pointer 1410 is coincident with an x-ray beam 1400; the light pointer 1410 can indicate the position 311 on a surface of an eye through which the radiation source enters by tracking angles of incidence of the collimator and x-ray beam. Cameras of imaging system 410 can track point 311 and image processors can be used to confirm this position to a user, or to trigger automated controls, if position 311 should be out of a threshold of accuracy, per a treatment plan.

As illustrated in FIG. 3A, for convenience certain dimensions relevant to beam collimation and treatment anatomy may be identified as L0, L1, L2 and L3, where:

- L0 is the total distance from the X-ray source anode 1420 to a treatment target 318 (e.g., macula or fovea);
- L1 is the distance from the X-ray source anode 1420 to the collimator exit aperture plane 1405;
- L2 is the distance from the collimator exit aperture plane 1405 to the tissue surface beam spot 311 (e.g., sclera surface at or near pars plana); and
- L3 is the length of the propagation path of the X-ray beam within tissue to reach the treatment target, the distance from beam tissue entry spot 311 to the treatment target 318.

In an exemplary ocular treatment plan having aspects of the invention, the collimator exit plane 1405 is typically within a distance L2 of about 1 cm to about 12 cm from the beam entry point 311 on the sclera. However, in alternative embodiments, the collimator may be configured to be in contact with the surface of the eye or adjacent face, and may include a suitable resilient or cushioning biocompatible contact surface. The distance D may be selected as a trade-off between the goal of minimizing penumbra of beam 1400 at the retina, and in avoiding interference and discomfort of the patent, e.g., due to space limitations when working close to the face. In certain embodiments, a high degree-of-freedom (DOF), high range-of-motion robotic positioner may be employed to position X-ray tube 112 and collimator 118, which can be programmed and/or controlled to maneuver so as to avoid interference with objects and parts of the patients body. See for example, high degree-of-freedom robotic surgical control systems such as employed in the CyberKnife® robotic radiosurgery system (Accuray, Inc. Sunnyvale, Calif.) and the da Vinci® minimally-invasive surgical system (Intuitive Surgical, Inc., Sunnyvale, Calif.). However, the da Vinci is not autonomous and requires an expert surgeon to move its arms. The Cyberknife is in fact autonomous. However, the linear accelerator which moves around the patient is over 1 ton in weight and cannot move close enough to the patient to deliver beams of X-ray to the eye. Furthermore, the system does not include an eye stabilization system to allow for alignment relative to the eye.

However, alternatively and advantageously, a limited range-of-motion positioner (see 115 in FIGS. 5-6) may provide greater precision and accuracy of radiotherapy, particularly where a single DOF is moved to stereotactically reposition the X-ray source 112 for sequential beam treatment applications, e.g., by minimizing positioning error, vibration and dynamic effects. In addition, a real or at least conceptual hazard of high degree-of-freedom robotic systems employing energy beam treatment, is the large possible range of beam paths (e.g., upon a control system failure), and associated risk issues, regulatory complexity, and high end-user installation and site modification costs.

In one example, L2 is selected to be about 55 mm and L0 is selected to be about 150 mm, suitable for use with APS 115 shown in FIG. 1A and described further in FIGS. 5-6. See, for example, embodiments described in the above noted U.S. application Ser. No. 12/100,398 filed Apr. 9, 2008; which is incorporated by reference.

In many embodiments, only a small amount of movement is required of the x-ray source 112 to treat a disease of the retina, such as macular degeneration and/or diabetic macular edema. In these embodiments, six degrees of freedom can be applied to the x-ray source 110, but the range of each degree of freedom is may be limited. Because each treatment dose is relatively short and applied over a small distance, the robot can sacrifice speed and travel distance for smaller size.

Alternatively, multiple X-ray source may be employed, e.g., having a fixed relationship to each other, to supply multiple stereotactic beams for treatment. However, embodiments employing an APS such as shown in FIGS. 1-6 can be more compact, lighter, and less expensive, and avoid the space limitations of excessive equipment working close to the face.

FIGS. 5 and 6 depict embodiments of a constrained X-ray positioning system to treat the eye (e.g., as included in APS 115). Positioning system 115 is depicted. Translation in the X-Y-Z motion is shown and in angular orientations $\phi$ and $\theta$. This positioning system is customized for close treatment and to treat the eye. The range of motion along each degree of freedom is limited and the positioning system 155 delivers x-rays to the eye. X-ray source 112 is positionable with respect to the eye, which can be tracked, in some embodiments, with a contact member 110 and module 625.

Note that imaging support 412 (see also FIG. 3B) is shown in this example projecting from XYZ stage 416, so that imaging system (410 in FIG. 3B) may be supported independently of the $\phi$ and $\theta$ actuators 413 and 414 respectively, but may be positioned by XYZ stage 416 so as to be in alignment with the eye geometric axis 2810 or treatment axis 2820, for example. However, it should be noted that all or portions of imaging system 410 may be supported either together with or independently of any of the degrees of freedom of positioning system 115, without departing from the spirit of the invention. For example, one component of imaging system 410 (e.g., a camera) may be mounted directly to tube 112, while other components are mounted to XYZ stage 116, and yet other components are mounted and positioned independently of all of the 5 DOF of the exemplary positioning system 115, e.g., by an independently actuated and controlled robotic support, or the like.

FIG. 6 depicts embodiments of a motion control system in which the collimator 118 is moved by the positioning system around the tip of a cone with the x-rays converging on a focal spot within the eye, such as the macula. The distance along the center of the cone to the collimator is constant for a given angle ϕ which refers to the angle the collimator 118 makes with treatment axis 2820. The distance from the edge of the collimator to the focal spot is constant for any ϕ or θ. Because the motion system is rigidly constrained around an axis, the error is very small in terms of positioning and movement.

In some embodiments, the distance L0 from the X-ray source anode 1420 to the retinal target 318 may be from about 200 mm to about 50 mm, and in an embodiment described in detail herein, this distance (L0) may be about 150 mm. In some embodiments, the distance from the end of the collimator (aperture 1405) to the center of the focus 318 on the retina (L2+L3) may be from about 120 mm to about 160 mm, and in an embodiment described in detail herein, this distance (L0) may be about 40 to about 60 mm.

Angle ϕ can change depending on the distance prescribed or desired. In some embodiments, the angle ϕ is variable and can be changed depending on the desired entry position of the beam into the eye. Nonetheless, to achieve the desired motion around the point of focus, the collimator moves around the rim of a cylinder such that the collimator can emit radiation from points at a constant angle with respect to the target. Such movement enables the positioning system to accurately position the collimator and x-rays tube along an arc. This single degree of freedom after positioning makes the therapy efficient and precise.

In the exemplary embodiment of positioning system 115 shown in FIG. 5, the system comprises a base (421 in FIG. 1A). Note that the base 421 is shown as a table-mount type base, but may be alternatively supported by other mounting structures known for medical devices, such as overhead mountings, cantilevered wall mountings, wheeled cart mounting, retractable or folding mountings, or the like.

In this example, base 421 supports a proximal XYZ stage 116 having three sequentially-supporting mutually-perpendicular linear actuators, which in turn supports a more distal rotational θ actuator 414 which has an axis of rotation parallel to the Z axis, which in turn supports a still more distal rotational ϕ actuator which adjusts the polar angle relative to the Z axis. The most distal X-ray source assembly 420 is supported by the ϕ actuator. This exemplary positioning arrangement shown may be operated in a number of alternative modes. However, it is particularly well suited to a stereotactic mode of operation wherein the X, Y, Z and ϕ degrees of freedom are adjusted and fixed relative to treatment axis 2820 and target 318, and subsequently X-ray source assembly 420 is re-positioned by motion of the θ actuator 414 to successive beam treatment positions, as shown in FIG. 6. Alternative embodiments of positioning system 115 for the X-ray source assembly 420 having aspects of the invention have differing proximal-to-distal ordering of the degrees of freedom shown, and may have greater or fewer than 5 degrees of freedom.

IID. System Computer and Machine-Readable Code

The processor in the system may be a conventional microcomputer having keyboard and mouse input devices, a monitor screen output device, and a computer interface that operably connects various components of the system, including the eye tracking assembly or device, a robotic arm that controls the position and thus the beam orientation of the of the source beam, and optionally, an arm that is mechanically linked to the eye guide, to carry out the various functions of the system.

As applied to treatment an ocular lesion, such as macular degeneration, these functions fall into one of four general areas: (1) target alignment, (2), treatment planning, (3) tracking target position during the course of treatment, and (4) control of the radiation beam, including beam position, duration, and intensity, to achieve a desired radiation dose at the target and to avoid or minimize potentially harmful effects on nearby radiation-sensitive structures. These four functions will now be separately considered with respect to the system designed for treating an ocular lesion, such as macular degeneration. Although the steps in the algorithm are described with respect to a method for treating a retinal lesions, such as macular degeneration, and with respect to tracking a geometric axis of the eye, it will be appreciated how the algorithms can be adapted for radiation therapies involving different targets, or where other body-target axes are employed. It will also be appreciated that machine readable code for executing the individual functions will preferably will be part of an integrated software or hardware system that encompasses all of the functions.

IID1a. Target Alignment, No Eye Guide

This algorithm, which is discussed and illustrated in other section of the applications, particularly in Sections VIIC and with respect to FIGS. 54-56, follows the general steps described below.

1. With the patient placed is a desired position, and looking straight ahead, an imaging system records an image of the patient eye, including corneal reflections from an external light source;

2. The image is converted to a digital image consisting of an N×M pixel array. Based on the known position of the imaging system in the external coordinate system, the pixels in the array correspond to known coordinates in the external system;

3. Standard or commercially-available imaging and image-processing system components may be adapted and employed, such as, for example, as provided by Edmund Optics, Inc. of Barrington, N.J. (e.g., an Edmund Optics-1312, progressive scan CMOS of 1280×1024 pixel dimensions) and The MathWorks, Inc. of Natick, Mass. (e.g., Image Processing Toolbox 6.2). The image processing system analyzes the image to identify the limbus and first corneal reflection, based on scanning pixel values in the array and identifying variations in localized pixel value that are consistent with the structures being identified, i.e., based on image structure boundaries characterized by expected changes in pixel values at certain boundary location in the image;

4. The pixel coordinates of the limbus and first corneal reflection are used to calculate derivative landmarks, such as the center of the limbus, and the resulting pixel values are used to assign external-system coordinates to an axis, e.g., the geometric axis of the eye, defined by the structure;

5. Knowing the external-coordinates of the geometric axis of the eye, and the distance between the camera and the eye, the three dimensional coordinates of the eye in the external coordinate system are assigned;

6. The coordinates of the ocular axis from step 5 in the external coordinate system are then used to determine the external-system coordinates of the target structure, e.g., the macula and optionally, any other structures of interest, such as nearby radiation-sensitive structures. This may be done using known spatial relationships in a standard eye model between the position of the ocular axis, e.g., geometric axis, at its point of intersection with the retina, and the positions of the macula and other structures, e.g., the optic disc, on the retina;

6'. In one embodiment, step 6 is carried out by aligning the patient-eye geometric axis with geometric axis of the eye model, and scaling the model to the patient eye by the known axial length of the patient eye, thus to superimpose the model on the patient eye. Based on the known coordinates of the selected structures in the model, the coordinates of the same structures in the patient eye can now be assigned and transformed to the external coordinate system; and 7. Knowing the coordinates of the patient target lesion in the external coordinate system, the program now determines the position and orientation of a beam axis that passes through the sclera, slightly above or below the midline of the eye, and intersects the center of the target lesion. A robotic arm carrying the beam source may be activated to place the beam along the calculated beam axis.

IID1b. Target Alignment with Eye Guide

This algorithm, which is discussed and illustrated in other section of the applications, particularly Sections IV-D AND VI-F and FIGS. 21-26, follows the general steps described below.

1. With the patient placed is a desired position, and looking straight ahead, and with an eye guide centered on the eye, e.g., centered with respect to the limbus, an imaging system records an image of the patient eye, and analyzes the digital image, as in steps 2 and 3 above, to confirm the positioning of the eye guide on the center of the eye.

2. With the patient looking straight ahead, information from the tracking system is used to calculate the external coordinates of the eye guide;

3. Knowing the external-coordinates of the eye guide, and matching the coordinates of contact portions of the eye guide and eye, the three dimensional coordinates of the eye in the external coordinate system are then assigned;

4. The coordinates of the eye from step 3 in the external coordinate system are then used to determine the external-system coordinates of the target structure, e.g., the macula and optionally, any other structures of interest, such as nearby radiation-sensitive structures, following step 6 in the algorithm above; and 5. Determining beam axis position and orientation are now carried out as in step 7 above.

IID2. Treatment Planning

This algorithm is discussed and illustrated below in Section IIIB and FIGS. 8-14 below.

1. From the known coordinates of the patient target area, e.g., retinal lesion, as determined from one of the alignment algorithms above, determining at least two treatment beam path axes directed from a source of a collimated x-radiation beam through the patient's sclera beyond the limbus and directed at the lesion on the patient's retina, 2. Calculating from an eye model superimposed on the patient eye (see step 6' in the first alignment algorithm above) the distance of travel of each beam through the eye along each beam axis;

3. Knowing the distance of travel from step 2, and the attenuation factor associated with beam travel through the medium of the eye, calculating a total expected beam attenuation for each treatment beam axis from entry point to target;

4. From the known radiation beam intensity settings, including beam intensity and spectral characteristics, the known total radiation dose desired, and the calculated attenuation of the beam through the eye along known beam axes, calculating a total beam duration time effective, when aimed at the target, to produce the desired dose; and 5. Dividing the total beam duration among the two or more beams.

II D3a. Tracking Absolute Target Position During the Treatment

The two tracking algorithm below are discussed and illustrated in Section V.G and FIGS. 29-36. Both are designed to track eye movement during the radiation treatment, and to convert the eye movement to a spatial map of radiation received in the region of the target area, including any radiation-sensitive structures. This first algorithm operates by constructing a spatial map of radiation exposure with respect to the absolute retinal positions in the region including and surrounding the target area lesion.

Steps 1-4 of the algorithm are carried out at regular intervals, e.g., every tenth second, during the course of treatment, that is, when the target lesion is being exposed to the radiation beam.

1. Receiving information from the tracking device on the position of the geometric axis or eye guide axis;

2. Comparing the eye-axis coordinates from step 1 with the known coordinates of the system axis;

3. From the variation in eye and reference axes coordinates from step 2, calculating the retinal coordinates of the beam axis, that is, the external-system coordinates at which the beam axis intersects the retina;

4. From the calculated retinal coordinates from step 3, and the known radiation equivalent at the retinal surface, calculating an instantaneous radiation equivalent received at the calculated retinal coordinates;

5. Using the accumulating instantaneous radiation equivalent values calculated in step 4 to construct a spatial map of radiation equivalent over an area of the retina that has received radiation; and 6. At periodic intervals, e.g., every tenth second, monitoring the total radiation equivalent received at the target and any radiation-sensitive structures.

II D3b. Tracking Target Position Excursions During the Treatment

This second algorithm operates to construct a map of eye excursion during the course of treatment, from which the radiation distribution as a function of distance from the target area can be calculated, for purposes of tracking total radiation received at any time at the target area and at known distances from the target area.

Steps 1-4 are carried out at regular intervals, e.g., every tenth second, during the course of treatment, as above.

1. Receiving information from the tracking device on the position of the geometric axis or eye guide axis;

2. Comparing the eye-axis coordinates from step 1 with the known coordinates of the system axis;

3. From the variation in eye and reference axis coordinates from step 2, calculating the retinal coordinates of the beam axis;

4. From the calculated retinal coordinates from step 3, calculating a vector between the target and the instantaneously measured excursion position of the beam at that time point;

5. Using the accumulating excursion vectors to construct a summed excursion-vector map;

6. From the summed excursion-vector map, calculating total radiation distribution as a function of distance from the target area;

IID4. Controlling the Radiation Beam (Gating Function)

This algorithm acts on information from the treatment planning algorithm and on information from a tracking algorithm, such as one of the two algorithms just considered, to control the beam intensity, duration, and timing of the beam from the radiation source, and the orientation of the beam axis.

1. At each point during irradiation along a single beam axis, comparing the total radiation equivalent received at a radiation-sensitive structure from one of the two tracking algorithms above with the maximum radiation equivalent allowed at the structure from that beam axis;

2. If the total radiation equivalent from step (1) is above a threshold level established during treatment planning, terminating beam exposure along that axis; otherwise go to step 3.

3. If all beam axes from the treatment plan have been exploited, terminate treatment; otherwise, go to step 4.

4. If total radiation equivalent at the radiation-sensitive structure is below threshold, continue irradiating the target;

5. Repeating steps (1)-(4) until an above-threshold value at a radiation-sensitive structure or a desired radiation equivalent at the target for that beam axis is reached;

6. Have all treatment axes been exploited? If no, direct the robotic arm controlling the position of the beam source to the next beam-axis position; if yes, then terminate the treatment.

III. RADIOTHERAPY TREATMENT METHOD

In one aspect, the invention includes a method of treating a lesion on or adjacent the retina of an eye of a patient with an external-beam radiation device. In a first step, the patient's eye is placed in alignment in alignment with a known system axis in an external three-dimensional coordinate system, and the eye's axial length is measured. Details of these steps step are given in Sections IIIA-IIIC below, where the eye is aligned based on natural features or landmarks of a patient, and in Section IV, with respect to the use of a eye guide to align the patient eye.

From the known position of the system axis and from the measured axial length, the coordinates of the lesion to be treated in the external coordinate system are determined, and a collimated radiation beam along a known beam axis in the external coordinate system at the lesion to be treated. Details of these steps, which are preferably carried out by processor in the above-described system, are described in Section IID above.

During the course of the treatment, and in particular, during the period when the lesion is being exposed to the external-beam radiation, the position of the eye is tracked with respect to the known system axis, thus allowing the position, i.e., coordinates of the lesion to be treated to be tracked in the external coordinate system. Details of the processor operations for carrying out this step are also detailed above in Section IID.

Based on the known beam axis of the collimated beam in the external coordinate system, and the instantaneous position of the lesion to be treated in the external coordinate system (as determined at least in part by the tracked position of the eye), the system processor operates to calculate a total radiation equivalent received at the lesion to be treated during the treatment.

In one preferred embodiment, the method is designed to delivery a desired dose of radiation to the target lesion, but without exposing one of more radiation-sensitive structures close to the lesion to a harmful does of radiation, i.e., a dose that could negatively affect the functioning of the structure. For example, in the case where the retinal lesion is the macula of the patient eye, one of the radiation-sensitive structures is optic disc. The method in this embodiment includes determining the coordinates of at least one radiation-sensitive structure in the external coordinate system; e.g., the optic, tracking the position of the radiation-sensitive structure(s) in the external coordinate system; and based on the instantaneous position(s) of the radiation-sensitive structure(s) in the external coordinate system, calculating a total radiation equivalent received at the at least one radiation-sensitive structure during the treatment. Details for carrying out these steps substantially follow those used in determining total radiation received at the target lesion, following the processor operations detailed above on Section IID.

IIIA. Eye Alignment

Figure 7:
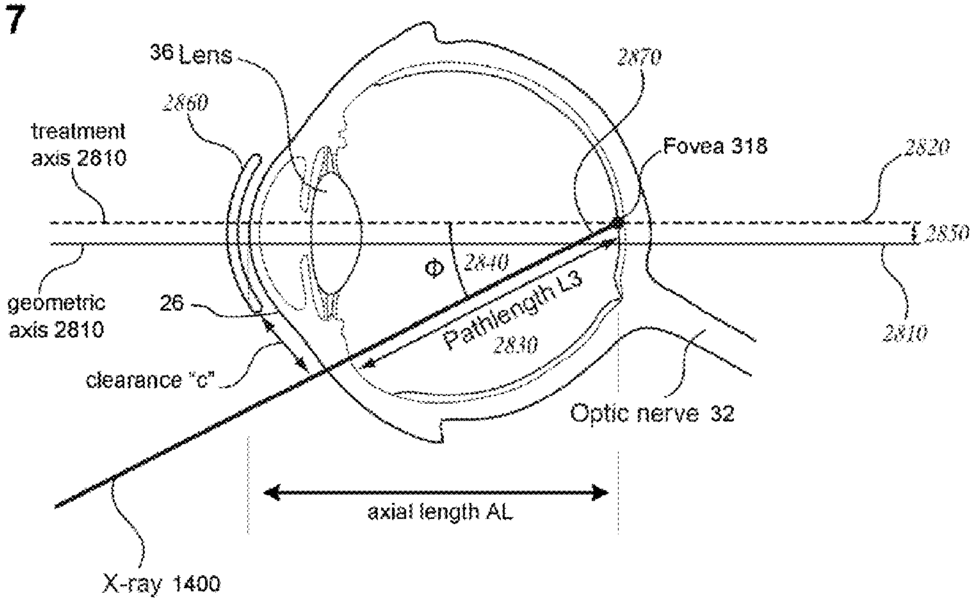
FIG. 7 depicts an anatomical targeting method for radiotherapy, depicting a cross section of a patient's eye.

FIG. 7 depicts an anatomical targeting method for radiotherapy. The central or geometric axis 2810 of the eye may be defined approximately by the eye-guide 2860 (or alternative eye-alignment methods), which in some cases is a lens which fits the curvature of the front of the eye. The geometric axis 2810 of the eye 30 may be defined as perpendicularly intersecting the cornea surface 35 at the center of limbus 26. In some embodiments, geometric axis 2810 can be the treatment axis, or a distinct treatment axis 2820 may be defined. In the example shown, the treatment axis 2820 is offset vertically and/or laterally and lies generally parallel to the geometric axis 2810, intersecting the fovea 318 of the eye (approximately the macular center). In one embodiment, angle $\phi$ is set so that the x-ray beam 1400 travels into the eye at a spot adjacent to the edge of the limbus 26 on the front of the eye, e.g., near the pars plana, so as to have a clearance "c" from limbus to center of beam entry point of about 2 to 6 mm).

The central axis, in some embodiments, may be the axis which is perpendicular to the center of the cornea or limbus and extends directly posterior and anterior to the cornea and to the center of the retina, as discussed previously. In some embodiments, the central axis is the treatment axis, about which a radiotherapy device can rotate; this axis can also be referred to as the system axis. In some embodiments, the treatment axis 2820 can be a parallel line to the central axis 2820 and offset from the geometric axis 2810 by a distance 2850.

The treatment axis can intersect the retina at the macula or the center of a lesion to be treated. The axis 2820 can be any axis in any orientation relative to the central axis 2810, axis 2810 being continually identified by the guide 2860. Path length 2830 (indicated also as "L3") is a distance of the path followed by the X-ray beam during propagation from tissue surface to the treatment target, and is helpful for predicting the dose at the intersection of the retina, as there will be attenuation of energy by the time the x-rays reach the retina and, to some extent, this attenuation will be dependent on the beam tissue propagation path length 2830. The tissue path length for a selected planned treatment procedure may be correlated with a measurement of the patient's eye, most conveniently to the eye axial length, as further described herein in detail with respect to FIGS. 14 and 15A-15B.

Optic nerve points in the medial (toward the midline) direction as it travels behind the eye. In addition, it has been demonstrated by inventors herein, that the typical path of the optic nerve is also inferior (downward or caudally) from the eye as it travels behind the eye. The example of a multiple-beam stereotactic treatment plan for macular irradiation having aspects of the invention, as depicted in FIG. 9, accounts for the path of the optic nerve in minimizing absorbed radiation dose to this structure. Reference is made to application Ser. No. 12/100,398 filed Apr. 9, 2008; and Ser. No. 12/262,031 filed Oct. 30, 2008 for further description; each of which applications is incorporated by reference.

Figure 8A:
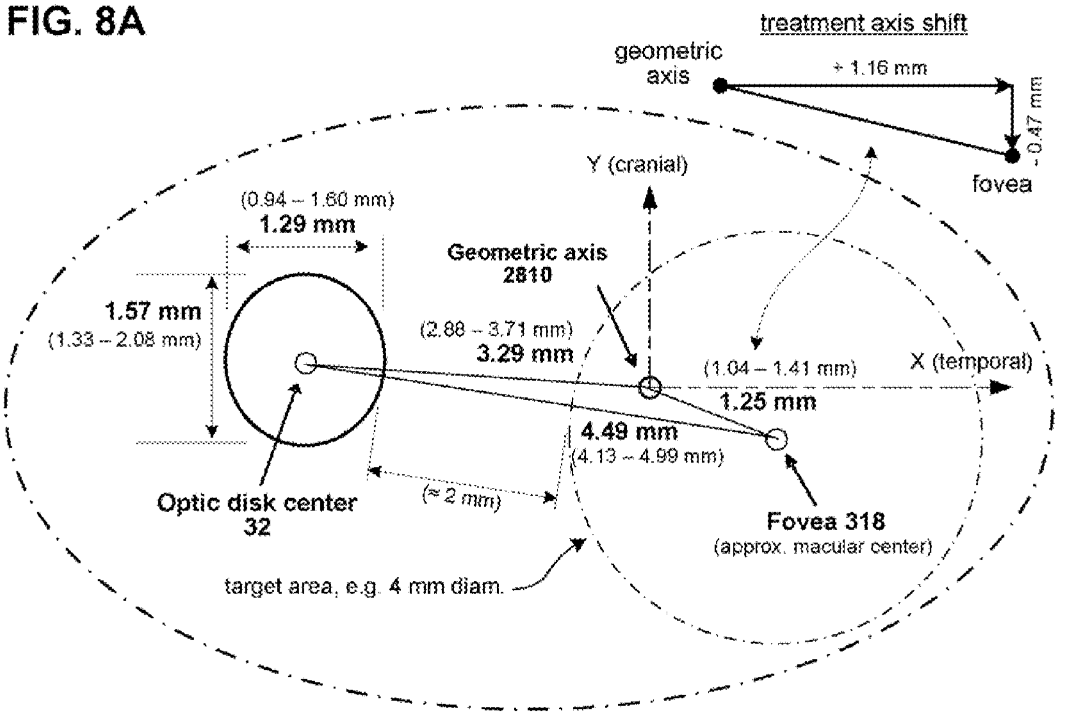
FIG. 8A is a schematic view of a fundus image on a patient's retina, showing retina anatomy and geometry.

FIG. 8A is a schematic view of a fundus image on a patient's retina showing one example of a treatment plan for AMD. The effect of the axis shift on the treatment region of the retina can be seen, the geometric axis 2810 is offset from is the treatment axis 2820 (centered on the fovea). Also shown are the dimensions defining relationship with the optic disk, as the treatment plan preferably assures low dosage to this structure. FIG. 8A below illustrates data from a study of several normal volunteers in which the intersection of the geometric axis with the retina was determined and related by distance to the fovea and the optic nerve. In some embodiments, only one shift geometry is used for all patients. Alternatively, a scaled shift geometry may be used based on one or more patient-specific parameters, such as axial eye length, e.g. determined by an A-scan or OCT. Shown are averages and maxima and minima for the depicted measurements. Also shown is a triangular diagram summarizing the average shift data to offset the treatment axis from the geometric axis: x=+1.16 mm temporally, and y=−0.47 mm caudally, and as further shown and described with respect to FIG. 21D. Inventors herein have demonstrated from clinical data that an exemplary radiotherapy treatment plan having aspects of the invention and incorporated treatment axis offsets at or near these values accurately predicts the center of a macular target. Reference is made to application Ser. No. 12/100,398 filed Apr. 9, 2008; and Ser. No. 12/262,031 filed Oct. 30, 2008 for further description; each of which applications is incorporated by reference.

It has been found that the average shift values shown lead to surprisingly small errors in the population studied, a maximum error of 0.20 mm in the horizontal direction and 0.08 mm in the vertical direction. Thus, when the geometric axis 2810 intersection with the retina is identified using guide 2860, the fovea or a lesion nearby can be targeted. A treatment plan can therefore be developed. For example, a known spot on the lens placed on the front of the eye can be determined and then the axial length can be used to locate the inner limit of the retina. After locating the point (either virtually by a model or visually through an imaging device) on the retina where the axis of the lens on the eye intersects the retina, any point along the retina such as a lesion center can be targeted with by the radiation positioning system.

Figure 8B:
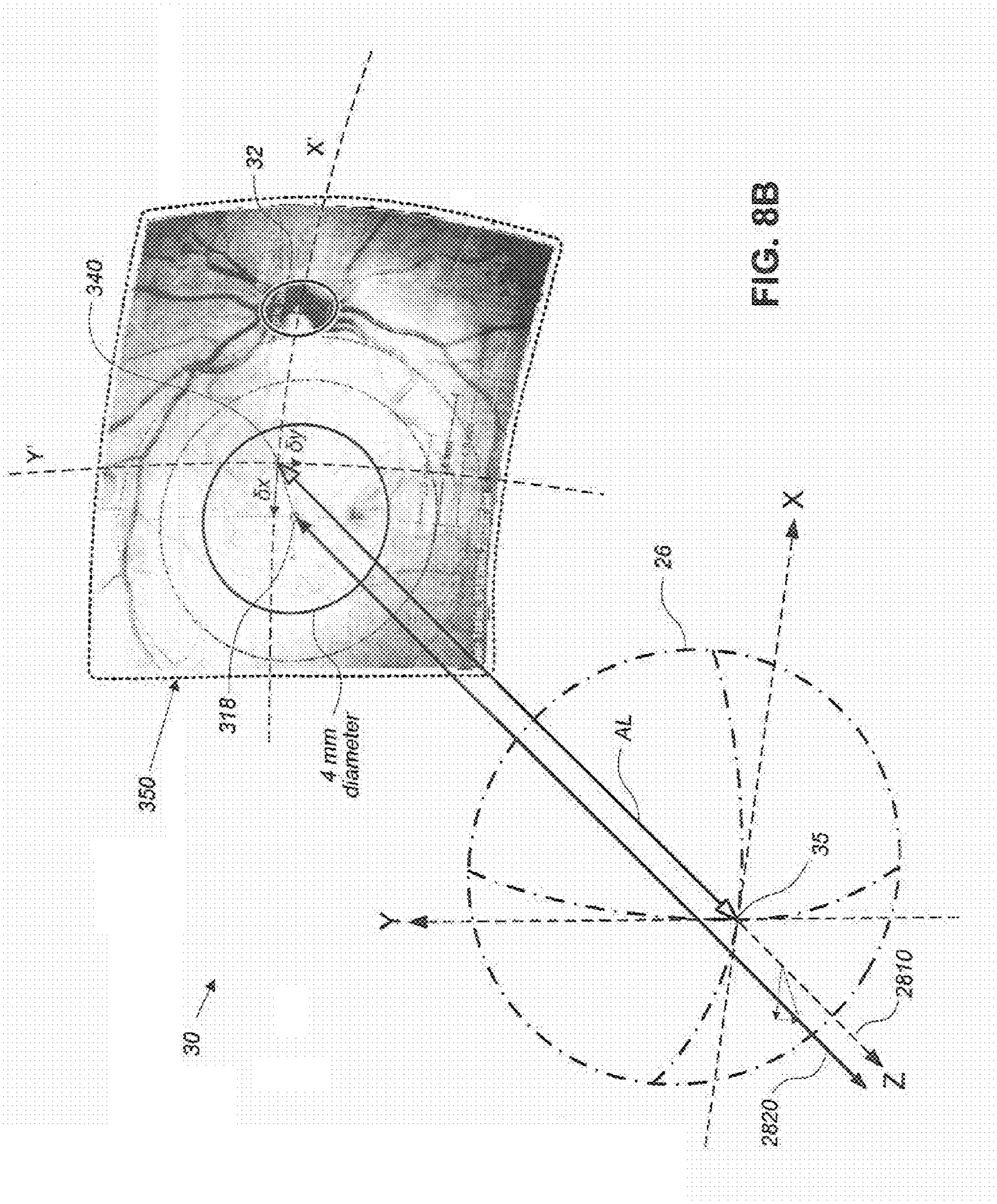
FIG. 8B is a perspective view of a virtual model of an eye, including a registered retinal image, such as an OCT image of a patient.

FIG. 8B is a perspective view of a virtual model of an eye 30, including a registered retinal image 350, such as an optical coherence tomography (OCT) image, a fundus camera image, or other medical image of a patient. In this example, the eye model 30 is shown as aligned with a radiotherapy system Z axis, which is collinear with the geometric axis 2810 of the eye. Axis 2810 perpendicularly intersects the cornea 35 at a central point defined by the center of limbus 26, the axis extending through the eye to the retinal pole 340. An X-Y coordinate plane for the eye model 30 is shown centered on the Z axis tangent to the cornea at the corneal center 35 (see the alignment method example described with respect to FIGS. 21A-21E).

A subsidiary retinal reference plane X'-Y' is defined centered on pole 340 (in typical patients, the retinal surface plane X'-Y' may be substantially parallel to the corneal X-Y plane). A opthalmologic retinal image may be incorporated into eye model 30, such as OCT image 350, for example by capturing an electronic image of a patient to be treated, and geometrically registering the image data with the model (aligning the image data to retinal plane X'-Y'). A convenient scale factor for sizing image data to the eye model is the eye axial length AL, the distance from the anterior corneal center 35 to the surface of the retina at pole 340, which may be measured non-invasively by an ultrasonic A-scan.

Figure 21A:
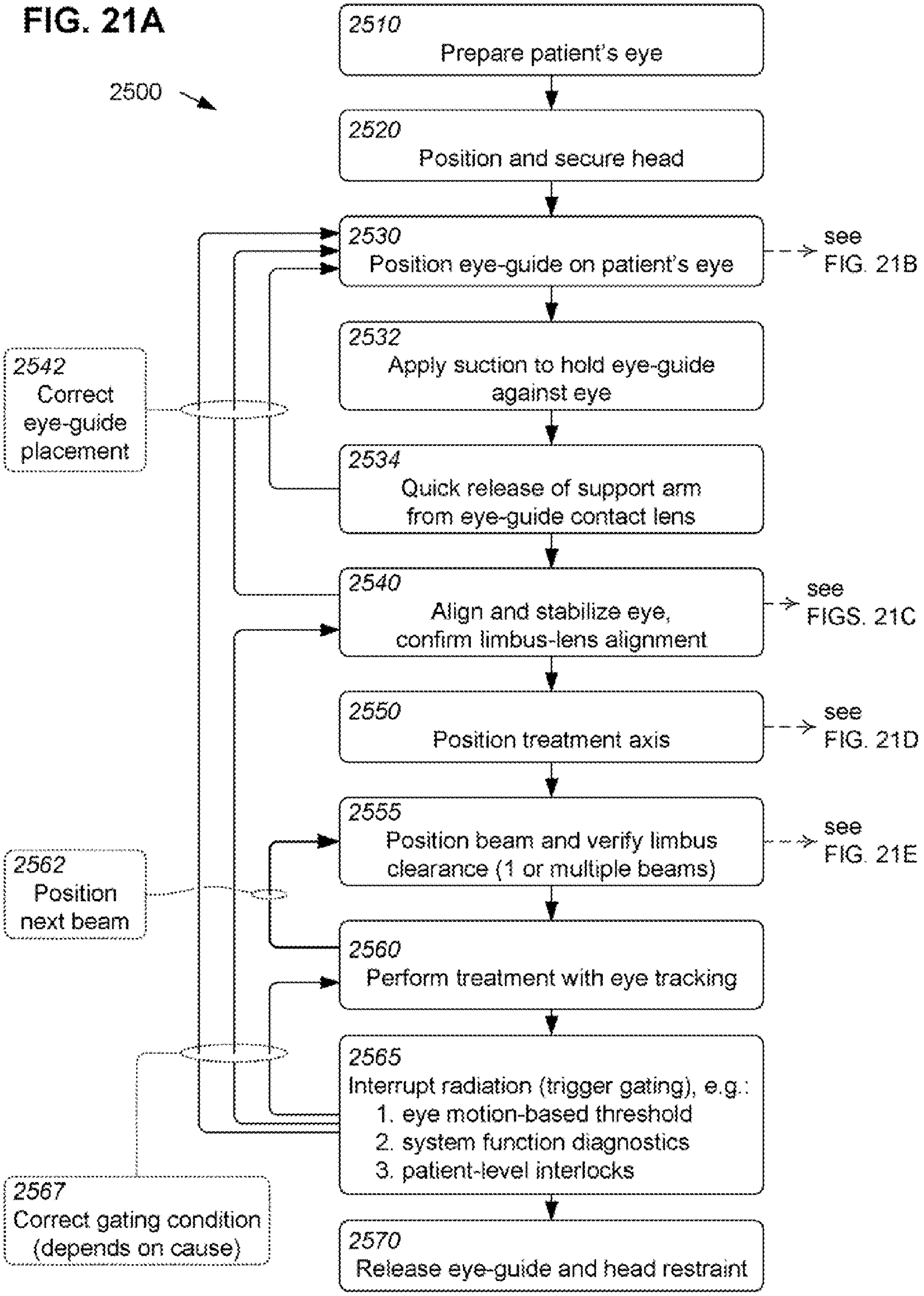
FIG. 21A is a flow chart illustrating one method of utilizing the system for stabilizing and positioning an eye for treatment.
Figure 21D:
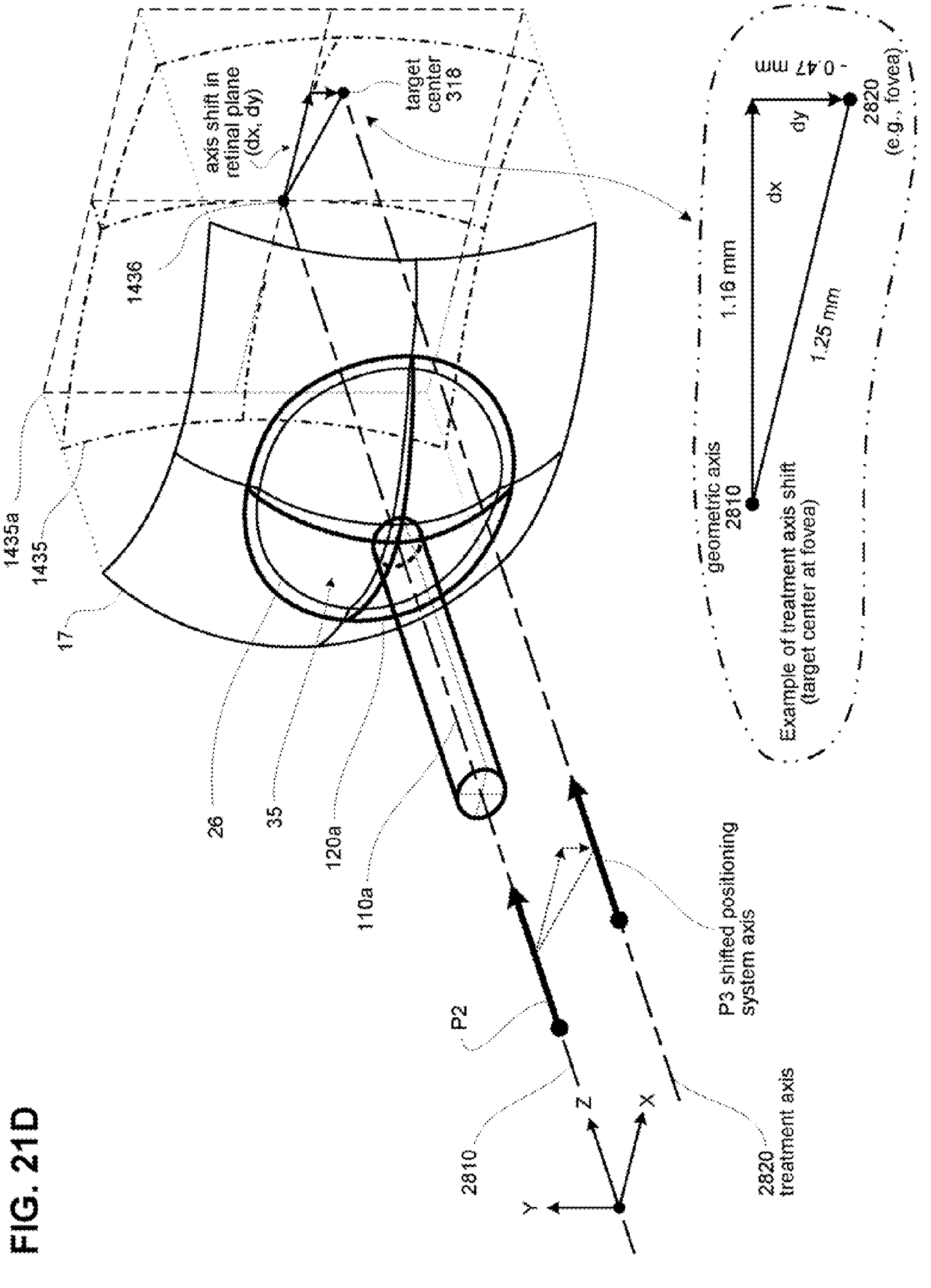
Figure 21E:
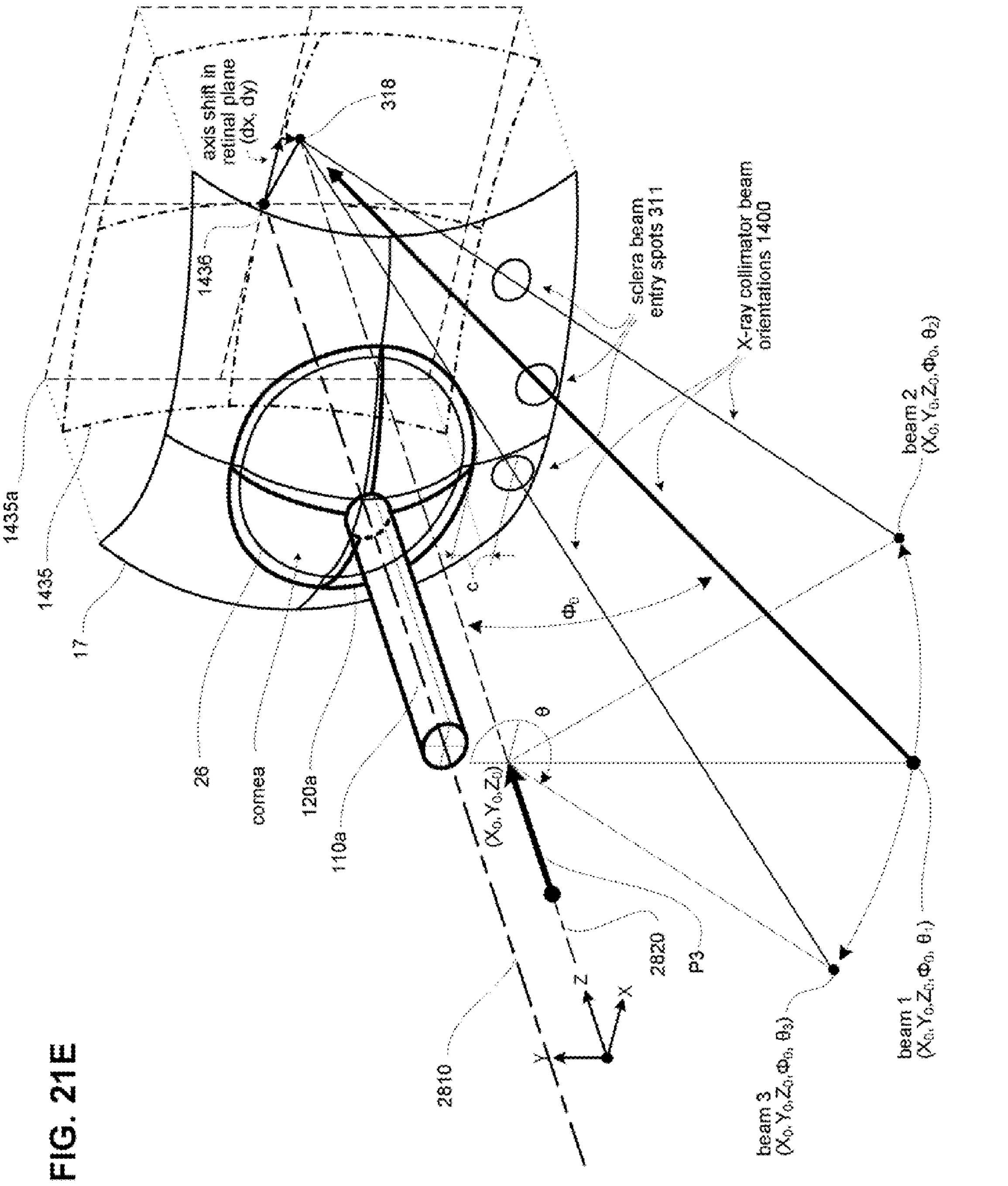

As described further with respect to FIGS. 8A and 21E, a treatment axis 2820 may be defined by offsets from pole 340 (δx, δy in the X' and Y' coordinate plane), the treatment axis intersecting the retina at a treatment target center 318. By incorporating a patient-specific retinal image 350 into an eye model 30 and registering the image congruently to the geometry of a radiotherapy treatment plan (e.g., as shown in FIGS. 8A and 9), the relationship between treatment axis 2820 and the patient's retinal lesion may be visualized by a physician. Radiation target parameters of the treatment plan may either be confirmed or modified, in preparation for treatment.

FIG. 9 is a frontal view of an eye as seen aligned with a system reference axis 18 (temporal to right, nasal to left), and depicting stereotactic X-ray treatment beam geometry, such as described in FIG. 7. Once reference axis 18 is identified (e.g., geometric axis 2810), treatment may be carried out by a device oriented with respect axis 18. Alternatively, a distinct axis 19 may be defined with respect to axis 18, for example by a shift of distance dy and dx, so that axis 19 intersects treatment target 318 positioned off-axis with respect to axis 18. Axis 19 may be called the "treatment" axis. Based on straightforward geometry, the device 312 can now be positioned so that its beam axis 311 intersects treatment axis 19 at tissue target 318. Axis 18 may be used to define one or more correlated geometric axes in the external coordinate system, and to define one or more additional intersection points with respect to beam 311. Note for treatment targets lying on reference axis 18, offset "d" may be about zero, and for treatment delivered through or to the cornea, angle "ϕ" may approach zero. The illustrated example is of an embodiment in which the alignment system is coupled to a treatment system adapted for orthovoltage X-ray treatment of a region of the retina generally including the macula.

Figure 11:
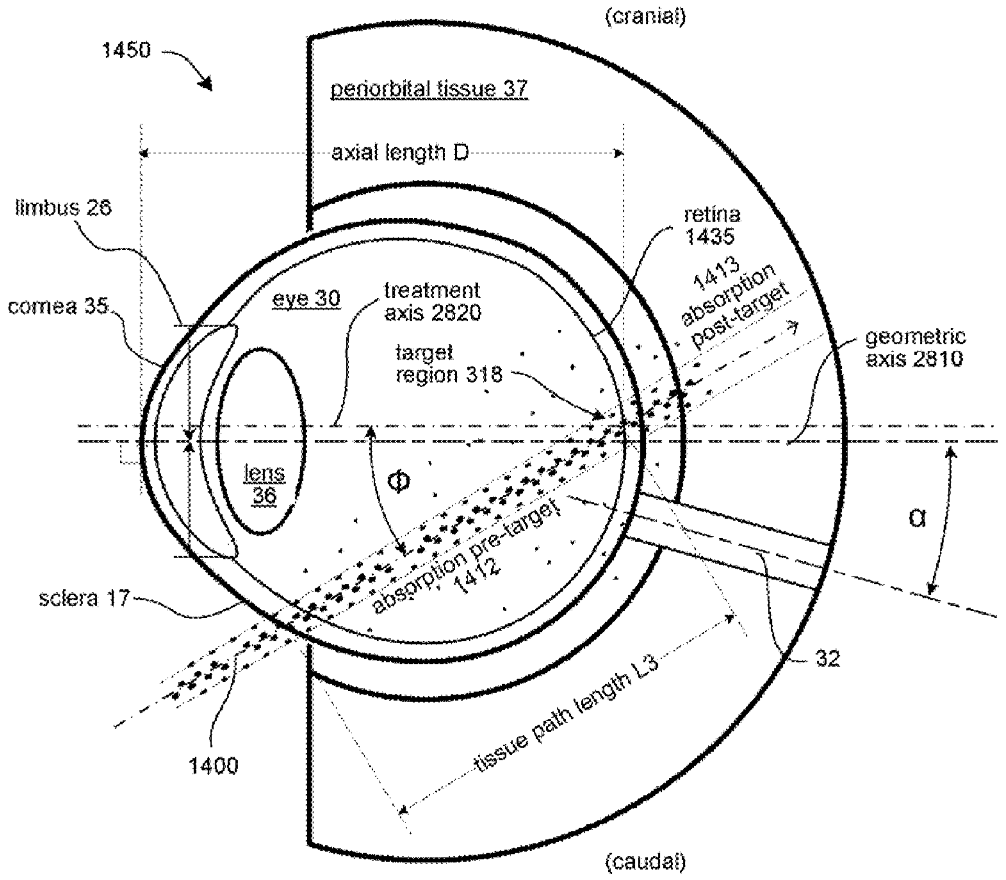
FIG. 11 depicts a phantom eye model includes a virtual representation of much of the ocular anatomy shown in FIG. 7, including the relationship between different anatomical features and eye geometry.

FIG. 9 can be correlated with FIGS. 7 and 11, which provide a generally comparable cross-sectional view of an eye, shown in association with a treatment system. As shown in FIG. 9, although a single beam axis 1400 may be employed, a plurality of beam axes may be defined in which two or more treatment beams are aimed to impinge on target 318 stereotactically. Treatment axis 19 may be chosen to intersect a selected target 318 within the eye, and employed as a reference to orient two or more treatment beams aimed to impinge on target 318 stereotactically.

In the example of FIG. 9, treatment axis 19 is chosen to intersect a selected target 318 within the eye, and employed as a reference to orient three treatment beams projected along three different beam axes 1400*a*, 1400*b* and 1400*c*, the beam axes defined so as to each impinges on target 318 from a different direction. Multiple beams may be projected simultaneously, or sequentially, with intervening periods of no treatment if desired. Likewise, multiple beams may be provided by multiple separately-positioned treatment devices. However, a preferred embodiment employs a single treatment device 312 (e.g. a collimated orthovoltage X-ray source), which is sequentially repositioned by positioning device 310 to administer treatment in sequential doses along each of a plurality of beam axes, such as axes 1400*a-c* (1400*a*, 1400*b* and 1400*c*). The beam axes each have a different respective point of entry into the body surface (311*a*, 311*b* and 311*c* respectively) and each follows a different tissue path leading to target 318. Likewise each beam follows a different tissue path for any propagation beyond target 318. In this way, treatment beam dosage penetrating tissue remote from target 318 may be minimized relative to the dosage received at target 318.

Figure 10:
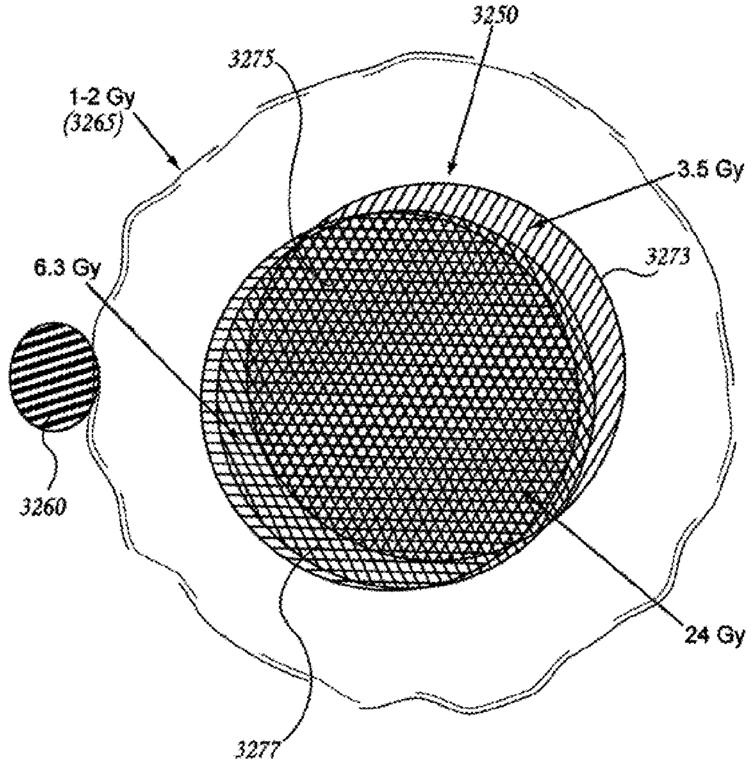
FIG. 10 depicts results of an experiment in which three beams were focused on the back of an eye using a robotic system.

Note that the number of stereotactic beam paths selected (for emission either sequentially or simultaneously) may be selected from a considerable range to achieve treatment goals. FIGS. 9-10 illustrate a 3-beam pattern example (1400*a-c*), and device embodiments described in detail herein (e.g., FIGS. 5-6) can conveniently administer such a pattern in sequence. However, alternative devices having aspects of the invention may have multiple X-ray source and/or collimators configured to administer such a pattern simultaneously. In other alternatives, treatment goals may be achieved with a single beam path 1400. In still further alternatives, treatment goals may be achieved with a number of beams exceeding three (e.g., 1 to n beams).

In yet further embodiments, a beam path 1400*i* may be continuously moved stereotactically during X-ray emission over a beam track on the sclera (or other body surface) having a selected scope or range, so that while the entry region for radiation is spread out along the surface track so as to reduce local tissue dose, at the same time the target region receives a concentrated dose as in target 318, the moving beam path reaching an effective focus on the target region.

In general, where a stereotactic beam pattern is described herein as "one or more beams", "a plurality of beams", or "at least one beam", these expressions include treatment configurations in which a collimated beam is moved continuously or incrementally over a selected stereotactic position range during radiation emission so as to achieve an equivalent treatment goal having a focused or concentrated target radiation dose.

Beam axis 1400 (or for multiple beams, each of axes 1400*a-c*) may be selected to follow a tissue path which avoid vulnerable structures or tissues which are remote from target 318, so as to minimize dosage received by such tissues. For example, in treatment of the macula for macular degeneration, axes 1400*a-c* may be selected to deliver a selected dose of beam treatment (e.g., a selected dosage of absorbed X-ray energy) to a target 318 on or near the retina 340, centered on the macula 342 while minimizing absorbed radiation by the optic nerve 350, the lens, and the like. In the example shown, three beam axis 1400*a-c* are defined, corresponding to three rotational angles about the treatment axis $\theta_a$, $\theta_b$, $\theta_c$, so that the beams directed towards the posterior eye enter the body on the surface of the anterior sclera 17 at points 311*a*, 311*b* and 311*c*, each entry point a selected distance beyond the limbus 26. Such beam orientation can avoid or minimize absorption by the lens and other structures within the eye, by appropriate selection of the beam paths.

As illustrated in FIG. 9 one or more of beam axes (e.g., 1400*a*, 1400*b* and 1400*c*) are defined such that each axis lies within a conical conceptual surface and whereby each beam intersects the apex of the cone. The cone may be defined having as its conical axis the treatment axis 19 with the apex disposed at target 318. In this example, treatment axis 19 is defined parallel to reference axis 18, having x-y offsets define in an perpendicular plane by "dx" and "dy" respectively (for a treatment target intersected by the reference axis the offsets are zero). Once the treatment axis 19 is defined, the base 34, the apex angle ("$\phi$" in FIG. 7), and rotational positions of axes 1400*a-c* with respect to axis 19, may be adjusted to provide both beam intersection at about target 318 as well as to provide entry points 311*a-c* located at a desired position of the body surface.

In one example of an orthovoltage X-ray treatment for macular degeneration, off-sets dx and dy are selected to define a treatment axis 19 centered on the macula, angle $\phi$ is selected to provide intersection of beams 1400*a-c* on the macular surface, and base 34 is selected to provide surface entry points 311*a-c* in a region of the lower anterior sclera beyond the boundary of limbus 26. In this example, an X-ray beam source may positioned by positioning device (see 115 in FIGS. 1 and 5) so as to project a collimated beam from a selected X-ray source distance so as to form a beam having a characteristic width at tissue entry "w". Note that although a treatment beam may be projected through an eye-lid or other tissue proximal to the eye, the eyelids (in this case the lower eyelid) may be conveniently retracted so as to expose an additional area of the anterior sclera 17.

Note that in the most general case, treatment axis 19 need not be parallel to reference axis 18, and target 318 may be located relative to axis 18 by other analytical methods not including a separately-defined treatment axis. On the other hand, a real or at least conceptual hazard of high degree-of-freedom robotic systems employing energy beam treatment, is the large possible range of beam paths (e.g., upon a control system failure), and associated risk issues, regulatory complexity, and high end-user installation and site modification costs.

FIG. 10 depicts results of a procedure in which three beams were focused on the back of a phantom eye model using the robotic system 10 described above, and represents a radio chromic film after bench top delivery of 100 keV overlapping x-rays at a target site 3250. A radio surgical phantom model was used in which a model eye was placed in the eye socket. Film was placed on the back of the model eye and x-rays were delivered to a target representing the macula. The region of overlapping x-ray beams 3275 are shown at their overlap region where the dose is 24 Gy. The optic nerve 3260 is depicted lateral to the overlapping set of beams at a scaled distance from the center of the overlap. A rapid isodose fall off 3273, 3277 occurs lateral to the overlapping region 3275 and well away from the optic nerve 3260. Notably, the isodose depicted at region 3265 is indeed between about 1% and about 10% of the dose (0.24 Gy-2.4 Gy) at the treatment spot 3275. These data are a consequence of the overlapping beam geometry as well as the fine beam collimation; they are physical proof of the ability of finely collimated overlapping orthovoltage x-ray beams to create well-defined treatment regions. Due to the 10-100 fold difference in treatment dose to optic nerve dose, fractionation is not required, and the entire dose can be given to the treatment region in one session with minimal concern for injury to important structures, such as the optic nerve. These overlap regions can be optimized and/or placed anywhere within the eye which is determined by the treatment planning system and depends on the beam energies, collimation, and filtering. The degree of overlap is also to an extent determined by system parameters. For example, treatment of the entire region of the retina for macular degeneration may be different than that for tumors or for hemangioma.

IIIB. Eye Models and Treatment Planning

Information such as described with respect to FIGS. 7-10 may be used to construct a virtual or phantom model of the eye having aspects of the invention (e.g., using software and interfaces with a computer processor). The eye model may represent the eye to be treated and related anatomy.

As used herein, "eye model" or "model of the eye" refers to any representation of an eye based on data, such as, without limitation, an anteroposterior dimension, a lateral dimension, a translimbal distance, the limbal-limbal distance, the distance from the cornea to the lens, the distance from the cornea to the retina, a viscosity of certain eye structures, a thickness of a sclera, a thickness of a cornea, a thickness of a lens, the position of the optic nerve relative to the treatment axis, the visual axis, the macula, the fovea, a neovascular membrane, a curvature of a cornea or a retina, a curvature of a scleral region, and/or an optic nerve dimension. Such data can be acquired through, for example, imaging techniques, such as ultrasound, scanning laser opthalmoscopy, optical coherence tomography, other optical imaging, imaging with a phosphor, imaging in combination with a laser pointer for scale, CT scan with or without contrast, and/or T2, T1, or functional magnetic resonance imaging with or without contrast. Such data can also be acquired through keratometry, refractive measurements, retinal nerve-fiber layer measurements, corneal topography, direct caliper measurement, etc. The data used to produce an eye model may be processed and/or displayed using a computer.

As used herein, the term "modeling" includes, without limitation, creating a model. The eye model is a virtual model which couples the anatomy of the eye with the coordinate system of the radiotherapy device 10. The eye model can be based on the geometry of the ocular structures and can be derived with parametric data and mathematical formulas to generate the model. Alternatively, the ocular geometries are derived from cross-sectional imaging, such as from CT scans or MRIs. With the treatment axis defined and the ocular anatomy defined, the coupling device can contact the ocular surface and link to the radiotherapy device via the eye model. The radiotherapy device may then positioned based upon the eye model.

The model may be based on generalized human ocular anatomy, and may be based on patient-specific ocular anatomy. Although human ocular geometry is distinctly variable within patient populations, appropriate adjustments and modifications to a generalized eye model may be made taking into account one or more patient-specific measurements, so as to accurately represent a particular patient's eye anatomy. For example, a virtual eye model may conveniently and economically include an overall structure based on generalized human ocular anatomy, which may then be adjusted or scaled by measurements taken from a patient to be treated, such as an A-scan measurement of eye axial length, routine type of diagnostic test used in ophthalmology (A-scan ultrasound biometry can provide, for example, the central or axial eye length from anterior corneal surface to retinal surface).

Figure 12:
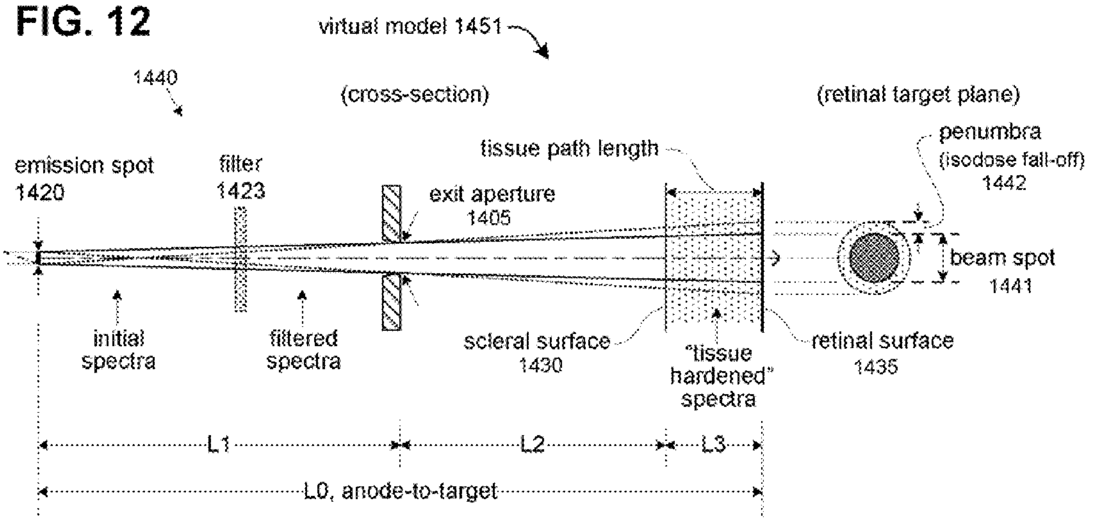
FIG. 12 shows an X-ray collimator system including the physical parameters that effect the radiation beam characteristics, as applied to a simplified anatomical representation of the anatomy of FIG. 11.

FIGS. 11 and 12 schematically depicts exemplary embodiments of virtual or phantom models of a human eye 30 and adjacent structures, such as may be digitally defined using conventional software tools, displays and input/output devices (or by using alternative graphic or representational modalities). A virtual model may include multiple components, which include different representations of the same anatomical structures. For example, in embodiment shown in FIG. 11, the eye model includes a virtual representation of much of the ocular anatomy shown in FIG. 7, including the relationship between different anatomical features and eye geometry.

FIG. 12 shows a model 1451 of an X-ray collimator system 1440 including the physical parameters that effect the radiation beam characteristics, as applied to a simplified anatomical representation of the anatomy of FIG. 11. However, in contrast to FIG. 11, the model 1440 of FIG. 12 is simplified, so that the surface of sclera 17 is depicted as a perpendicular planar surface 1430, and retina surface 1435 is likewise depicted as a plane perpendicular to the beam axis 1400.

Note also that "emission spot" 1420 is depicted in FIG. 12 as a planar surface of a defined cross-sectional dimension perpendicular to beam path 1400, and represents an idealized X-ray emitting surface emitting photons through collimator 118. Actual X-ray devices may have an X-ray emitting source having an number of alternative shapes, orientations and configurations. For example, the X-ray-emitting electron-beam target of an linear accelerator source may be high atomic number material aligned in the path to the electron beam and presenting an exit plane which may be substantially perpendicular the collimated X-ray beam 1400. Alternatively, the target anode material of an commercial orthovoltage X-ray tube may comprise a surface at a substantial angle to the collimated X-ray beam 1400, the output X-rays being emitted through a window (e.g., thin Be sheet) oriented in a generally transverse direction to the cathode beam impinging on the anode surface. The anode material may be formed to have a planar surface, or a truncated conical surface in the case of a rotating anode. To simplify the model 1440, the effective X-ray emission spot 1420 from the perspective of aperture 1405 may be represented as a disk of defined diameter oriented perpendicularly to beam 1400 and uniformly emitting X-rays of a certain initial spectrum. For convenience, such an emission source 1420 is referred to herein as an "anode" or "anode spot" without loss of generality.

Likewise, the aperture 1405 is represented in FIG. 12 as single circular opening, but need not be circular and need not comprise a single opening. See for example, collimator embodiments described in Ser. No. 11/873,386 filed Oct. 16, 2007, which is incorporated by reference. Where an collimator exit opening and/or projected radiation beam-spot on a tissue surface or target plane is non-circular (elliptical, rectangular, elongate, irregular or the like), the diameter may be conveniently considered to be a selected geometrically characteristic dimension, such as maximum width, a major or minor axis, a mean width or the like.

A model such FIG. 12 permits convenient modeling of photon energy spectral change as the beam propagates from anode to treatment target. The initial spectra emitted by anode spot 1420 may pass through a filter 1423 which shifts the spectrum to a higher mean photon energy by absorbing predominately lower energy photons. The effective filter 1423 may comprise any device structure material in the beam path (inherent filtration, e.g., an X-ray tube window, a laser beacon deflection mirror, aperture covering, or the like) and any additional filter material positioned for this purpose (e.g., one or more aluminum plates of selected thickness mounted at a selected position in along the axis of collimator 118).

A filter for penetrating radiation is often characterized by its absorption properties scaled relative to a half-value-layers or half-value thickness (HVL), related to mean free path of a photon or particle. An HVL may be defined as the thickness of specified material which reduces the intensity of a particular input radiation spectrum entering the material by half. However, a filter element need not be an integral HVL and may be of any selected thickness. Likewise, a filter element need not be of a single or uniform material. For example, filters may have a series of layers, such as layers in decreasing order of atomic number such as tin, copper, and aluminum layers in the direction of propagation. Although the examples described may have filters of uniform cross-sectional thickness or composition, in alternative embodiments, a filter may be non-uniform with respect to the beam cross-section, so as to produce a spectral variation from one side the beam to another (wedge shaped), radially variation about a center, or other variable distribution.

The filtered spectrum is further "hardened" by upward shift in mean photon energy as it propagates along tissue path L3 of eye 30 towards retina plane 1435 ("tissue hardened spectrum"). The intersection of beam 1400 with retina 1435 ("retinal target plane") may be represented in this simplified model as a circular central 1441 and a concentric penumbra or "isodose fall off" margin 1442. However, in alternative embodiments, the beam-spot geometry (1441, 1442) may be configured to be non-circular. See application Ser. No. 12/262,031 filed Oct. 30, 2008 (which is incorporated by reference), such as FIGS. 8-12 and 22-29 of that application and related description.

It is apparent that the relevant anatomical structure can be defined mathematically and geometrically, optionally including convenient simplifications and generalizations, without loss of utility in planning and predicting radiotherapy treatment.

Empirically and/or theoretically determined radiation beam characteristics and human tissue characteristics may be correlated with the eye model to allow modeling of radiation transmission and absorption along a beam propagation path. For example radiation propagation and absorption through tissue may be simulated employing software such as the Monte Carlo Radiation Transport Code developed by Los Alamos National Laboratory. As shown in FIG. 11, a virtual model may include a geometric representation of position of the optic nerve extending posteriorly from the optic disk of the retina (in this example characterized by angle $\pi$), which is useful in determining beam propagation paths which minimize dosage to the optic nerve, such as from the portion of applied radiation passing through and beyond a treatment target adjacent the macula.

In the examples shown in FIGS. 11 and 12, the virtual or phantom eye model 1440, 1450 is configured to represent a narrowly collimated external radiation beam directed to enter an exposed scleral surface 17, such as the pars plana 1430, and propagate to the surface of the retina 1435 at or near the macula 318. See co-invented application Ser. No. 12/100,398 filed Apr. 9, 2008 (which is incorporated herein by reference) for further description of methods having aspects of the invention for determining suitable beam paths for ocular treatments, and in particular, beam paths which may be used to treat a macular region, while minimizing absorbed dosage to such structures as the lens and optic nerve.

In an embodiment of a treatment planning method having aspects of the invention, beam tissue path length L3 is determined (i.e., radiation beam distance through tissue from air entry point to treatment target), and the path length is in turn employed with a radiation transport model to account for reduction in beam strength and spectral profile as it passes through tissue. This permits determination the dosage at the target relative to the air kerma beam dosage. In actual treatment, the magnitude of radiation can then be adjusted to provide an accurately predictable absorbed dosage at the target (e.g., by adjusting the radiation duration).

As one example, it has been shown in studies conducted by inventors herein that, for a treatment plan to irradiate the macular region via a beam entry point near the pars plana, that the tissue path length of a wide range of patients can be accurately predicted using a virtual model and a single A-scan measurement of a patient's ocular axial length. Indeed, an linear approximation can give good results for a particular treatment plan, such as a formula: PL(mm)=AL(mm)−k; where k is a constant such as about 3. See further description with respect to FIGS. 14-15. In addition, patient-specific imagery may be incorporated into the eye model, such as is schematically depicted in FIG. 8. In one embodiment, a fundus image is obtained from a patient prior to radiotherapy treatment, the image may then be scaled in proportion to a patient measurement such as ocular axial length, the image being aligned and superimposed on the virtual model.

An eye model may be used in planning treatment, as is depicted in FIG. 9, such as by determining a treatment axis 19 with reference to a radiotherapy system reference 18, and defining one or more radiation target regions 318 suited to the disease being treated. One or more radiation beam paths 1400 may also be defined with reference to the model. In the example shown, three stereotactic beam paths 1400*a*-1400*c* are planned so as to be coincident adjacent target region 318 centered on treatment axis 19. Planned positions/orientation of X-ray beam 1400 may likewise be superimposed on the model by correlation of the model coordinate system with the planned system coordinates. A image displayed to an operator/physician may thus include model data; scaled and registered fundus image data (and/or other medical image data); together with planned radiotherapy beam geometry data. Among other things, this permits a physician to confirm that the planned treatment is appropriate for the lesion of the patient, as seen in the fundus image.

The model may be used to determine patient-specific parameters relevant to radiation propagation, such as a tissue path length along a beam path 1400 to a target region 318 to apply radiation dosage to a target beam spot 1441 (see FIG. 12). In this manner, an eye model having aspects of the invention may be used to compile a patient-specific treatment plan which accurately predicts radiation dosage levels and distribution in a target region 318 as shown in FIG. 11, and which accurately predicts radiation dosage distribution relative to anatomical structures such as the lens 36 and optic nerve 32 (see optic disk 3260 in FIG. 10). See for example the retinal dose map of FIGS. 37A-37B. Data from such radiographically-measured and/or computationally simulated dose distribution may be incorporated and registering with a phantom or virtual model. Planned radiation beam geometry (See FIGS. 9 and 11) may then be included in the model as virtually-projected radiation beams 1400 from a virtual radiation source, and used to simulate dose deposition at a target region 318 in the phantom model.

A combination of anode size, anode-to-target distance and collimator length may be selected by methods having aspects of the invention for an X-ray source providing a tightly collimated beam spot of appropriate maximal intensity, sized to a selected target region dimension, and having sharply defining penumbra or area of dosage fall-off surrounding the beam spot. A combination of X-ray tube field potential and filter dimensions may be selected by methods having aspects of the invention which provides a favorable ratio of radiation dosage at a scleral entry point to target region (pre-target absorption or "tissue hardening"), while permitting rapid attenuation of beam dosage beyond the target region, such as be absorption in orbital skull bone (post-target absorption). See co-invented application Ser. No. 12/100,398 filed Apr. 9, 2008 (which is incorporated herein by reference) for further description of the characteristics of radiotherapy beams and configuration of X-ray treatment devices having aspects of the invention. The embodiments have selected parameters which provide radiation treatment beam characteristics which are particularly well suited to the treatment of ocular lesions, including lesion of the retina such as occur in AMD.

Figure 13A:
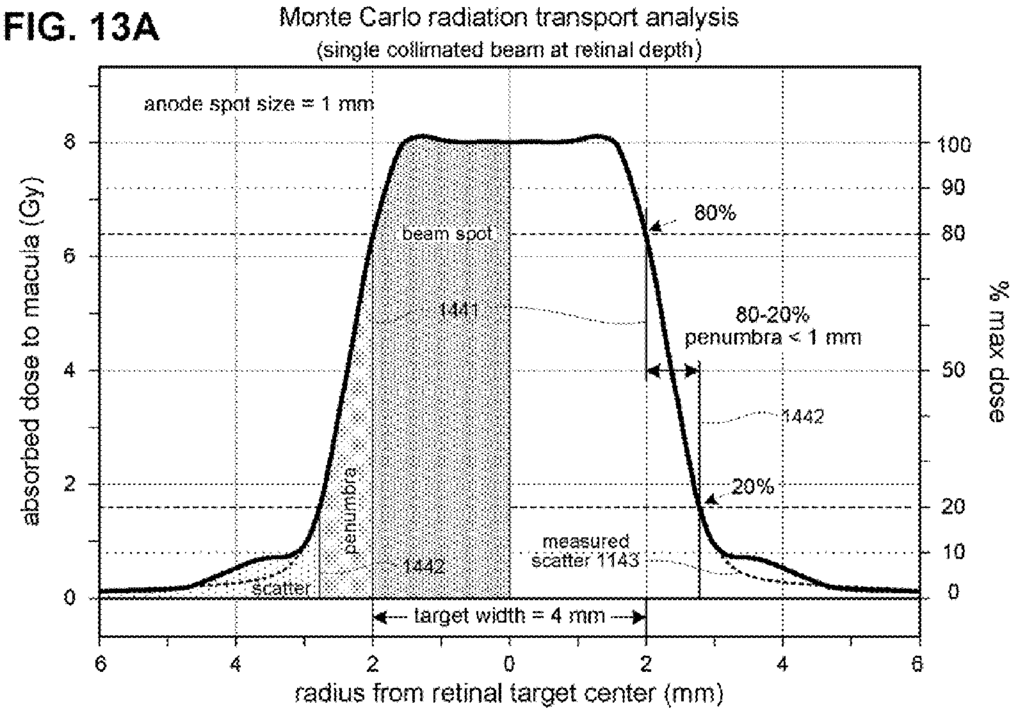
FIG. 13A is a plot showing the results of a Monte Carlo computational simulation for absorption of X-ray energy in a configuration generally similar to that of FIG. 12.

FIG. 13A is a plot showing the results of a Monte Carlo computational simulation for absorption of X-ray energy in a configuration generally similar to that shown in FIG. 12. The computational simulation accounts for radiation propagation effects, such as scattering in tissue, on the resulting dose profile across a retinal target. Cross sectional profile to the absorbed dose to the macula target for a 100 kVp X-ray beam. A collimator was selected to create approximately a 4.0 mm beamspot, and to simplify the MCNP geometrical setup, a non-clinical normally incident beam angle is assumed. The absorbed dose profile at the center of macula is shown for X-ray tube anode focal spot size of 1.0 mm, positioned 100 mm from the target, for a targeted central dose of 8 Gy. Vertical lines 1441 are placed at +2 mm and −2 mm radius, delineating also the 80% isodose in this model. The ±2 mm region approximates the anatomic size of a macular lesion target region of 4 mm diameter. The penumbra 1442 is indicated as bounded by the 20% isodose, with low dose or "scatter" region 1443 adjacent the penumbra margin.

Monte Carlo (MC) simulations are used to model x-ray absorption, scatter, and dosing to structures impinged on by x-rays. An example of a tool useful for this type of analysis is the MCNP Radiation Transport Code developed by Los Alamos National Laboratory (see D B Pelowitz; MCNPX User's Manual Version 2.5.0, LA-CP-05-0369; Los Alamos National Laboratory, Los Alamos, N. Mex., 2005, which is incorporated by reference herein). Monte Carlo methods are widely used computational algorithms for simulating the behavior of various physical and mathematical systems, and for other computations. They are distinguished from other simulation methods (such as finite element modeling) by being stochastic, that is, non-deterministic in some manner. Computational radiation simulations, such as Monte Carlo analysis and the like, are included in embodiments of treatment planning systems having aspects of the invention, and may be used to assist in treatment planning where radiation is involved.

Monte Carlo simulation can also be used to predict and dictate the feasibility and other elements of the radiotherapy system 10 (e.g., optimization of the collimator and treatment planning schemes); for example, the collimation designs, the energy levels, and the filtering regimes, can be predicted using Monte Carlo simulation. The results of Monte Carlo simulation have been experimentally verified and further improved, based on initial MC simulation. In some embodiments of radiotherapy where the anatomy, beam energies, and treatment volume are similar, the Monte Carlo simulations can be run once and then the path variables altered (e.g., through ray tracing or other geometric methodology) without need to repeat Monte Carlo simulation. For example, MC simulation can predict the penumbra of an X-ray beam.

In FIG. 13A, the dose coefficient in the central region was estimated to be 7.7 Gy/Gy, where the reference air kerma value is again set at 100 cm from the x-ray source. The sharpness of the falloff of the target spot from full dose to zero or very low dose is measured by the penumbra. Penumbra represents the portion of the target that does not "see" the entire anode focal spot and hence does not receive the full dose. The sharper the penumbra, the tighter and more conformal the dose can be delivered. One metric that may be used to characterize the dose profile and size of an the X-ray beam spot and effective penumbra dimension makes use of isodose contours, conveniently expressed as a percentage of a maximum central region dose.

Penumbra may be given an empirically convenient definition as the distance between selected dose intensity levels, such as the 80% the 20% isodose lines (the 80-20 penumbra) or alternatively the distance between the 90% and 10% isodose lines (the 90-10 penumbra). The 80-20 penumbra in FIG. 13A is indicated to be less than 1 mm in extent for the 4 mm beamspot diameter. Note that the model also shows a degree of scattered dosage at 10% of less of the maximum dose intensity, extending outward beyond the 20% isodose line, trailing off thereafter to a low level of dosage (>1% of maximum) as the radius from target increases.

Figure 13B:
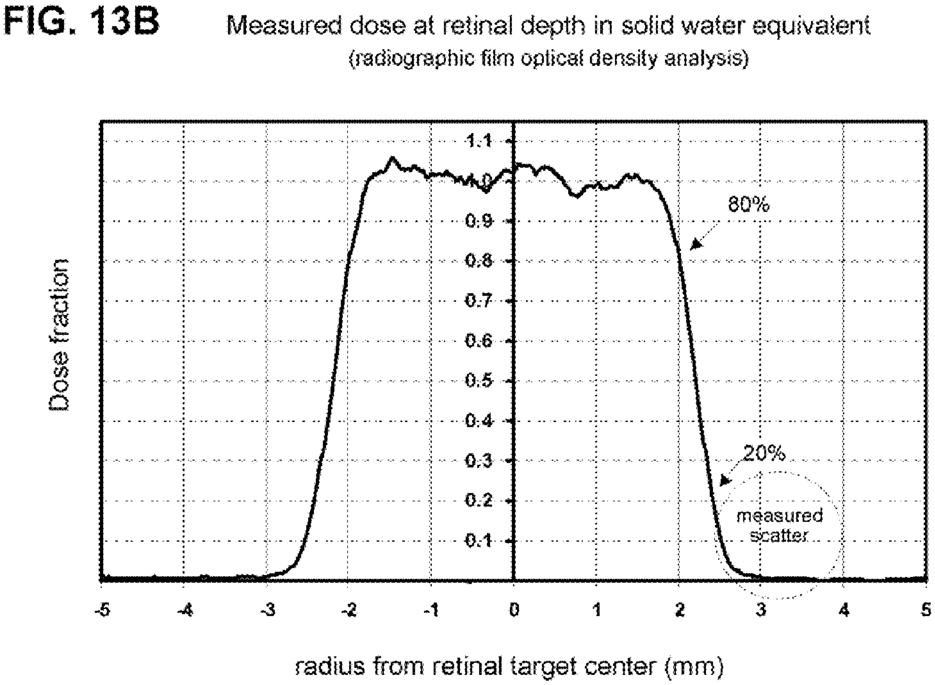
FIG. 13B shows a plot of measured dose intensity at retinal depth for an X-ray/collimator configuration comparable to that of FIG. 13A.

For purposes of comparison and validation, FIG. 13B shows a plot of measured dose intensity at retinal depth for an X-ray/collimator configuration comparable to that of FIG. 13A. In this example, a radiographic film was place behind an approximately 20 mm thickness of "solid water" type water-equivalent radiographic phantom material, to simulate the tissue thickness depth of the retina. The optical density of the film, exposed to about 10 Gy of absorbed X-ray dose, was converted mathematically to an equivalent absorbed dosage. It may be observed that the general shape of the beamspot and penumbra is very similar to that shown in the Monte Carlo simulation of FIG. 13A. However, no bolus of scatter immediately beyond the penumbra (believed to be an artifact) is observed in the measurements, the dosage level instead dropping consistently and rapidly to a low level beyond the 20% isodose ("measured scatter"). This distinction between the modeled scatter and the measured scatter is indicated also in FIG. 13A by a dashed line. Note that although the measured penumbra and scatter region is smoothly and consistently characterized in the radiographic measurements of FIG. 13B, the central beamspot is depicted somewhat irregularly, apparently due to saturation exposure of the film at maximum dosage.

In embodiments of radiotherapy methods and devices having aspects of the invention, the overall eye axial length (distance from cornea surface to retinal surface) and the beam tissue path length (the path length of tissue to be penetrated by the treatment beam in propagating from surface to target) are relevant to important of treatment parameters. For example, the tissue path length is relevant to (a) the selection of X-ray input beam spectral characteristics such as the determination of tube potential and filters (see application Ser. No. 12/262,031 filed Oct. 30, 2008), and (b) for a given X-ray treatment beam, the tissue path length as the beam is actually administered to a patient determines the dose rate at target in Gy/min (see pre-target absorption indicated in the eye model of FIG. 11). Similarly, the eye axial length and other eye geometry are relevant to tracking motion of the retina during administration of treatment, as is described further herein.

Thus it may be seen that measuring and/predicting the tissue path length for the patient permits accurate calculation of the rate at which radiation is absorbed by target tissue. In certain radiotherapy embodiments, for a known dose rate based on tissue path length, the duration of beam emission is conveniently controlled (e.g., a timer to shut off power to tube) so as to administer a planned dose to the target (e.g., one third of total planned dose for a 3-beam stereotactic procedure).

For this purpose, a series of experiments were performed to determine appropriate eye measurements to establish the depth of target on the retina. A correlation model was established to show the relation of the path-length to axial length of the eye. Using a 3D laser scanner, a device which can precisely map the coordinates on a surface, a series of points in three dimensional space was derived from the surface of several cadaver eyes.

Figure 14:
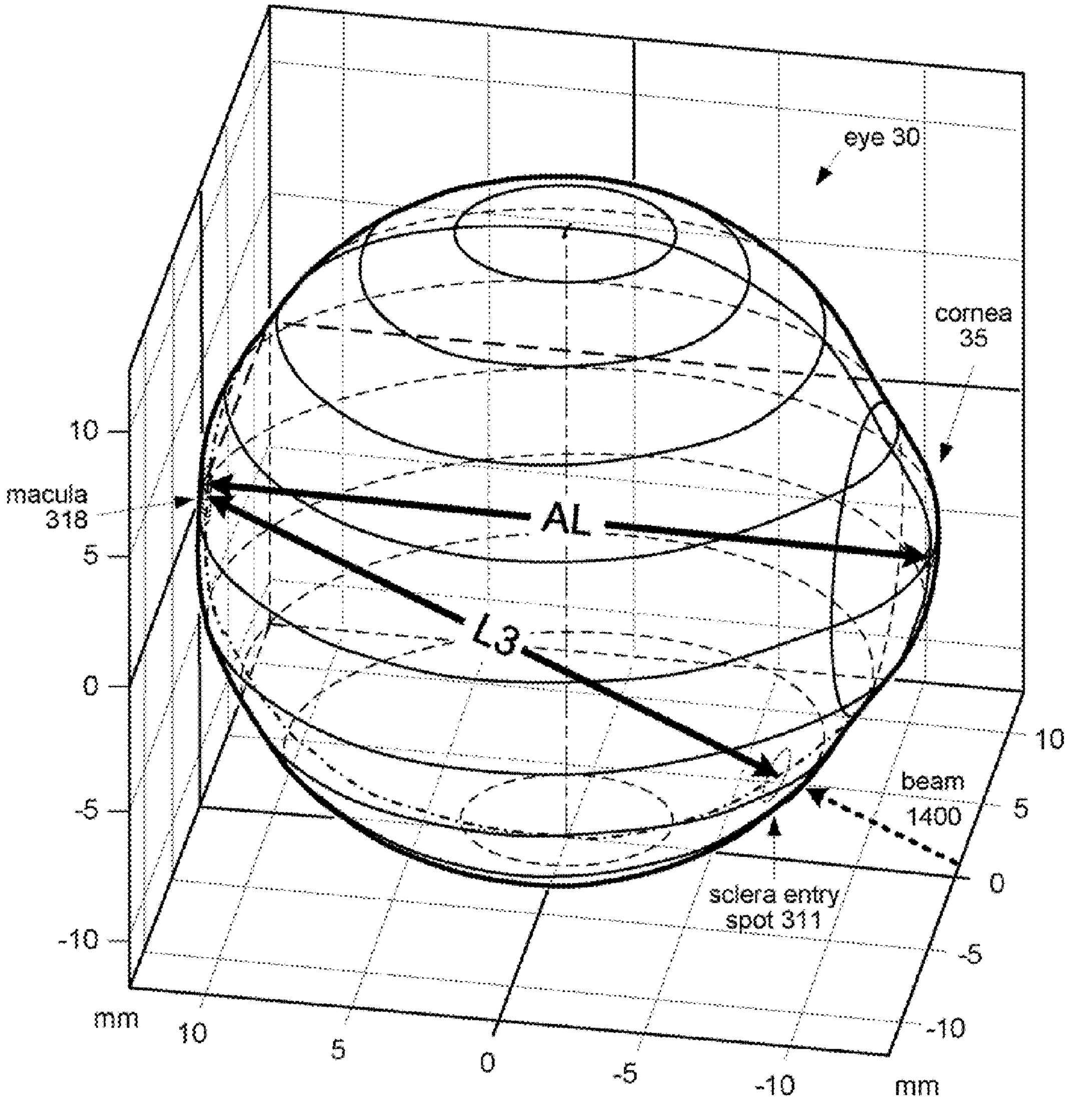
FIG. 14 shows an example of the mapping using a 3D laser scanner to determine points in three dimensional space from the surface of several cadaver eyes.

FIG. 14 shows a typical example of the mapping results from this protocol, which permits mapping the shape and contours of the cadaver eye to a high degree of accuracy. With this model derived from the surface of cadaver eyes, the axial length and path-length, and other anatomical dimensions can be measured directly. The axial length (AL) and tissue path length (L3) are indicated in, the beam path corresponding approximately to the beam path shown in FIGS. 7 and 11, directed through the sclera entry spot 311 to the target center 318 (e.g., macula or fovea), the beam entering the eye beyond the limbus of cornea 35 of eye 30.

Figure 15A:
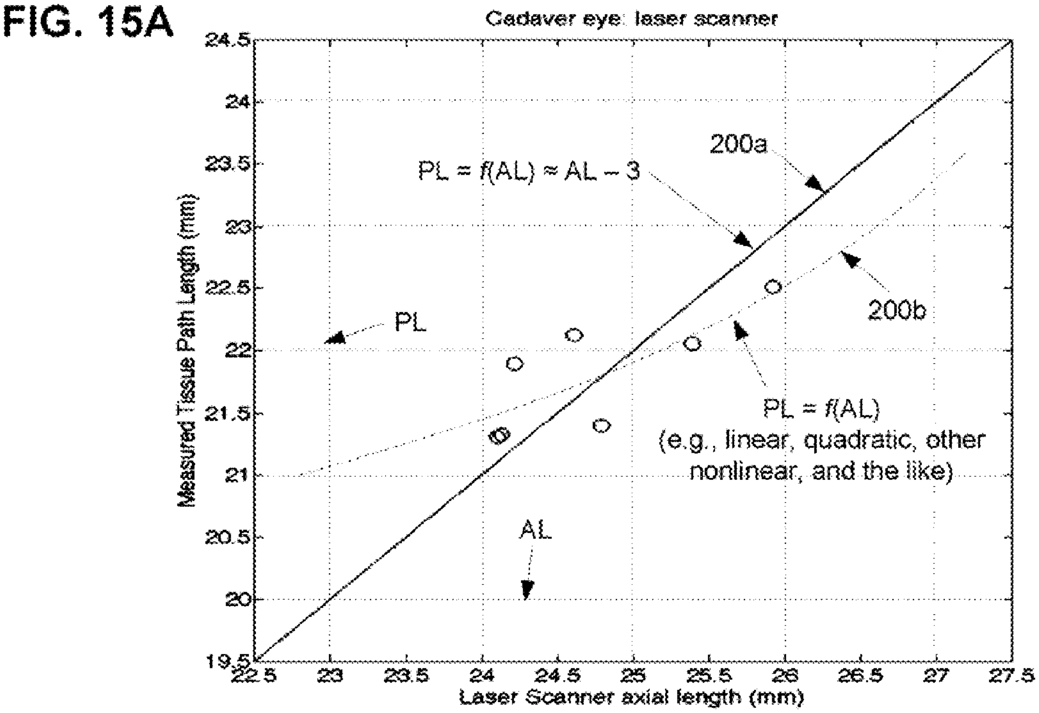
FIG. 15A is a plot of the tissue path length versus axial length from data such as shown in FIG. 14.

As shown in FIG. 15A, which depicts the measurements on a series of seven cadaver eyes, the tissue path length (PL) and axial length (AL) can then be correlated or related to one another. In living patients and study populations, axial length may be obtained by an A-scan. An A-scan is an ultrasonic measurement conventionally used in ophthalmology where eye geometry is relevant, such as in refractive vision correction. It has be found by inventors herein that A-scan measured axial length can usefully be performed on the example cadaver eyes and compared with Axial lengths determined from the laser scanner data. In general, this relationship can be conveniently and usefully approximated by a variety of linear or non-linear equations or curve fits where tissue path length is a function of axial length, or PL=ƒ(AL). In this example dataset, this correlation can be represented effectively as a linear function. This may be an equation of the form Y=aX+b, where Y=tissue path length (PL), and X=axial length (AL). An example where a=1 and b=−3, the equation is PL=AL−3, expressed in millimeters (curve 200*a* in FIG. 15A).

It should be understood that different equations may be used as effective mathematical representations of this data or similar data (e.g., PL=AL/2+9.5) without departing from the spirit of the inventions. Likewise, this or similar data may be expressed as a non-linear function, such as a quadratic equation or the like (curve 200*b* in FIG. 15A). Alternative expressions may be used, and additional data (or more specialized data sets) may also be analyzed by the methods shown. For example, such ocular data may be represented by alternative non-linear functions, or may be embodied or carried out by look-up table interpolations rather than function evaluations, and the like. Additionally, anatomic data sets correlating additional patient attributes (age, gender, or the like), may be assembled, and predictive relationships obtained relevant to these patient populations. Mathematical relationships representing this data may be including in the software of radiotherapy system 10, and used to predict treatment tissue path length, based on physician measurements and inputs for a particular patient.

In certain alternative embodiments, the functional relationship for tissue path length may be based on more than one anatomic measurement, other measureable patient characteristics (e.g., refractive data), or other patient history data (age, gender, and the like). Advantageously and more generally, the method illustrated in the above example may be extended to other radiotherapy procedures in addition to its use in ocular treatments for to the macula. One embodiment of the method may be summarized as comprising the steps:

(a) selecting one or more input parameters (anatomical measurements, other human measurements and/or other patient-specific characteristics such as age, gender, and the like), such as $P_1, P_2 \ldots P_i$;

(b) characterizing variation in a relevant patient population with respect to the selected parameters (e.g., studies of anatomical or other measurement variation in patient populations, optionally as a function of other patient-specific characteristics);

(c) correlating the population variation with the treatment tissue path length PL for a radiotherapy treatment plan;

(d) determining a mathematical function and/or calculation algorithm effectively expressing a relationship between the selected parameters and the tissue path length, which may have the form $PL=f(P_1, P_2 \ldots P_i)$;

(e) determining data for the selected parameters for a specific patient to be treated (f) using the mathematical function and/or calculation algorithm to determine PL for specific patient to be treated ($PL_0$);

(g) modifying or adjusting one or more parameters of the radiotherapy treatment plan based on the value of $PL_0$. (e.g., beam duration or dose, spectral energy, filtration, collimation geometry, beam orientation, or the like); and (h) treating the patient according to the modified or adjusted treatment plan Method embodiments such as the above example may be integrated into radiotherapy treatment devices having aspects of the invention, such as by including effectuating software code in computer processor-controllers of a radiotherapy system, so as to enable the treatment device to carry out one or more of the steps of the method.

Figure 15B:
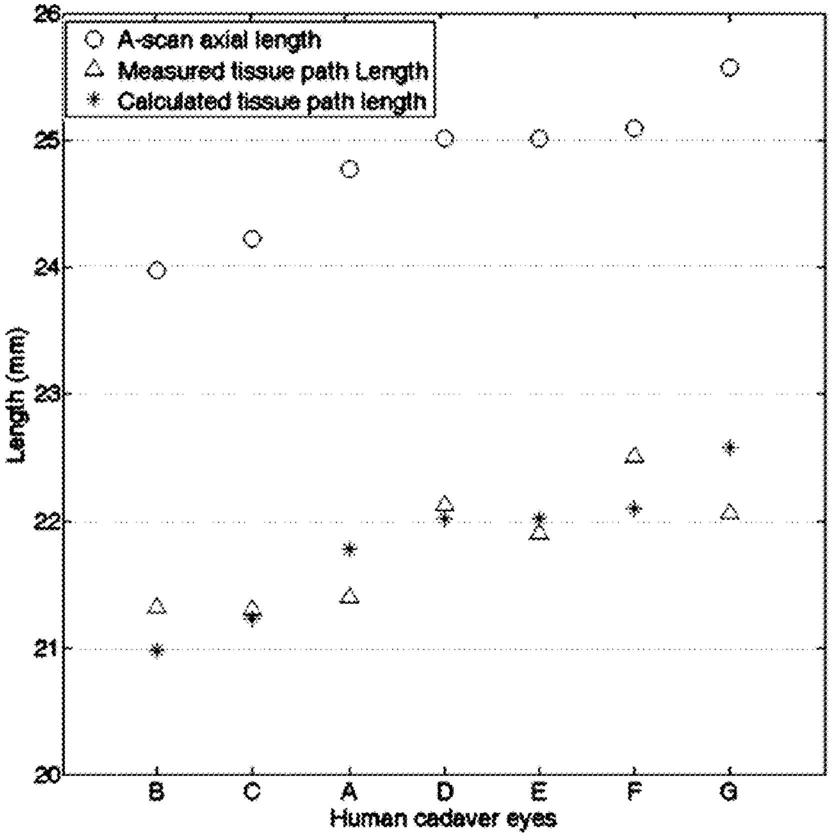
FIG. 15B is a plot of tissue path and A-scan derived axial length seven example cadaver eyes.

In FIG. 15B, for each of seven example cadaver eyes, the A-scan derived axial length is shown, together with the laser-scanner value of tissue path length, and a calculated tissue path length according to the linear formula PL=AL−3. For clarity of presentation, the seven example eyes are ordered by increasing A-scan axial length. It can be see that with minimal scatter, the results of A-scan are a good predictor of path length. The maximum error introduced by the A-scan in these data is approximately 0.3 mm. It has been shown by inventors herein that an error of 1 mm in path length would introduce approximately 3% error into the dose calculation for absorption at a retinal target. Therefore, an error of 0.30 mm introduces approximately 1% error in dose, which quite small and clinically acceptable. Based on this discovery, a method embodiment having aspects of the invention comprises determination a patient's eye axial length by means of a pre-operative A-scan, and then predicting the tissue path length of a treatment beam, and adjusting at least one treatment parameter based on the tissue path length (e.g., beam duration time).

IIIC. Eye Alignment, Stabilization and/or Tracking

FIG. 16 illustrates a top view of one embodiment of a system for controllably positioning and/or stabilizing the eye of a subject for therapeutic treatment. The upper portion of FIG. 16 shows a block diagram of a system 100 for carrying out a method having aspects of the invention. The lower portion of FIG. 16 shows an eye-guide module to permit alignment, stabilization and/or tracking of an eye prior to and during treatment.

In the illustrated embodiment, system 100 includes one or more cameras 102 positioned to image eye 10 along the geometric axis 810 (or 2810). Camera 102 provides video image data of eye 10 to a processor 106 and preferably to a display 104. Coupled to display 104 is an image generator/processor 106, such as a personal computer programmed with commercially-available computer aided design software, capable of generating and overlaying geometric images onto the image of eye 10 appearing on display 104, and preferably configured to perform image recognition algorithms using eye images. Processor 106 may also include patent specific data and images obtained prior to operation of system 100, e.g., to include in displayed images, and/or to be used to provide patient specific geometry for treatment.

Eye-contact device 110 may be equipped with a plurality of position indicators that are capable, in combination with detectors located in the external coordinate system, to locate the position of the contact device in the external coordinate system. This type of tool-tracking system, has been described for use in image guided surgery, where it is necessary to place a movable surgical tool, and typically also pre-op patient images, in a common surgical frame of reference containing the patient. In the present application, the position indicators may be three or more beam-directing elements designed to reflect external positioning beams, e.g., microwave beams from known-position beam sources to known-position beam detectors, with the position of the contact device being determined by a processor operatively linked to the beam detectors. Alternatively, the beam-directing elements in the eye-contact device can be equipped with a plurality of LEDs mounted on the device for directing, for example, a plurality of beams at known-position detectors to determine the position coordinates of the contact device in the external coordinate system. Such tool registration systems have been described, for example, in U.S. Pat. Nos. 7,139,601, 7,302, 288, and 7,314,430, all of which are incorporated herein by reference in their entirety.

In a third general embodiment the position-determining means takes the form of a collimated light-beam assembly, including a laser light source and one or more optical components, such as a half-silvered mirror, for aligning the laser beam with the collimated irradiation beam produced by beam source 108; such that the two beams are essentially coincident, along the same axis 810. In this embodiment, the beam-positioning assembly is moved with respect to the patient's eye until the laser beam is aimed directly onto the selected target region of the patient's eye, e.g., the macula region at the central rear portion of the retina. As can be appreciated, this will place the selected target region of the eye in registry with the therapeutic irradiation-beam; that is, the laser beam acts as a reference beam that functions to place the eye in the same frame of reference (coordinate system) as the irradiation beam.

More generally, the spatial registration and guidance of the contact device 110 may be through optical or electromagnetic sensor detection. In general, cameras or other detectors are mounted either on the system, or optionally in the treatment room, and are used to track and register the position of the eye or contact device 110. Cameras or detectors are then able to determine and record the three dimensional position of the contact device 110 in real time, and therefore the position of the eye as it is positioned. A calibration process can be used to determine the relative spatial position of the contact device to a known reference frame, as well as in combination with optional images. The calibration information can be stored in a reference file on the computer and used by a software program.

System 100 also may includes a processor or control unit which has a graphical user interface for receiving instructions from, and presenting information such as alignment and system functionality data to, a system operator. Further, the control unit may be in electronic communication with one or more of the other components of system 100 described above, e.g., the motors controlling the beam-positioning assembly, the motors controlling the eye-positioning assembly, and sensors, detectors and beam sources for determining the position of the eye-contact device in the external coordinate system, as described above.

IV. EYE GUIDE AND ALIGNMENT METHODS

This sections details features and applications of the eye guide in the treatment system and method of the invention.

IVA. Eye Guide Devices

Figures 17A, 17B:
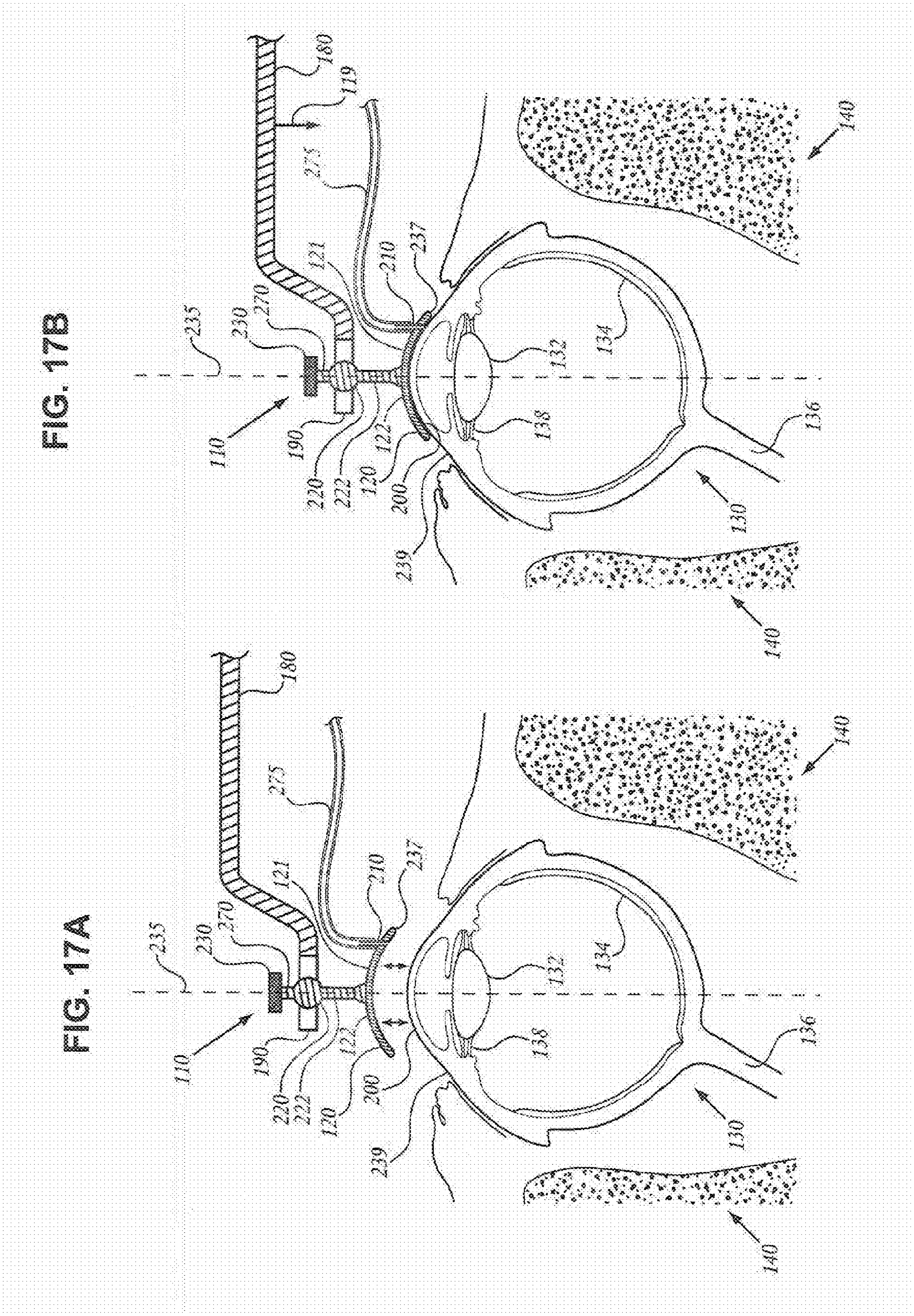
FIGS. 17A-B illustrate top views of an embodiment of a system for engaging the eye of a subject.

FIGS. 17A and 17B illustrate top views of an embodiment of a system for engaging the eye of a subject, the contact device 110 being reversibly and controllably coupled to the cornea 200 and/or limbus and/or sclera 239 of the eye 130 is schematically illustrated. The eye 130 includes a cornea 200 and a lens 132 posterior to the cornea 200. The eye 130 also includes a retina 134, which lines the interior of the rear surface of the eye 130. The retina 200 includes a highly sensitive region, known as the macula, where signals are received and transmitted to the visual centers of the brain via the optic nerve 136. The retina 200 also includes a point with particularly high sensitivity known as the fovea. The eye 130 also includes a ring of pigmented tissue known as the iris 138. The iris 138 includes smooth muscle for controlling and regulating the size of an opening in the iris 138, which is known as the pupil. The eye 130 resides in an eye socket 140 in the skull and is able to rotate therein about a center of rotation.

As contemplated by the present invention, the eye-contact member 120 can be made of a number of materials well known in the art. Preferably, the eye-contact member can be fashioned from a material with attention to biocompatibility. In an exemplary embodiment of the invention, the contact member 120 is made from poly(methylmethacrylate), or PMMA (e.g., Vistracryl®, FDA MAF 1189). Thermoset and/or thermoplast PMMA are contemplated by the present invention and are supplied by a number of sources, such as Perspex CQ (ICI Derby, England). Teflon and tantalum are also noted. It is also possible to coat eye-contact member 120 with biocompatible materials if elements of the eye-contact member 120 are not biocompatible. In some embodiments, the eye-contact member 120 contains pigments or dyes. In particular embodiments, the eye-contact member 120 is coated or impregnated with bioactive substances including anti-inflammatory agents/immunomodulating agents and/or anti-infective agents. Particular eye-contact members will contain radiopaque, radioactive, fluorescent, NMR contrast or other reporter materials. The contact member 120 or the entire eye-guide assembly 110 may be supplied to a user as a packaged, disposable, pre-sterilized unit.

A certain degree of rigidity, or hardness, of eye-contact member 120 is of use in physically coupling with the eye and with the pivot which attaches to the control arm as described in further detail below. However, the eye-contact member 120 includes, in certain embodiments, a certain degree of flexibility, or softness, such that the eye-contact member 120 has a degree of flexibility, but still retains an arcuate shape in its resting position. The internal contour 122 may replicates the curvature of a typical photocoagulation lens used in ophthalmology practice (e.g. Haag-Streit). In operation, a lubricant (e.g., Genteal) may applied to the lens to keep the eye moist during the procedure. A light vacuum (e.g., from about 10 to about 50 mm Hg, and preferably less than about 25 mm Hg) may applied to the device through the vacuum tube (e.g., by a spring loaded syringe device, which may be clipped to patient clothing), and the eye-guide positioner 600 may apply a bias force against the eye (e.g., spring loading of arm 180). The combination of light vacuum and light bias force has been demonstrated by inventors herein to provide adequate eye stabilization, while promoting patient comfort. The I Guide may have a breakaway feature (e.g., a axial post-and-ferrule connection of lens 120 to post 222) that allows the patient to exit from the positioning arm quickly and seamlessly as needed (e.g. during a sneeze). In this case, the vacuum and cup 120 may remain on the patient in the event of movement away from the positioning arm, allowing easy re-attachment.

The eye-contact device 110 functions to stabilize the eye in a first position to provide interactive support (e.g. stabilization and/or controllable movement) for the eye while the eye is being treated. The contact device 110 includes a cup or eye-contact member 120 which contacts eye 130. The contact member 120 can be positioned on the eye in a variety of positions, and is therefore useful in a wide variety of ocular treatment procedures. In one embodiment, the eye-contact member is in at least partial contact with the cornea 200. In the embodiment illustrated in FIG. 17B, the eye-contact member covers a substantial portion of the cornea (but does not necessarily touches the cornea). The member 120 may also cover portions of the sclera. The contact member 120 includes preferably a curved structure or “lens” that is substantially centered on the axis 235 and overlying the cornea 200.

The curved contact member 120 is preferably shaped with a concave eye-contact surface that will substantially conform to the anterior surface of the cornea 200 of the eye 130. The contact surface of the contact member 120 preferably has a radius of curvature that is greater than about 5 mm. In one embodiment of the invention, the radius of curvature of the inner surface of the eye-contact member 120 is about 7.38 mm. Likewise, in a preferred embodiment, the radius of curvature of the outer surface of the eye-contact member 120 is preferably 7.38 mm. It will be appreciated that a 1:1 ratio of inner and outer curvatures minimizes or eliminates refraction of energy through the eye-contact member 120 in certain embodiments of the invention; in this embodiment, the contact member 120 is a simple cup for the eye 130. Alternatively, the inner and outer curvatures may differ to permit desired focusing or diffraction of energy as it is transmitted through the eye-contact member 120. In some embodiments, the contact member 120 is produced in a variety of shapes, one or more of which can be chosen for a given patient depending on his or her specific anatomy.

With continued reference to FIGS. 17 A and 17B, the contact member forms, with a back plate 121 of the contact device, an internal reservoir 122 by which a negative pressure (partial vacuum) applied to the device, through a vacuum port 210, is distributed across the contact surface of the device, as can be appreciated. The vacuum port is connected to a suitable vacuum source though a tube 275. In this embodiment, the vacuum port 210 is positioned through the eye-contact member 120 such that an air or fluid communication space is formed through eye-contact member 120 to allow air trapped between eye-contact member 120 and the anterior surface of the cornea 200 of eye 130 to be reversibly removed, thereby reversibly engaging the eye-contact member 120 with the anterior surface of the cornea 200. In an alternative embodiment not shown, vacuum port 210 is attached to connector 270 which can contain a hollow lumen along axis 235 through eye-contact member 120 such that air between eye-contact member 120 and the anterior surface of the cornea 200 is capable of being reversibly removed as described above. Vacuum or suction assistance is useful for locating and adhering the scleral lens base on the eye 130 of the subject and securing the contact device 110 to the subject’s eye 130. Once in a desired treatment position, the contact device 110 can couple with the system 100 during the treatment procedure, as described below. Following treatment, the contact device 110 can be decoupled from the system 110 and removed from the subject.

In one preferred embodiment, negative pressure applied to the eye, for example, a negative pressure of 20-50 mm Hg, is effective to stabilize the position of the eye on the device, that is, substantially prevent movement of the eye with respect to the device, but by itself is not sufficient to hold the eye-contact device on the eye. Rather, the contact device is secured to the eye by a biasing force acting to bias the device against the patient’s eye, acting in combination with the negative pressure applied to the eye by the device. In the embodiment illustrated, the contact device is secured to the eye by the biasing force acting through arm 180, where the negative pressure applied to the contact device functions to prevent the eye form moving with respect to the device. As noted above, the contact device is typically biased against the eye with a force of between about 1-25, typically 5-25 grams, by a biasing spring, electromagnetic force, or the like. The advantage of this system is that the negative pressure applied to the eye can be substantially less than that which would be required if the vacuum alone were acting to hold the device to the eye, and this substantially lower negative pressure increases comfort and reduces irritation and deformation of the front portion of the eye. The biasing force is illustrated in the figures, e.g., FIGS. 2A and 2B, by an arrow 119, which indicates the direction of action of the force in the figures.

When the eye-contact member 120 contacts eye 130, negative pressure is applied to remove air from between the eye and contact member, to stabilize the position the eye 130 with respect to the contact member. A primary vacuum fitting is in fluid communication with the air passage. A vacuum line 275 is connected to the vacuum port 210. Additionally, a vacuum pump is in air or fluid communication with the vacuum line 275 for evacuating the air trapped between eye-contact member 120 and the corneal surface 200. Collectively, the vacuum port 210, line 275, and pump (not shown) constitute a primary vacuum subsystem. The degree of strength of the vacuum required to seal can be varied, and preferably controllably and continuously monitored, by the system of the invention. In one embodiment of the invention, between about 0.5 mm Hg and about 50 mm Hg are utilized to provide the negative pressure effective to stabilize the position of the eye with respect to the contact member 120. Preferably, the vacuum is between about 20 mm Hg and about 50 mm Hg. More preferably, the vacuum force applied is about 25 mm Hg and is monitored by pressure sensors and/or by directly monitoring the vacuum source. In some embodiments, the pressure is held passively, for example, by a bladder. The bladder can be produced such that it can apply a given maximum pressure.

It should be noted that the vacuum pressures described herein are dramatically lower than are used in many prior art forms of ocular surgery, such as laser radial keratotomy. This system having aspects of the invention also avoids the need for temporary paralysis of the eye, and avoids patient discomfort. Contact member 122 may be mechanically biased by a light force (such as a spring applied to support arm 180) to bear against the eye, assisting in maintaining engagement with the cornea, without heavy suction.

By engaging the contact member 120 with the eye 130, the eye 130 becomes fixed in a first position, the patient unable to move the contact member with intra-ocular movements. The contact member can, however, be moved using control arm 180; the movement by the control arm rotates the eye through the eye-contact member. Thus, one embodiment of the invention includes substantially stabilizing the eye 130 in a selected position with the eye-contact member 120.

FIGS. 18A-18D depict perspective views of the contact device with the control arm attached having aspects of the invention. As shown in the figures, a preferred embodiments of contact device 110 includes a pivot joint or connector 220 which accommodates pivot movement between the contact member and positioning arm 180, as the arm moves the contact device to a desired orientation in the external coordinate system. In one embodiment, pivotable connector 220 is a spherical or ball pivot joint which allows rotation in three dimensions. In the example shown, positioning arm 180 may be releasably coupled to the contact device through a stem-and-socket arrangement which fastens the end of arm 180 to a socket formed in ball joint 220.

Figure 18A:
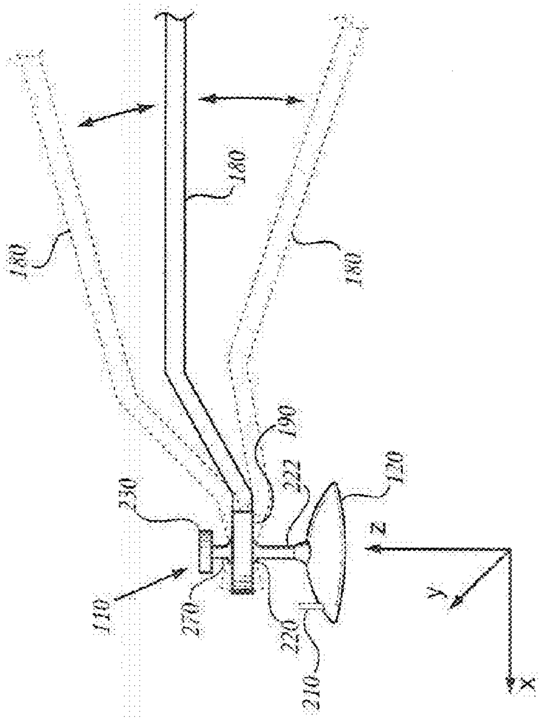
FIG. 18A-D depicts perspective views of the contact device with the control arm attached having aspects of the invention.
Figure 18B:
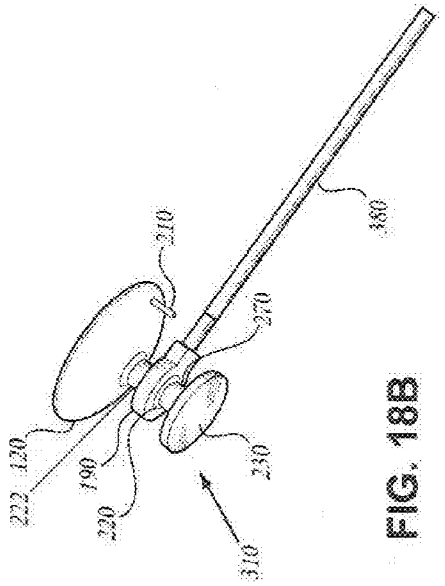
Figure 18C:
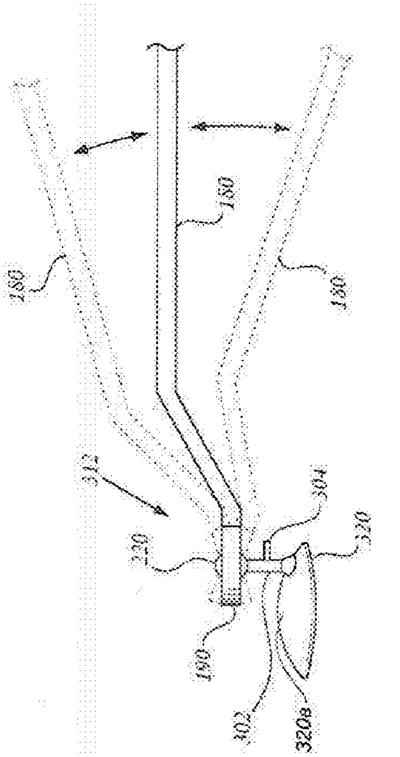
Figure 18D:
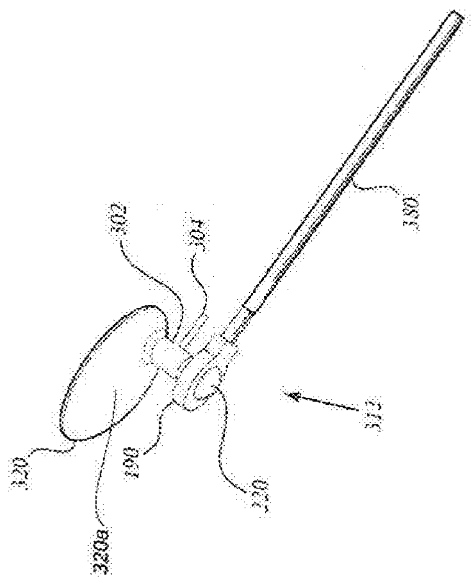

FIGS. 18C-18D show an alternative embodiment in which the contact member or lens 320 is supported from one or more off-center points (e.g., by side-post 302) so that a central portion may be transparent, permitting retinal imaging while the eye is engaged by device 312 (e.g., by a fundus camera, which may be employed as a module in system 10, or may be separate). With a contact which is transparent in its center, direct imaging of the retina can be performed so that rather than fiducials, the retinal coordinates and movement can be imaged directly. Pivot point 220 is off center and post 302 is off center as well. The apex 320*a* of the lens 320 is free to transmit incident and reflected light, allowing the retina and other ocular structures to be seen through the lens 320.

IVB. Eye Guide Fiducials

FIG. 19 schematically illustrates an eye-guide device for use in an eye stabilizing system having aspects of the invention, and having patterned fiducials, and a method of determining orientation by image recognition. The figure shows a perspective view of an embodiment of contact or eye-guide device 512 including the contact member 120, spherical pivot 220, mirror 230 and vacuum port 210. In this embodiment of the invention, the contact device 110 includes one or more fiducial markers 240, 242, 244, 246, 248 which define the geometry of the contact device 110 or geometric relationships between the contact device 110 and additional components of the system and/or eye as described throughout the specification. The fiducial markers, in one embodiment of the invention, contribute to the positional knowledge of the eye when the contact device 110 is engaged with the eye 130, and a coordinate system is known. Spatial registration can be used record and monitor the three dimensional spatial position of the contact device 110 relative to a known reference point.

Figure 23:
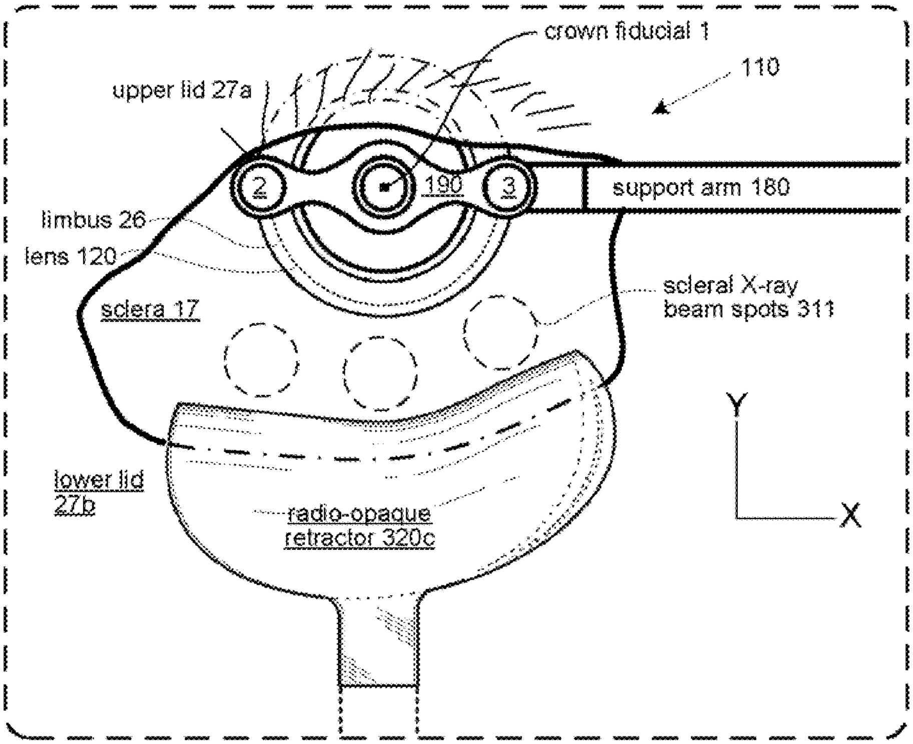
FIG. 23 depicts an alternative embodiment of an eye-guide having aspects of the invention engaged with an eye having an alternative embodiment of an eyelid retractor.

The example shown of an eye stabilizing system 512 has a reflecting mirror 230 attached. As described herein, alternative embodiments do not require a mirror surface, and image-based tracking of the eyeguide 110 may employ non-mirror fiducials. the mirror and central pivot 220 can be replaced with. For example, as shown in FIGS. 23-25, fiducials may be carried on a horizontal cross arm and pivoted center post, and/or on the lens itself, or (as shown in FIGS. 18C-18D), the lens may be supported by a offset member or side post, so that visualization can take place through the lens.

In the embodiment illustrated, one or more of the fiducial markers 240, 242, 244, 246, 248 includes an imageable fiducial locator. The fiducial locator is locatable using one or more imaging system modalities. In this embodiment, the fiducial is capable of being mounted in or on the eye-contact member 120, such as being either flush to, or recessed from, an outer surface of eye-contact member 120. However, in alternative embodiments, the fiducial need not be configured for mounting flush to or recessed from contact member 120, and can be mounted to extend from eye-contact member 120. In another embodiment, one or more fiducials are positioned on, within, or on the perimeter of mirror 230. This allows the mirror 230, along with contact device 110, to be centered or aligned with respect to the limbus or other ocular structure.

The fiducial may include a liquid or gel housed in a sealed interior cavity. Preferably, the fiducial is a solid. The solid, gel, or fluid may be visible by one or more imaging modalities (e.g., MR, CT, etc.). In one embodiment, the fiducial is integrated into the eye-contact member itself. The imaging fiducial is visible and provides good contrast on images produced by at least one imaging modality. In one embodiment, the imaging fiducial is multimodal (i.e., locatable by more than one imaging modality), such as by using a mixture of different imaging fluids, gels or solids that are locatable on different imaging modalities.

In one embodiment, the one or more of the fiducial markers 240, 242, 244 includes a substance that is viewable on a first imaging modality, while one or more of the fiducial markers 246, 248 includes a substance that is viewable on a different second imaging modality. In one such illustrative embodiment, the one or more of the fiducial markers 240, 242, 244 includes, or is doped with, a substance having a high atomic number (Z), such as barium, titanium, iodine, gold, silver, platinum, stainless steel, titanium dioxide, etc. that provides good contrast on a CT or other radiographic imaging system. In this embodiment, one or more of the fiducial markers 246, 248 include gadopentatate dimeglumine, gadoteridol, ferric chloride, copper sulfate, or any other suitable MRI contrast agent, such as described in chapter 14 of Magnetic Resonance Imaging, 2nd ed., edited by Stark and Bradley, 1992, which is incorporated herein by reference.

In an alternative multimodal embodiment, the fiducial marker is constructed of a substantially solid plastic or other material that is hygroscopic, i.e., capable of receiving and retaining a fluid, such as an imaging fluid that is viewable on an imaging system (e.g., an MRI imaging system or the like). In a further embodiment, the plastic forming the fiducial marker is doped or otherwise includes a substance that is viewable on a different imaging system, such as, for example, a CT or other radiographic imaging system. Illustrative examples of solid plastics that can be made hygroscopic include, among other things, nylon and polyurethane. Using a hygroscopic material avoids the complexity and cost associated with manufacturing a sealed cavity for retaining an imaging fluid. Moreover, by adapting the solid hygroscopic plastic for imaging using a first modality, and by using the imaging fluid for imaging using a second modality, each of the solid and the fluid can be separately tailored toward providing better contrast for its particular imaging modality.

In a further embodiment of the fiducial markers illustrated in FIG. 19, the outer surface of one or more of the fiducial markers is reflective of light or other electromagnetic energy. Consequently, it is locatable by a camera in an optical positioning system that is coupled to an image-guided workstation (e.g., during subject registration). One additional function of such fiducials is measurement calibration where the distance between fiducials is used to calibrate distance on or within the eye. In one such example, the outer surface of the imaging spherical fiducial marker includes light-reflective microspheres (e.g., embedded in an adhesive covering the fiducial or eye-contact member 120). In another such example, the outer surface of the fiducial is covered with an adhesive-backed light-reflective tape, such as SCOTCHLITE 9810 Reflective Material Multipurpose Tape sold by Minnesota Mining and Manufacturing Co. ("3M"), of Saint Paul, Minn.

In one embodiment of the invention, the spherical pivot 220, mirror 230 and/or the control arm 180 includes one or more fiducial markers. In an alternative embodiment of the invention, the one or more fiducial markers are configured to be locatable by a remote positioning system as well as imagable using one or more imaging modalities. In one such embodiment, the outer surface of the eye-contact member is configured to be light reflective, such as discussed above. The fiducial markers are still advantageously locatable using one or more imaging modalities (e.g., MR, CT, or other imaging system providing 3D or other internal images within a subject) as well as also being locatable external to the subject, such as by using a remote camera or like component of an optical or other positioning system, e.g., that is coupled to an image-guided workstation. In one embodiment, this permits automatic registration of the actual location of the subject's eye (e.g., using cameras to locate the light reflective fiducial markers) to pretreatment images of the system on which additional imageable fiducial markers are positioned. This eliminates the need to register the eye of the subject by inserting an optically-locatable positioning control arm onto the contact device, and eliminates the need for other absolute position reference, because the fiducial markers themselves are optically locatable and registerable to known locations on pretreatment images of the system.

Control arm 180 may be coupled to an image-guided workstation or platform (not shown). In this embodiment, control arm 180 includes an end that is sized and shaped to permit being coupled to spherical pivot 220. The control arm 180 includes, in this embodiment, a plurality of fiducial markers 520, 522, 524, 526, 528, 530 that are locatable by a camera or other like device of the optical positioning system. The fiducial markers 520, 522, 524, 526, 528, 530 on the control arm 180 are positioned in a known spatial relationship to each other and to the tip of the control arm 180. By recognizing the locations of the fiducial markers, the optical positioning system is capable of computing the location of the control arm tip, which is in a known spatial relationship with the configuration of the fiducial markers. This permits the control arm 180 to be used in conjunction with the optical positioning system to register the eye of the subject and to further plan and/or perform the treatment procedure using an image-guided workstation. An image guided treatment computer workstation, which is capable of displaying previously acquired and loaded pretreatment images of a the system. The optical positioning system connected to the workstation includes an infrared light (or other energy source) that provides light that is reflected from the reflective fiducial markers. This permits the reflective fiducial markers on the control arm 180 to be located and recognized by the cameras.

IVC. Detection of Eye-Guide Fiducial Patterns

FIGS. 20A-20H schematically illustrate an eye-guide device for use in an eye stabilizing system having aspects of the invention, and having patterned fiducials, and a method of determining orientation by image recognition. In the exemplary embodiment shown, a pattern of highly reflective fiducials is mounted to the device. In the example shown this is a triangular three-fiducial pattern (4), comprising fiducial 1 (on center bar 190) and fiducials 2 and 3 (on lens 120), although other patterns may be used. For example, the fiducials may have a surface including an adhesive-backed light-reflective tape, such as SCOTCHLITE 9810 Reflective Material Multipurpose Tape sold by Minnesota Mining and Manufacturing Co. ("3M"), of Saint Paul, Minn. Likewise, other methods of applying or forming a reflective surface may be used, such as reflective ink compositions, and the like.

Placement of the fiducials may conveniently be chosen such that they form right triangle (90-45-45) when eye-guide is in alignment—perpendicular and coaxial to system center (see FIG. 20B). For two lens fiducials, angle of 45 degrees is preferred as a best compromise for horizontal and vertical sensitivity during measurement (i.e., if for example selected angle is 60 degrees it would provide greater horizontal sensitivity, but less vertical). Also, lens fiducials are surrounded by the dark area in order to provide for easier detection.

By virtue of the center pivot 220 the center fiducial 250 can move in horizontal and vertical direction in relationship to lens fiducials. That movement causes triangle relationship of the angles to change, which provides feedback of the alignment position, and hence the patient's eye.

Reference is made to the description above with respect to the imaging system pattern recognition functions, illustrated also in FIGS. 3A-3B. In summary, the fiducials as illuminated by lights 405 provide a high-contrast image to axial camera 401 Computer processor 501 may be programmed by suitable software to process the electronic image signals to delineate the image regions corresponding to the fiducials (using known image processing algorithms, such as contrast enhancement, filtering, intensity thresholds, edge recognition, and the like). The processor can then define a center of mass for each fiducial image, and locate the corresponding points in a coordinate frame of reference, so as to create a mathematical representation of the fiducial pattern from the camera perspective. The mathematical representation then permits calculation of relevant angles and dimensions, and so derive eye-guide position and orientation information. Note that scaling information can be used to derive Z axis distance information, alternatively or additionally to the off-axis camera 402 described with respect to FIGS. 3A and 3B. The process can be repeated from sequential camera images at any selected position update rate (e.g., about 1 to 50 Hz) to provide continuing position and motion data.

Once fiducials are recognized, and triangle angles and leg lengths calculated, the processor 501 may provide feedback (e.g., via display images) to the user indicating which direction to move the eye-guide in order to have it aligned. All three angles and their spatial relationship may be considered in order to provide feedback to the user, for people it is easier to understand, and react to, one variable per direction (.i.e. up/down for vertical, and left/right for horizontal), lens fiducial angles are represented as a ratio to the user—A2/A1. This gives only one number for direction of movement. For example, in aligned condition ratio would be one because 45/45=1; if mirror is tilted at some angle to the right ratio might be 48/52=0.9231, etc.

In FIG. 20A the angles are identified as a, b and c, where a is the angle of the center fiducial 250 with respect to the lens fiducials. Angles b and c are the left hand and right hand angles. Angles a, b, and c determined by fiducial image recognition. Leg lengths l1, l2 and l3 may be scaled to confirm Z position. A pattern height h (or width) may also be defined from detected data representing the distance between fiducial 1 and a line joining fiducials 2 and 3. Similarly, pattern widths may be defined (w1, w2). It should be understood that the same detected image data may be expressed and organized as a number of alternative sets of geometric parameters as steps in calculations, without departing from the spirit of the invention.

FIG. 20H illustrates the effect of tilt of eye-guide 110, the rotation of the center-post 222 about pivot 220, causing fiducial 1 to move in the opposite direction to lens 120. Tilt may be horizontal, vertical or combinations of these. Note that the effect of tilt is to cause a ±change in the distance between fiducial 1 and the lens fiducials 2 and 3, depending on direction of tilt (compare h1 untilted with h2 tilted).

Six cases are illustrated in FIGS. 20B-20G:

FIG. 20B shows the eye-guide aligned with geometric axis, where a=90 deg.; b=45 deg.; and c=45 deg. This corresponds to the left-hand image of FIG. 20H.

FIG. 20C shows the eye-guide positioned upward (post tilted up relative to lens), but aligned horizontally, where a<90 deg.; and b=c>45 deg. This corresponds to a tilt in which height h is increased.

FIG. 20D shows eye-guide positioned downward (post tilted down), but aligned horizontally, where a>90 deg.; and b=c<45 deg. This corresponds to a tilt in which height h is decreased, as shown in the right-hand image of FIG. 20H.

FIG. 20E shows eye-guide positioned to the right (post tilted right), aligned vertically, where a<90 deg.; b>45 deg.; and c<45 deg. This corresponds to a tilt in which width w1 is decreased and width w2 is increased.

FIG. 20F shows eye-guide positioned to the left (post tilted left), aligned vertically, where a<90 deg.; b<45 deg.; and c>45 deg. This corresponds to a tilt in which width w2 is decreased and width w1 is increased.

FIG. 20G shows general case: eye-guide positioned off-center vertically and horizontally, where a≠90 deg.; and b≠c, specific angles values determine orientation This corresponds to a case in which each of h, w1 and w2 differ from the nominal values as shown in the aligned case of FIG. 20B.

Note that the methodology described with respect to FIG. 20A-G may be applied to fiducial patterns distributed in different structural elements of eye-guide 110. See for example the eye-guide 110 of FIGS. 23-25. In that example, the fiducials 2, 3 are on an extended cross bar 190 and fiducial 1 is on an elevated center-post 222, so as to create a linear pattern when aligned. In the case of alignment with the system coordinate axis (see FIG. 24D, compare with FIG. 20B), the angles b and c=0°, the angle a=180° and the lengths l2=l3. Note the effect of the horizontal tilt of center-post 222 (FIGS. 25A and 25B) is to render the lengths l2 and l3 unequal, even when the eye-guide center pivot 220 intersects the system axis 2810. In the similar case of vertical tilt (not shown), the angles a,b are not zero.

V. EXAMPLES OF AND DETAILED METHODS

This section describes various examples and more detailed methods of the therapeutic system and applications disclosed above.

V.A. Therapeutic Method that Employs an Eye Guide

FIG. 21A is a flow chart illustrating one method of utilizing the system for stabilizing and positioning an eye for treatment. It should be noted that the devices described having aspects of the invention may be used in a wide variety of ocular treatment methods. FIGS. 21B-21E are diagrams of an eye associated with the radiotherapy system, illustrating examples of steps included in the flowchart of FIG. 21A.

The method embodiment 2500 may be summarized as including all or some of the steps:

a) Prepare eye 2510.
b) Position and secure head 2520.
c) Position eye holder (eye-guide) on subject's eye 2530.
d) Apply suction to hold eye holder against eye 2532.
e) Quick release of control arm from eye contact member 2534 may be provided.
f) Align and stabilize eye 2540.
g) Position treatment axis relative to eye 2550.
h) Position and verify beam axis 2555.
i) Perform treatment with eye and/or eye-guide tracking 2560.
j) As required, interrupt radiation (gating) based on eye-motion 2565.
k) Release eye from eye holder 2570.
l) Additional or alternative steps may be included (e.g., corrective eye realignment, or automatic correction of beam path to follow retinal target motion).

The steps included in FIG. 21A and further illustrated in FIGS. 21B-E are described in detail below:

Step 2510

Prepare eye—Preparing a subject's or patient's eye for treatment which can include delivering an anesthetic, taping the upper or lower lid, fitting an opposite-eye patch, measuring biometric parameters such as axial length, corneal diameter, etc. Optionally the eye may be dilated, particularly when employing alternative device/method embodiments having aspects of the invention which include integrated retinal imaging optics (not shown) with radiotherapy treatment system 10 (e.g., OCT or fundus camera). Preparation may include applying eye numbing drops to the eye of the subject. The untreated eye may be covered with a patch, e.g., so as to avoid distraction. Scleral clearance can be provided by securing the lower eyelid downward with a lid retractor as further described herein, or with tape (see FIG. 2) or eyelid eversion.

Step 2520

Position and secure head—Following preparation, the subject's head is secured in a suitable position to the system, such as in head and chin rest 160 and head fastening 161. The subject's head is positioned in a head support and the chin is rested on a chinrest. Fastening 161 may include with straps or the like, and may have an adjustable tensioner, optionally with a force-limiting fitting or clutch. This assembly may include a gating interlock detector (see Step 2565) to assure it remains engaged during radiation emission. Other patient position detectors may optionally be included, such as contact-sensitive hand grips 163.

Step 2530

Position eye holder on subject's eye—The eye contact member or eye-guide 110 is then positioned on the subject's eye. The eye-guide contact lens 120 and/or eye surface may be coated with an ophthalmic lubricating solution or gel (e.g., GenTeal® formulations, produced by Novartis Ophthalmics). In one example, the eye-contact member is placed on the cornea by tilting the eye-contact member to contact the upper portion of the sclera. As the eye-contact member contacts the upper scleral region of the eye, the eye-contact member is tilted downward to achieve full contact with the eye.

As further shown in FIGS. 11 and 21B, the limbus 26 comprises the generally circular boundary of sclera 17 and cornea 35, the limbus lying substantially within the projected plane 26*a*. A corneal tangent plane 35*a* projected parallel to limbus plane 26*a* intersects the cornea center 35*b* closely adjacent the limbus center 26*b*. The geometric axis 2810 of the eye 30 may be defined as an axis through the center 26*b* of the limbus 26, perpendicular to the center 35*b* of the external surface of cornea 35, and intersecting the surface of retina 1435 at retina pole 1436).

The alignment in step 2530 includes engaging the eye-guide 110 with eye 30 so that the eye-guide has a known or measurable orientation and position relative to the center 26*a* of limbus 26. In the example shown, the eye-guide contact portion or lens 120 may advantageously be formed to be substantially circular and concentrically aligned with an eye-guide center axis 110*a*. Similarly, the central axis 110*a* of the eye-guide 110 in the example shown is substantially collinear with the eye-guide support post 222. This symmetry conveniently assists a physician to positioning of the holder or eye-guide 110 on the eye 30 by visually aligning the lens 120 symmetrically with limbus 26. In this position, the post 222 of the eye-guide 110 is aligned with the center of the limbus 26 so as to indicate the geometric axis of the eye. The lens 120 may be transparent, advantageously permitting visual confirmation of concentric alignment of the lens edge 120*a* on the limbus 26 in embodiments in which lens 120 is larger than limbus 26 (i.e., covering a portion of adjacent sclera 17).

However, the lens 120 need not be circular, and the eye-guide support post 222 need not be collinear with the eye-guide axis 110*a* (see examples FIGS. 18C-D). As described herein in detail, camera image-based feature recognition methods having aspects of the invention provide for computer processor determination of the position of the center 26*b* of limbus 26, and fiducials located on eye guide 110 may similarly be tracked to determine the relative position and orientation of eye-guide 110 with the center of limbus 26. These determinations provide a non-visual method to guide and confirm the alignment of the eye-guide 110 with the geometric axis 2810 (see step 2540).

The eye-guide placement and alignment can be performed by a physician while observing the both the holder and the eye of the patient directly, or on a computer monitor, or both of these interactively. Alternatively, an imaging camera-processor of imaging system 410 can determine the center of the limbus automatically and aid in the positioning of the holder with its center aligned with the center of the limbus (see axial camera view of FIG. 21C(2)). In some embodiments, the holder is positioned in place automatically rather than manually by the device operator. Note that at this step the X-ray source positioning system (see 115 in FIG. 1A) need not be aligned with the geometric axis 2810, and is shown in FIG. 21B at an arbitrary relative orientation P1.

Step 2532

Apply suction to hold eye holder against eye—Once the position of the holder or eye-guide lens 120 relative to the limbus is determined, suction may be applied through the holder to appose it to the eye, and secure coupling of the lens to the eye surface. With the holder firmly attached to the eye, the holder (and eye) can be moved into position relative to the treatment device in known coordinates within the system. Note that the degree of vacuum suction is selectable, and greater or lesser levels may be employed. In the embodiments described in detail, a relatively light suction (e.g., about 25-50 mm Hg), has been shown to adequately couple the eye-guide lens 120 to the patient's cornea 12. Such modest levels of suction may promote patient comfort and acceptance of treatment.

Step 2534

Quick release of control/support arm from eye-guide contact lens—As described above, a quick release is built into the contact device in some embodiments of the invention. In case of an emergency or fatigue, the patient can release from the holder by a applying a modicum of force which results in the eye-contact member or lens 120 releasing or breaking away from the remainder of the eye-guide device 110. In such a case, the method step returns to the step prior to positioning and securing the head 2520, or to the step of positioning the eye-guide contact device on the subject's eye 2530, as indicated in FIG. 21A.

Step 2540

Align and stabilize eye—As shown in FIG. 21C(1), the treatment device and positioning system axis is adjusted as needed to be positioned relative to the eye so as to bring as to bring the X-ray source positioner reference axis (system Z axis) into alignment with the geometric axis of the eye. In the figures, the system axis when aligned relative to the eye geometric axis 2810 is depicted as P2. The movement, indicated in the figure as M(x,y,φ,θ), may include movement or rotation of either or both of the patient's head and/or eye, and alternatively or in combination, may include movement or rotation of the treatment system components. For example with reference to FIGS. 1A,B and 2A,B, either one or both of the patient's head, eye and/or treatment system 10 may be moved so as to accomplish alignment.

In certain embodiments, the adjustments may include principally X and Y direction adjustments of eye-guide positioner 600, which may include a manual or powered multi-axis micro manipulator. An auxiliary display (see 503*b* in FIG. 1B) may be positioned to give an physician imaging system feedback while operating the eye-guide positioner 600. With the head stable, movement of the eye guide 110 in the X and Y direction by eye-guide positioner 600 may be used to rotate the eye geometric axis 2810 (e.g., by rotating the eye globe in the orbit) to lie parallel to the reference axis of positioning system 115 (system axis). Movement of the positioning system 115 in the X and Y direction can then be employed to bring the two axes into collinearity. Alternatively or additionally, the system axis may also be rotated to align parallel with an initial orientation of eye geometric axis 2810. Additional adjustments may be provided to adjust the patient's head in rotational degrees of freedom, such as rotation in the X-Y plane. However it has been demonstrated that providing a comfortable but firm head and chin restraint assembly 160 typically is effective to stabilize the patient's head in a generally level and horizontal orientation. See examples shown in FIGS. 1-2 including chin rest 172, forehead support 171 and head fastener 173, preferably used together with adjustable patient seating height.

FIG. 21C(2), depicts an example of a view as captured using an Z-axis camera (e.g., camera 401 in FIGS. 1A and 3A) showing an example contact device or eye-guide 110 positioned on patient's eye 30 (see FIGS. 23-25). The eye-guide post fiducial 1 is shown centered on the Z axis and the left and right hand support bar fiducials 2 and 3 are shown horizontally aligned and equally-distant from the post fiducial 1, indicating that the eye guide is aligned parallel and coaxially with the camera axis. This alignment is confirmed and calculated automatically by image recognition software from captured camera images by the system processor 501, and such data may be displayed as a image superimposed on a camera image to the operator (display 502). Note that in alternative embodiments employing a Z-axis laser pointer or beacon (403 in FIG. 3A, see also FIGS. 30A-B), the eye-guide 110 may be positioned by coaxially aligning the reflected laser spot.

Note in FIG. 21C(2) that eye-guide contact lens member 120 is shown positioned slightly off-center with respect to the limbus 26 (boundary of iris 24 and sclera 17 on patients eye 30). The image processor 501 may also track the limbus position as described herein, and compute a divergence of the center of the limbus from the Z alignment axis (indicated as δx and δy). This divergence may be automatically compared to a preselected tolerance threshold, and also may be displayed to the operator within the camera image frame.

Step 2542.

In the event that the limbus divergence is determined to be unacceptable (either at Step 2540 or at any other step), Steps 2530 through 2540 may be repeated as shown by the return arrows on flow chart FIG. 21A.

Note that the processor 501 may be programmed to monitor eye camera image data (e.g., cameras 401, 402) to re-determine limbus-to-lens alignment on an ongoing basis during treatment, and to determine an error condition (one example of patient-interlock diagnostic in Step 2565) linked to radiation or X-ray source 420 so as to trigger gating when a selected alignment threshold is exceeded.

Note that in certain embodiments having aspects of the invention, a treatment system reference coordinate system may have an arbitrary, but known, orientation/position to an eye anatomical reference, as shown in FIG. 21B. From this known eye reference orientation/position, suitable mathematical transformations may be performed, e.g., by a control processor of a robotic positioner, to move an X-ray source to a selected treatment orientation with respect to an treatment target. However, it is advantageous in ocular radiotherapy devices having aspects of the invention, to have a principal mechanical movement axis of the X-ray source positioning system aligned parallel to, and preferably collinearly with, the geometric axis of the eye. For example, the geometric axis of the eye 2810 may be aligned, as shown the Z axis of positioning system 115, which may also be the θ rotational axis. In embodiments described in detail herein and illustrated in FIGS. 21C-E, such an alignment method is conducive to precision calibration and control of X-ray source movement. With this initial system alignment relative to eye anatomy accomplished (FIG. 21C), only a limited set of subsequent movement ranges and directions are required for carrying out a stereotactic treatment plan. For example, these may include a small X/Y shift to treatment axis 2820 (step 2550, FIG. 21D), small ϕ and/or Z adjustment to target convergence angle and limbus clearance, and a modest θ adjustment for each subsequent beam path (step 2555, FIG. 21E). Such limited and constrained motion serves to minimize mechanical backlash, uncertainties and vibration, and to maximize accuracy, repeatability, patient confidence and intuitive operation.

Step 2550

Position treatment axis—A radiotherapy treatment plan for an ocular condition may be developed specifying a target location relative to an anatomical reference point such as the macula or fovea as described herein (see also the examples and description in U.S. Ser. No. 12/100,398 filed Apr. 9, 2008, which is incorporated by reference).

In certain embodiments, the X-ray source may be positioned for treatment while maintaining the system Z coordinate axis aligned with the geometric eye axis 2810, either for central axis targets, or by suitable robotic controls transformations for off-axis targets.

However, in the embodiments described in detail herein, and as shown in FIG. 21D, the system Z-axis (e.g., the Z axis of X-ray source positioning system 115) may be shifted to realign with treatment axis 2820 which intersects the center of treatment target 318. The system axis thus realigned is indicated as P3 in the figure. In this example, a lesion of the macula is treated by radiation to a target 318 approximately centered on the fovea. An exemplary treatment plan may define offsets relative to the pole of the retina (intersection of geometric axis 2810 with the retinal anterior surface), the offsets being defined as X and Y movements in the plane tangent to the retinal pole (dx, dy). The detail diagram indicates offset dimensions taken from fundus images of a representative sample of persons, defining mean values of offsets of the fovea from the retinal pole of about 1.16 mm and −0.47 mm respectively, although these values are purely exemplary. In this example, the X-ray source positioning system 115 is moved the specified dx and dy offsets by action of the X and Y axis actuators (see FIG. 5), so as to shift the system Z axis (translate without rotation) so as to intersect the defined target 318.

Step 2555

Position beam and verify limbus clearance—FIG. 21E illustrates the motion of the X-ray source to carry out an exemplary stereotactic treatment following the shift of the system Z axis to intersect the target 318, as depicted in FIG. 21D.

The Z and ϕ axis actuators may be moved to orient the collimator assembly 118 so that the beam axis 1400 intersects the Z axis at the target 318, forming a triangular arrangement (see FIGS. 3A-6). With the Z and ϕ axis positions thus fixed (values $Z_0$ and $\phi_0$), the collimator assembly 118 may be subsequently re-oriented solely using the θ actuator to selected treatment beam positions (e.g., beams 1, 2 and 3 at values $\theta_1$, $\theta_2$ and $\theta_3$ respectively) to align the beam axis 1400 to propagate to target 318 and intersecting the body surface at respective selected beam entry points (e.g., sclera beam-spots 311). Note that while it is advantageous to re-orient the collimator assembly 118 for multiple beam paths by single degree-of-freedom motion, it need not be so, and alternative embodiments may provide for more complex movement.

The clearance c of the (each) X-ray beam 1400 at scleral entry spot 311 may be confirmed both visually by the operator and/or by image recognition by the processor 501. As shown in greater detail in the camera-frame image of FIG. 21C(2), a laser beacon 1410 (see FIG. 4) may be aligned along the beam axis 1400 (the intended beam path as aimed prior to X-ray emission) to create a small visible spot on the sclera of known position relative to the beam 1400 (e.g., concentric), the spot lying within the camera frame. The laser spot may be recognized by processor 501, its position calculated, and compared with the tracked position of limbus 26, so as to calculate the beam-center-to-limbus-edge clearance c. The clearance c may then be compared with a minimum tolerance (optionally also a maximum tolerance). For example, based on a predicted collimated beam radius of about 1.5 mm at the sclera, a selected limbus minimum margin of 2.0 mm may be determined by a value of c≈1.5+2.0=3.5 mm. The beam margin from the limbus may be specified in a treatment plan, e.g., from about 1 to about 5 mm. The X-ray beam radius at the sclera (e.g., from about 0.5 to about 5 mm) may also be predicted, such as by calculation of collimator geometry and/or radiographic measurement as described in detail herein. The clearance c may be adjusted if needed, e.g., by small movements of the X-ray source 420 in Z and/or ϕ directions.

Step 2560

Perform treatment with eye tracking—X-ray treatment may be administered according to the treatment plan, such as at a pre-selected beam configuration, intensity and spectrum, the beam being emitted for a time interval selected to deposit a desired absorbed dosage to the target. Multiple beams may be emitted stereotactically to delivery a desired total target dosage, while exposing non-target regions (such as sclera beam entry spots 311) to less dosage than that of an equivalent single-beam treatment.

During treatment, the eye position relative to the system 10 may be continually tracked as described in detail herein and the eye position data so obtained by be automatically monitored by processor 501 on a real time basis as treatment progresses, including calculation of the motion of target and other eye anatomy (an resultant dose variation) based on eye tracking motion data. See description regarding FIGS. 26-36, and detail description in co-invented Application No. 61/093,092 filed Aug. 29, 2008 and well as the other applications which are incorporated by reference. As described below with respect to Step 2565, such eye tracking data and calculations may serve as a basis for radiation interruption or gating.

In the embodiments described in detail herein, the X-ray collimator assembly 118 may remain fixed during the emission of an X-ray treatment beam. However, in alternative embodiments, positioning system 115 may be configured to provide real-time repositioning of the X-ray source during X-ray emission, for example, to compensate for residual motion of the retinal target during treatment. Alternatively In certain embodiments, all or certain ones of the actuators described with respect to FIG. 5 for positioning of the X-ray source (X,Y, Z, ϕ and θ of positioner 115) may be used to re-position the X-ray source so as to compensate for motion of the retina. Alternatively, additional actuators and/or degrees of freedom may be provided so as to provide fast-response, small-range (Vernier) adjustment of the X-ray beam orientation (e.g., re-aiming the retinal beamspot) and/or shaping (e.g., responsively blocking a portion of the beam spot, such as proximal to the optic disk), so as to permit rapid adaptation of the beam to compensate for a moving retinal target. Such embodiments are describe further in co-invented Application No. 61/093,092 filed Aug. 29, 2008, which is incorporated by reference.

Step 2562.

For multiple beam path or stereotactic treatment, method Steps 2555-2560 can be repeated as indicated by Step 2562 until a desired treatment is completed, for example for a pattern of three stereotactic beams as described in detail herein.

Step 2565

Interrupt radiation (trigger gating)—During the course of Step 2560 as radiation is being emitted along beam path 1400, radiation may be interrupted (gating of X-ray source 420) in response to selected criteria, such as threshold values of measured criteria, discrete system-level diagnostic error or failure states, or patient-level interlock or diagnostic triggers. Upon triggering of gating, various devices may be used to interrupt X-ray or other radiation emission, as described herein.

Step 2567

Following gating, corrective action may be taken as indicated in depending on the particular triggering cause (may require repeating one or more preceding steps), and treatment irradiation then resumed until a desired beam fractional dose is delivered.

(i) In motion-threshold gating, such as Subsection 1 below, all or portions of alignment and positioning steps 2540-2455 generally are repeated to bring the beam center into alignment with target center, prior to completing the treatment fraction.

(ii) In some cases, such as transitory system conditions in Subsection 2 below, the corrective action may involve brief system corrections not requiring repetition of pre-radiation steps 2555 or before, and treatment may be resumed at step 2560. In other cases, the positioning actions included in steps 2450-2550 may not need to be entirely repeated, but verification of alignment and position (visually or by image processing) may be desirable before resuming treatment.

(iii) if the gating is triggered by decoupling of limbus 26 and eye-guide lens 120, as in the example of Subsection 3 below, corrective action may include repeating the eye-guide positioning steps 2530 and 2354 as well as steps 2450-2550.

Examples of gating criteria may include one or more of:

1. Exceeding retinal motion threshold. As described herein and in the incorporated applications, the eye tracking data may be employed to determine one or more discrepancy or error values based on a target movement or motion-related dose distribution, such as a maximum target displacement, a cumulative retina displacement vector, a dose distribution indicator, or the like. The error value may in turn be compared on a real-time basis with a gating threshold value to trigger a gating event. Optionally, eye tracking algorithms may be used to track motion or dose relative to non-target structures, such as the limbus, lens of the eye, optic nerve and the like, with respective gating thresholds.

(a) In a one motion-threshold example embodiment for a retinal target region, the error value may be the current scalar magnitude of a summation vector representing cumulative retina target motion derived on a time increment basis (e.g., camera frame-by-frame rate or a selected sub-sampling rate) from eye tracking data. For example the vector inputs may include components in the X and Y directions of the retinal target plane, indicating the X and Y deviations at each measured time of the beam center from the target center. The vector summation accumulates these components as directional vector quantities, the scalar magnitude representing the radial distance from the target center of the summation vector (square root of the sum of the squares of the components). Such a summation vector magnitude represents the time-weighted cumulative displacement error in the position of the beam-spot center from the planned retina target center point. The vector may be linear, or alternatively have quadratic or other non-linear distance weighting so as to de-emphasize small fluctuations in position (e.g., jitter or vibration) relative to larger, continuous displacements. Upon reaching a pre-selected scalar magnitude threshold, gating (interruption) of the X-ray source can then be triggered.

(b) A calibrated "motion-free" dose distribution may be determined experimentally and/or computationally (e.g., Monte Carlo simulation and/or radiographic beam-spot measurements) representing the dose distribution either at the target region (e.g., macula surface) or at any other tissue location within or adjacent to the radiation beam path. From the calibrated dose distribution, an equivalent time-increment dose distribution may be determined for a desired time increment (e.g. video frame rate). Retina or other tissue motion can then be derived from eye tracking data as described herein, and such motion data can be used to modulated with time-increment dose distribution so as to yield a contribution for each time increment to a cumulative dose distribution accounting for measure eye motion. Such motion-modulated dose distribution may be used to validate or determine a motion-threshold value as in 1(a) above by determining the dose distribution at the gating trigger point. Alternatively the motion-modulated dose distribution may be used to evaluate the adequacy of treatment dose level within the planned target region 318.

(c) Alternatively, the motion-modulated dose distribution of 1(b) may be determined on a real-time basis at any desired anatomical location within the distribution, and such dose may compared to a dose-threshold be used to trigger gating. For example, a maximum cumulative dose at the edge of the optic disk may be used to trigger gating.

(d) Alternatively or additionally, the real-time determined cumulative dose distribution of 1(c) may be evaluated within the planned target region, and may be used to trigger termination of treatment at a desired target treatment profile, including motion-related eye-dose distribution effects. Examples include triggering gating-termination upon (i) reaching a selected maximum treatment dose level at highest-dose point in a defined target region; (ii) reaching a selected minimum treatment dose level at the lowest dose point within a defined target region; (iii) reaching a selected average dose within a defined target region; (iv) a combination of these (e.g., reaching at least a selected average dose after achieving a selected low-point minimum); or the like.

2. System-level functional diagnostics. Gating may be triggered by error or failure conditions such as loss of eye tracking by the system, loss of limbus tracking, or other system-based failure deemed justification for interruption of radiation treatment, e.g., due to electronic conditions, camera conditions, lighting conditions, inadvertent blocking or interference with imaging, and the like. Alternatively or additionally, processor 501 may determine and monitor a selected number of different diagnostic conditions which can be used to trigger gating, such as X-ray tube parameters, lighting parameters, laser pointer 1410 position tracked relative to the limbus (limbus clearance), and the like.

3. Patient-level interlocks. Alternatively or additionally, processor 501 may determine and an monitor a selected number of patient-based interlock or diagnostic conditions which can be used to trigger gating.

(a) These may include specific patient interlock sensor signals, such as indicating disconnect of head restraint fasteners, disconnect of eye-guide lens mounting (see step 2534); patient hand grip 163 contact sensors (See FIG. 1A), and the like.

(b) The patient-based condition may also be determined by image processing/recognition from one or more cameras or other remote sensors. For example, the relative positions of eye-guide 110 and limbus 26 may be monitored continuously during treatment via camera-based eye tracking and compared against a selected threshold indicating disconnect or decoupling of the eye-guide lens 120 from the patients eye (such as by sliding of the lens over the cornea). An error condition may be determined so as to trigger gating of radiation. (c) In a further example, transitory "blinking" compensation gating embodiments are described in co-invented Application No. 61/093,092 filed Aug. 29, 2008, which is incorporated by reference. The transitory gating embodiments compensate for sudden, brief, large magnitude, generally vertical displacements which result from involuntary blinking or spasmodic movements of the eye, typically followed by a quick return to a generally well-aligned eye position. These eye movements may be rapidly detected by image-based eye tracking so as to trigger a rapid-response radiation gating. Treatment radiation may be automatically resumed, either after a fixed time delay or an automatic realignment confirmation. This "blinking" type gating may be used independently or in combination with retinal motion threshold gating described in Subsection 1 above.

Step 2540

Release eye holder—Following treatment, the patient may be released from the eye-guide 110 (e.g., release of vacuum suction) and head restraint 160.

VB. Pixel-Level Image Alignment Methods

In certain embodiments having aspects of the invention, the image recognition and processing may be conveniently and advantageously performed on a digital pixel-level of camera resolution based on camera image signals (e.g., cameras 401, 402), such as a selected video frame representing an image at a defined image capture time. The eye alignment method of Step 2540 may be applied similarly to the alignment of other anatomic features as a step in carrying out treatment with a radiation device.

Conventional video frame image data may be stored for processing in a manner known in the electronic arts, such as by defining a two-dimensional array of pixel data in a computer memory, wherein each array element is mapped to a particular pixel position of the camera image and wherein each array element is associated with one or a plurality of values indicating pixel color and/or intensity. For example, a 24-bit RBG color-encoded pixel values of an array for a 1000×1000 pixels image dimensions may be stored. Where the image capture is focused and delimited by a specific area of interest, (e.g., a portion of the patient's face including an eye, eye lids and adjacent skin surface), the pixel position may be mapped to a particular point on the area of interest. For example, where the area of interest is an approximately 10 cm×10 cm area of the patients face, each pixel of a 1 Mega-pixel image represents about region of about 0.1 mm×0.1 mm, or about 100 micron resolution. A 4 Mega-pixel image represents about region of about 0.05 mm×0.05 mm, or about 50 micron resolution.

The imaging camera may conveniently be aligned with the radiotherapy coordinate system axes (or alternatively, at a known orientation and position relative to the coordinate system). For example, and axial camera may be aligned so that the camera optical axis is parallel to the system Z axis, and so that the center pixel of the camera sensor chip corresponds accurately to the system Z axis. For this orientation, the camera "sees" its field of view in direct relation to the system X-Y plane origin, as shown in FIG. 21C(2). Deviations and directions of imaged features may then be measured in pixel scale in this reference frame.

The storage of image data may continue for subsequent video frames. If desired, image processing and feature recognition may be carried out on a real-time basis on all, or a selected sub-sample, of the captured video frames. Camera sensor resolution and image size (e.g., conventional CCD image sensor chip), frame capture rate, and other imaging parameters may be selected in consideration of associated optical and mechanical components, to optimize system performance, cost, speed and the like, as is known in the electronic arts.

Referring to the axial camera view shown in FIG. 21C(2), in an example sub-method embodiment, the processor 501 may be programmed with suitable software code, acting on image data in computer memory, to carry out all or a portion of the sub-steps of an image alignment algorithm, including:

(a) Identifying a pixel of the image representing the eye-guide central axis. For example, the processor may:
  - (i) determine the portion of the image including center-post fiducial 1 (e.g., by contrasting edge detection);
  - (ii) determine the geometric center of the fiducial image area; and
  - (iii) select the pixel lying closest to the fiducial center.

(b) Determining that the eye-guide 110 is aligned with the camera (system Z axis). For example, the processor may:
  - (i) repeat step (a) with respect to each of fiducials 2 and 3 so as to select a pixel representing the center of each fiducial;
  - (ii) calculate the horizontal (X) center-to-center the distance between each of fiducials 2 and 3 and fiducial 1 (e.g., count number of intervening pixels);
  - (iii) determine whether fiducials 2 and 3 are equidistant from fiducial 1 (no horizontal tilt) [*optionally display any error magnitude to operator];
  - (iv) calculate the vertical displacement (Y) of the fiducials 2 and 3 from fiducial 1;
  - (v) determine if fiducials 2 and 3 lie on a horizontal line including fiducial 1 (no vertical tilt) [*optionally display any Y and θ error magnitudes to operator];
  - (vi) determine if the pixel representing the eye-guide center is located at (0,0) of image system Z axis (center pixel of camera image) [optionally display any X and Y error magnitudes to operator];
  - (vii) determine, if (iii), (v) and (vi) are true, that eye-guide 110 is aligned with the system Z axis [*optionally compare with selected tolerance thresholds and display compliance or non-compliance to operator];

(c) Determining the location of the center of limbus 26 in the system coordinates. For example, the processor may:
  - (i) determine the portion of the image including all or the exposed portion of the limbus boundary (e.g., by contrasting edge detection) and identify the pixel locations corresponding to the limbus boundary image;
  - (ii) mathematically determine a "best fit" shape corresponding to limbus boundary data, for example using boundary pixel locations as inputs to determine an equation for a circle or ellipse with lowest error function;

(iii) calculate the center of "best fit" shape, and identify the image pixel closest to center.

(d) Determining any deviation of the location of the center of limbus 26 from either or both of the system Z axis. For example, the processor may calculate the horizontal (X) and vertical displacement (Y) of the limbus center from pixel representing the system Z axis (e.g., by counting intervening vertical and horizontal pixels) [*optionally displaying the X and Y values to operator].

(e) Registering the positions and/or orientations determined in steps (a-d) of one or both of eye-guide 110 and limbus 26 in a virtual eye model, e.g. eye anatomic geometry stored in computer memory. For example, the eye model may additionally include measured patient-specific data and/or imagery such as eye axial length, and a scaled OCT or fundus image.

(f) Calculating the position of the retina (or other structures) in the system coordinates based on the registered eye model.

As described above with respect to FIG. 21A, the placement of eye-guide 110 relative to the limbus 26 on the eye surface may be adjusted until the limbus-to-lens alignment (measured step (d) above) is reduced to as close to zero as is desired. Likewise, alignment of eye-guide 110 relative the system Z axis may be adjusted (e.g., by positioner 600 in FIG. 1A) until the eye-guide alignment error (measured in step (b) above) is reduced to as close to zero as is desired.

A related method having aspects of the invention, including an algorithm for aligning a body part with a radiation device, may be summarized: (a) defining a normal axis to said body part; (b) aligning said normal axis to a pixel on a camera image visualizing said body part; and (c) linking said pixel on said camera image to a coordinate frame of a robotic positioning system thereby linking said normal axis of the body part to an axis of the robotic positioning system.

The algorithm may further comprise determining the distance between said body part and said robotic positioning system wherein said distance is measure along said normal axis. The algorithm may further comprise defining a normal step comprises locating fiducials on said body part. The algorithm may include that the detection of said fiducials directs said aligning of said normal axis, such as where the fiducials are attached to a device which contacts the sclera of an eye, and which may have a contact member fitted to the limbus of the eye. The algorithm may include that an axial length of an eye is used to define a position on a retina of the eye and said position is utilized to define movement to a macula from said position.

V.C. Eye-Guide Placement and Eyelid Retraction

Figure 22:
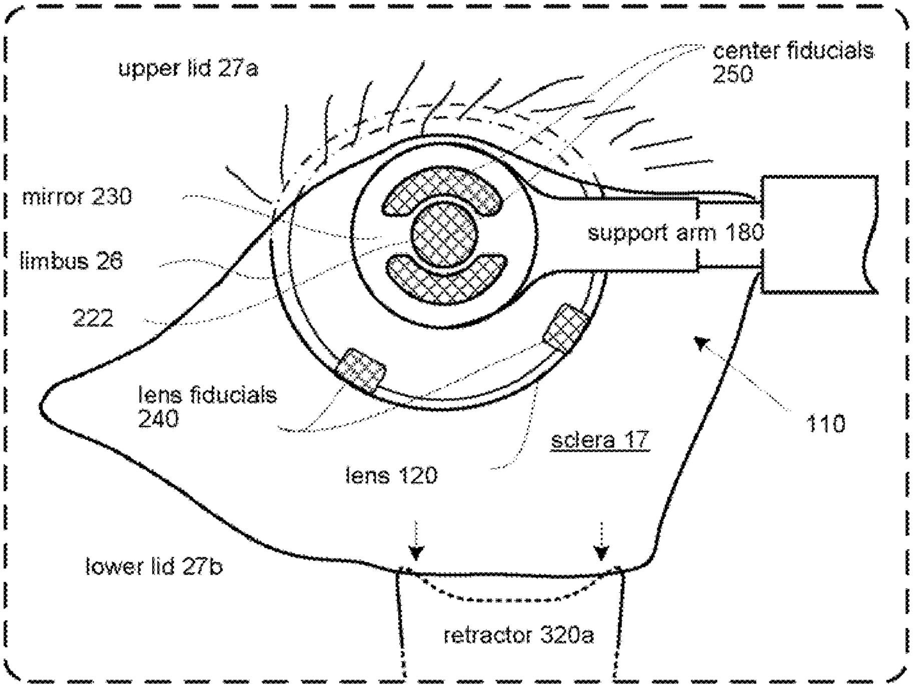
FIG. 22 depicts one embodiment of an eye-guide having aspects of the invention engaged with an eye having one embodiment of an eyelid retractor.

FIGS. 22 and 23 are drawings of a patient's eye showing two different embodiments of an eye-guide 110 having aspects of the invention as engaged with the eye in an operative position, in this case with the eye substantially as it appears when aligned with the eye-alignment axis 2810 of radiotherapy system 10. The eye-guide lens 120 is shown approximately centered on limbus 26, the lens being supported by arm 180.

In the example of FIG. 22, the eye-guide 110 includes one or more reflective fiducials (as further described herein), in this example having two or more fiducials 240 positioned spaced-apart on the lens 120, and one or more fiducials 250 positioned on the crown of center post 222. In this example, the center post may also include a mirrored surface 230, which may be used to track alignment with a axial pointer beacon or laser beam, as further described herein (see also FIGS. 2AB and 29-31). The eye-guide embodiment shown is of the type employed during acquisition of the example eye-tracking data shown in FIG. 26A-E. using an eye alignment/tracking system having an alignment-axis-centered low powered laser pointer 403 (see FIG. 4).

In this example, the lower eyelid is retracted downward by a retractor or lid speculum 320*a* to expose an area of the sclera for treatment beam entry (see FIG. 46A and related description). The upper lid may ride over the eye guide lens 120 upper portion, but the system cameras can effectively track both the lens fiducials 240, and detect and compute the image of the limbus (as further described), permitting the positions of each to be determined automatically (including extrapolations to covered portions shown as dashed lines). The retractor 320*a* includes a smooth and non-abrasive hook-like portion 323 comprising a wire-loop configured to overlap and engage the eyelid. The retractor hook 320*a* may be supported a number of alternative ways (e.g., hand-held, taped to a support, mounting to a base, an elastic tether, or the like).

Figures 48A, 48B, 48C, 48D, 48E:
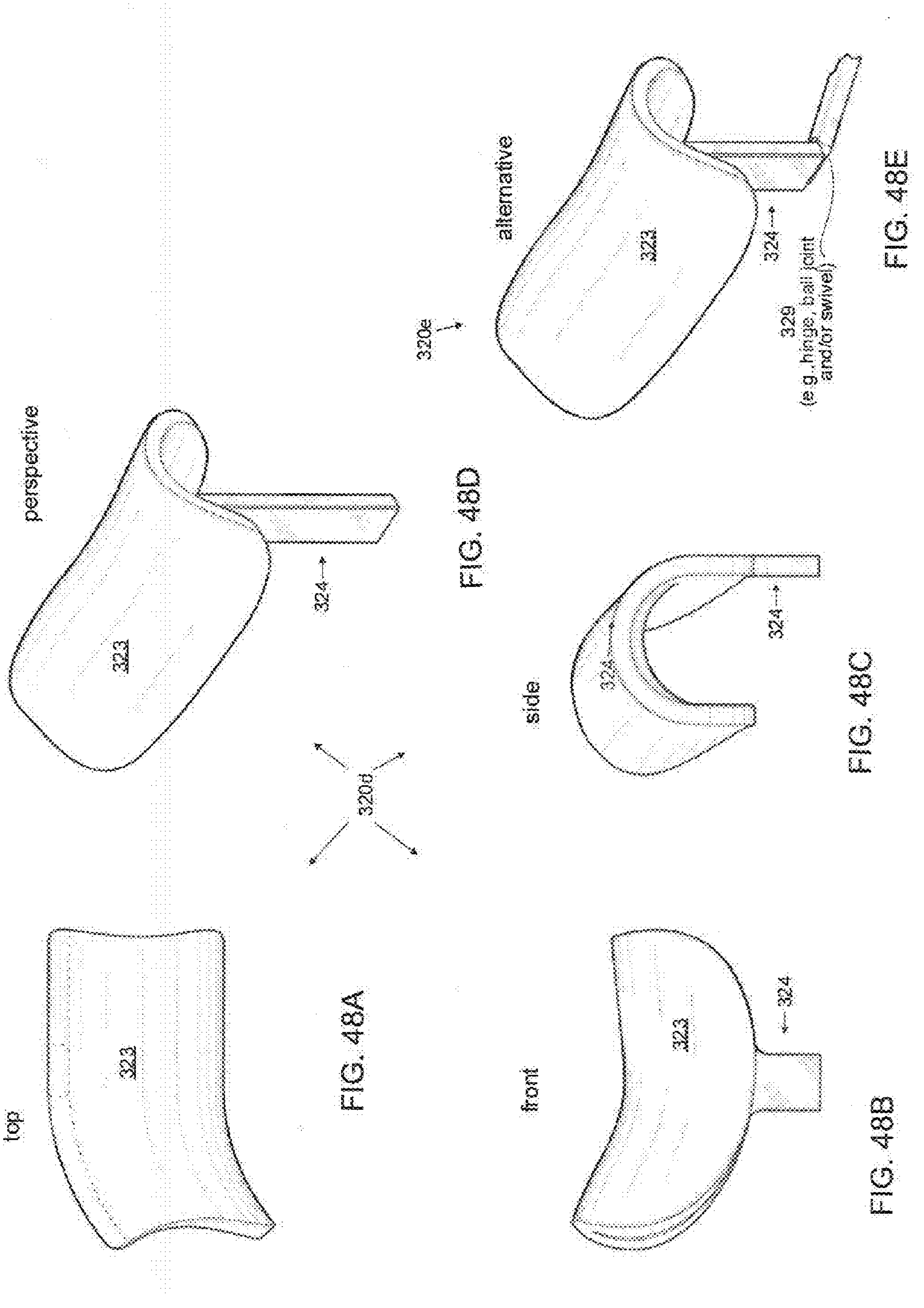
FIGS. 48A-E illustrate further alternative embodiment of an eyelid retractor having aspects of the invention.

FIG. 23 shows the alternative eye-guide embodiment 110 as engaged with the eye 30 in an operative position. The eye-guide shown is of the type described in detail herein and shown in FIGS. 24A-D and 25A and 25B. The lower eyelid in this example is retracted downward by retractor embodiment 320*d* (see FIGS. 47-48 and related description), which has a non-abrasive smoothly curved or saddle-shaped spoon-like hook member 320*c*, optionally composed of radio-opaque material.

FIGS. 24A-24D illustrate an eyeguide device embodiment 110 having a pattern of fiducials, the guide for use in a eye stabilizing system having aspects of the invention, shown in contact with an eye and depicting the method of determining alignment. In the example shown, the eye-guide does not have a mirror surface, but includes 3 fiducials having a highly reflective material (e.g., "Scotchbright"), one at the top of the center post 222 (fiducial 1), and two on the cross arm 190 on either side of the center post pivot 220 (fiducials 2, 3).

The fiducial arrangement shown permits a transparent lens 120 to be free of fiducials, which promotes digital image-recognition of the limbus. In addition the eye-guide may be tracked by camera image processing without a collimated and aligned light source (e.g., a laser), and may be tracked under simple lighting, such as LEDs positioned adjacent the eye.

FIGS. 24B-24D show series of perspective views of an eyeguide embodiment 110 from several different orientations to the viewpoint, which can be a camera. View B is angled substantially, so that the fiducials 1-3 form a triangular pattern 4, which may be measured by image recognition methods. View C is angled less and presents a correspondingly smaller triangular pattern. View D is aligned with the view point, and show a straight line arrangement, with equal right (2-1) and left (3-1) legs between fiducials. Note that the aligned pattern of View D is very easy for a operator to recognize visually, either directly or as displayed on a user interface.

FIGS. 25A-25B illustrate that rotation of the center post 222 about pivot 220 will result in a shift of the center fiducial 1 (in X or Y or both), even when the eye-guide support arm 190 is perpendicular to the viewing axis.

IV.D. Example of Alignment Method

As shown if FIGS. 3-5, the imaging system 410 has a known position and orientation relative to X-ray source positioning system 115 of radiotherapy system 10 in a global coordinate system. In preferred embodiments, the imaging system is supported to be movable by positioner 115. For example, as shown in FIGS. 3B and 5, imaging system 410 may be mounted to imaging support 412, which in turn may be mounted to move in concert with XYZ stage 416 while remaining independent of φ actuator 413 and θ actuator 414.

In an example method using particular device and sub-method embodiments described in detail herein (e.g., as shown FIGS. 1-2, and 23-25, using methods shown in FIGS. 21A-21E), the method may include all or some of the following:

(a) Initially, the patient is positioned in head restraint 160 of system 10, with eye guide 110 engaged and lens 120 centered on limbus 26.

(b) The imaging system 410 is moved into a position (e.g., by positioner 115 X, Y and/or Z motion) where the retro-reflecting fiducials 1-3 of the I-Guide 110 can be viewed by the imaging system 410 (e.g., by cameras 401-402 in FIGS. 3A-3B communicating with a system processor and an operator display).

Figure 27:
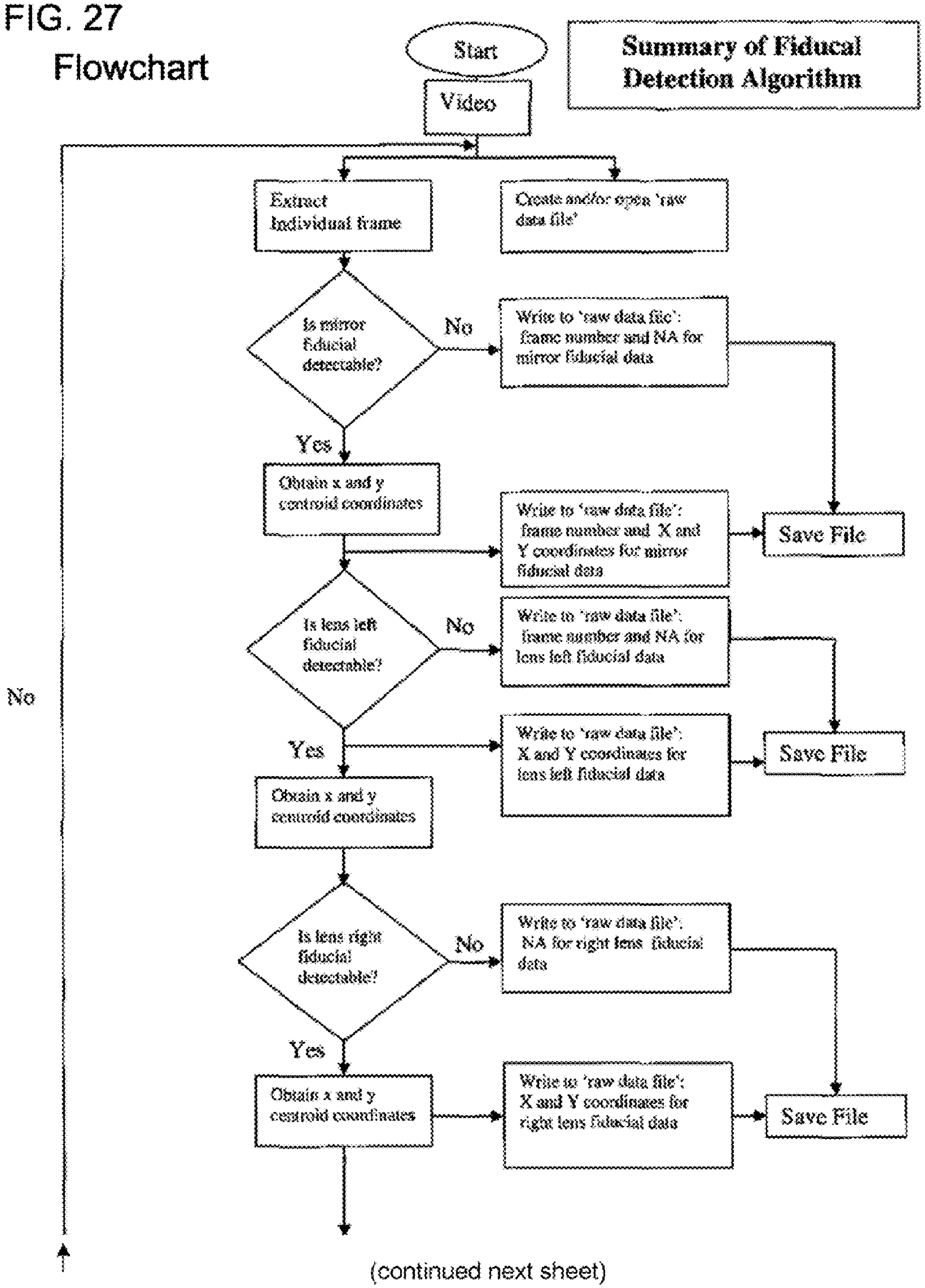
FIGS. 27 and 28A-B are flowcharts illustrating data acquisition and processing.
Figure 27:
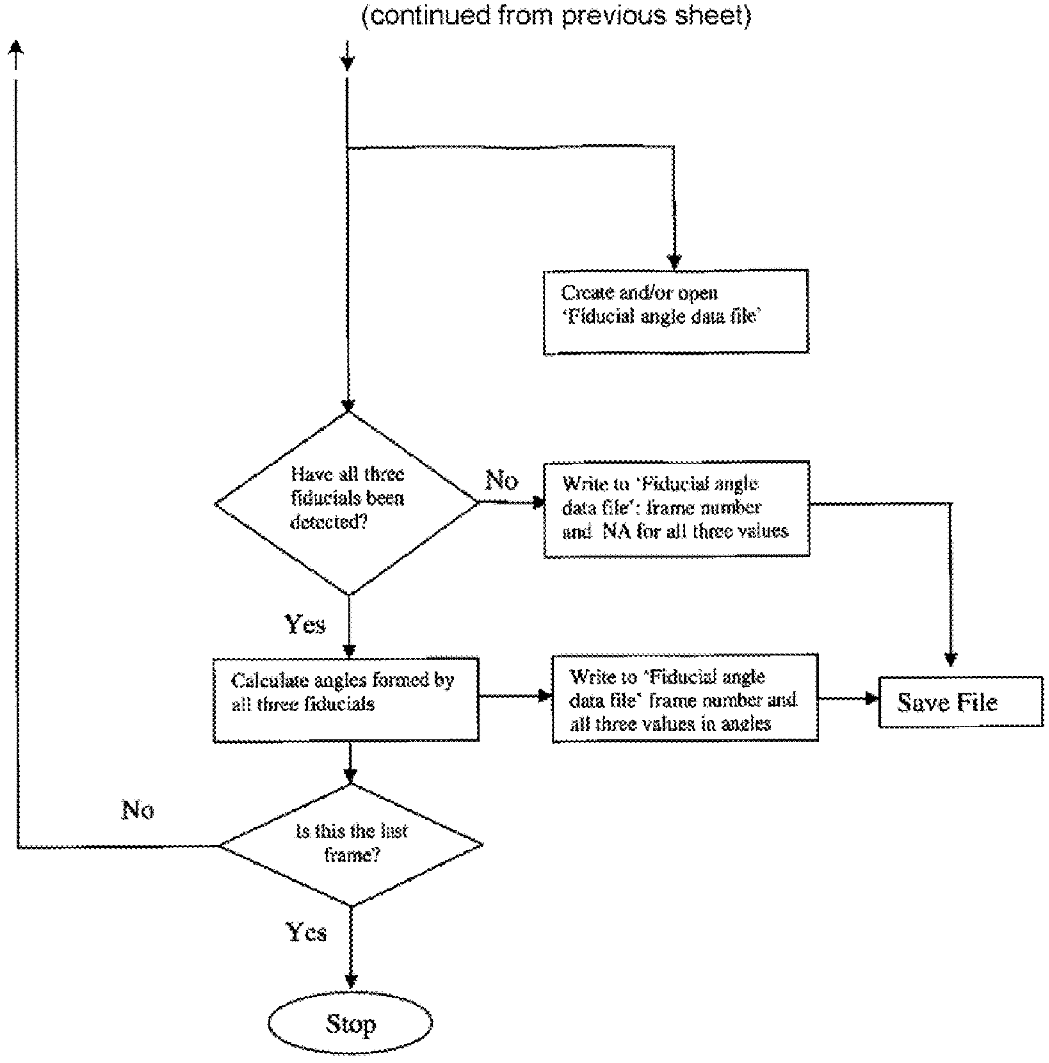

(c) As image data from the fiducials is processed into spatial information (see flowchart FIGS. 27-28, the positioner 115 may be configured so as to auto-align (or manually) to the center of the I-Guide crown in X and Y (center fiducial 2 in FIGS. 23-25).

(d) The operator then adjusts the I-Guide angle until it is oriented along the system axis as shown in FIG. 21C, for example by rotation about eye-guide pivot 220 by adjustment of eye-guide positioner 600 along X', Y' and/or Z' axes. Further auto-alignment of the X and Y axes of positioner 115 brings the eye-guide axis into co-linearity with the system Z axis. In this configuration the eye geometric axis 2810 is collinear with the Z axis of positioner 115.

(e) The positioner 115 may then be offset in X and Y to shift the system Z axis from alignment with geometric axis 2810 to align with an off-set treatment axis 2820 ($X_0$, $Y_0$ in FIG. 21E). In one treatment plan example, this is a shift of 1.16 mm temporally (may be ±X depending on if the left or right eye is being treated) and −0.47 mm caudally (−Y), as shown in FIG. 21D. Note that this shift may alternatively be done before or after the $Z_0$ and $\phi_0$ adjustments.

(f) With the eye-guide 110 and positioner 115 aligned as described, the positioner 115 is moved axially along the Z axis until it reaches the selected treatment position ($Z_0$ in FIG. 21E), and the x-ray source 112 is rotated about the φ axis to the selected beam angle ($\phi_0$ in FIG. 21E). In this configuration, the spot of laser beacon 1410 is directed to appear on beam entry spot 311 (see FIGS. 3A and 4). The operator may confirm beam position and clearance of the beam from the limbus 26 by visual display via cameras 401-402, and the system 10 may confirm alignment by image processing and recognition of both laser beacon and limbus.

(g) (i) In a preferred treatment practice, the system is maintained in this configuration in four degrees of freedom ($X_0$,$Y_0$,$Z_0$,$\phi_0$), and further stereotactic re-positioning of the X-ray source assembly 420 is confined to rotation about the θ axis of positioner 115.

(ii) Note that where the treatment axis 2820 at ($X_0$,$Y_0$) intersects a retina-surface target center 318 (e.g., center of the macula) and the combination of ($Z_0$,$\phi_0$) aims the beam path 1400 to intersect the treatment axis 2820 at the target center, subsequent rotation about the θ axis causes the stereotactic beam paths to describe a cone with the apex at the target center 318. The combination of ($Z_0$,$\phi_0$) may also be selected to provide clearance from limbus 26 and eye lens 36, so as to have sclera entry points 311$_i$ distributed spaced-apart in a roughly circular arc outside but adjacent to limbus 26 (see FIG. 9).

(iii) For example, the first treatment beam may be at an angle of θ=1800. For convenience, a θ angle of 180 degrees (referenced from 0° north) may be referred to as the 6 o'clock position (beam 1 at $\theta_1$ in FIG. 21E). Other treatment positions may be selected by adjusting the θ angle e.g., beam 2 at $\theta_2$ and beam 3 at $\theta_3$, at roughly the "5 o'clock" and "6 o'clock positions" (θ≈150° and 210°, respectively).

(iv) Alternatively or in combination, adjustment of other DOF may be performed, targeting beam 1400 to suit an alternative treatment plan.

V.E. Example of Image-Based Eye and Eye-Guide Measurements.

The exemplary embodiment of the imaging system 410 may be configured to acquire data at a selected rate for each camera, and typically the processor processes and calculates data at a selected update rate, e.g. about 10-50 HZ. In one example, a set of direct measurements are made at an update rate of 30 Hz, and used to calculate an additional set of inferred measurements as data is updated.

As shown in the eye-guide example shown in FIGS. 23-25, the direct measurements are performed automatically using image processing and pattern recognition software on a frame-by-frame basis from camera video input signals, and include:

1 Eye limbus center X-Y position.

Viewed from the on-axis main system camera 401.

Locates anatomical transition between the dark of the iris and light of the sclera (limbus margin 26 in FIG. 9).

Defined by center of mass of the best fit circle using limbus detection software.

2 Eye-guide 110 yoke X-Y position (yoke or tie rode 190 in FIG. 23).

Viewed from the main system camera 401.

Locates 2 fiducials on the tie rod 190 (fiducials 2 and 3 in FIG. 23).

Defined by the center of mass between 2 fiducials (Yoke).

Note that the relative positions of yoke 190 and crown.

3 Eye-guide 110 crown X-Y position.

Viewed from the main system camera 401.

Uses infrared light from the IR LED bank of lights 406, close to axis of camera 401.

Locates the fiducial on the tip of the Eye-guide 110 (fiducial 1 in FIG. 23).

Defined by the center of mass of the fiducial (crown).

4 Eye-guide 110 yoke 190 Z position.

Viewed from the off axis range Z camera 402.

Defined by the center of mass between the 2 fiducials on the tie rod (fiducials 2 and 3 in FIG. 23).

The calculated measurements are performed automatically using system computer processors on a real-time basis as direct measurements are updated, and include:

5 Base lens 120 X-Y position.

(a) This is a projected estimation of the center of the base lens 120 approximately at the same plane of the limbus measurement. The inputs include measurements 2 and 3 (X-Y of yoke 190 and crown fiducial 1, respectively), which define an eye-guide longitudinal axis, which can be extrapolated from the known structural geometry of eye-guide 110 to determine the lens X-Y.

(b) Note that the relative detected X-Y positions of yoke 190 and crown fiducial 1 also define an eye-guide axis angle relative to system 10 coordinates (analogous to eye-guide 110 "pitch and yaw", designated here as eye-guide ϕ).

(c) Note also that the relative detected vertical positions of fiducials 2 and 3 on yoke 190 define an eye-guide angle in the system X-Y plane (analogous to eye-guide 110 "roll", described here as eye-guide θ). In certain embodiments, this may be largely be controlled by the support of head-chin restraints 160 and eye-guide positioner 600, and the eye-guide θ value may be small or negligible.

6 Limbus-to-lens coupling.

This is a functional measure based on the amount of relative movement between the base lens 120 X-Y position and the limbus 26 X-Y position.

Relative motion that exceeds a threshold value (e.g., 500 microns) may be interpreted as an indication that the base lens 120 has shifted from its original location at eye alignment or has become decoupled.

7 Retinal target 318 X-Y-Z position.

This computation involves all detected motion parameters so as to estimate the related motion at the back of the eye, inferred as motion of the retinal target 318 (See embodiments of FIGS. 29-36).

Gating algorithms and criteria are based on these calculations (See embodiments of FIGS. 39-42).

Note the eye alignment method flowchart and geometric diagrams of FIGS. 21A-21E in regard to examples of the use of the measurement as described above by the system 10 computer processors 501 (via suitable software) and displays 503*a,b*: For example:

Measurements 1, 5 and 6 (relative position of eye-guide lens 120 and limbus 26) may be displayed to assist a physician in placement of eye-guide 110 as shown in FIG. 21B as centered on the limbus, and used to automatically confirm eye-guide placement accuracy.

Measurements 2, 3 and 5*a,b* (eye-guide angle and eye-guide X-Y) may be used to guide and/or automatically drive the motion M(x,y,ϕ,θ) of FIG. 21C to align the eye geometric axis 2810 coaxially with system Z axis (relative values eye-guide X,Y,ϕ,θ versus system 10 coordinates and Z axis become zero).

Measurements 2, 3 and 5 may be used to confirm accuracy of the X-Y shift of positioning system 115 from geometric axis 2810 to treatment axis 2820, as shown in FIG. 21D.

Measurement 4 may be used to confirm accuracy of positioning system 115 movement to the treatment Z position ($Z_0$) as shown in FIG. 21E.

All the above measurements may be used to track eye position and retinal position on a real-time basis during treatment.

V.F. Example of Eye-Guide Data Extraction and Eye Motion

FIGS. 26 through 41 pertain to measurements of eye motion of patients who are engaged by an eye alignment, stabilization and tracking system having aspects of the invention, such as are depicted in FIGS. 1, 2 and 16-26. These aspects also include mechanisms and methods for assuring that any residual motion of the stabilized eye does not prevent radiotherapy to be effectuated with dosage distribution adjacent a target region remains within planned parameters.

Figures 26A, 26B, 26C, 26D, 26E:
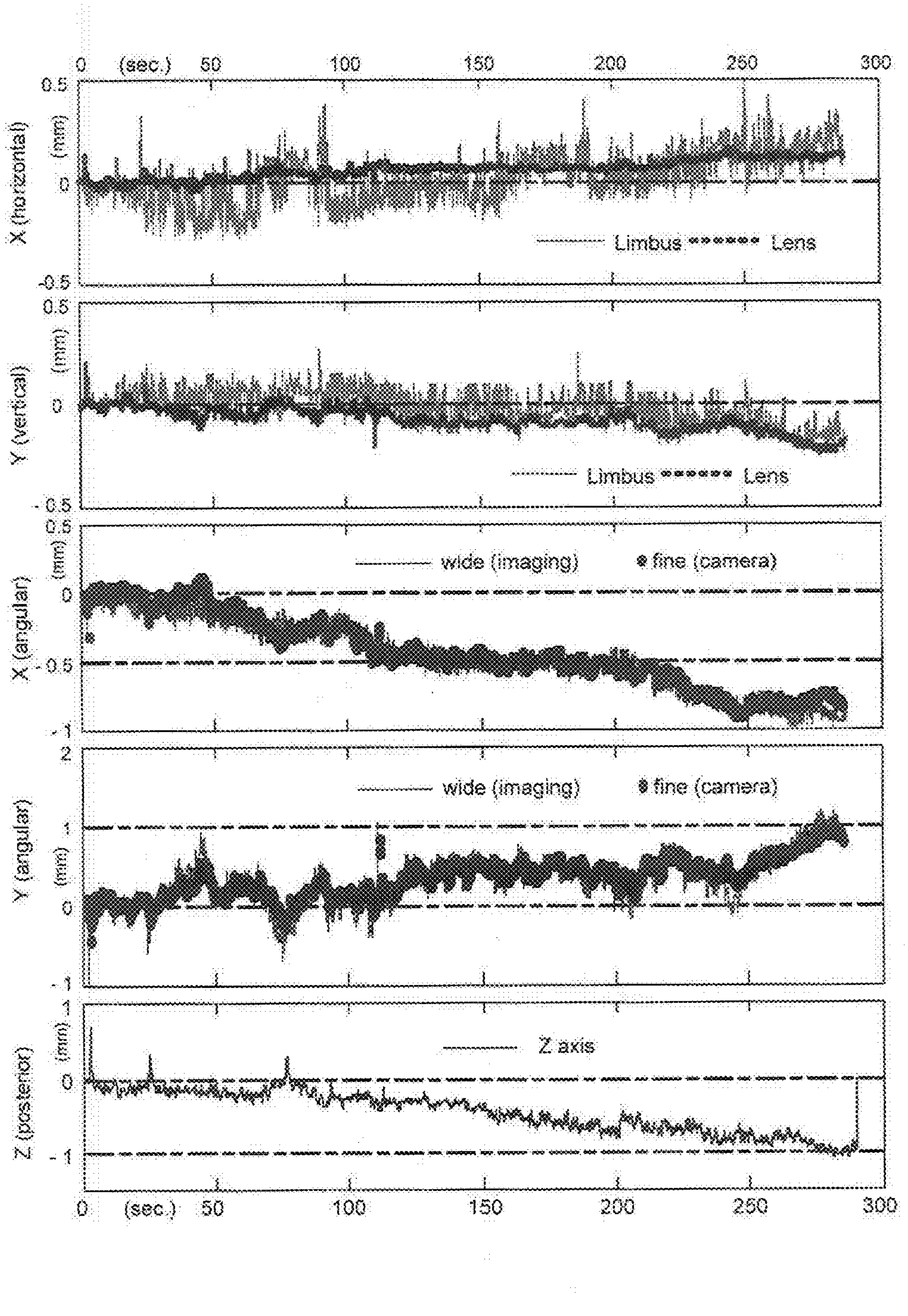
FIGS. 26A-E are plots showing eye movements experimentally measured with an embodiment of a system for controllably positioning and/or stabilizing the eye.

FIG. 26 A-E are plots showing eye movements experimentally measured with an embodiment of a system for controllably positioning and/or stabilizing the eye of a subject. In the this particular embodiment, the data was acquired using three video cameras mounted on an embodiment eye stabilization and tracking system having aspects of the invention, and employing a laser beacon 810 coaxial with a system axis (see FIGS. 2A and 2B) and reflecting from a mirror-surface eye-guide fiducial 230. Note that the particular camera/imaging configuration used in the example illustrates only one of a range of alternative embodiments comprising cameras and/or other sensor configured for acquiring motion data of the nature shown. For example, FIGS. 3A and 3B illustrate and imaging system employing two cameras, capable of acquiring comparable eye motion data. In the example of FIGS. 26A-26E, for each patient, video from each camera was processed, frame by frame, in order to extract desired data. The cameras were configured as follows:

"PSD camera", also referred to as "fine angle data". Coaxial laser beam is reflected from the eye guide's mirror and detected by the camera. Although enabling high resolution data to be extracted, this setup can only collect data within very limited range of +/−1.25 deg.

"Central camera"—the eye-guide fiducial data; camera is mounted perpendicular to patient's eye and can view eye guide's lens and mirror, as well as anatomic data such as limbus position.

"Z-range" camera—distance data; camera is able to see eye-guide mirror but is mounted to the side of central axis. eye guide's, and hence patient's fore and aft movement (Z axis) is accurately easily detected.

Fine Angle Data

PSD camera is set up such that reflected laser beam is visible as a white (bright) area contrasted on the dark background in the camera view. Every frame from the video is individually extracted, and using custom algorithm and software, location and centroid of the laser area is determined. Centroid data is expressed in (x,y) pixel coordinates and using predetermined conversion factor translated to angle in X direction and angle in Y direction. Conversion factor is (pre)determined based on set-up and calibration data. Since knowing patient's head movement during the treatment was desired (i.e. relative movement) each angle in X and Y direction was subtracted from the very first recorded data point.

Fiducial Data

Using custom algorithm and software each frame from the central camera's video is extracted, and fiducials on Eye guide's lens (2) and mirror (1) are detected. Center of each fiducial is expressed in (x,y) pixel coordinates. By design fiducials form a triangle, therefore it is possible to calculate angles within a 'fiducial' triangle. Angle formed at center of the eye-guide mirror is used for vertical determination (Y angle), and ratio of angles formed by fiducials on the lens is used for horizontal determination (X angle). Relative motion data was desired so each acquired data set was subtracted from the first data point. During the study, the fiducial location differed slightly on each lens, without effecting the method. Fine X and Y angles were paired to X and Y fiducials and correlation factor was determined per each patient's data set. Correlation factor was determined by using line equation y=ax+b, where y is fiducial data, a is slope, x is fine angle data, and b is offset. Variables a and b were determined using few points from data set (in future whole set should be interrogated).

Distance Data

Laser spot reflection on the eye-guide's mirror, as seen by set "Z-range" camera was used to determine distance data. For each video frame, center of laser spot was detected using custom algorithm and software (see further description of measurements under caption "Example of image-based eye and eye-guide measurements.". Note that in addition to the image-based methods described, range data may be obtained by ultrasound or other reflected-signal techniques. Using predetermined calibration and correlation factors, each detected location was converted from pixels to millimeters. Other image data may be used in lieu of laser spot, such as light impinging on eye-guide 110 from an LED lights source (e.g., visible or IR)

The measurements shown in FIGS. 26A-26E are from a typical patient who was tolerating the procedure well for the administered period of about 300 seconds (5 min.), and are as follows:

A. Horizontal X motion of the eye-guide and the limbus, plotted together to show relative motion of these.

B. Vertical Y motion of the eye-guide and the limbus, plotted together to show relative motion of these.

C. Horizontal X motion of the eye-guide mirror due to angular deflection about the pivot.

D. Vertical Y motion of the eye-guide mirror due to angular deflection about the pivot.

E. Z motion of the eye-guide due to motion of the eye posteriorly.

It may be seen that each parameter includes movements of on the order of 1 mm or less, and most less than 0.5 mm, over a substantial period of 5 minutes without any re-alignment procedures.

Figure 28A:
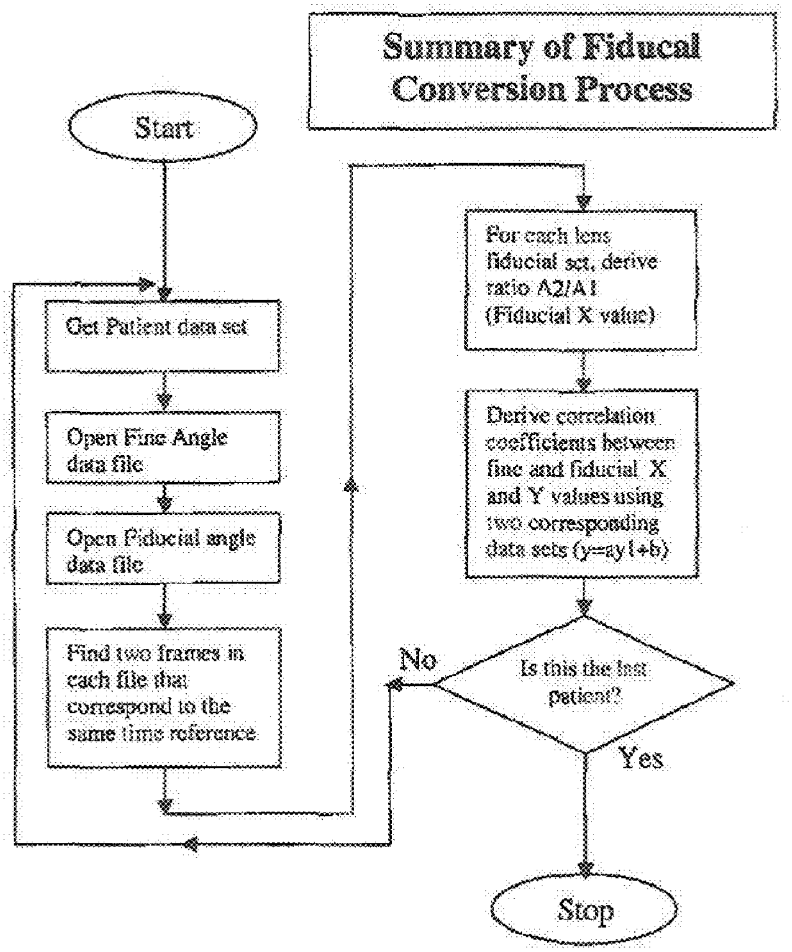
Figure 28B:
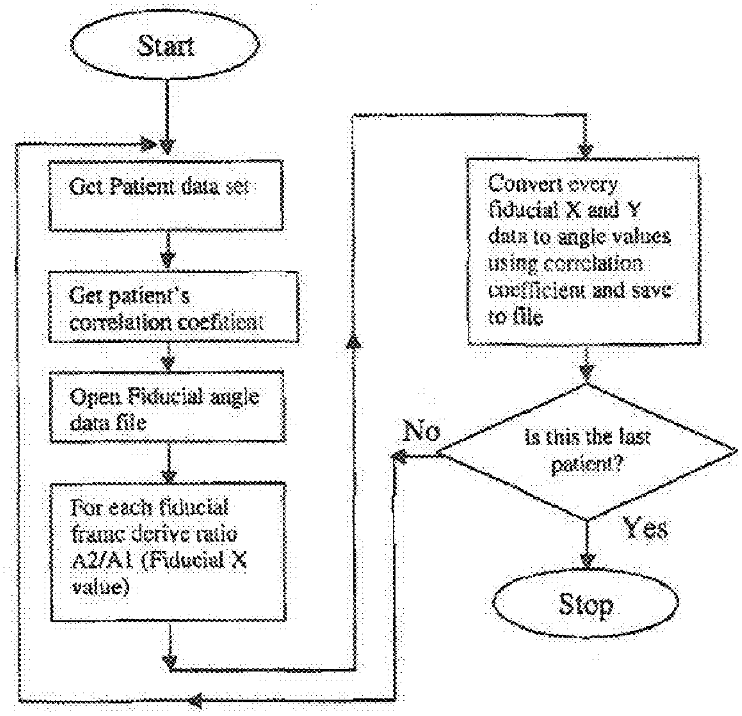

FIGS. 27, 28A and 28B are flowcharts illustrating data acquisition and processing used in this example, and are self-explanatory to one of ordinary skill in the art. It should be understood that the algorithms and methods depicted are merely an example to demonstrate the functionality of one embodiment of the system, and alternative or additional particulars and sub-methods may be included without departing from the spirit of the invention.

The flowchart of FIG. 27 (on two sheets) is a summary of the fiducial detection algorithm employed in obtaining the data of FIG. 26. The input to the method is a video signal captured by system cameras. The data flow is a loop which processes each frame of video data, preferably on a real-time basis as each frame is captured. Alternative methods can select particular frames for data computation (e.g., in a timed sequence to support a desired data update rate), for example where a greater frame rate is desired for a user visual display than is desired for data computation. As may be seen, the output from the method are particular computed values, which in this example are depicted as being written as correlated with the particular video frame to memory media, indicated as "save file". It is to be understood that these output values may additionally or alternatively be directly accessed by system electronic processors for further display, computation or control functions.

The flowcharts of FIGS. 28A and 28B depict further processing and conversion steps based on raw date obtained from the video frames, such as in the process of FIG. 27.

FIGS. 26A-26E are plots showing eye movements experimentally measured with an embodiment of a system for controllably positioning and/or stabilizing the eye of a subject. The measurements may be used as inputs for methods herein of determining motion of retinal structures of interest during radiotherapy.

V.G. Extrapolation of Eye Movement to Retinal Movement, and Dosage Mapping

Tracking of eye motion as described above may be correlated with a virtual eye model having aspects of the invention, such as are described herein to assess movement of particular eye anatomy during radiotherapy treatment, for example, the movement of a retinal target region relative to the path of an X-ray beam during treatment. Such anatomical movement may in turn be used to assess actual absorbed radiation dosage and its distribution in relation to a planned radiotherapy treatment.

It has been demonstrated the low levels of suction (e.g., 25-50 mm Hg) are sufficient to provide reliable coupling of the eye-guide 110 to the eye, so as to maintain the eye guide at a selected position (e.g., with lens 120 centered on limbus 26 in contact with cornea 12 and sclera 17).

However, eye motion may still occur on the scale of a fraction of a millimeter to a few millimeters even where the eye-guide 110 and eye-guide support assembly are substantially rigid and coupled to the eye, and where chin-head restraint assembly 160 provides firm head support (e.g., generally firm chin and forehead members 171, 172 and a snug head fastener 161). Sources of residual voluntary or involuntary eye movement include: (a) the eye is movably mounted in the skull, and may be moved within the orbit and adjacent soft tissue, such as by the eye muscles or head motion; and (b) the skin and soft tissue covering the skull, face and chin is generally loose and free to move within limits over the underlying boney support, and such motion may permit in small head movement, which then applies rotational and/or translational forces to the eye, as the eye tends to follow the head motion.

It should be understood that the certain eye stabilization methods and devices having aspects of the invention may omit aggressive measures sometimes used in opthalmologic and cranial surgery, such as temporary eye paralysis, high-suction contact eye-holders, orbital socket clamps, and/or rigid mechanical clamping of the skull. Less aggressive stabilization measures can lower treatment costs, improve patient acceptance, and reduce treatment time. Trade-offs in patient comfort, convenience, and cost can be made which favor of tolerating a selected modest level of eye position/orientation change during treatment versus absolute eye motion prevention. Alternative retina target tracking, dosage mapping and compensation method and device embodiments having aspects of the invention provide safe dosage control where a residual level of eye motion is present during treatment. In addition, the methods and device embodiments provide a "fail-safe" functionality for treatment procedures which have low levels of eye motion.

FIGS. 29-31 graphically illustrate the effect of particular eye motions of an eye engaged by an eye-stabilization system having aspects of the invention on motion of the retinal, including a treatment target (e.g., the macula) and a sensitive structure (e.g., the optic disk). In each case a radiotherapy beam is targeted on a region encompassing at least a portion of the macula, and the views show the beam initially aligned on the target, and show the effect of a particular movement away from alignment. The structure of the assembly 117 is essentially similar to that shown in FIGS. 17-18.

These figures demonstrate the effects on retinal dosimetry of real patient eye motion during radiotherapy. Anterior eye motion data from several patients was collected with an embodiment of an eye stabilization and tracking system as described herein (but no X-ray source was present in this test system). These data were analyzed to obtain retinal motion during the 5 minute study period. Using a measured dose map from a stationary mannequin study, the dose on the retina was modulated by the calculated motion to determine the effects on macular target and optical disc dosimetry. The following inputs and assumptions were used in this example analysis:

(a) 3-beam overlap dose map from an actual phantom mannequin radiometric dose study.

(b) Calculated retina motion based on measure eye movement.

(c) Eye assumed to be solid, with no shape-change during study, and retinal curvature assumed to have a negligible effect on dosimetry.

(d) Eye and head assumed to move together to accommodate rotation around pivot point (220 in FIG. 17), pivot point (220 in FIG. 17) assumed not to move, and eye-guide-to-limbus relative motion (decoupling) assumed to be about a fixed cornea curvature (note alternative models described herein).

(e) "Typical" retinal geometry and positions of macula and optic disk.

(f) Initial tracking alignment assumed to be perfect; beams centered exactly on fovea.

Figure 29B:
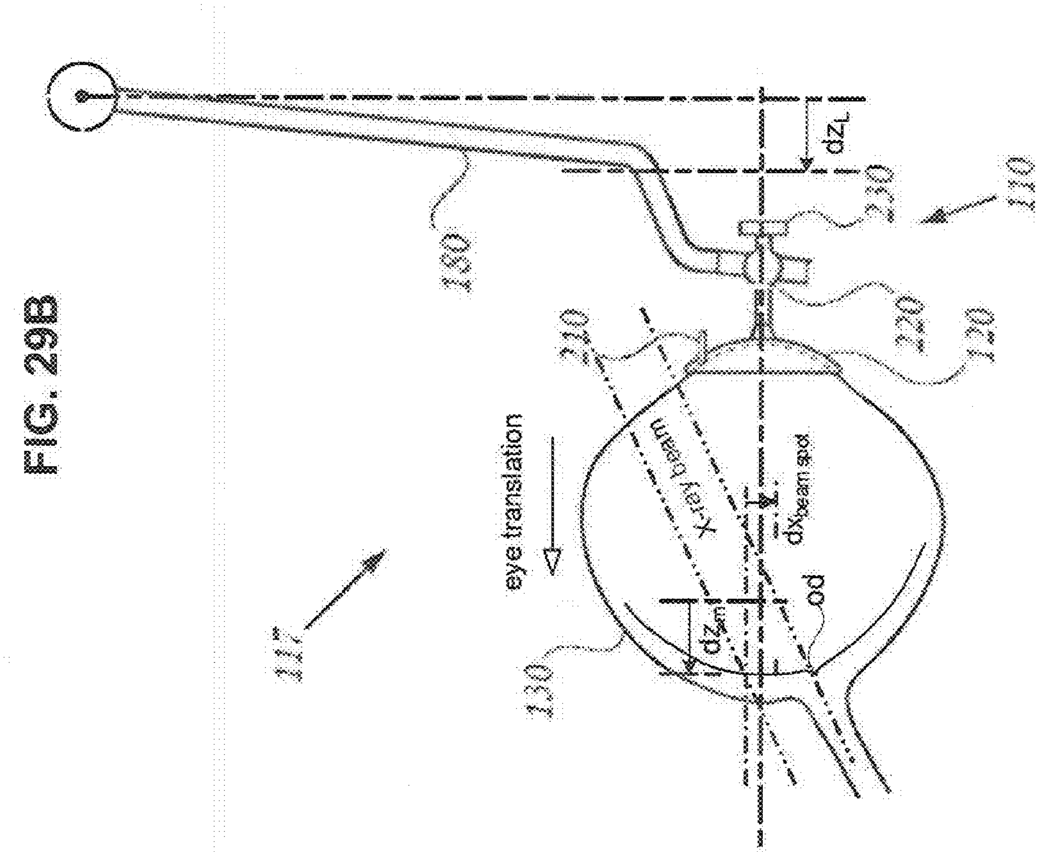
FIGS. 29A-B are two views plan view of an eye-guide included in a eye stabilizing system having aspects of the invention, shown in contact with an eye during X-ray treatment, illustrating the effect on retinal position of motion of the eye.
Figure 29A:
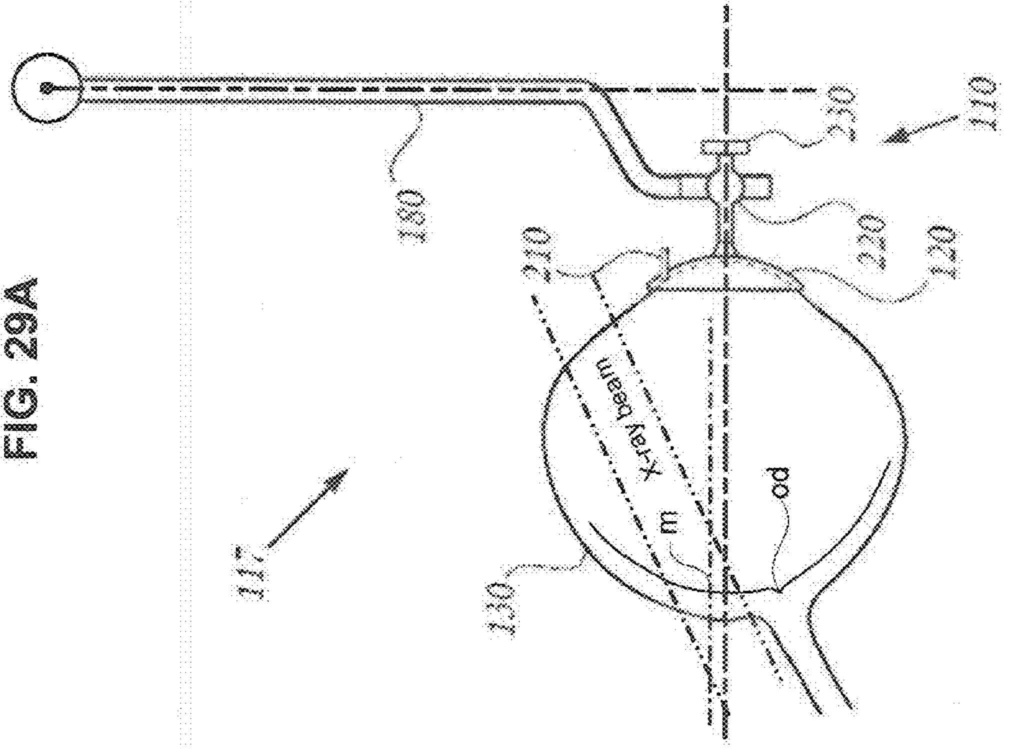

FIGS. 29A and 29B are two views plan view of an eye-guide included in a eye stabilizing system having aspects of the invention, shown in contact with an eye during X-ray treatment, illustrating the effect on retinal position of motion of the eye in the system Z direction. In this case, a posterior Z movement (see FIG. 26E) can be seen that the eye motion translates the retina along the Z axis without components of motion of the retina in the X or Y axis. However, the eye motion does result in a relative motion of the beam spot on the retina due to the angled alignment of the beam with the retina. In this illustration, the beamspot moves relatively in the X direction as shown, for a beam angled from the opposite direction.

It will be apparent that the direction of relative motion of the beamspot is dependent on the X-ray beam orientation relative to the Z axis (see angles $\phi$ and $\theta$ in FIGS. 5-9), and in the general case of an arbitrary angle $\Theta$, a motion of the eye in the Z direction will result in both X and Y components of the relative motion of the beamspot in relation to the planned target. It will also be apparent that the scale of such relative motion is dependent on the angle $\phi$ of the beam with the treatment axis, a small angle $\phi$ resulting in a relatively small movement of the beamspot in relation to eye motion on the Z axis. In a preferred embodiment, angle $\phi$ is kept constant during stereotactic re-positioning, with angle $\theta$ changed for each beam application.

Figures 30A, 30B:
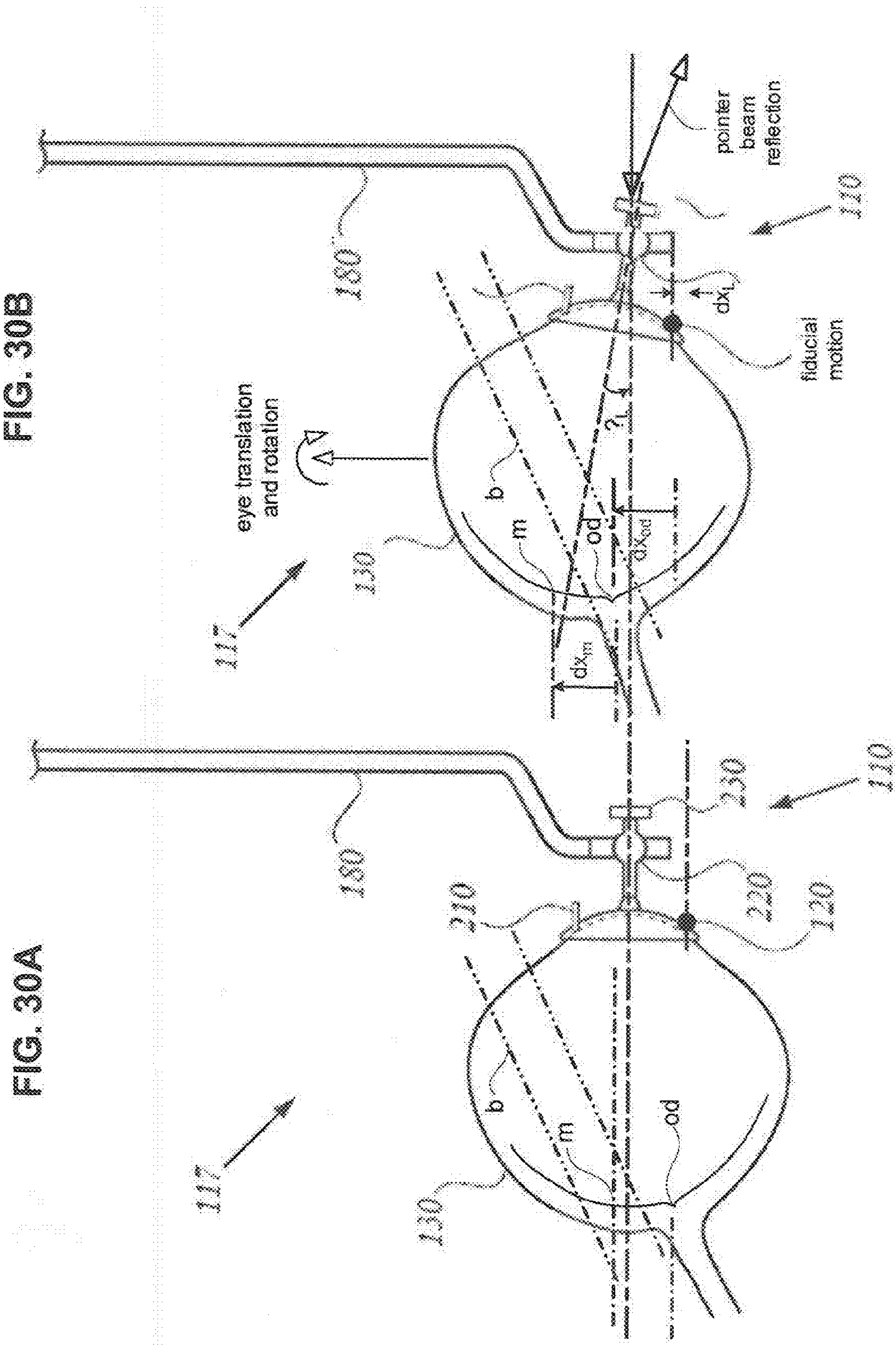
FIGS. 30A-B are two views plan view of an eye-guide having aspects of the invention in contact with an eye during X-ray treatment, illustrating the effect on retinal position of rotational motion of the eye.

FIGS. 30A and 30B are two views plan view of an eye-guide in contact with an eye during X-ray treatment, illustrating the effect on retinal position of motion of the eye angularly about the pivot of the eye guide. In this case, the eye and lens are pivoted through a small angular change da (see FIGS. 26C and 26D). Note that although the pivot is assumed here to be fixed, the eye motion is both in translation and in angular orientation. This can be seen to result in a motion both of the eye-guide lens fiducials (shown in the X direction, but generally in both X and Y), and in a larger motion of the retinal target in the same direction, due to the longer moment arm pivot-to-retina relative to the shorter moment arm pivot-to-lens.

Figure 31A:
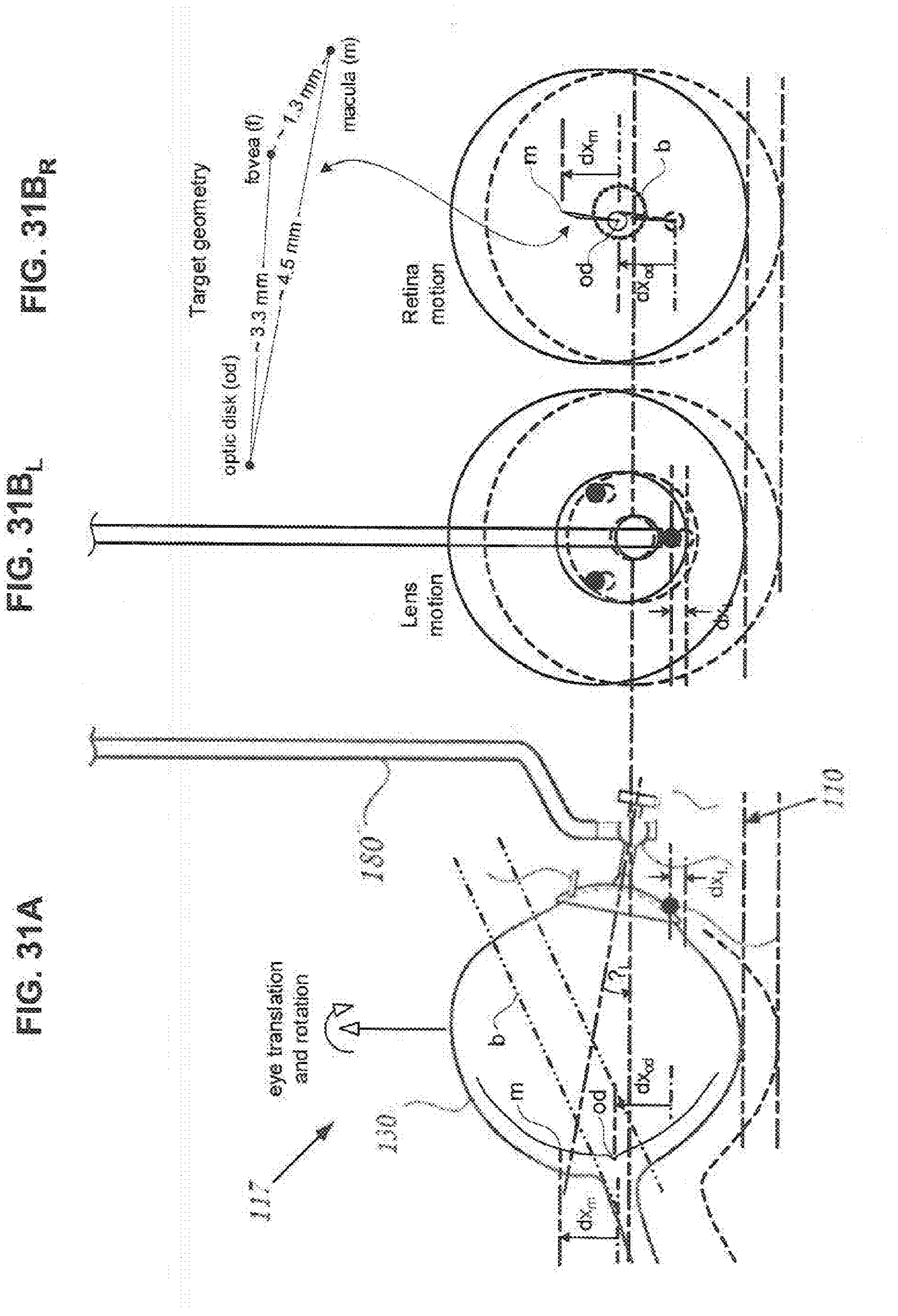

FIGS. 31A and 31B are a comparison between the lateral illustration of FIG. 29B (reproduced as FIG. 31A) and two frontal schematic views of a phantom eye, wherein FIG. 31$B_L$ shows frontal projection of lens movement, and FIG. 31$B_R$ shows frontal projection of corresponding retinal movement. Note that FIG. 31$B_L$ shows a relatively small movement lens fiducials relative to the movement of the eye body.

FIG. 31$B_R$ has a projection of retinal target geometry, as show more clearly in attached detail view, and shows retina beamspot b. Note that the motion of the retina in this example moves the optic disk (od) into the path of beamspot b, and move the macula out of the treatment beamspot, both undesired effects with respect to the exemplary treatment plan.

FIGS. 32-36 are diagrams depicting one example of a transformation procedure having aspects of the invention for converting detected input signals related to eye movements (see FIGS. 29-31) into corresponding movements of a beamspot relative to the retina. These figures relate to the example data shown in FIGS. 26A-26E.

Note that the set of input signals is only exemplary, and alternative measurement modalities and detectors may be employed without departing from the spirit of the invention. Likewise, the alignment and tracking system and the set of input signals shown in this example are presented by way of demonstration of certain inventive principals and aspects, and alternative measurement modalities and detectors may be employed without departing from the spirit of the invention. For example, the alignment of an eye-guide (e.g., 110 in FIGS. 17A and 17B) need not be determined by a beacon reflecting off a mirror, as shown in FIGS. 2 and 30, but may be determined by a variety of other tracking methods. In certain embodiments, one or more cameras linked to processing and pattern recognition software may be used to track motion of fiducials (e.g., located on eye-guide lens, supports, pivot post or on the patient eye), so as to determine geometric eye alignment and eye-guide position relative to eye anatomy.

Likewise, particular eye features may be tracked my such imaging methods independently of eye-guide structure (or without the use of an eye contact member), such as imaging of the limbus, a Purkinje reflection, a retinal image, and the like. See examples and description herein with respect to FIGS. 54-56. Eye position and orientation data from such non-eye-contact tracking systems (e.g., time sequenced values of eye geometric axis angles and eye X, Y and Z positions in a radiotherapy device coordinate system) may then be used to calculate target position and motion in the posterior or medial eye, such as the position of a fovea or macula target, e.g., by the methods illustrated and described with respect to FIGS. 29-36. For further examples and description, see the co-invented priority applications, such as Ser. No. 12/103,534 filed Apr. 15, 2008 and Ser. No. 12/027,083 filed Feb. 1, 2008; each of which is incorporated herein by reference.

Figure 32:
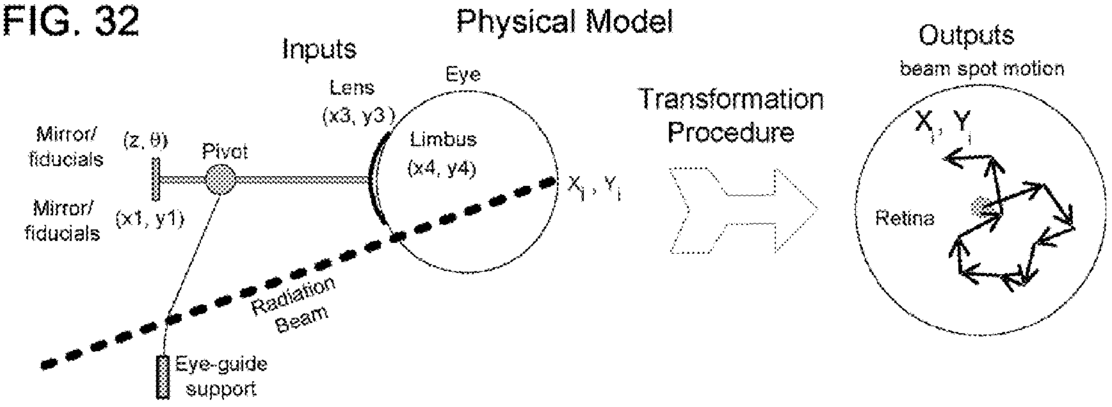

FIG. 32 is a diagram of a physical model of a transformation procedure. The figure shows on the left-hand side the eye-guide mounted on an eye relative to a radiation beam, with indications of input signals detected from fiducials and mirrors on the eye-guide lens, pivot post and/or support arm, and input signals from imaging of the limbus of the eye relative to lens. The figure shows on the left-hand side a diagram of the retina as an X-Y plane, on which are superimposed a time-sequence of the relative movements of the radiation beam-spot, each successive position indicated as $x_i$, $y_i$, where $(x_i, y_i)_t$ is a function of inputs.

Figure 33:
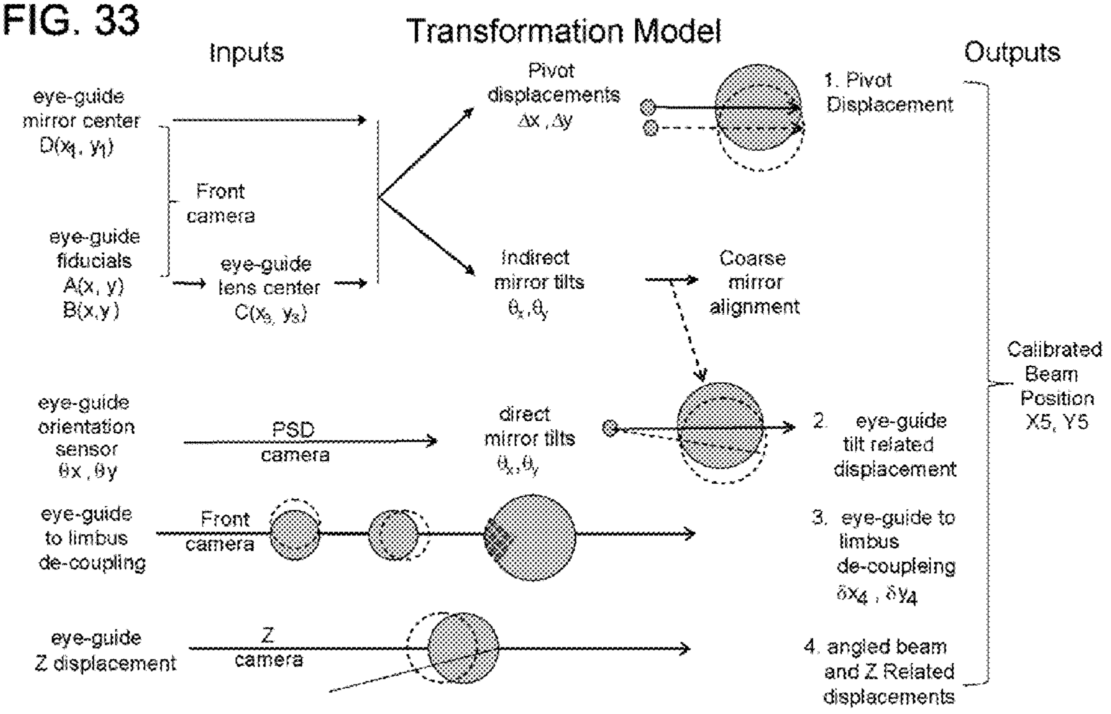

FIG. 33 is a diagram showing data flow from individual measurements to intermediate outputs, then to a final summation output. The inputs shown, and the detection methods are described above with respect to FIGS. 26A-26E. The input measurements may be performed at a selected acquisition update rate, for example about 10 Hz (or greater or less), with the incremental positions representing successive data acquisition cycles. As noted in FIG. 33, intermediate analysis from inputs produces for each input cycle:

(1) Values for pivot displacement in the X-Y plane, in turn reduced to corresponding components of retinal displacement.

(2) Values for eye-guide tilt angular components in the x and y directions, in turn reduced to corresponding components of retinal displacement by rotation on the pivot-to-retina moment arm.

(3) Values for eye-guide lens motion relative to the limbus of the eye (de-coupling), in turn reduced to corresponding components of retinal displacement; and (4) Values for eye-guide motion along the Z-axis, in turn reduced to corresponding relative motion of the intersection point of the retina with a fixed radiation beam path (a function of beam rotation θ and beam angle ϕ), which can be expressed as components of retinal motion in the X-Y plane.

(5) Summation of intermediate values (1) through (4) to produce output values expressed as x and y components of relative motion of the radiation beam spot on the retina, as depicted in the right hand of FIG. 32.

FIG. 34 illustrates schematically the relation between rotation of the eye-guide (see FIG. 18) measured as components of angular change or eye-guide tilt θx and θy (note that in this context, θ is distinct from radiation source rotation θ in FIG. 5), and offsets of the limbus of the eye relative to the eye-guide lens, measured as displacements in the x and y directions. The diagrams illustrate the components in the X directions, and the method is similar in the Y directions. Note that in certain embodiments, the eye-guide support (see FIG. 2) may be configured to be relatively rigid, so that the eye-guide pivot tends to remain stationary in the X-Y plane, and eye-guide tilt and limbus motion corresponds to head and eye motion as indicated in the diagrams. In certain embodiments, the eye-guide support may be hinged to permit a range of motion along the Z axis.

(1) The retinal displacement $x_0$ due to rotation about the eye-guide pivot is a function of the pivotal moment arm, which is the sum of the eye-guide pivot-to-cornea distance L and the axial length of the eye D (retina-to-cornea) and the angle change: $x_0=(D+L)*\tan\theta_x$. The vertical (Y direction) component is determined similarly.

(2a) In one modeling embodiment, the retinal displacement $\delta_x$ due motion of the eye relative to the eye-guide, detected as change in the position of the limbus boundary relative to the eye-guide lens (eye-guide decoupling), may be modeled as a rotation about a center of rotation which is approximately the center of the eye axial length or center of eye globe, such that the displacement at the retinal center is approximately equal to but opposite the displacement at the cornea (i.e., D,axial≈2 R,eye). Consequently, the equal lever arm results in: $\delta_x\approx 1*(x3-x4)$, where x3 and x4 are positions of lens and limbus respectively.

(2b) In an alternative modeling embodiment, the retinal displacement $\delta_x$ due motion of the eye relative to the eye-guide may be modeled as a rotation along the curved surface of the cornea, such that there is modeled a virtual center of rotation (radius of curvature of the corneal surface $R_c$). This may vary by patient and is typically substantially shorter than ½ the axial length. $R_c$ may be approximated empirically, e.g., D,axial≈$k_c*R_c$, where $k_c$ is from about 3 to about 4. Consequently, $\delta_x\approx(k_c-1)*(x_3-x_4)$.

(2c) In one sub-method embodiment, the models of (2a) and (2b) are combined using a weighting factor to determine an effective motion due to lens-to-retina relative motion: $\delta x\approx(k_e-1)*(x3-x4)$, where $k_e$ is a constant such that D,axial=$k_e$*Re (effective rotation radius), and $k_e$ is selected to be from about 2 to about 4 (e.g., $k_e\approx 2.25$). The vertical (Y direction) component is determined similarly.

(3) The combined effect of eye-guide tilt and limbus decoupling motion may be determined as the sum of these components in the X and Y directions, such that:

horizontal: $\Delta x=x0+\delta_x$ vertical: $\Delta y=y0+\delta y$.

FIG. 35 illustrates schematically the relation between displacement of the eye and eye-guide in the Z direction and change of intersection point of an angled radiation beam with a retinal target center. The diagram illustrates the component in the Y direction (for a beam angle β in the Y-Z plane), and the method is similar for components in the X direction where the beam is also angled in the X-Z plane). As may be seen, a displacement $\delta_z$ measured at the eye-guide implies an equal displacement of the retinal target along the Z axis. Although the position of the target in the X-Y plane is unchanged, there is relative motion of the "beam spot" formed by the angled radiation beam on the retinal surface, in effect a displacement of the beam spot in the X-Y plane, in this example indicated as $\delta_y$. The trigonometric relationship with respect to beam angle β may be expressed as $\delta y=\delta z*\tan\beta$.

FIGS. 36A and 36A show details of the formulas for conversion, in this case performed for each of three stereotactic beam paths aligned to a common target region, as shown for example in FIGS. 6 and 9. As shown in FIG. 36A, the formulas yield intermediate values which are then summed to yield collective horizontal and vertical components. Note that the beam alignments are indicated in shorthand notation as 5 o'clock, 6 o'clock, and 7 o'clock beams, referencing an exemplary treatment plan in which three beam rotational positions with respect to the treatment axis (angle θ in FIG. 5) are roughly 150, 180, and 210 degrees from the vertical respectively, while the beam angle with the treatment axis ϕ remains constant. While this has been shown by inventors herein to be an advantageous treatment plan in terms of minimizing dose to the optic nerve during application of a pattern of 3 overlapping macular treatment beams with pars plana entry points, alternative positions are, of course, possible. As shown in FIG. 36B, the individual x and y components of relative motion are functions of both angles θ and ϕ, and thus are computed with different constants of conversion.

As shown further in FIGS. 39-41 the incremental retinal beam spot positions determined as described in FIGS. 29-37 may be employed to "paint" incremental radiation dosage depositions on the representation of the retina in the phantom model. For example, experimentally and/or theoretically determined dosage distribution and irradiation rates for a fixed retina (e.g., a model distribution rate pattern in Gy/sec), may be adjusted for retina motion, and the cumulative radiation dosage distribution and levels to the actual moving retina may be accurately calculated in a real-time basis. As described further below, such real-time dose accumulation distribution may be used to modify the radiation treatment in progress. For example, irradiation may be stopped (gated), the eye-to-source alignment corrected, and irradiation may be resumed. Alternatively, the radiation source may be actively re-positioned to correct for any change in retinal alignment (e.g., "driving" the source to reduce and error function to zero). In another alternative, irradiation may be temporarily stopped, and resumed when retinal position is determined to have realigned by patient motion. This latter alternative has been shown by inventors herein to be convenient an effective for "blinking" type effects which may induce brief displacement transients, without greatly effecting overall eye alignment.

Figure 37A:
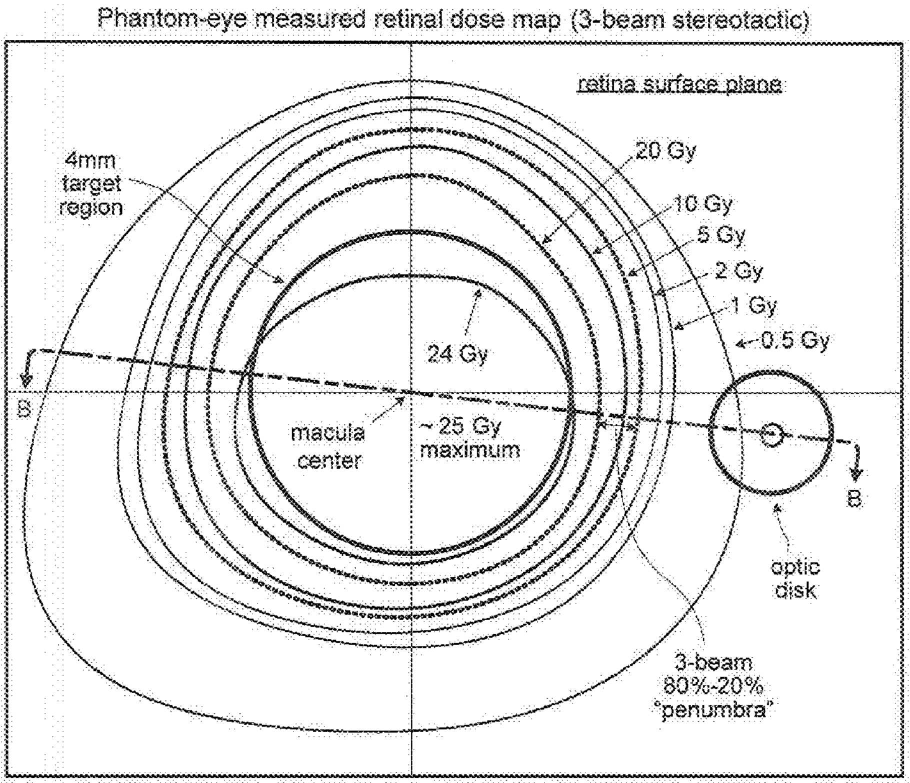
FIG. 37A-B are plots illustrating a stereotactic 3-beam dose map of retinal dose measured by radiometry on a phantom eye or mannequin.
Figure 37B:
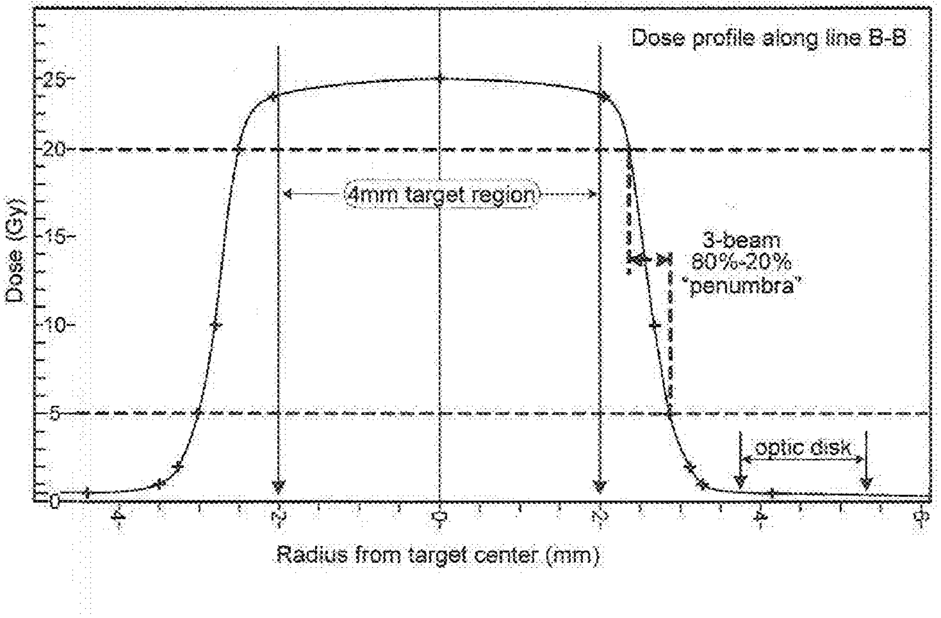

FIGS. 37A and 37B are plots illustrating a stereotactic 3-beam dose map of retinal dose measured by radiometry on a phantom eye or mannequin (by optical density analysis of the exposed film), without eye motion, as described herein, which serves as a basis for comparison for the eye motion modulated examples shown in FIGS. 39-41. Note the beam trajectories are substantially as shown in FIG. 9.

The contour dose map of FIG. 37A shows that the 4 mm target region lies entirely within the 80% isodose (20 Gy based on a maximum level of ~25 Gy). Indeed the area of the 24 Gy isodose (about 96%) is roughly co-extensive with the 4 mm target region. The optic disk lies entirely beyond the 1 Gy isodose, and thus receives substantially less that 4% of the maximum dose. Note that while the term "penumbra" is used herein specifically to refer to dose distribution from a single collimated beam, it is instructive to note the concept as applied to a stereotactic multiple beam dose map, and an 80%-to-20% isodose cumulative "penumbra" is indicated in FIGS. 37A-B as the span between the 20 Gy isodose and the 5 Gy isodose, based on a maximum dose level of approximately 25 Gy. Note that dose levels may vary substantially depending on treatment plan particulars. For example, a particular treatment plan may provide for a mean dose level within a retinal target region of less than about 8 Gy; or about 16 Gy; or about 24 Gy or more, depending on specific medical goals to the treatment. Likewise, treatments may be repeated at selected time intervals for fractionation purposes, without departing from the spirit of the invention.

Figure 38A:
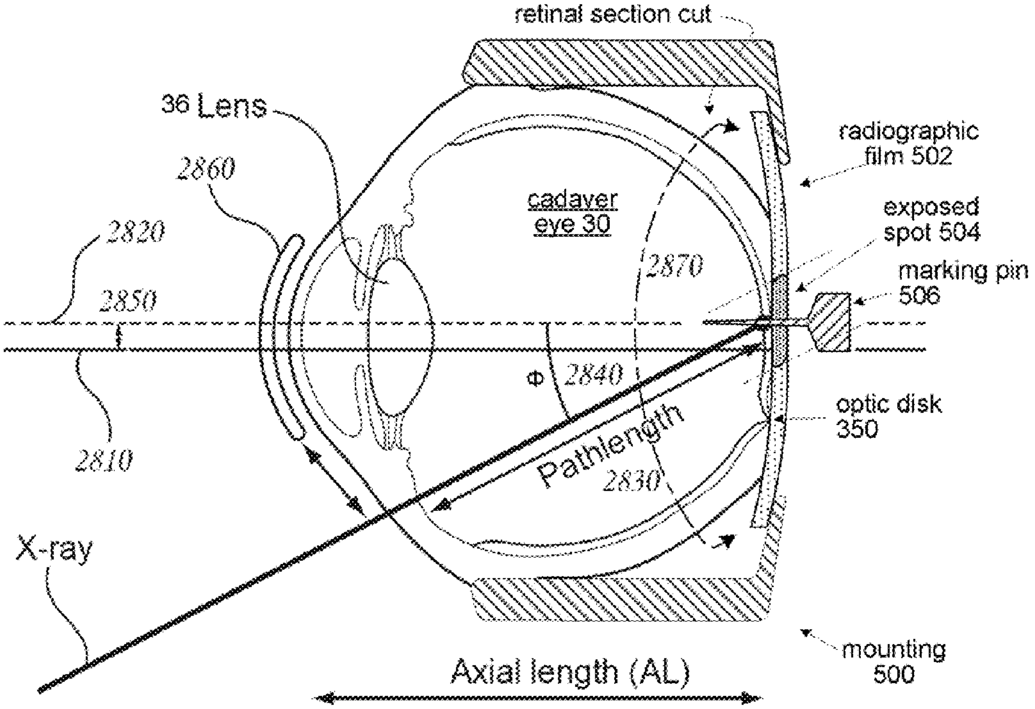
FIGS. 38A-B depicts a method of confirming an exemplary radiotherapy treatment plan having aspects of the invention using radiographic measurements on a cadaver eye.
Figure 38B:
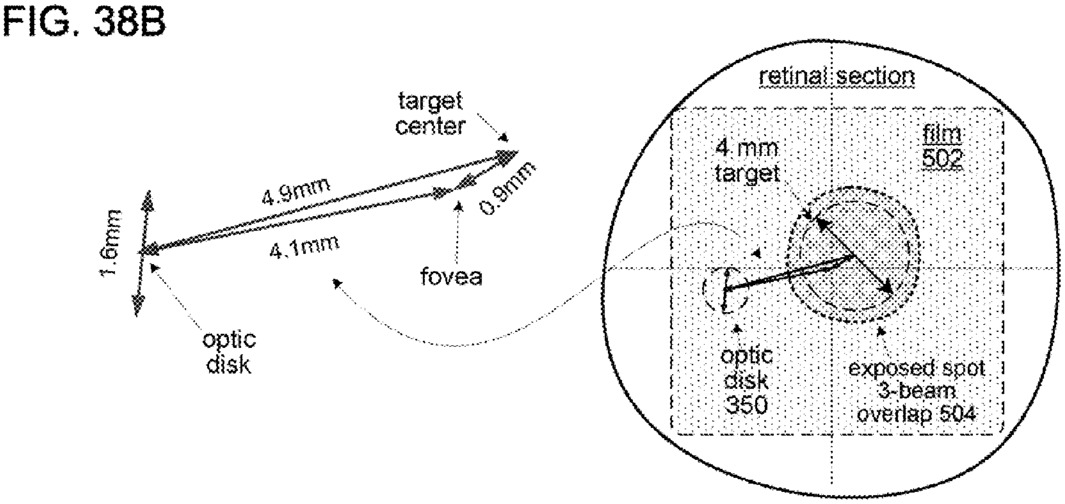

FIG. 38B is a plotted dose profile corresponding to the line B-B in FIG. 37A, which is a transect through the target center and the optic disk center. This profile provides a clear illustration of the isodose fall-off in the "penumbra" region, decreasing rapidly to a low value at the margin of the optic disk.

Figure 37C:
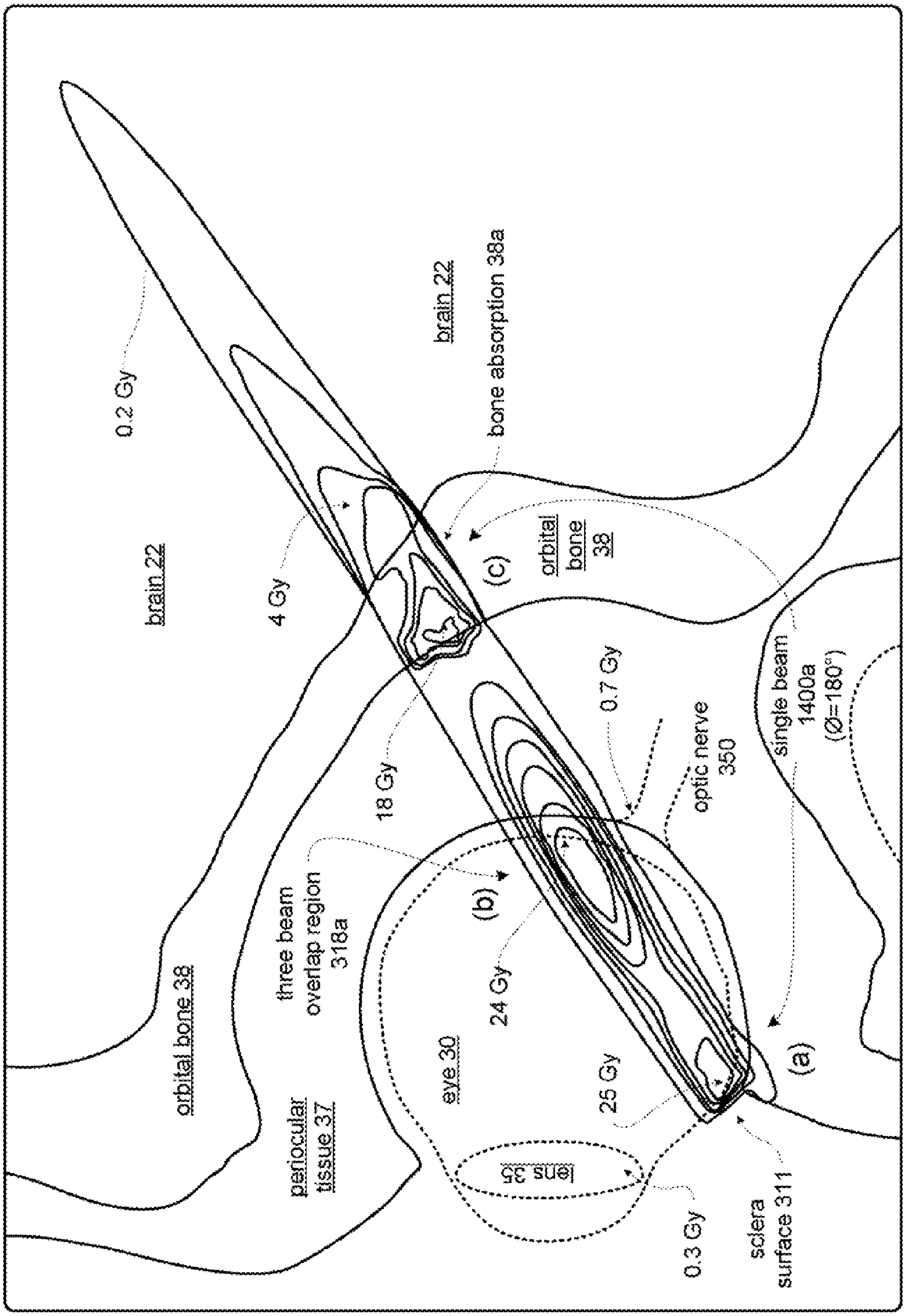
FIG. 37C is a dose distribution plot prepared by means of Monte Carlo numerical radiation transport simulation employed in conjunction with a tissue-characteristic model derived from human anatomy revealed in CT scan imagery.

For purposes of comparison, FIG. 37C illustrates dose distribution in tissue both anterior and posterior to the retinal plane mapping of FIGS. 37A and 37B. FIG. 37C is a dose distribution plot prepared by means of Monte Carlo numerical radiation transport simulation (see methodology re FIG. 13A) employed in conjunction with a tissue-characteristic model derived from human anatomy revealed in CT scan imagery. The mapping of FIG. 37C is a vertically-oriented planar cross-section taken through the treatment axis 2820 (see FIG. 21E), which corresponds with the plane containing a central treatment beam path (beam 1 at θ=180 degrees in FIG. 21E). The model includes the lens 35 and optic nerve 350 of eye 30, the globe being surrounded by particular tissue 37 within boney orbit 38, and showing tissue of brain 22.

The mapping includes radiation dose contribution 1400*a* from central beam 1 as well as radiation applied at the cross-sectional plane from two angled stereotactic beams (beans 2 and 3 in FIG. 21E,) which are directed so as to intersect the plane of the mapping only in a region adjacent the central retina ("3-beam overlap" region 318*a*). The Monte Carlo simulation showed dose level at selected structures as noted in Table 1 below:

TABLE 1

| Dose at Selected Structures | |
|---|---|
| Structure | Dose (Gy) |
| Lens | 0.3 |
| Optic Nerve | 0.7 |
| Cornea | 0 |
| Sclera | 25 |
| Brain | 4 |
| Orbital Bone | 18 |
| Macula | 24 |

Three Beams Delivering 24 Gy To Macula

The isodose contours of FIG. 37C illustrate three principal regions of higher dosage:

(a) the scleral surface area 311 (25 Gy), which represents only the single central beam 1, since angled beam 2 and 3 have distinct and separated entry regions;

(b) the 3-beam overlap region 318*a* (24 Gy at the macula) in which each beam makes an approximately equal contribution; and (c) high absorption by comparatively dense orbital bone (18 Gy), which again represents only the central beam. Note that in part due to higher bone absorption and consequently reduced penetration beyond, the residual dose to the surface of the brain is only about 4 Gy, diminishing rapidly to a small fraction of a Gy at depth.

FIG. 37C illustrates a treatment method and device having aspects of the invention, for radiation treatment to a retinal target, including providing a positionable orthovoltage X-ray source configured to emit a tightly collimated X-ray beam, the beam emitted on a path that avoids both the lens and optic nerve of the eye, the beam being filtered so that surface dose fraction is minimized relative to a retinal dose fraction, the beam also having a maximum photon energy low enough to minimize the dose fraction penetrating deeper than the boney orbit of the skull.

VH. Radiometric Confirmation of Eve Alignment and X-Ray Dose Targeting

FIGS. 38A and 38B depicts a method of confirming an embodiment of a radiotherapy treatment plan having aspects of the invention. FIG. 38A illustrates a cadaver eye 30 which has been fixed in a mounting 500, configured to be aligned with radiotherapy system 10 using a suitable mechanical support (not shown) in generally the manner and orientation shown in FIG. 3B. The mounting 500 positions the cadaver eye as, in effect, a phantom eye for purposes of confirming both eye alignment method and the dosimetry of the treatment system. FIG. 38A shows that the cadaver eye 30 has been partially dissected to expose the tissue adjacent the posterior retina, so as to permit a backing of radiographic film 502 to be positioned behind the eye parallel to the retina.

The procedure includes the following: The eye in mounting 500 with film is mounted in the eye alignment and stabilization system 625 (see FIGS. 2 and 16 for example) by a suitable mechanical support (not shown), and the eye is aligned using the methodology described with respect to FIGS. 21A-21E, is the same general manner as the alignment of the eye of a human patient. The eye-guide (represented by eye-guide lens 2860 in FIG. 38A) is applied to the cornea so as to be centered on the limbus, vacuum suction is applied, and X-ray source 420 is moved into treatment position as shown in FIG. 3B. As with the treatment plans described herein, the X-ray beam is aligned to a treatment axis 2820, which is positioned relative to eye geometric axis 2810 by a pre-determined offset 2850.

A series of three treatment beams are applied to eye 30 (see FIGS. 9-10), so as to expose the radiographic film 502 adjacent the retina so as to produce an exposed spot 504 indicative of the target absorbed dose distribution. The radiographic film is formulated to produce a visible spot, permitting a marking pin 506 to be inserted through the film into eye 30, in this example at the center of spot 504, so as to register and maintain the orientation of the film 502 as exposed with the eye tissue.

Eye 30 is then dissected along a retinal section as shown in FIG. 38A to expose a the posterior retina, registered to the exposed film 502. The flattened retinal superimposed on exposed film is depicted in FIG. 38B. The retinal geometry is shown in the detail on the left at the left, the retinal dissection shown schematically on the right view of the figure. As may be seen, the exposed film spot 504 is substantially centered on the macular target, covering the 4 mm target region. The spot 504 is also substantially separated from the optic disk 350. The geometry of dosage may be compared with the phantom mannequin dose map of FIG. 37A.

The procedure thus confirms the effectiveness of the eye alignment method and ocular targeting methods having aspects of the invention, by demonstrating that the applied radiation dose is targeted to the macular tissue (and avoiding the optic disk), as provided by the treatment plans described herein.

Patient Study Results

FIGS. 39A-39E are plots showing the extrapolated retinal motion based on the eye motion data of FIGS. 26A-26E. The computed retinal motion was used to modulate the 3-overlapping beam dose map derived from a mannequin study shown below in FIGS. 37A and 37B.

Note that preferably such extrapolations are carried out automatically by a digital processor as the eye motion data is acquired, more preferably in real-time. It will be apparent to one of ordinary skill in the art how this can be done without undue experimentation.

Figure 39A:
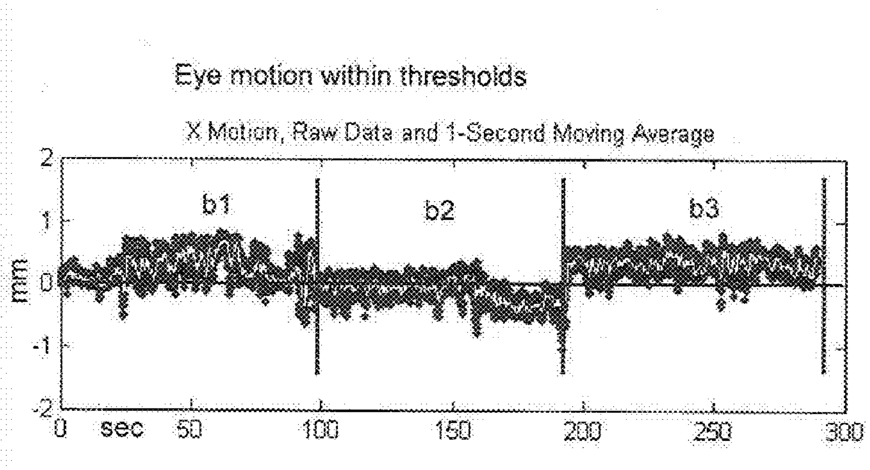
FIGS. 39A-E are plots illustrating retinal motion determined form the eye motion measurements shown in FIGS. 16A-E, and showing the effect on radiation dosage absorbed on the retina.
Figure 39B:
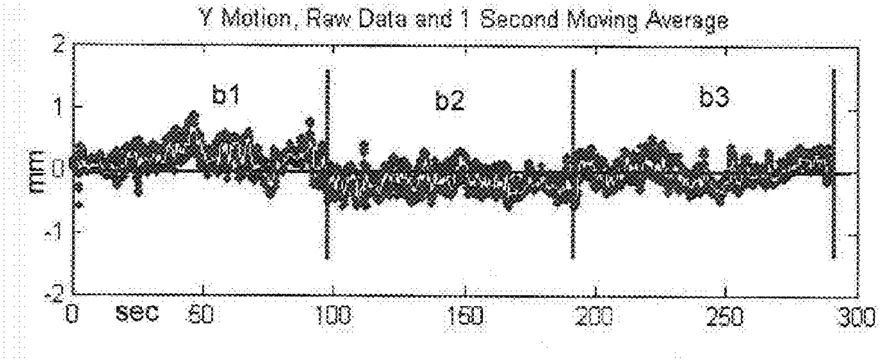

FIGS. 39A and 39B show the X and Y components of actual patient retinal motion for a period of about 5 minutes. This data is presented as a simulated model for an X-ray treatment procedure (no irradiation of human patients was performed in acquiring the eye motion data presented in FIGS. 26-41). The duration has been divided into three segments representing stereotactic beam applications. The eye-guide has been assumed to be re-aligned with the treatment system coordinate system after each repositioning of the X-ray source, i.e., twice during the 5 minute duration, indicated as b1, b2 and b3 on the plots.

The plots include both complete data (broad band) and also 1-second filtered or averaged motion plotted on the same axis (narrow center plot). Note that the eye tracking system can have a selectable update rate. In the example case, the imaging system update rate was about 10 Hertz, resulting in about 3000 samples in the 5 min. duration. In general, the data shows a saccadic eye motion or jitter, of high frequency and low amplitude, which tends to spread the raw data to a broader band. The short period filtering makes trends in eye motion more apparent. In addition, the data are computed wherein the retina is treated as flat.

Figure 39C:
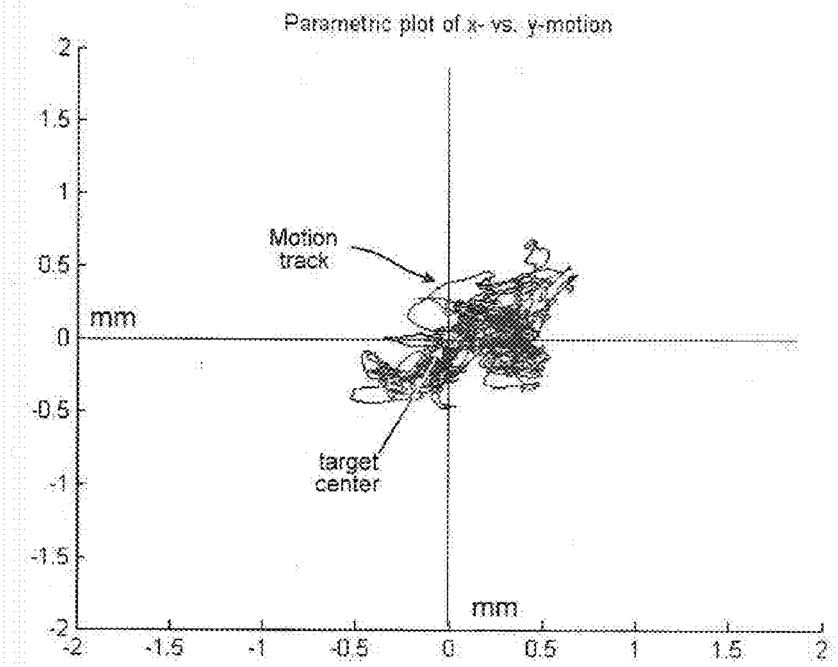

FIG. 39C is a parametric plot of the data of FIGS. 39A and 39B, and graphically depicts the departures of the retina from the target center, in both X and Y directions. It may be seen that nearly all the motion, weighted by duration, remains within about a 0.5 mm radius of the target.

Figure 39D:
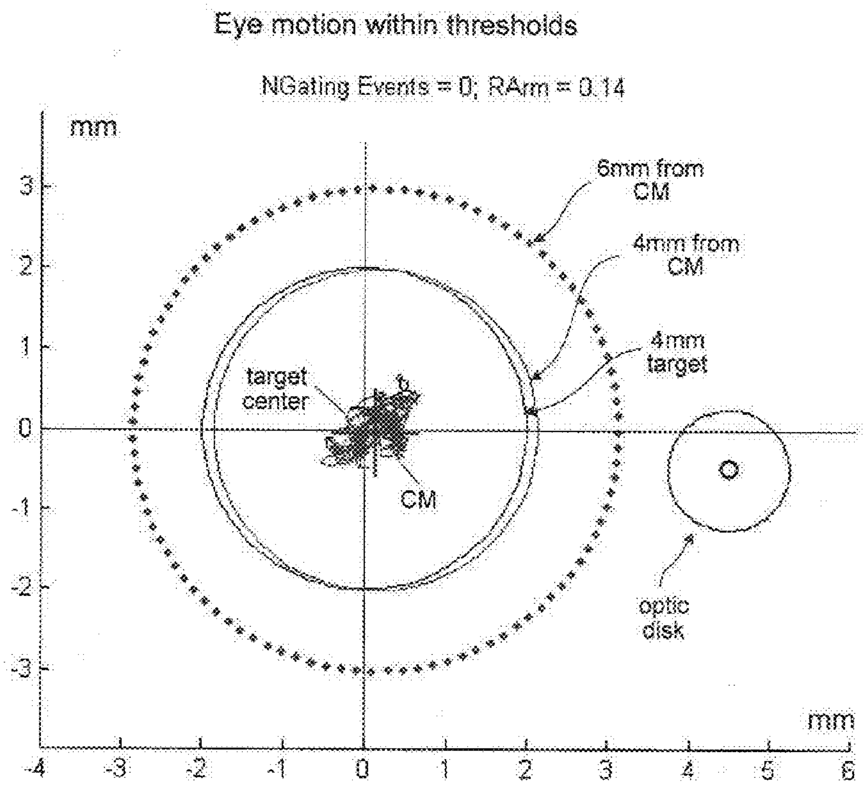
Figure 39E:
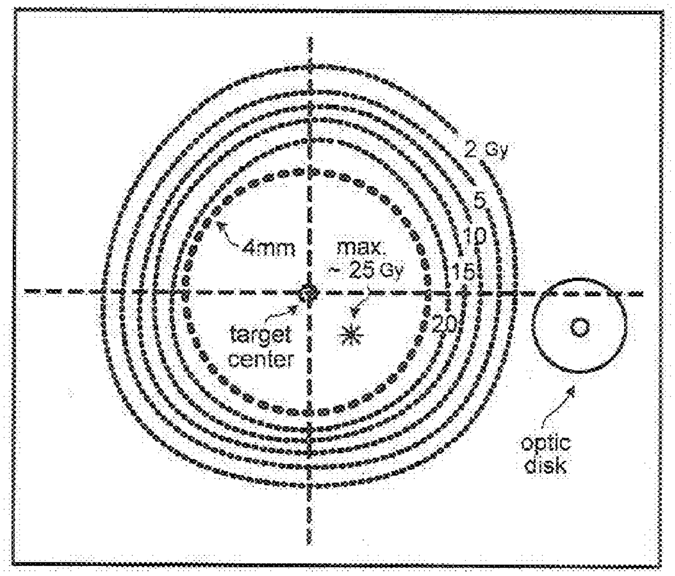

FIG. 39D is a plot similar to that of FIG. 39C and showing retinal geometry of the optic disk as well as indication of a planned treatment target as a 4 mm circle about a target center. A center of mass CM was computed based on the retinal motion, weighted by duration in position, to yield a cumulative indicator of shift of radiotherapy dose application. For convenience, 4 and 6 mm circles about the CM are shown, the 4 mm circle about CM being directly comparable with the 4 mm circle about the target center (the equivalent with no motion). It may be seen that the shift of the CM is less than about 0.2 mm, and in the adverse case (shift towards optic nerve), makes little difference in the dosage pattern.

FIG. 39D is a dose map based on the data of FIG. 39D and employs date for a non-motion X-ray study using a simulated eye (mannequin model assuming perfect alignment, no motion), the X-ray study data being used to assess the tissue absorbed dose distribution implied by the actual eye motion of the patient study. Isodose contours are shown for gradations from maximum level (about 24-25 Gy), to a inner fall-off boundary of 20 Gy (80% isodose), and outer beam spot boundary of about 5 Gy (20% isodose), and a lower scattered boundary of 2 Gy.

In an example of a radiotherapy treatment plan having aspects of the invention, it is desired to maintain a dose of between 25-20 Gy within about a 4 mm treatment target centered approximately on the fovea, and to maintain less than about 5 Gy outside of a 6 mm treatment region around the target center. In addition the example treatment plan includes avoiding greater than about 2 Gy dosage, and preferably much less, to the optic nerve and optic disk.

It can be seen the motion-modulated dose map of FIG. 39D achieves the treatment plan goals with realistic patient motion data, by use of the eye-stabilization system having aspects of the invention.

VI. GATING CONTROL AND ALGORITHMS

This section details various methods and algorithms by which the processor in the system controls total beam exposure, e.g., intensity and duration, in response to eye motion position detected during therapeutic treatment.

VI.A. Eve Position and Exposure Control

FIGS. 40A-40H are plots showing the extrapolated retinal motion of a patient in which a consistent pattern of side-drift was noted. The eye-motion data was of the same nature as shown in FIGS. 26A-E, and acquired by the same methods and with the same eye-tracking devices, but in a the case of a patient exhibiting different eye motion behavior. In these plots, generally the same methodology and presentation is used as in FIGS. 39A-39E, and the following discussion will focus only on differences.

Figures 40A, 40B, 40C:
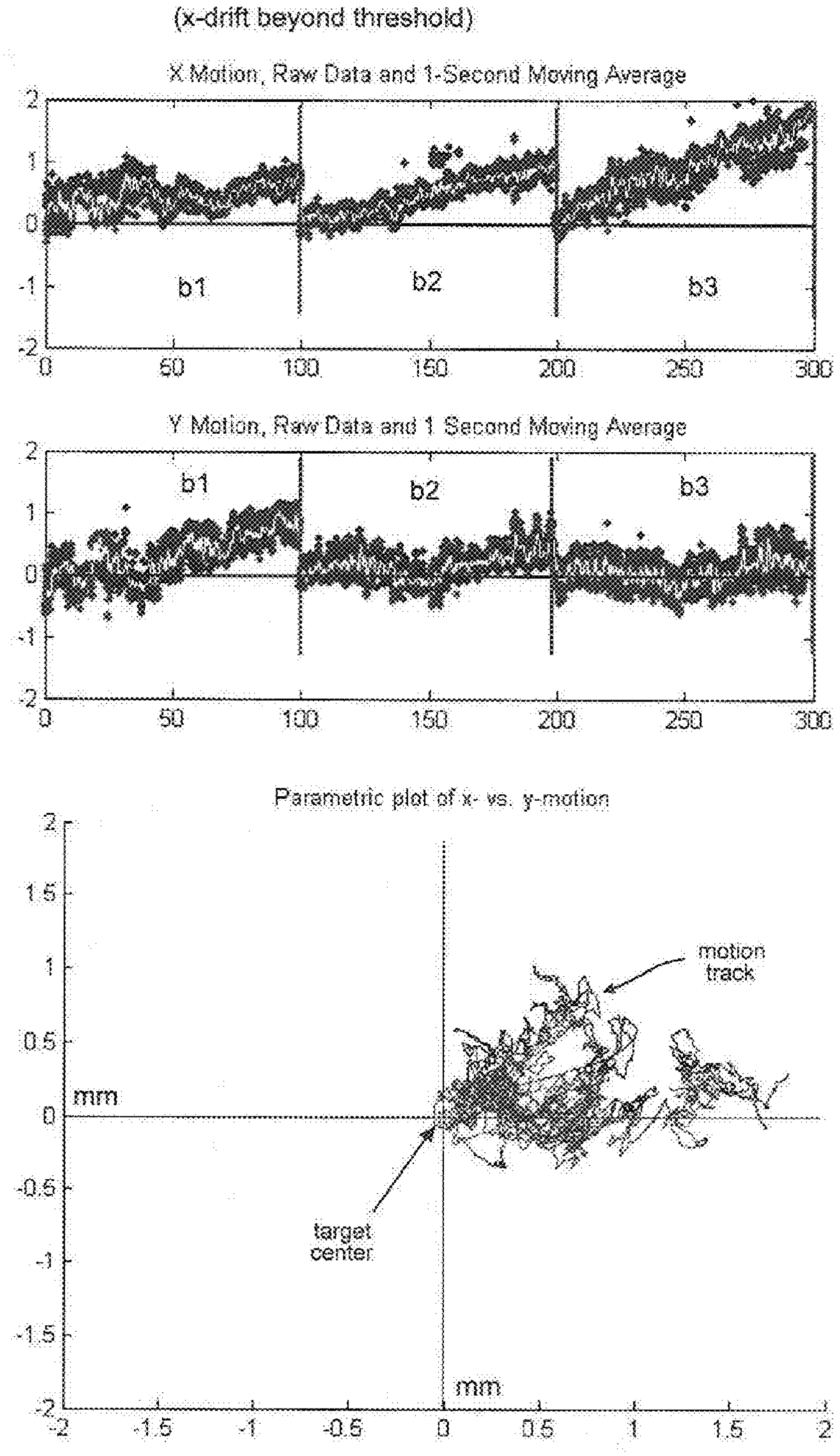
FIGS. 40A-H are plots illustrating retinal motion determined form the eye motion measurements, and illustrating a method of preventing unplanned radiation dosage to the retina by gating the X-ray source and realigning the eye stabilizing system.

FIGS. 40A and 40B show the X and Y components of a patient's retinal motion for a period of about 5 minutes, divided into three "beams" as described above. It can be seen that there is at trend to a relatively large shift in X direction, due to motion of the patients head and rotation of the eye-guide lens about the pivot point. The deviations vertically are relatively small, but the horizontal deviations of the retina exceed 1 mm for substantial periods. FIG. 40 C show a parametric plot of the motion.

Figure 40D:
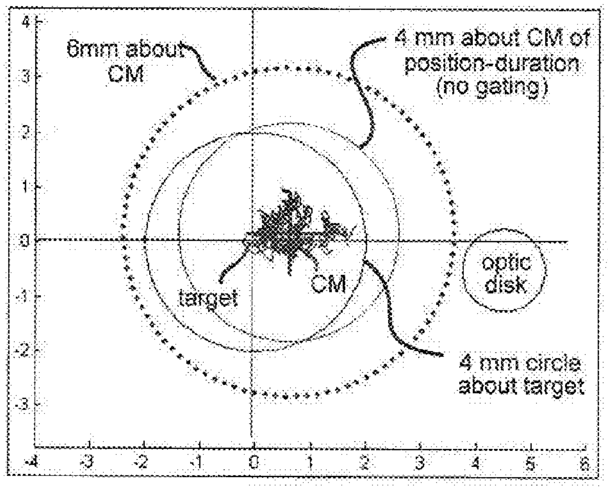
Figure 40E:
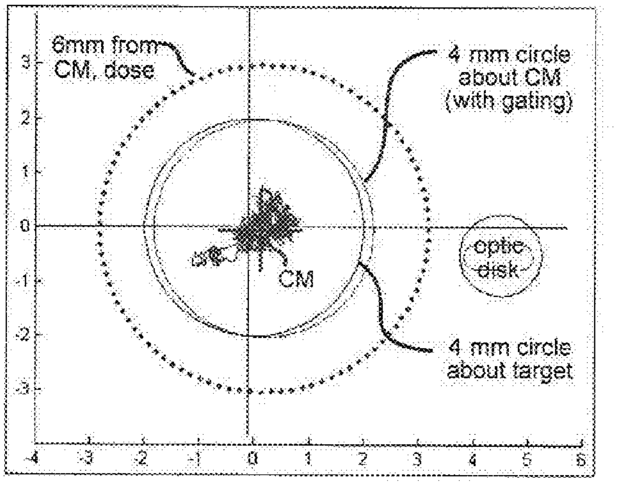
Figure 40F:
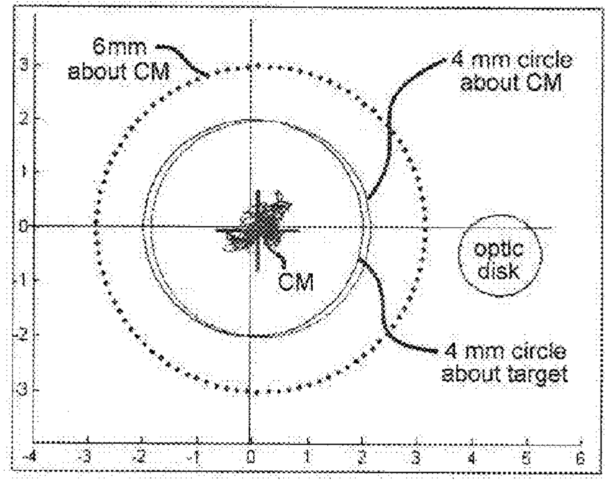

FIGS. 40D-40F are three CM shift plots made in the manner of FIG. 39D wherein of FIG. 40D shows the uncorrected drift data, FIG. 40E shows compensated data as described below, and of FIG. 40F is a reproduction of FIG. 39D for purposes of comparison.

FIG. 40D shows that the CM of the motion-duration of the data of FIGS. 40A and 40B is shifted about 0.75 mm from the target center, and that the 6 mm circle is shifted to extend close to the optic disk.

FIG. 40E shows that the CM of the motion-duration following a drift compensation procedure with employs a "Time-Displacement Moment" analysis to trigger gating (shutting off) the X-ray source (simulated here), followed by realignment of the patients eye with the system alignment axis. An example procedure includes:

a) Defining a Time-Displacement Moment vector such that TDM=(Displacement from center)*(Time away from center). This is less sensitive to brief, large displacements than long lingering ones.
b) In exemplary treatment system embodiments, the dose rate is relatively low (about 4 Gy per minute) which allows time to respond to deviations by gating.
c) Defining a gating threshold for a selected magnitude of the cumulative TDM, which is the trigger point for gating. A "Spring constant" term may be included to dampen or adjust sensitivity. In one example, the threshold is selected to prevent CM deviation from exceeding about 0.2 mm from target center. A larger or smaller threshold may be selected.
d) Realigning the patient and treated eye to system coordinates (a) following beam repositioning, simulated here by ⅓ of treatment period, and (b) following gating of X-ray source per criteria.
e) Resuming treatment, extending the treatment period as needed to obtain full treatment dosage.

A comparison of FIGS. 40E and 40F shows that the drift compensation procedure (in this case 5 gating events within the 5 minute treatment period) results in a CM offset much reduced, and comparable to the data of a patient without systematic drift.

Figure 40G:
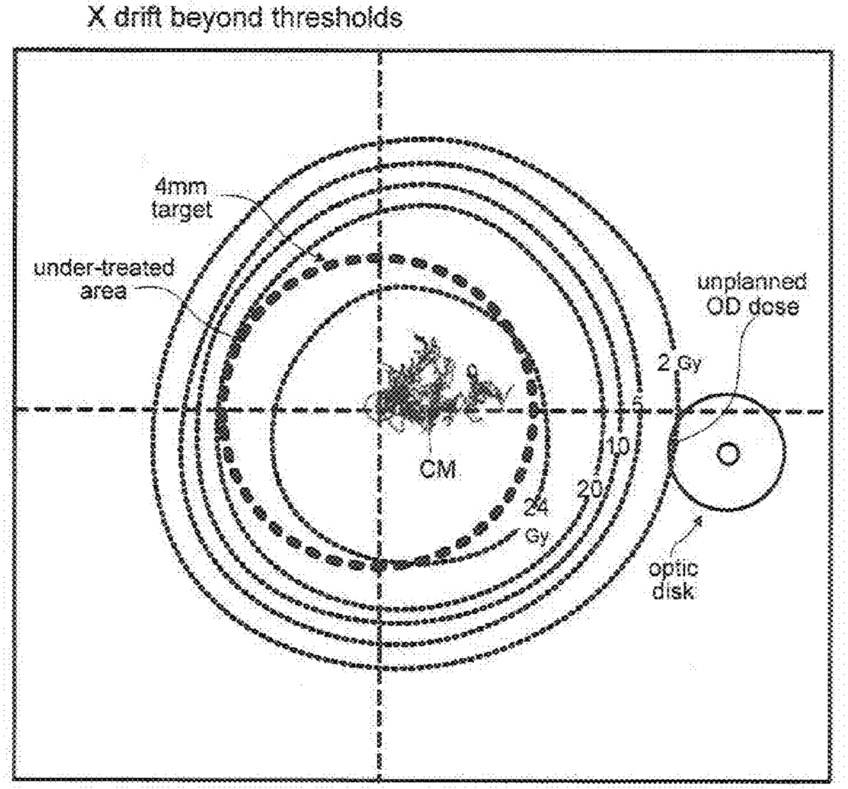
Figure 40H:
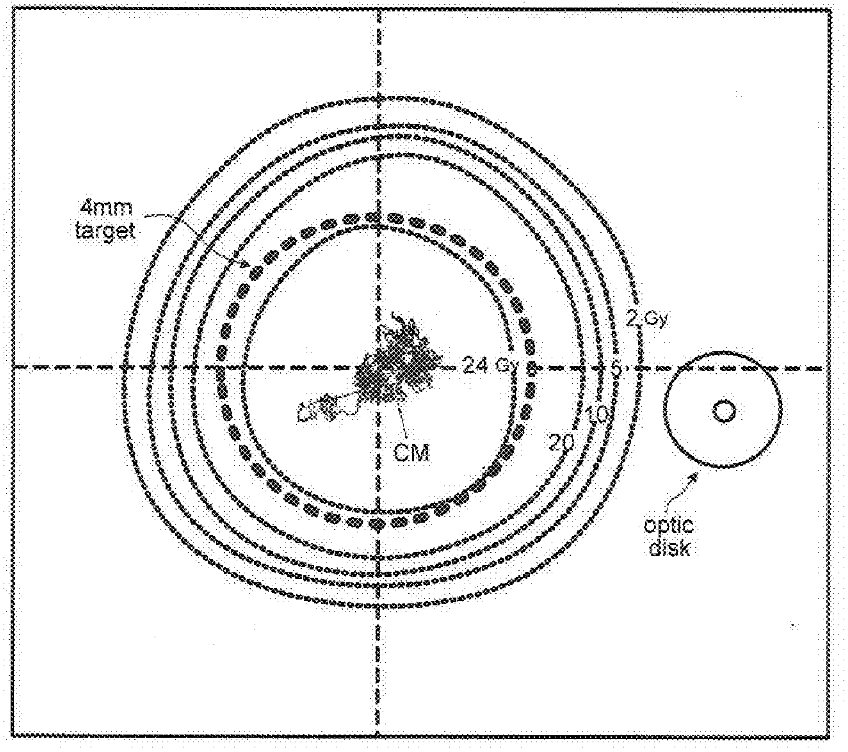

FIGS. 40G and 40H are uncompensated and compensated dose map plots corresponding to the data of FIGS. 40D and 40E. Note that in FIG. 40G shows both an under-treated area, the 20 Gy isodose only marginally encompassing one side of the 4 mm target circle, and unplanned doses exceeding 2 Gy to portions of the optic disk. Both of these effects are avoided by the gating-realigning procedure, as shown in steps 2565, 2540 of FIG. 21A.

VIB. Motion-Based Gating Algorithms.

Method and device embodiments having aspects of the invention provide for a figure of merit for the displacement of radiation dosage "center of mass" from a target center, based on tracking of retinal motion relative to beam center in X and Y components (nasal-temporal and cranial-caudal respectively). This may be configured to accept small excursions from target center, but will prevent lingering large excursions, and may be configured to provide enhanced protection for sensitive structures, such as the optic nerve. Note that alternatively or additionally, generally similar method and device embodiments may be used to track a radiation beam path relative to other anatomical structures, such as the cornea or the lens of the eye.

In experiments by inventors herein, relevant eye motions have been shown to typically fall into certain categories: (a) high frequency jitter (+/−x and y directions); (b) steady directional drift for extended periods; and (c) large-magnitude, short-duration excursions, (e.g., blinking+/−y direction), generally not changing long duration alignment. Small positive and negative changes without cumulative drift result in a modest "spreading" of the beam spot, but typically are not problematic.

Linear Response Algorithms:

Advantageously, with respect to (b) steady drift, a "center of mass" or CM vector representing cumulative deviation may be defined, where the incremental contributions to the vector sum have the components:

$$Q_x=x_i*dt$$

$$Q_y=y_i*dt$$

Where $x_i$=x displacement [mm] at sample time $y_i$=y displacement [mm] at sample time dt=time [s] between samples (e.g., sample rate of about 1 to about 50 Hz)

Optionally, alternative embodiments may include smoothed data to suppress high frequency "jitter" (e.g., 1 sec. average values for 30 Hz sample rate to yield equivalent xi, yi values for dt=1 sec).

Additional attributes may include:

CM(sumQx, sumQy)=running vector sum of X and Y components, where:

magnitude is distance from target center=SQRT (sumQx^2+sumQy^2)

direction is the angle arctan(sumQy/sumQx).

Gating/realignment criteria=threshold CM magnitude=CM*k k is an adjustable constant to define gating sensitivity: k="spring constant" [Gy/mm/s].

CMmax=CM for total treatment time, final of vector summation (with or without gating/realignment during treatment).

magnitude may define a general beam-target registration error (TRE).

direction may be used to analyze dose to and/or protect particular structures.

In the embodiments described in detail, re-orientation of the X-ray source/collimator may be done quickly and quietly by an automated positioner under operator monitoring, and it is preferable to continue treatment with successive stereotactic beams without necessarily realigning the treated eye relative to the system coordinates. In this method of practice, the realignment is performed only when gating occurs pursuant to pre-established displacement vector criteria.

In other alternative embodiments, a separate calculation may be performed to enforce a maximum clearance of CM from a vulnerable structure (e.g., separately tracking the component of CM in the direction of the optic disk, with gating at a clearance threshold). Likewise, further alternative embodiments may include real-time dose mapping to vulnerable structures (e.g., optic disk, cornea, lens, etc.) using data such as is depicted in FIGS. 37A and 37B. Gating and realignment may be performed when a dose threshold is re Note that in some commercially available X-ray tubes, a bias grid may be included providing for rapid quenching of the electron flux by field neutralization. In others, the high voltage power supply may be switched to provide an effective gating response.

Non-Linear Response Algorithms:

In alternative method and device embodiments having aspects of the invention, a non-linear algorithm may be employed, which provides an adjustable weighting to provide greater response to large deviations than small deviations. As with the linear algorithm described above, a modified "center of mass" vector representing a non-linear accumulative deviation factor (AF) may be defined, where the incremental contributions to the vector sum have the components:

$$Q_x=k*(x_i)^n*dt$$

$$Q_y=k*(y_j)^n*dt$$

Where k=sensitivity constant which adjustably scales components to optimize treatment (e.g., k=1 to about 5). Note that sensitivity may also be adjusted as a factor in the Gating Criterion.

$x_i$=x displacement [mm] at sample time $y_i$=y displacement [mm] at sample time n=selected exponent (e.g., n=1 to 3, such as 1 for linear, 2 for quadratic, etc.)

dt=time [s] between samples

Note for a quadratic form (n=2), the weighting of the incremental contribution is proportional to the square of the instantaneous displacement (e.g., $Q_x$ (2 mm)=$^4$*$Q_x$ (1 mm)), thus placing an emphasis on large drift magnitudes, with less emphasis on minor fluctuations near zero. To avoid directional ambiguity, the sign relative to a zero axis of the displacement may be accounted for in a vector summation where n is an even integer, e.g., n=2, where sign(x)=x/|x|, and thus ±1, such as:

$$Q_x=\text{sign}(x_i)*k*(x_i)^n*dt$$

$$Q_y=\text{sign}(y_i)*k*(y_i)^n*dt$$

The accumulation factor may be integrated over time as AF(sumQx, sumQy)=vector sum of X and Y components, where:

magnitude=SQRT(sumQx^2+sumQy^2), which represents a non-linear target offset.

direction=arctan(sumQy/sumQx), which is an angle in x/y coordinates lying within the retinal surface plane.

AF(total or terminal)=final cumulative value of AF at end of treatment, may be considered to define a target registration error (TRE) for the treatment.

The gating criterion may be formulated in a number of alternative ways. In one example, a maximum value for AF offset (MaxDist) may be selected which can be deemed acceptable if maintained for the entire treatment period as a constant value (e.g., from about 0.1 mm to about 1.0 mm, and preferably about 0.2-0.4 mm), such as Gating Criterion=MaxDist*TreatmentTime.

An additional or alternative sensitivity factor or constant may be applied to the Gating Criterion, such as Gating Criterion=MaxDist*TreatmentTime/SensitivityFactor. For example, the gating sensitivity may be made more/less conservative by adjustment of the sensitivity factor. For example, the Sensitivity Factor may be about 3.

The treatment factor may also be adjusted in response to a typical or mean target registration error (TRE) for a patient population. Simulated treatments (non-radiation with real eye stabilization/tracking) have been used by inventors herein to gather patient population data to assist in establishing gating criteria. For example, a reasonably conservative MaxDist may be established initially for a treatment plan, which may result in infrequent gating events for an acceptable TRE. Population experience may show that improved treatment accuracy is possible without excessive gating (e.g., up to about 21-5 gating events per treatment), and thus the SensitivityFactor may be increased to lower the achieved mean TRE. Similar adjustments may be made to other computational factors, such as the exponent n.

One approach to determining a maximum distance or value (MaxDist) for the accumulation factor (AF) is an estimated error analysis. For example, the distance from idealized "no error" beam edge to a vulnerable structure, such as the optic disk, may be determined from measured collimated beam characteristics and typical patient ocular anatomy. For example, with reference to FIGS. 37A and 37B, the distance or structure clearance from the penumbra edge to the optic disk edge might be estimated to have a mean value of 0.75 mm or 750 microns. Likely sources and magnitudes of potential error may be then be identified, including a proposed value forMaxDist. For example, three sources of potential error and a representive maximum magnitude may be considered: (a) I-Guide lens-to-limbus centering (~0.4 mm), (b) positioning system targeting error (~0.4 mm), and (c) eye motion effects (~0.4 mm). An RMS value of these three sources can be estimated as SQRT $(0.4^2+0.4^2+0.4^2)$=0.69 mm. Since this is within the structure clearance of 0.75 mm, the proposed value of MaxDist of 0.4 mm (400 microns) appears reasonable.

Motion-Based Radiation-Equivalent Parameters.

Note that alternative mathematical and statistical algorithms than those described herein may be used to define accumulated displacement factors and gating/realignment criteria serving the same medical treatment goals, without departing from the spirit of the invention.

As may be seen from the above examples, a motion-based parameter, such as a targeting error accumulation factor, may be defined, without calculation of actual radiation absorption, to function as an equivalent or surrogate for radiation dosage distribution on a treatment target (e.g., a defined macular region) or a sensitive non-target anatomical structure (e.g., the optic disk). Known radiation properties of a treatment beam (e.g., a calibrated isodose rate and distribution in beam cross section) may be used to determine equivalency. Thus a known beam dose intensity (e.g., in Gy/sec at retinal tissue-depth) may be used to select a motion-based property reliably associated with radiation effects.

A software-processor-based treatment system controller may calculate such an eye motion-based radiation equivalent parameter (e.g., AF in examples herein) and monitor this parameter relative to pre-determined numerical thresholds. The motion of a target and/or sensitive structure may be detected directly (see discussion FIGS. 49-52); or determined by an extrapolation algorithm based on overall eye motion (as in FIGS. 29-36).

Alternatively, a software-processor-based treatment system controller may calculate actual radiation dose distribution at targets and/or sensitive structures (see methods with respect to FIGS. 37A and 37B), taking into account of the effects of the detected motion of the eye. Threshold for gating (or other motion compensation) may be based on specific radiation dose levels.

VIC. Gating Examples

Figure 41A:
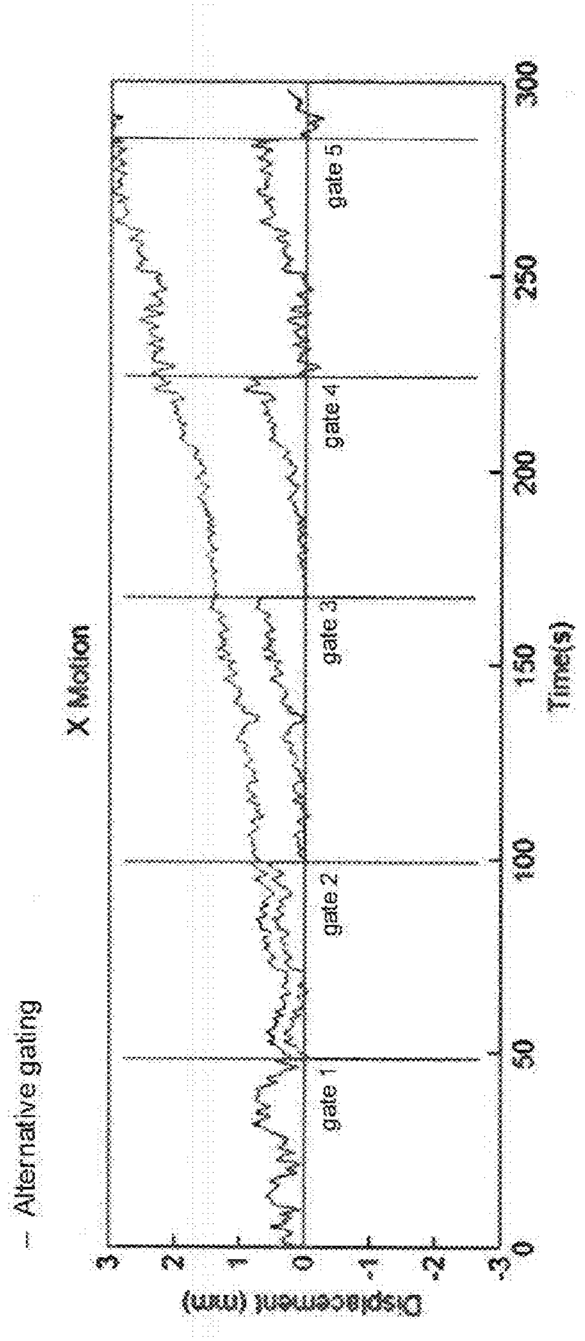
FIGS. 41A-D are plots illustrating alternative gating methods based on retinal motion determined form the eye motion measurements.
Figure 41B:
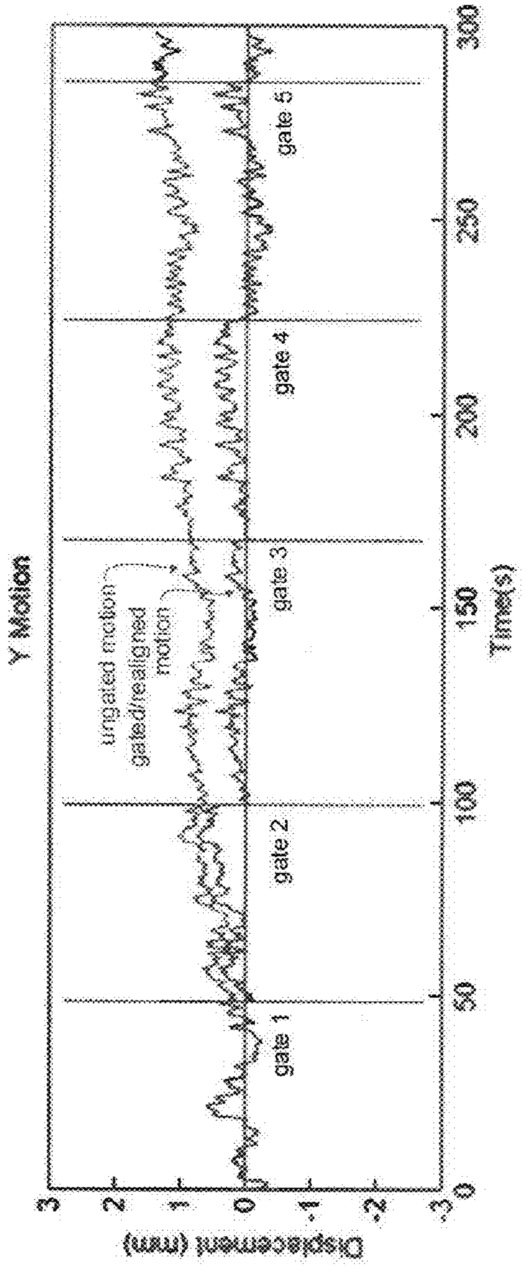

FIGS. 41A-41D illustrate one example of method and device embodiments for gating and controlling dose distribution in response to retinal motion. FIGS. 41A and B are plots showing X and Y components of retinal motion respectively. In this case, eye alignment and stabilization was performed, but no irradiation was performed, yielding the input eye motion data as shown in FIGS. 26A-26E. A retinal motion conversion was performed (see FIGS. 32-36), and gating control was simulated using a linear algorithm as describe above with a trigger sensitivity of about 3 (gating example) and 0 (ungated example). The re-alignment in the gating example in this patient was simulated by re-zeroing the X and Y displacement of the data when the gating threshold was reached, resulting in gates 1-5 as indicated in the figures. Both the "ungated motion" and "gated/realigned motion" are shown as indicated in each figure.

Figure 41C:
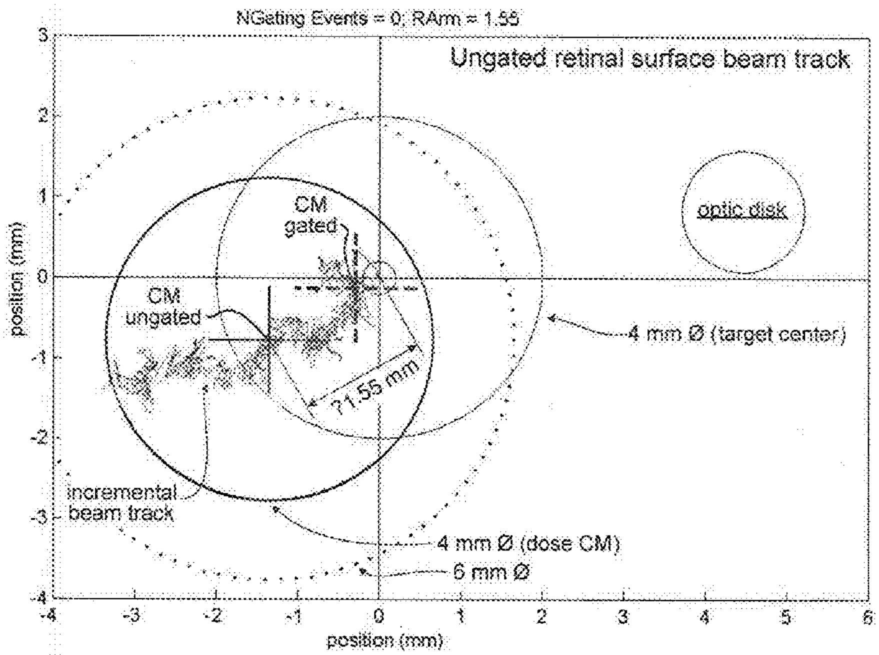
Figure 41D:
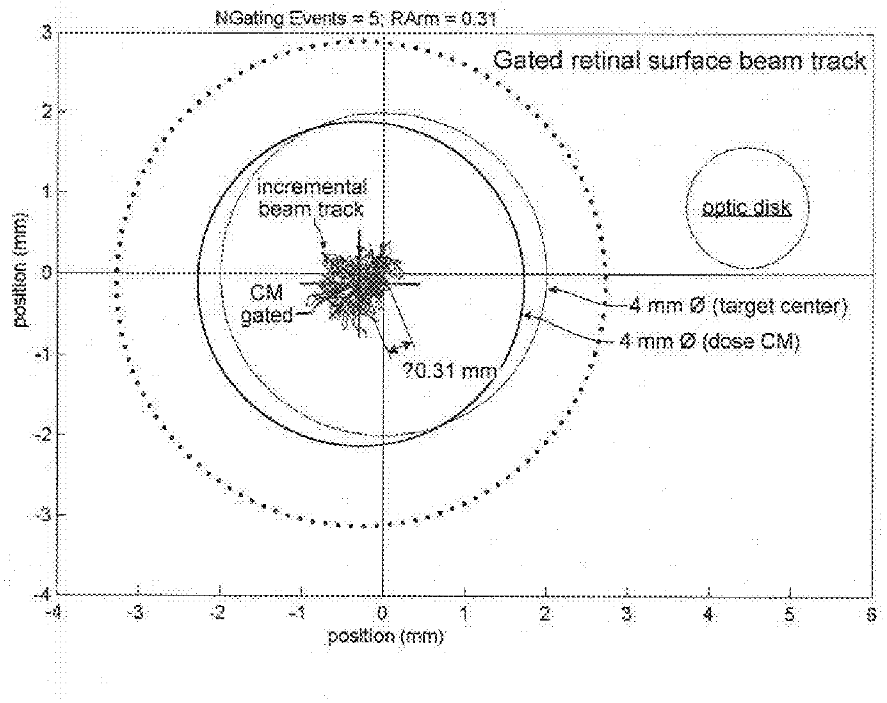

FIGS. 41C and 41D are X-Y parametric plots showing the ungated and gated retinal surface beam tracks, respectively, relative to the target center (0,0), and showing also the optic disc and a 4 mm target zone around the target center. In each case, there is superimposed the location of the vector position of the terminal "center of mass" of the beam position (CM), as described above together with 4 mm and 6 mm circles around the CM. As can be seen in FIG. 41C, the terminal CM (indicated also as RArm) without gating is about 1.55 mm as indicated by dimension arrows. In contrast, where the gating sensitivity is adjusted to result in 5 gating/realignment events, FIG. 41D based on the same input data shows a terminal CM of only about 0.31 mm, or roughly a 5-fold reduction in targeting error.

Gating trigger algorithms and devices effectuating such algorithms (e.g., a computer processor/controller of a radiotherapy system, communicating an automatic gating signal to an associated X-ray source) have been demonstrated in conjunction with eye alignment/stabilization system embodiments to provide a TRE accuracy within less than about 0.5 mm, while effecting a maximum of about 3-5 gating/realignment events for a substantial patient population.

FIGS. 41E-41H are plots illustrating additional examples of method and device embodiments having aspects of the invention for gating and controlling dose distribution in response to retinal motion. The plots are arranged in pairs (41E and 41F and 41G and 41H), one pair for each of two subjects being treated using a radiotherapy system embodiment according to FIGS. 1-6. Each plot has the same horizontal time axis and each pertaining to a single X-ray beam emission interval in which a macular dose of about 5.3 Gy was delivered as part of a 3-beam stereotactic treatment totaling about 16 Gy at the macula.

In each pair of plots, the upper plot shown the time-variable values of retinal X displacement from the system treatment axis 2820, shown as a light solid line, and the values of retinal Y displacement, shown as a heavy solid line. These values are calculated based on fiducial and limbus tracking signals, as described herein with respect to FIGS. 21-36. In these examples, the data update rate during treatment was about 10 Hz. For purposes of clarity of display without loss of meaning, the displacement data plotted in the figures is filtered (averaged point-by-point over a few data cycles) to suppress the display of high frequency perturbations or jitter in the frame-by-frame data.

In the lower plot of each pair, the Accumulation Factor (AF) is plotted as a heavy solid line, relative to the left hand vertical axis as a fraction of the pre-determined maximum allowed gating criteria threshold. The time-increasing total accumulated central X-ray dose at retinal depth (TD) is shown as the light solid line, relative to the right hand vertical axis, in Gy. The AF was computed as a summation of a quadratic displacement vector magnitude, as described above. The total accumulated dose is a summation of incremental doses for each time increment during X-ray treatment ("beam ON time"). Each incremental dose is based on calibrated air kerma X-ray tube emission properties using system-measured tube field potential voltage and cathode current. The determination of incremental dose includes calibrated propagation of the X-ray spectrum through collimator filters and intervening ocular tissue to retinal depth, the tissue path length being determined from beam path geometry as scaled to the particular patient's eye based on an ultrasonic A-scan measurement.

Figure 41E:
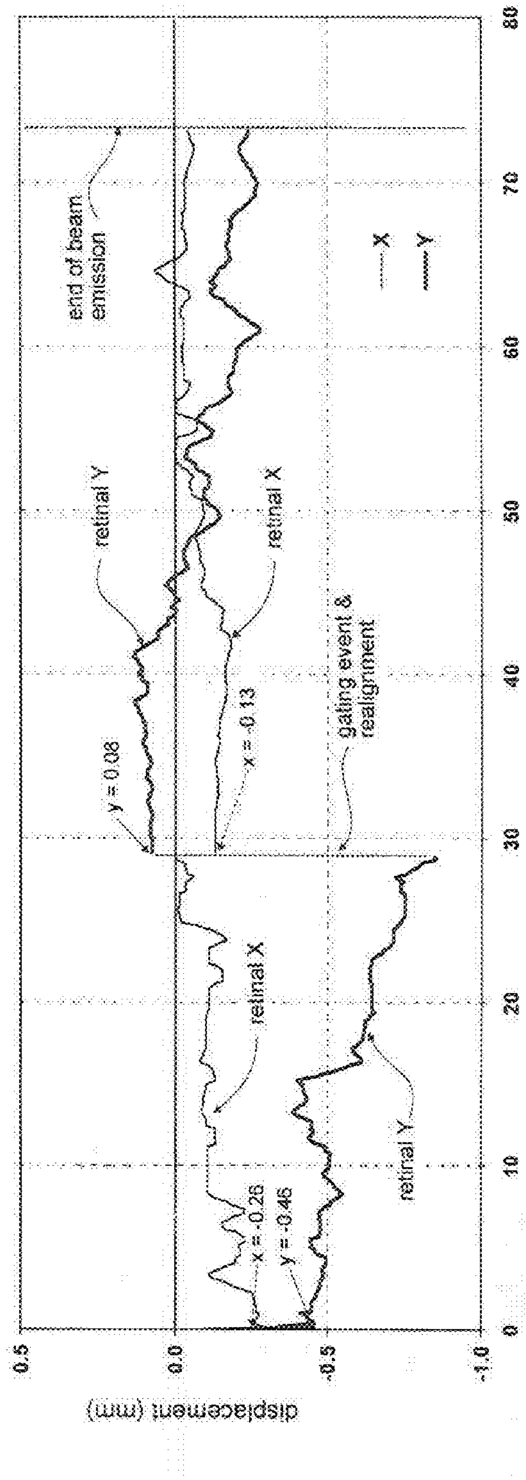
FIGS. 41E-H at plots showing the operation of retinal tracking and X-ray gating controls during patient treatment.
Figure 41F:
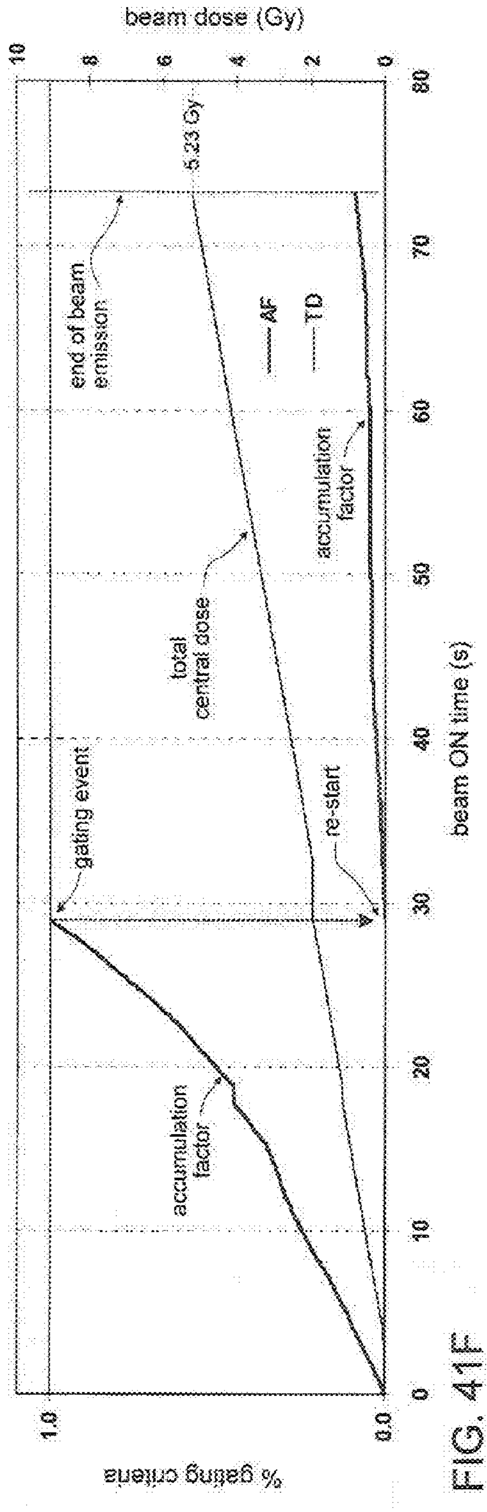

Turning first to FIGS. 41E and 41F it may be seen that the macular center alignment at the beam start time was displaced a fraction of a millimeter in both the X and Y directions (−0.26 and −0.43 mm respectively). The AF plot may be seen to slope upwards a moderately steep angle initially. Over the first 20-25 seconds, the retinal displacement in the Y direction increased while displacement in the X direction decreased. It will be appreciated that the trigonometric magnitude of the displacement vector (square root of the sum of the squares of the X and Y components) is increasing during this interval, and this increase is reflected in a steeping of the slope of the AF curve. As the AF reached the gating criteria threshold (AF=>1*GC) at about 29 seconds beam ON time, the system processor triggered X-ray source gating, shutting off the X-ray source tube.

Following gating, the operating physician realigned the eye and eye-guide with the treatment axis 2820 (X, Y displacements of −0.13 and 0.08 mm respectively), and the X-ray source was re-started. Note that the TD line is briefly flat as the emission intensity ramps up at re-start over a period of about 1-2 seconds. Over the remainder of the beam emission, the retinal X and Y components remain within a fraction of a millimeter, and the AF curve is has only a shallow upward slope, accumulating only to a small fraction of the maximum GC at the time of beam termination at about 73 seconds ON time, the total dose delivered reaching 5.23 Gy.

Figures 41G, 41H:
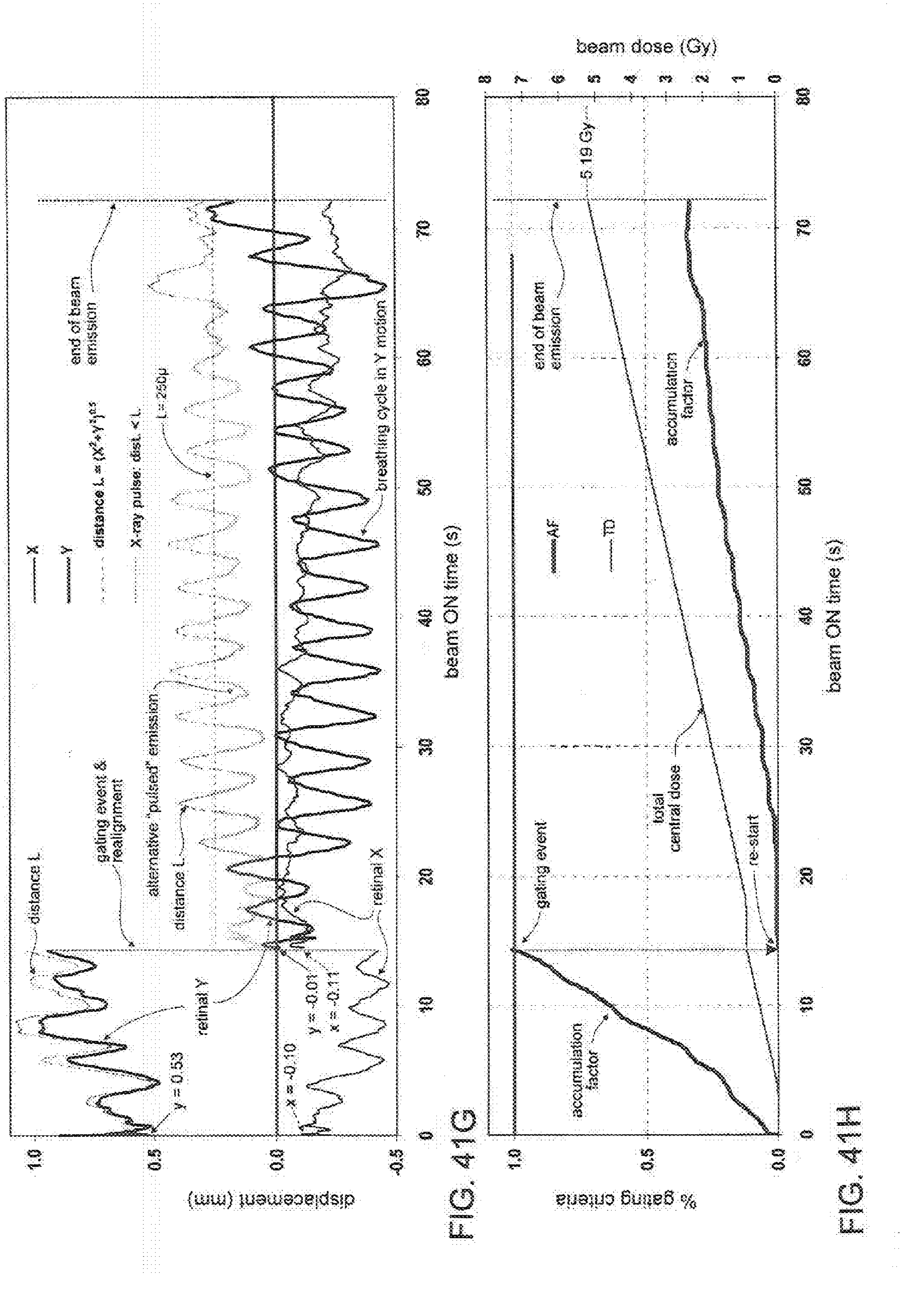

Turning next to FIGS. 41G and 41H it may be seen that the displacement data in this case shows a marked and persistent periodicity, particularly in the Y displacement, with a period of about 3.5 seconds and a Y amplitude of about a third of a millimeter. It is believed that this is due largely to the particular breathing behavior of the patient, which caused slight head and eye movements. For a linear algorithm for the accumulation factor (AF), periodicity does not effect the AF, while for a quadratic algorithm for the accumulation factor (AF) in which the displacements are weighted with the square of their magnitude (as employed in these examples), periodicity of this nature increases the AF relative to a non-oscillating curve of the same mean value. [Note, in addition to the retinal X and Y displacement curves in FIG. 41G, there are curves for the "distance" L of the retina target from beam center where $L=(X^2+Y^2)^{0.5}$, and for an X-ray "pulse". These are discussed below with respect to an alternative method of treatment].

As in the previous case, the it may be seen that in FIGS. 41G and 41H, the macular center alignment at the beam start time was displaced in both the X and Y directions (−0.10 and 0.53 mm respectively). The AF plot may be seen to slope upwards at a steep angle initially, reaching the gating trigger level (AF=>1*GC) after about 14 seconds beam ON time. Following gating, the operating physician realigned the eye and eye-guide with the treatment axis 2820 (X, Y displacements of −0.11 and −0.01 mm respectively), and the X-ray source was re-started. Over the remainder of the beam emission, the mean trend of retinal X and Y components remain small, although as noted, the amplitude of periodicity was significant. The AF curve is has a modest upward slope, accumulating to about 35% of the maximum GC at the time of beam termination at about 72 seconds ON time, the total central dose delivered reaching 5.19 Gy.

Pulse-Modulated Radiation Control.

In the examples described in detail herein, the systems utilize a substantially constant-intensity X-ray source, such that the cumulative time of exposure is generally linearly related to absorbed dose to a tissue in the beam path. However, depending on selected X-ray source characteristics, either or both of variable-intensity beams or pulse-modulated beams may be used to apply radiotherapy, without departing from the spirit of the invention.

As an illustrative example, and turning again to FIGS. 41G and 41H, it may be seen that the cyclical excursions in foveal target location due to patient breathing motion (principally in the vertical or Y direction) place the target intermittently very close to zero-displacement from the treatment beam center.

FIG. 41G shows a curve of the displacement or "distance" magnitude L (as a dashed curve) of the retina target from beam center where $L=(X^2+Y^2)^{0.5}$, noting that L is thus always a positive magnitude regardless of whether the X and Y vector components are positive or negative.

The X-ray source 420 may be controlled to emit beam radiation only when the value of retina displacement L is less than a selected threshold (e.g., 0.25 mm or 250μ is illustrated), although this was not the actual treatment procedure for the subject in this case. The distance curve is thickened with a solid grey overlay for those portions for which L<250μ, indicating an alternative treatment example in which the X-ray source would be modulated to only emit radiation when L is within this threshold.

Very precise X-ray emission or pulse control for X-ray tubes is known in the radiological art, such as for cine-radiographic techniques and the like. Rapid switching of X-ray emission from the anode spot can be obtained, for example, by use of high voltage switching in the secondary circuit of a constant potential X ray generator; by starting and stopping the inverter in a medium frequency generator; or by using a grid controlled X ray tube. See for example the grid-controlled G-1078 Rotating Anode X-Ray Tube by Varian Medical Systems, Inc. Alternatively, controlled physical blocking of the X-ray beam may be performed by a shutter, such as a rapid-acting electro-mechanically driven radio-opaque shutter, e.g., mounted in the collimator.

A method of pulse modulated X-ray treatment having aspects of the invention may include, for example, monitoring (summing) the modulated or "pulsed" beam ON time via the control processor, and continuing beam treatment until a desired dose is applied. A gating/realignment criteria may be included, such as a "duty cycle" criteria in which the treatment is interrupted if the percent of beam ON time falls below a selected level for a selected period, such as about 50% duty cycle. Thus if the eye motion is such that the distance L is continuously beyond the pulse threshold, the eye is re-aligned to provide a useful duty cycle. In the example of FIG. 43G, the gating at about 14 seconds would have served as such a re-alignment gating, putting alignment close enough for about a 50% duty cycle.

In further alternatives, a constant rate and length pulse may be used, in which each such pulse has a fixed duration, and the pulses are enabled at a selected rate. The system may determine a GO/NO GO decision for each pulse based on the current target-beam displacement, the pulse only being triggered when GO criteria are met (e.g., L<250μ). The treatment duration may be a pre-determined number of triggered pulses, corresponding to a selected dose.

VI.D. Gating Controls for Blinking Motion

FIGS. 42A-42H are plots showing the extrapolated retinal motion of a patient in which a consistent pattern of involuntary blinking during the simulated treatment was noted, each blink resulting in a rapid strong, though temporary, shift of the eye upward. It should noted that upward shifts do not tend to increase dosage to the optic disk, but may result in under-treatment of a macular target region.

Figure 42A:
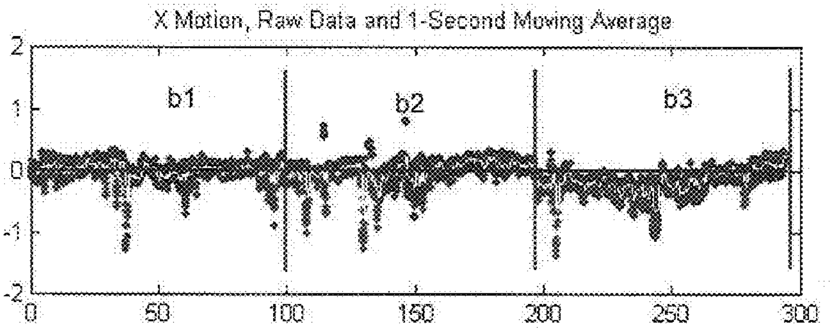
FIGS. 42A-H are plots illustrating retinal motion determined form the eye motion measurements, and illustrating a method of correcting for patient blinking during treatment, so as to control radiation dosage to the retina.
Figure 42B:
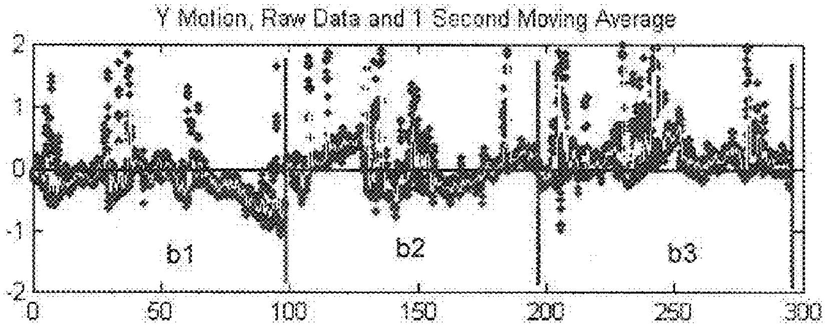
Figure 42C:
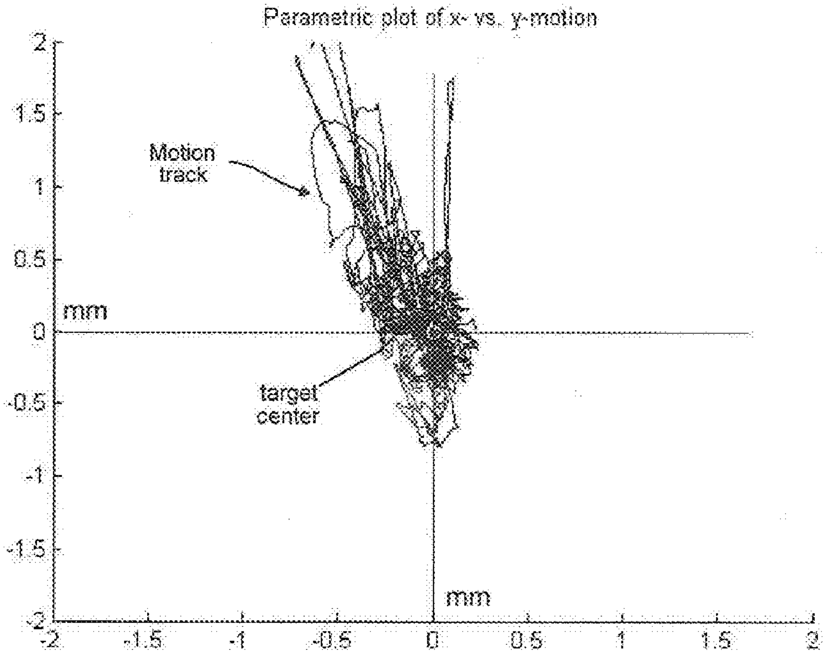

FIGS. 42A and 42B show the X and Y components of a patient's retinal motion for a period of about 5 minutes, divided into three "beams" as described above. It can be seen that there are a large number of very brief vertical or Y excursions, in some cases exceeding 2 mm, although there is much less motion in the X direction. The eye tends to return to alignment fairly rapidly after each blink. FIG. 42C show a parametric plot of the motion.

Figure 42D:
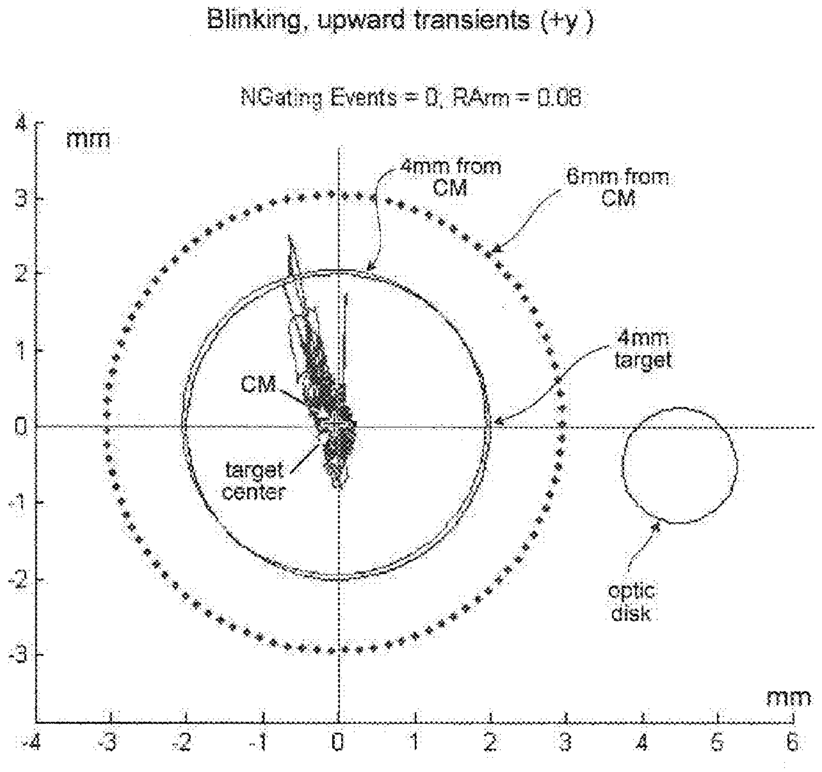
Figure 42E:
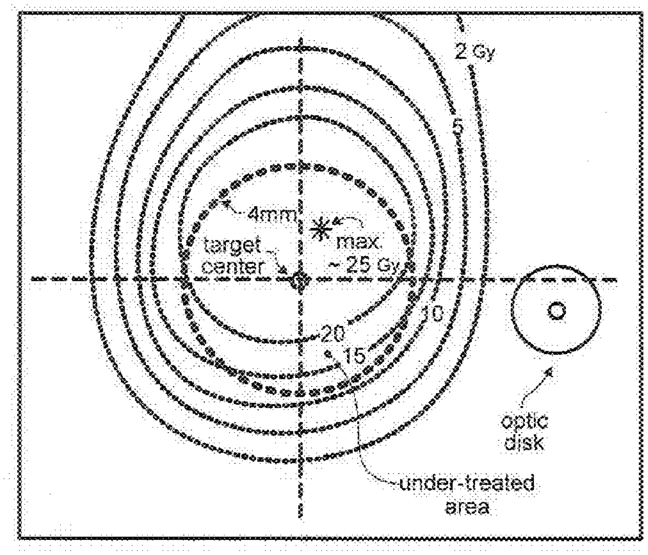

FIG. 42D shows that the CM of the motion-duration of the data of FIGS. 42A and 42B undergoes only a very small shift in spite of the large vertical excursions of motion. However, FIG. 42D shows that the corresponding dose map is more strongly effected because of the high magnitude deviations (beam spot isodose fall-off gradient is highly non-linear), resulting in a vertical "smearing" of dose upward, and a loss of dose in the lower part of the treatment region, resulting in a substantial under-treated area (dose less than 20 Gy within the 4 mm target circle.)

Figure 42F:
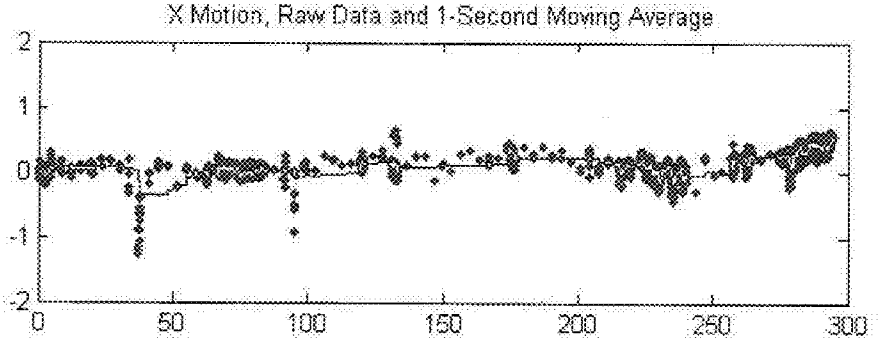
Figure 42G:
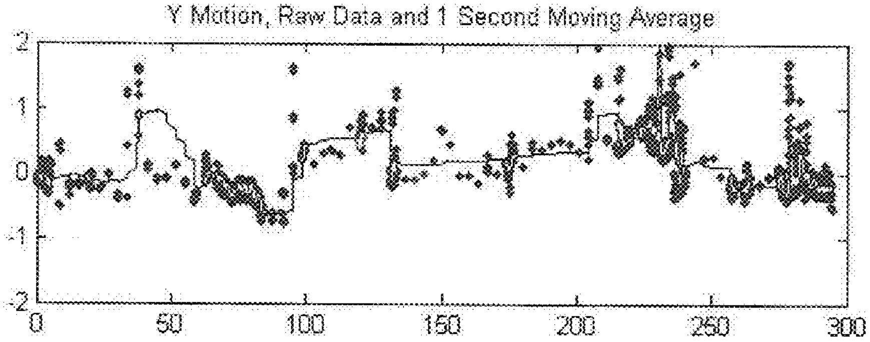
Figure 42H:
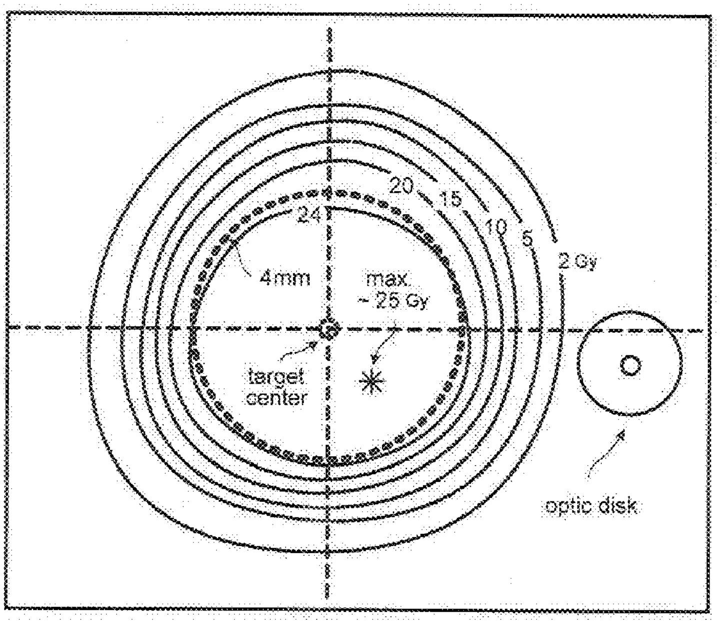

FIGS. 42F-42H show the results of a "de-blinking" method having aspects of the invention. The exemplary method includes.

- Defining a gating trigger parameter responsive to blinking movements. One example of a trigger parameter is to look for large first difference from one sample to next (suitable for an update rate of 10 Hz), for example a difference of about 0.5 mm in the 1/10 second between measurements.
- Triggering results in simple gating of the X-ray source, such as shutting of the high voltage power supply or HVPS (moderate response), or alternatively activating a cathode bias grid to prevent electron acceleration (faster response). Any HVPS ramp down/up time may be allowed for in dosage mapping and treatment duration.
- Waiting a defined period for patient to spontaneously realign, e.g., 3 seconds.
- Resuming treatment and optionally add beam-off time to treatment period.

FIGS. 42F and 42G show the data of FIGS. 42A and 42B after it is filtered to illustrate the above method, discarding samples during a 3 second waiting period following triggering. FIG. 42H shows the resulting change to the dose map, which removes the dose "smearing" effect.

VI.E. Real-Time X-Ray Source Repositioning to Follow Retinal Motion

In certain embodiments, as an alternative to or in addition to the X-ray source emission controls and realignment methods described above with respect to FIGS. 39-42, either or both of the X-ray source (e.g., via X-ray source positioner actuators) or patient eye (e.g., via eye-guide and/or head restraint actuators) may be re-positioned and/or reoriented to compensate for patient eye motion, as detected on a real time basis.

For example, the manual eye-guide positioner 600 shown in FIG. 1 may include actuators effective to move the eye-guide automatically under control of system processors, in response to retinal motion as detected during treatment. As shown in FIGS. 29-31, just as motions of the eye and/or head (causing retinal motion) can be detected as translation or rotation of components of eye-guide 110. For example, as shown in FIGS. 29A and 29B, relative motion of the eye and X-ray beam source in the system Z axis (dZ) results in a relative motion of the beamspot on the retina (dX), the direction of relative motion being dependent on the particular angular orientation of the treatment beam with the eye geometric axis 2810. Similarly, as shown in FIGS. 30A and 30B, translation of the eye in the X or Y directions relative to the eye-guide 110 induces rotation and retinal motion in the direction of translation. Conversely, motion of the eye-guide 110 may be employed to induce compensatory retinal motion, so as to reposition the retinal beam-spot relative to target.

X-ray source positioner motion. In alternative embodiments, the actuators of positioning system 115 depicted in FIGS. 1-6 may be used to reposition the X-ray source assembly 420 so as to reorient a treatment beam in response to retinal motion as detected during treatment (e.g., automatically under control of system processors). As shown in FIG. 21E, the X-ray beam path 1400 is brought to bear on the target 318 by a sequence of movements of the actuators of positioner 115 to an adjusted position ($X_0$,$Y_0$,$Z_0$,$\phi_0$), at which position the change of rotational variable θ about the treatment axis 2820 results in substantially no relative motion of the retinal beamspot. Conversely, motion of one or more of the X,Y,Z, and/or ϕ actuators of positioner 115 may be controlled so as to re-position the retinal beamspot in response to patient eye motion, as detected on a real time basis, such as by actuation to move X-ray source 420 from ($X_0$,$Y_0$,$Z_0$,$\phi_0$, θ1) to (X',Y',Z',ϕ', θ1). In alternative embodiments, positioning system 115 may comprise additional actuators configured for rapid and precise motion (e.g., small-range "Vernier actuators") in addition to primary actuators for one or more of the X,Y,Z, and/or ϕ system axes.

Likewise, positioning system 115 may comprise additional or alternative degrees of freedom or mechanical axes in addition to the X,Y,Z, and/or ϕ system axes, and these may be configured for real-time reorientation of beam path 1400 in response to detected retinal motion.

Beam steering by collimator aperture lateral translation. In the example shown in FIG. 43 A-C, one or more additional degrees of freedom are provided for structure to move the retinal beamspot relative to the initial beam axis 1400. Advantageously, the X-ray source mass (weight and inertia) which must be moved for fine scale re-orientation of the beam may be reduced by having an actuator configured to reorient only a portion of the collimator assembly structure 118 to delimit the beam to a slightly adjusted beam path. In the example shown, only a very small fraction of the mass of the X-ray source assembly need be moved to make small compensatory movements of the retinal beamspot, where one or more actuators 119*a* are configured to engage and move a collimator exit aperture plate 1405*b* of modest mass, the actuator assembly 118*b* being arranged adjacent the distal end of collimator assembly 118. Typically, a small mass may be repositioned more responsively and accurately than a relatively large mass, such as the total mass of X-ray source tube 112.

Figure 43A:
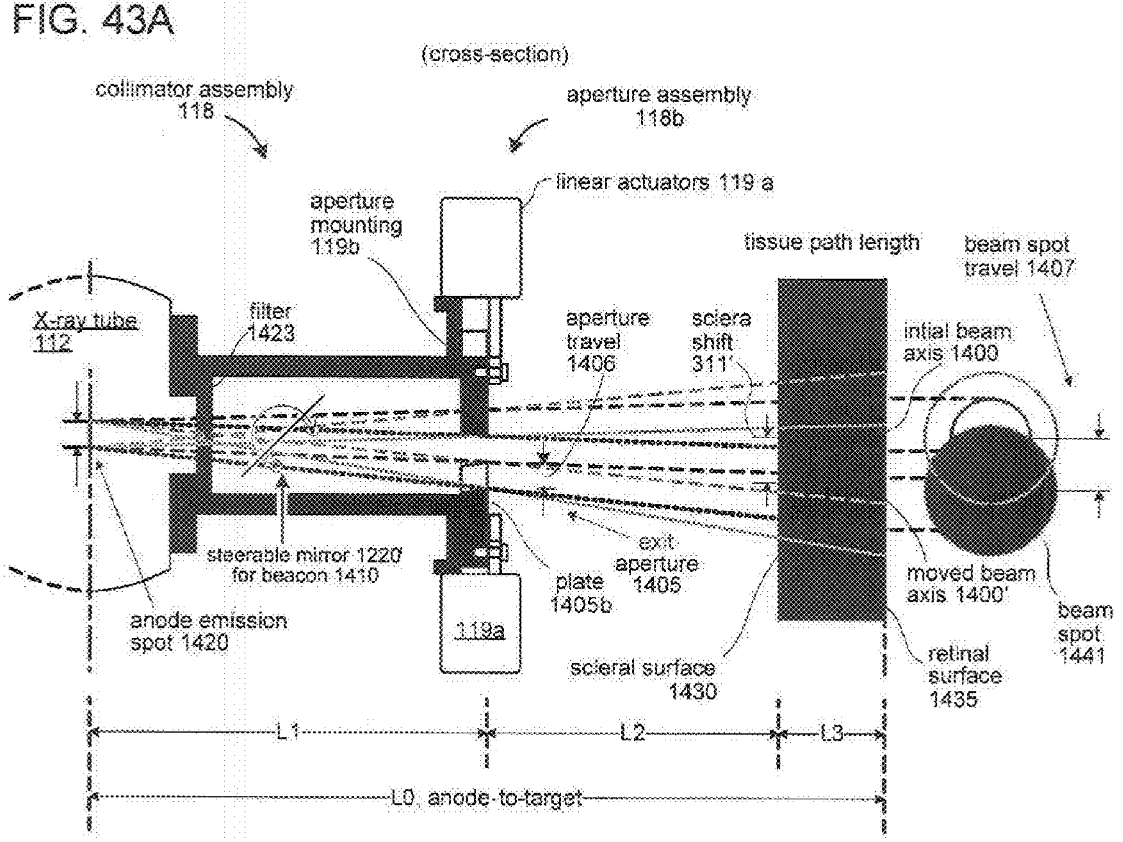
FIGS. 43A-C illustrate an embodiment for tracking retinal motion by altering beam path using a moveable collimator exit plate.
Figure 43B:
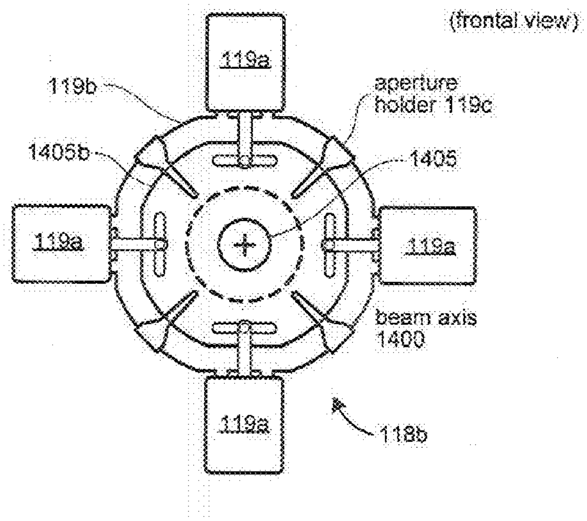
Figure 43C:
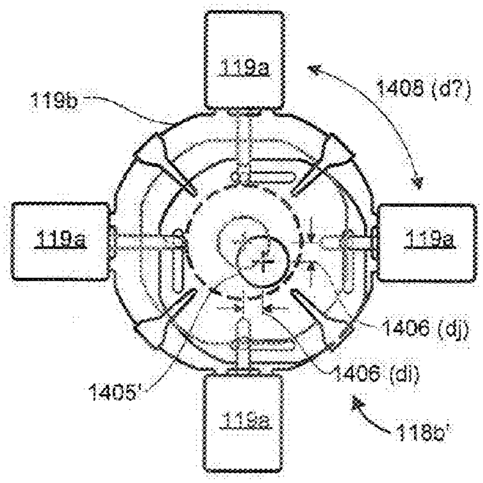

As shown in FIGS. 43A-43C, aperture plate 1405 is supported by aperture mounting 119*b* (e.g., may be held in position by holders 119*c*) and engaged by actuators 119*a*. In the example shown, the plate is supported to move in two dimensions (directions I and J for relative motion di and dj respectively) in a plane perpendicular to the beam axis 1400, but this need not be so. Similarly, the example depicts pairs of linear actuators in a parallel "push-pull" arrangement for each direction, but this is purely exemplary. For example, the actuator assembly 118*b* may alternatively provide a rotational degree of freedom (not shown) in addition to a lateral translation of plate 1405*b*, so as to provide motion via polar coordinates lateral to axis 1400.

FIG. 43A provides a cross-sectional "ray-tracing" beam model similar to that of FIG. 12, with elements generally identified by the same numerals, and having collimator dimensions similarly identified as L0, L1, L2 and L3. X-ray tube 112 emits a beam 1400 via collimator 118 to propagate to sclera surface 1430, penetrating to retinal surface 1435 to form retinal beam spot 1441. Lateral motion of aperture plate 1405*b* moves the exit aperture 1405 through a distance indicated as aperture travel 1406. Both the aperture plate 1405*b* and the beam 1400 is shown both in an initial position/orientation (dashed or light lines) and a shifted position/orientation (solid or dark lines) as beam 1400'.

FIGS. 43B and 43C are frontal elevations of collimator 118, showing the arrangement of linear actuators 119*c* to plate 1405*b*, wherein figure B represents an initial position, and C represents a shifted position, where the plate 1405*b* has moved in two directions (di, dj respectively). Because plate 1405*b* is mounted at a distance between anode 1420 and retina 1435, the aperture travel 1406 results in a respective retinal beam spot travel 1407 which is magnified to a degree. For example, if aperture 1405 is exactly at the midpoint (L0=2*L1), the beam-spot travel 1407 will be twice the aperture travel 1406. Thus a movement of 1 mm by plate 1405*b* would in this case result in a shift of approximately 2 mm in beamspot 1441. Note from FIGS. 40A-40H that retinal motion of a restrained patient may be on the order of 1-2 mm or less over reasonable treatment periods. For embodiments in which the aperture is close to sclera surface 1430, the magnification of motion may be modest.

Note from FIG. 43A that the entry point 311 of beam 1400 at sclera 1430 is shifted by a distance comparable to beamspot travel 1407. In the treatment systems described herein, the relationship of sclera beam-spot 311 may be actively tracked by imaging system and processors, and accurately predicted based on eye motion detection. The collimator assembly 118 may include a steerable mirror 1220' (see laser beacon 1410 and mirror 1220 in FIG. 4) to permit a beam-aligned laser beacon to be steered to remain aligned with beam 1400', so as to assist in automated or operator monitoring of beam shift. System processors may be configured (e.g., by suitable software) to predict motion sclera beamspot 311 so as to avoid motion of plate 1405*b* which would bring the sclera beamspot 311 within a selected threshold distance of a vulnerable structure, such as the cornea or the lens of the eye (e.g., source-gating could be used to control retinal dose distribution in this case). In many cases, the motion of spot 311 will be away from or at least not towards a vulnerable structure.

In one alternative, the actuators 119*b* comprise one or more electromechanical actuators known in the art. In another alternative, the actuators 119*b* comprise one or more piezoelectric actuators, such as a 2-D a piezoelectric actuator stage. Such actuators may be configured to controllably translate rapidly (e.g., millisecond order response) over a distance a few mm with accuracy on the order of a few microns.

Collimator aperture axial rotation. The aperture 1405 may be moved in a axial rotational degree of freedom about the longitudinal axis of the collimator 118, as shown in FIG. 43C, by axial rotation 1408 (dβ). Suitable actuators and support bearings (not shown) may be included in collimator assembly 118 to accomplish this motion, either by rotation of all or a portion of the collimator 118, or by rotation of a distinct aperture plate 1405*b*, and these may be actuated manually and/or by motion control software operating via system processor 501.

Aperture rotation may be particularly useful when aperture 1405 is offset from the collimator axis (as in FIG. 43C), or to align an aperture shape with a target in embodiments (not shown herein) where the aperture 1405 includes a non-circular opening or opening pattern, such as an elliptical, elongate, or crescent-shaped opening or the like (see aperture embodiments described in application Ser. No. 12/103,534 filed Apr. 15, 2008 and Ser. No. 12/100,398 filed Apr. 9, 2008, which are incorporated by reference).

For example, the robotic positioner 115 of FIGS. 5 and 6 is configured to rotate the X-ray source assembly through an angle θ to adjust beam position for successive stereotactic treatment paths. Collimator aperture rotation in the opposite direction may be employed as shown in FIG. 43C to maintain a desired orientation of an asymmetrical collimator aperture 1405 relative to the target 318 as the X-ray source 112 is repositioned.

Collimator longitudinal extension. The example of FIG. 43D is shown in the form of an extensible "zoom-lens"-like mounting of an exit-aperture 1405 on a collimator body 118'. The telescoping, tube-mounted structure shown is exemplary only, and it should be noted that in alternative embodiments may be made with substantially different structure without departing from the spirit of the invention. For example, outer portion 118*b* need not be directly mounted to base portion 118*a*, but may be independently supported, the independent support configured to permit movement of aperture 1405 distally and axially away from anode 1420, so as to increase distance L1. In this fashion, certain embodiments may be made which omit base portion 118*a*, such as where any desired beam conditioning components (e.g., choke plate, filter, stray radiation shielding) are independently provided.

Note that an extensible collimator may be included as, in effect, an additional degree of freedom for initial X-ray source positioning, as well as for tracking target motion during treatment. For example, it in certain embodiments of radiotherapy systems having aspects of the invention, the X-ray source 112 and retracted collimator 118' may be first positioned in one or more degrees of freedom, for example in the X-Y-Z volume and with a selected polar angle $\phi$. The azimuth angle $\theta$ may be selected in sequence for each beam position (e.g., b1-b2-b3 in FIG. 6). For each beam position, prior to emission of radiation but after positioning the X-ray source and collimator, extensible outer portion 118*b* of collimator 118' in may be extended axially (extension 118*c*) or "zoomed" so as to place collimator exit 1405 a selected distance from the surface of the eye 30. Following emission of radiation, the extensible outer portion 118*b* may be retracted prior to repositioning of the X-ray source and collimator.

Note that collimator 118', and/or the system in which it is used, may contain detectors and safety mechanisms permitting a close approach to sensitive tissue. For example, aperture 1405 may have a covering of compliant, biocompatible material 119 so as to cushion and protect the sclera or other ocular structures, which may be shaped to conform to an eye surface, facilitating operation close to the face or permitting safe eye contact. Likewise proximity detectors and/or servo-controls may be used to automatically maintain a selected non-contact clearance from tissue, and/or to limit any force applied on tissue contact.

FIGS. 43E and 43F schematically depicts a ray tracing model similar to that of FIG. 12, comparing graphically the effect of collimator extension, illustrating a series of two different examples of collimator exit plane-to-target distance (L2+L3 in FIG. 12), with aperture size 1405 and anode-to-target distance L0 held constant, FIG. 43E may be considered to be representative of a contracted value L2*a* per FIG. 43D, and FIG. 43F may be considered to represent an extended or "zoomed" value L2*b*. Note that the values of L0, L1 and L2 and aperture diameter as illustrated are purely exemplary, and these may be varied substantially without departing from the spirit of the invention. The comparison of the two figures shows that variation in aperture distance has an effect both on penumbra width 1442 and central beam spot size 1441, both are reduced as the aperture approaches the target plane, for a given aperture diameter. If desired, the aperture 1405 may be sized for a selected treatment configuration and remain of fixed dimension.

Alternatively, the aperture diameter (and/or shape) may be made adjustable. FIG. 43G shows the same configuration as FIG. 43F ("extended collimator"), but has an enlarged aperture (25% larger in this example) to compensate so as to maintain a constant target central beamspot diameter (4 mm as illustrated). In certain embodiments, the aperture diameter is adjusted to suit a specific treatment plan, e.g., based on the dimensions of a patients macular lesion.

Figures 43H, 43I:
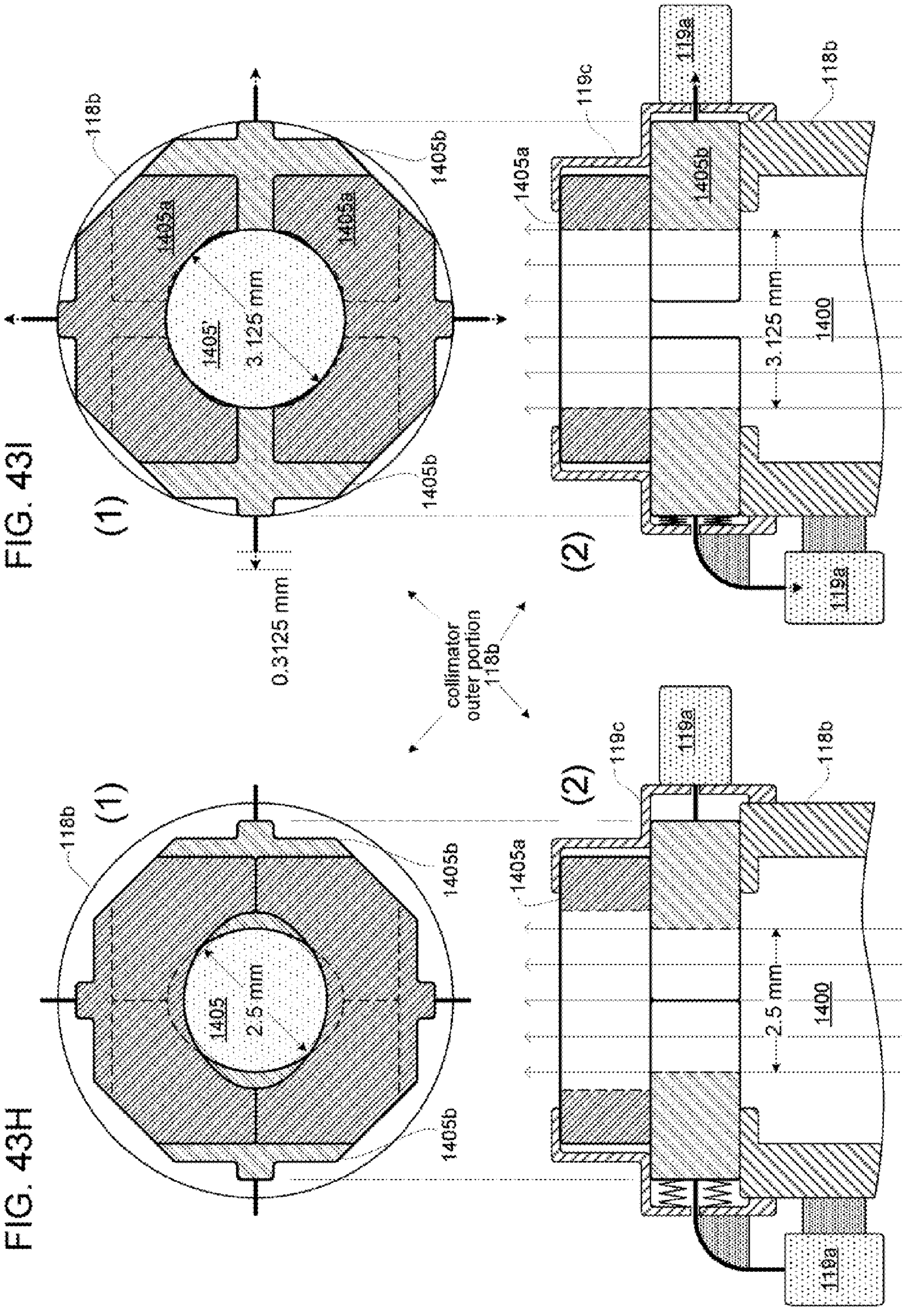
FIGS. 43H-K illustrate alternative embodiments of collimator assemblies having aspects of the invention, which have a variable collimator aperture diameter.

Collimator adjustable aperture diameter. FIGS. 43H and 43I schematically a distal portion of a collimator assembly 118 having aspects of the invention and having adjustable aperture, comprising a plurality of movable aperture plates (1405*a*-1405*b*), arranged to be moved radially outward from the axis of collimator 118, so as to increase the effective aperture radius. In each figure, view (1) is a plane or frontal view of the aperture plate arrangement, and view (2) is a longitudinal cross section of the collimator 118. In the example shown, the assembly includes two opposed pairs of aperture plates disposed in upper and lower overlapping perpendicularly oriented parallel layers. In this example, each plate has a quasi-elliptical opening serving to define one quadrant of the perimeter of the aperture opening 1405. An plate support ring 119*c* is shown schematically (alternative support arrangements may be included) and hold the plates 1405*a*-*b* in position at the distal exit of collimator 118, while permitting lateral sliding movement in one radial dimension for each plate. FIG. 43H illustrates the contracted aperture (2.5 mm diameter) and FIG. 43I illustrates the dilated aperture (3.125 mm).

For each plate, a schematic linear actuator 119*a* engages the plate so as to controllably move the plate radially inward or outward. It should be understood that a wide range of alternative mechanical and electromechanical assemblies may be included as plate actuators, which may be automatically or remotely controlled, or may be manually adjustable.

One of the advantages of orthovoltage radiotherapy is that radiation-control components such as collimator aperture plates may be much smaller, lighter and more compact than comparable components employed with multi-MeV X-ray and gamma ray treatment devices, due to the reduced penetrating effect of low energy photons. This permits a compact remotely-adjustable aperture assembly having aspects of the invention to be mounted on a collimator assembly suitable for use close to the face of a patient.

For example, miniature motors and linear actuators are commercially available providing accurate, remotely controllable actuation for the device of FIGS. 43 H and 43I as well as for devices such as camera lenses, film advance, shutter motion control and the like (e.g., piezoelectric linear actuators, by New Scale Technologies, Inc. of Victor, N.Y., and by Dynamic Structures & Materials, LLC of Franklin, Tenn.). Alternative actuation arrangement may employ cable or link drive arrangements, or the like as are known in the mechanical and electromechanical arts. Note that in the right hand portion of FIGS. 43H and 43I the actuator 119*a* is mounted directly to the aperture assembly 119*c*, while in the left-hand side, the actuator 119*a* is mounted at a certain distance from the actuator assembly 119*c*, linked mechanically to the actuator plate 1405*a,b*, which can be via a pulley-cable, crank-cable, slide or link, conduit-cable or other mechanical linkage known in the art. Springs or other bias components may be included (see left hand actuator) to counter the force of an actuator, to permit reversible motion upon relaxation of actuator, or the motion may be positively driven in each direction (contraction and dilation).

It may be noted by comparison of FIGS. 43 H and 43I that the "contracted" state of the aperture plates 1405*a,b* (2.5 mm opening, FIG. 43H) closely approximates a circular opening with only very small portions of the opening exceeding the inscribed 2.5 mm circle. The dilated state of the aperture plates (3.125 mm opening, FIG. 43I) presents substantially an exactly circular opening, in that the arc portions of the plate have this curvature. The shape of the plates need not be as shown, the figures exemplifying the principal of the adjustable aperture assembly. Likewise, non-circular adjustable aperture opening shapes are possible. Note also that the dimension range of the examples (2.5-3.125 mm) is purely exemplary, and the range may be from substantially smaller to substantially larger than the example shown.

Figures 43J, 43K:
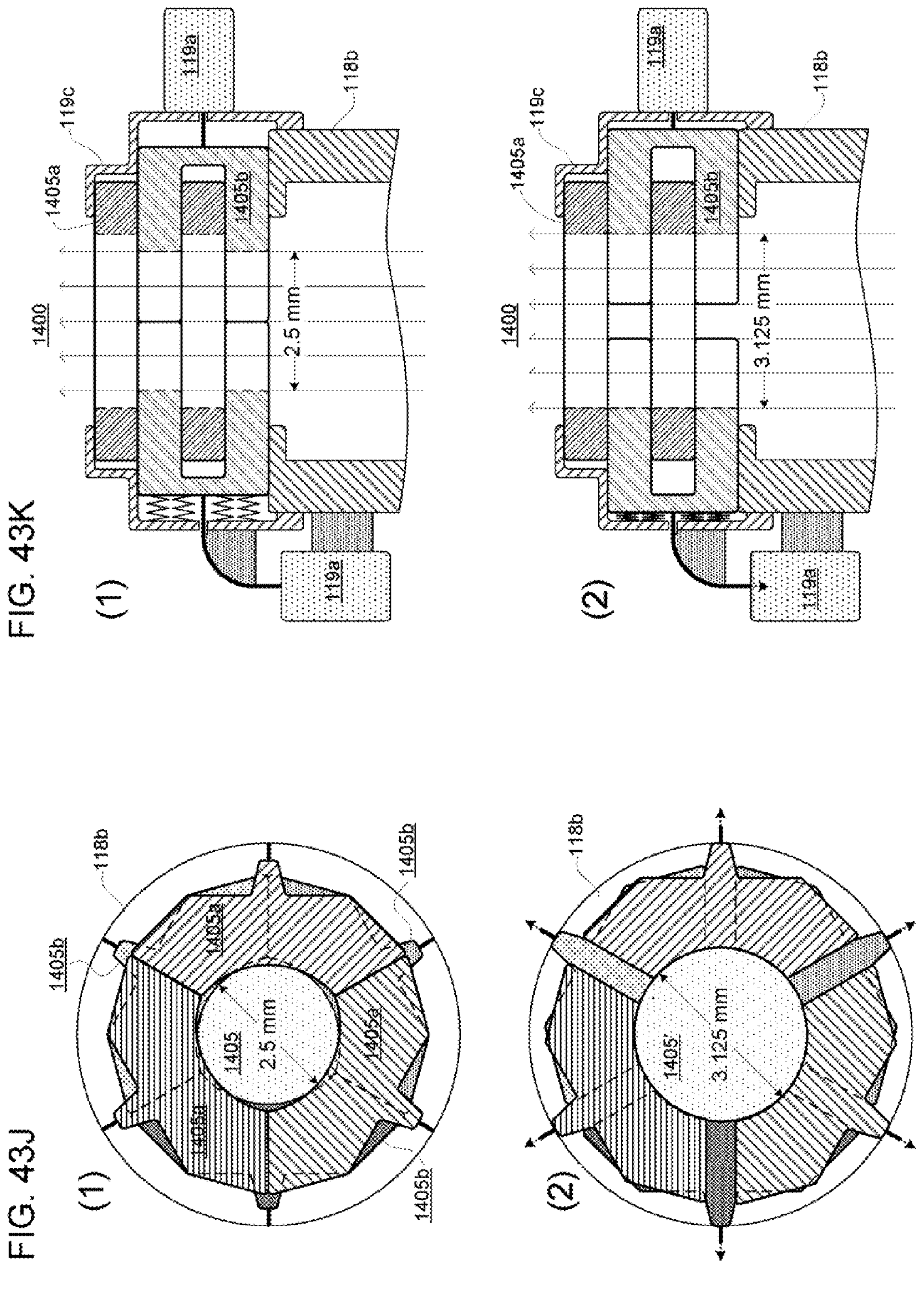
Figure 44A:
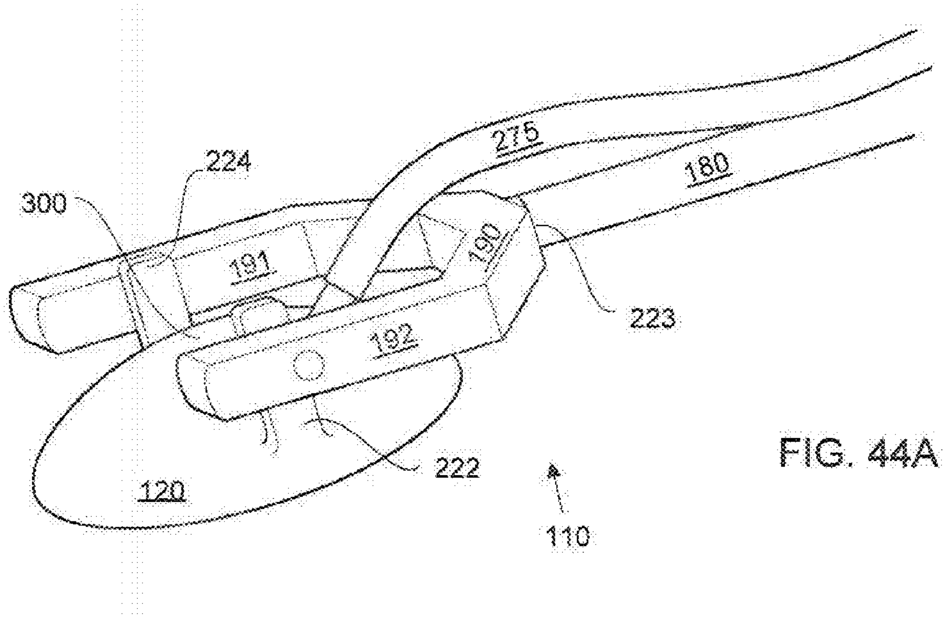
FIGS. 44A-D illustrate an eye-guide device for use in a eye stabilizing system having aspects of the invention, the guide having a window or transparent portion permitting retinal imaging during treatment.
Figure 44B:
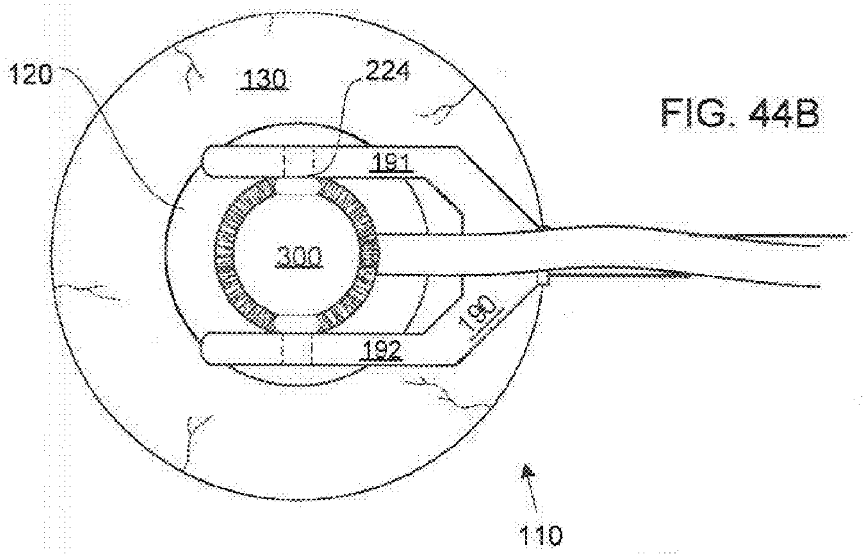
Figure 44C:
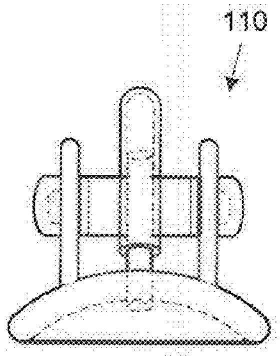
Figure 44D:
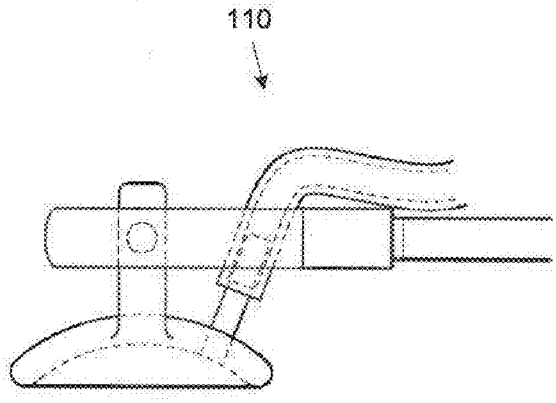

FIG. 43J illustrates an example of a collimator assembly 118 having adjustable aperture 1405, generally similar to the embodiment of FIGS. 43H and 43I, but having a hexagonal plate pattern, in two layers of three plates each layer (1405*a* and 1405*b*), in which each plate defines a 60 degree segment of the perimeter of the aperture opening 1405. View (1) shows the contracted state (2.5 mm) and View (2) shows the dilated state (3.125 mm).

FIG. 43K, Views (1) and (2) illustrates an example of a collimator assembly 118 having adjustable aperture 1405, generally similar to the embodiment of FIGS. 43H and 43I, but having a plurality of digitated interleaved double plates 1405*a* and 1405*b* forming a series of four linked layers. The doubled plates (greater plurality of leaves is possible) may be actuated in the manner of the assembly of FIGS. 43H and 43I.

Combined aperture motion. The embodiments of FIGS. 43A-43C having a laterally moveable aperture 1405 may be combined with embodiments of FIGS. 43H-43K having radially adjustable aperture diameter, so as to have simultaneous (or sequential) lateral aperture motion while varying aperture diameter. For example, each plate 1405*a,b* of the aperture assemblies 119*c* may be supported and actuated to have complex motion, radially relative to each companion plate, and collectively laterally (e.g., X and/or Y) so as to produce lateral motion of a changing aperture. Alternatively, a discretely adjustable diameter assembly may be mounted on a laterally movable support, so that aperture dilation/contraction may be combined with overall support motion.

VII. ADDITIONAL EMBODIMENTS

This section describes additional eye guide and treatment method embodiments of the invention

VIIA. Additional Eye Guide Embodiments

FIGS. 44A-44D illustrate an eye-guide device 110 for use in a eye stabilizing system having aspects of the invention, the guide having a window or transparent portion 300 permitting retinal imaging during treatment (note alternative example in FIGS. 18C and 18D). In the example shown, the lens 120 is supported by one or more posts or extensions 222, which engage a Y-shaped yoke 190 comprising arms 191, 192. Yoke 190 is mounted to support arm 180 by a swivel 223. Arms 191-192 mount to extensions 222 by means of pivots 224. Pivots 224 and swivel 223 provide freedom of motion for lens 120 two perpendicular directions. Window 300 is formed in the center of lens 120 (which may be entirely transparent), so as to permit an image to be obtained from the interior of eye 130 while eye-guide 110 is engage to the eye. Vacuum connection 275 communicates off-center on lens 120 and does not obstruct window 300.

FIGS. 45A-45D illustrate an alternative eye-guide device 110 for use in a eye stabilizing system having aspects of the invention, similar in many respects to the embodiment shown in FIGS. 44A-44D. As in the eye-guide of FIG. 44, the guide has a window or transparent portion permitting retinal imaging during treatment, and has a vacuum line to provide suction at the lens contact surface. In this example, the lens is supported by two posts, each of which engages a pivot joint, such as a ball joint, one post linked thereby directly to the support arm, and the companion post linked via a tie bar and second ball joint mounted at the side of the support arm. The arrangement of these components forms a frame, which may be made adjustment mechanism, in this case the tie bar being jointed to a slide-and-set screw assembly, which may be selectively repositioned along the axis of the support arm. The arrangement shown permits the eye-guide to have asymmetric pivoting characteristics, whereby pivot resistance may be selected to be different is the X and Y directions.

Figure 45A:
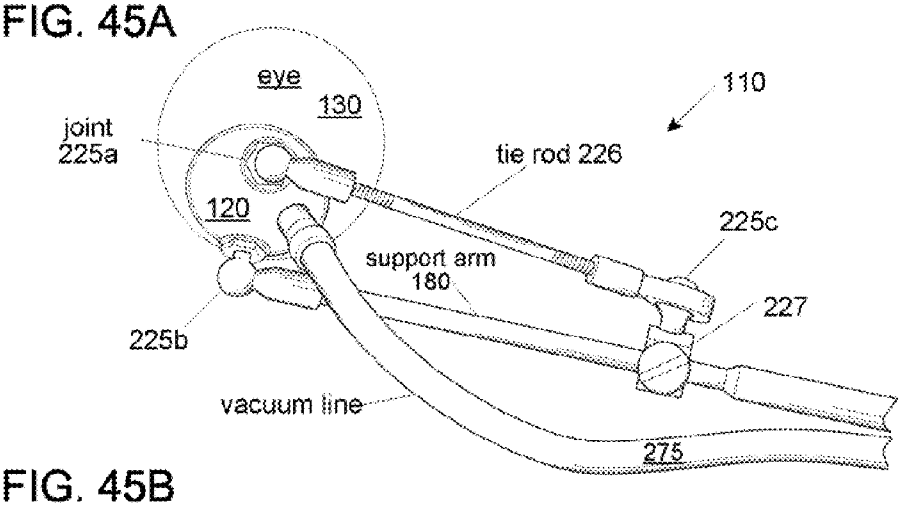
FIGS. 45A-E illustrate eye-guide devices having a widow or transparent portion, and having an adjustable support arm structure comprising a plurality of joints.
Figure 45B:
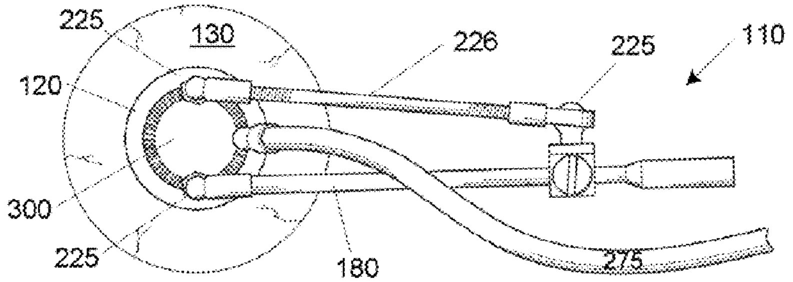
Figure 45C:
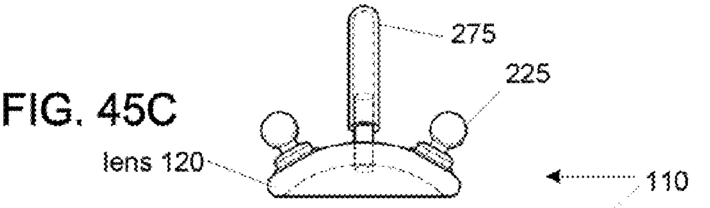
Figure 45D:
Figure 45E:
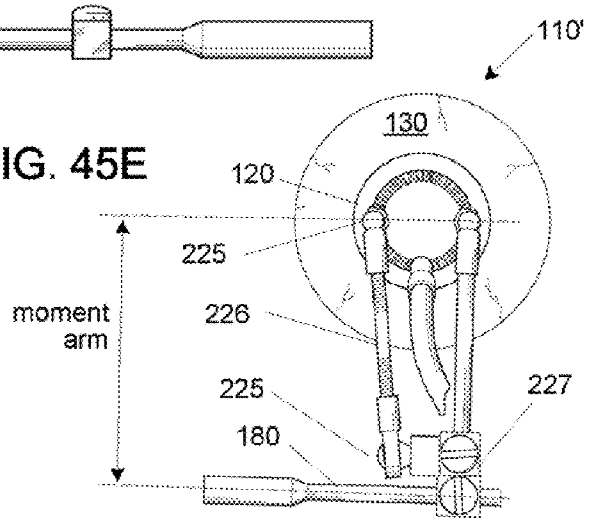

FIG. 45E illustrates an alternative embodiment similar to that of FIGS. 45A-D, in which the support frame for lens 120 is rotated approximately 90 deg. with respect to the support arm 180, so that the lens 120 is at the end of a moment arm about the axis of the support arm 180. The moment arm permits a bias or reaction force of the lens 120 upon eye 30 to be transmitted as a torque about the support arm 180. This may be exploited or regulated by means of a torque spring or other actuator within eye guide support (600 in FIG. 2).

Eye-Lid Retractors

FIGS. 46A and 46B illustrate two exemplary embodiments of elastically-tethered eyelid retractors 320*a*, 320*b* having aspects of the invention, generally similar to those that were used during acquisition of the data shown in FIG. 26A-26E. Each of retractors 320*a*, 320*b* includes a smooth and non-abrasive hook-like portion 323 configured to overlap and engage the eyelid, the hook mounted on a handle portion 324. FIG. 46A shows a wire-loop type hood and handle portion, and FIG. 46B shows a Desmarres type retractor member having a smoothly curved spoon-like hook member.

The handle portion may be supported a number of alternative ways (e.g., hand-held, taped to a support, mounting to a base, or the like), but a advantageous alternative is to connect the handle via an elastic tether portion 325 to an attachment 326, such as a spring clip or the like. The tether may comprise a stretchable elastic member, which may comprise an elastic strap, an elastomeric tube or the like. A terminal attachment is included to mount the tether to a convenient base, such as a spring clip, snap fitting, or the like. Either or both of the tether length or attachment position may be adjusted to provide a selected tether tension acting upon the eyelid. A length-adjustment fitting (not shown) may be included in the tether 325, such as a friction loop, Velcro fitting, or the like.

In certain embodiments, the tether is configured to be attached to the patient so that the relation of attachment to eye is relatively constant, notwithstanding patient movement. For example, the attachment 326 may include a spring clip which can be clamped to patient clothing adjacent the face, such as a shirt collar, button hole, pocket, or the like.

FIG. 46C shows an optional tension release fitting 328, which includes a force-limiting coupling, such as a magnetic or adhesive coupling, the coupling configured to release if excessive tension is applied to the tether. For example, the coupling may include a pair of adhering disks 327*a,b* of magnetically-patterned ferric oxide composition, each disk fixed to one adjoining (upper or lower) elastomeric tube section 325*a,b* by a pin inserted into and bound in the tube lumen.

FIGS. 47A-47C illustrate an alternative embodiment of an eye-lid retractor upper portion 320*c* (A. frontal view, B. side view, and C. perspective), having an extended hook portion 323 configured to slip behind the eyelid, and a saddle shaped top surface. The dimensions shown are purely exemplary.

FIGS. 48A-48D illustrate an further alternative embodiment 320*d*, generally similar to that of FIG. 24, and having an widened and asymmetrically curved hook portion 323, configured to align with the eyelid in a comfortable engaged configuration, while covering a substantial portion of the eyelid. The complex curvature of the hook portion allows it to follow the shape of the eye to minimize eyelid stress to that required to expose the sclera for treatment. As shown in FIG. 48E, the retractor portion 323 may be mounted to a handle 324 including a hinge mechanism 329 configured to align the handle with the retracting stress on the eyelid, for example to relieve sideways bending stress on the eyelid due to mounting alignment. The hinge mechanism 329 may be flexible in one or more directions, and may comprise one or more mechanical hinges or live hinges, and may comprise a swivel and/or ball joint.

Attention is directed to FIG. 23, which shows the retractor embodiment 320*d* of FIGS. 48A-48D as operationally engaged with a patients lower eyelid. The saddle-shaped and curved upper surface is configured to provide a border adjacent scleral X-ray beam spots 311. All or a portion of the body of retractor 320*d* may comprise a radio-opaque material so as to provide effective shielding of the eyelid and adjacent tissue from stray or scattered radiation during X-ray treatment beam emission.

VIIB. Additional Retinal and Ocular Imaging Embodiments

In addition to imaging devices used in eye alignment, motion tracking and beam position confirmation (see FIGS. 3A and 3B), embodiments of radiotherapy system 10 having aspects of the invention may include additional or alternative imaging devices to provide images of ocular structures such as the retina. For example, system 10 may include a direct or indirect opthalmoscope, a slit-lamp biomicroscope, a fundus camera, an optical coherence tomography system (OCT), a Scanning laser opthalmoscope (SLO), a line-scanning laser opthalmoscope (LSLO), an ultrasonic ocular imager, and the like.

FIGS. 49-52 illustrate aspects a exemplary embodiment of a radiotherapy system including an LSLO instrument mounted so as to obtain images of a patient's eye before, during and/or after treatment. An LSLO is a simple, compact device which scans a focused laser line on the fundus or other ocular structure, and processes the reflected light to form an image.

Figure 49:
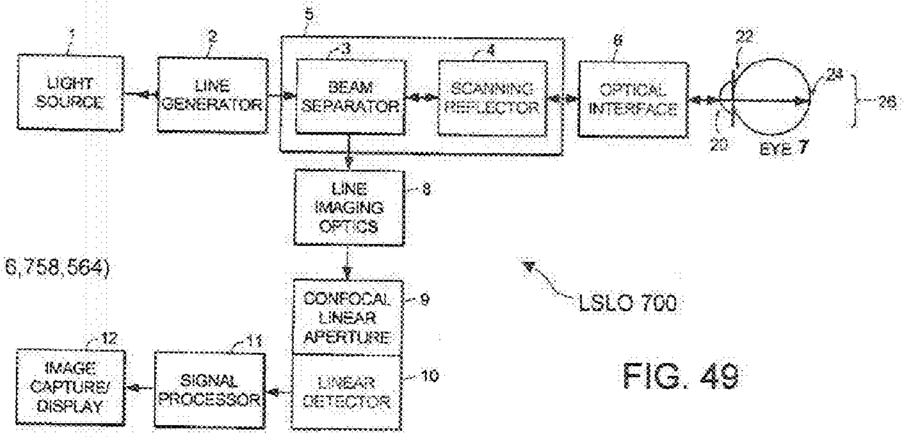
FIG. 49 is a schematic structure diagram of a LSLO embodiment, configured for retinal imaging

FIG. 49 is a schematic structure diagram of a LSLO embodiment 700, the structure boxes of the diagram also being indicative of steps of an operational process or method of use. This figure is taken (with certain modifications) from U.S. Pat. No. 6,758,564, which is incorporated herein by reference. In summary:

(a) Light source 1 (e.g., including one or more lasers or LED) provides a substantially point source of visible, infrared and/or ultraviolet light. The light propagates initially in a optical path towards eye 7 (incoming light), and subsequently propagates in an optical path reflected from eye 7 (reflected light).

(b) Initially, light from source 1 is received and converted to a line of light in line generator 2 (e.g., including one or more lenses, a fixed cylindrical optic, or a holographic optical element). The line of light emitted from the line generator 2 is received by beam conditioner 5, which includes beam separator 3 and scanning reflector 4.

(c) Beam separator 3 (e.g., turning mirror or turning prism) and scanning reflector 4 are collectively configured so that the incoming light and the reflected light are caused to follow separate paths in the distal portion (relative to eye) of the instrument 700: (i) incoming light propagates between the light source 1 and the beam conditioner 5; (ii) both incoming and reflected light propagate through optical interface 6 disposed between beam conditioner 5 and eye 7; and (iii) reflected light is diverted to propagate between the beam conditioner 5 and the linear detector 10.

(d) Eye 7 includes a cornea 20, a pupil 22 and a retina 24, and the region of the interior rear wall of the eye 7 is generally referred to as fundus 26. Optical interface 6 (e.g., an assembly of one or more lenses) receives and focuses a line of light, the light being scanned by reflector 4 in a direction perpendicular to the line so as to move across a portion of the eye 7 such as the fundus 26.

(e) The eye can interact with impinging light in different ways. The light can pass through the eye in transmission, and can be reflected from some regions of the eye, including the surfaces of cornea 20 and fundus 26. Structures in the eye 7, such as such as layers from the front of and behind the fundus 26, may absorb and re-emit some of the light. The transmission, absorption/reemission, and reflection properties of portions of eye 7 are a function of the light wavelength and the structure and composition of the portions of the eye.

(f) The light that returns from eye 7 to LSLO 700 via interface 6 (collectively "reflected light") includes the reflection and/or the absorption-reemission of the incoming line of light, with possible contribution from ambient environmental light. The reflected light is received confocally by the optical interface 6, and then is reflected by the scanning reflector 4 in a synchronous manner with the scanning of the incoming line of light, so that the reflected light passes to the line imaging optics 8. Beam separator 3 may be disposed at the conjugate to cornea 20, and scanning reflector 4 may be disposed at the conjugate to pupil 22.

(g) The line imaging optics 8 reconfigures the reflected light into a line, which passes a confocal linear aperture 9 and impinges on a linear detector 10. The confocal linear aperture 9 may be positioned to be conjugate to the line illumination on the retina 24. The confocal linear aperture 9 can be designed to prevent light that is not confocally received by the apparatus from passing through to the linear detector 10. The linear detector 10, which may be a linear CCD array detector (e.g., a 1×512 pixel linear array) or a 1×n linear CMOS array (n equals the number of array pixels), generates electrical signals corresponding to the image received.

(h) Electrical signal processor 11 receives the electrical signals from linear detector 10, and may include an analog-to-digital (A-to-D) converter that converts analog light levels to digital signals, and may include a digital processor (e.g., one or more operationally-mounted semiconductor microprocessor chips, or a commercially-available personal computer) to receive, store, and analyze the signals, such as by use of a frame grabber.

(i) The signal processor 11 may be connected to an image/capture/display module 12, which can include any of a computer monitor, video display, a image storage medium, printer or the like. As is well known in the art, power supplies and motors are provided to operate the scanning reflector 4, the light source 1, the linear detector 10, and the signal processor 11 and the image capture/display 12. The components of instrument 700 described may be miniaturized and compact if desired, and image data can also be transmitted for remote processing, use and viewing.

Figure 50A:
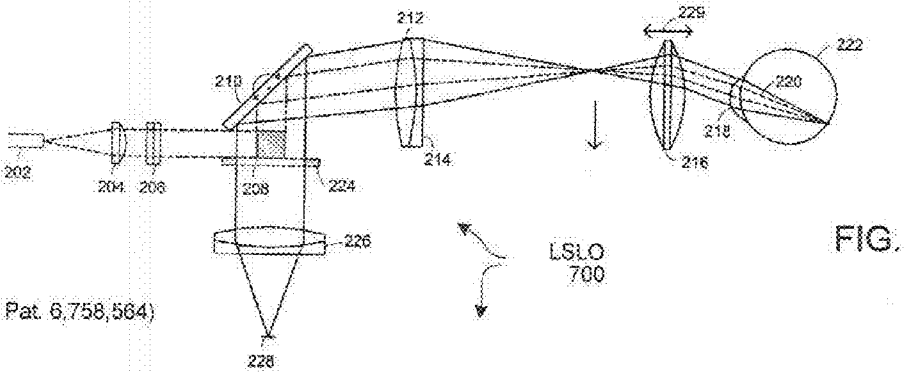
FIGS. 50A-B are an elevation view hand a plan view respectively of one exemplary optical layout of a LSLO instrument.
Figure 50B:
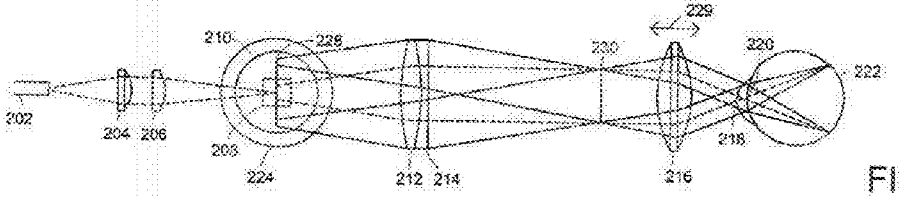

FIGS. 50A and 50B are an elevation view and a plan view respectively of one exemplary optical layout of a LSLO instrument 700 configured to image the fundus of an eye, the example having particular elements functionally corresponding to the embodiment schematically diagramed in FIG. 49. In summary:

(A) Light 202 (e.g., a single-mode fiber coupled 3 mW 830 nm laser diode) provides a substantially point source of light, which is expanded to a line of light by cylindrical lenses 204, 206, such that the beam remains collimated on one transverse axis, but focuses near the pupil conjugate and then rapidly diverges on the other transverse axis. The line of light impinges on turning prism or mirror 208 so as to be directed to the scanning mirror 210, which is mounted to be moved by a drive such as a galvanometer motor. The line of light is scanned by mirror 210 and directed to pass through one or more lenses 212, 214, and 216, which are positioned and/or adjusted to pass the line of light through a cornea 218 of an eye 222 and through an undilated pupil 220 of the eye so as to impinge as a line focused on a fundus of the eye, which includes the retina 222.

(B) The reflected light exits the eye through the pupil 220 and the cornea 218, passes through lenses 216, 214, 212, and is redirected by the scanning mirror 210. The redirected path of the reflected light passes around the turning mirror 208 and passes through the pupil stop 224, then passing through one or more objective lenses 226. The laser line is imaged by the lenses 216, 214, 212, and 226 confocally to a linear CCD array 228 (e.g., a digital line-scan camera). The side view of FIG. 50B shows the pupil separation at the small turning prism mirror 208 (the incoming light is focused at the pupil conjugate) so as to allow the illuminating (incoming) beam to pass to the retina 222 while acting as a stop for corneal reflections in the reflected light. The line 230 is scanned on the retina 222 by the scanning mirror 210 and the reflection is de-scanned and imaged to the linear CCD array 228.

(C) The linear CCD readout is synchronized with scan motion of mirror 210 and an image is acquired with a frame grabber. A focus adjustment for the laser, and line rotation and displacement adjustments to align the laser line with the linear CCD array may be provided with commercially available tip/tilt mounts, rotary mounts, and slidemounts. The line confocal system is quickly aligned and optimized over the length of the array. An opthalmoscopic lens slide 229 holding lens 216 may be used to focus the light line on the eye, such as to correct for ametropia. A rectangular image of the fundus is thus obtained. The camera body may house one or more circuit cards including signal processing chips, and power and computer cables may attach to the camera body.

Figure 51:
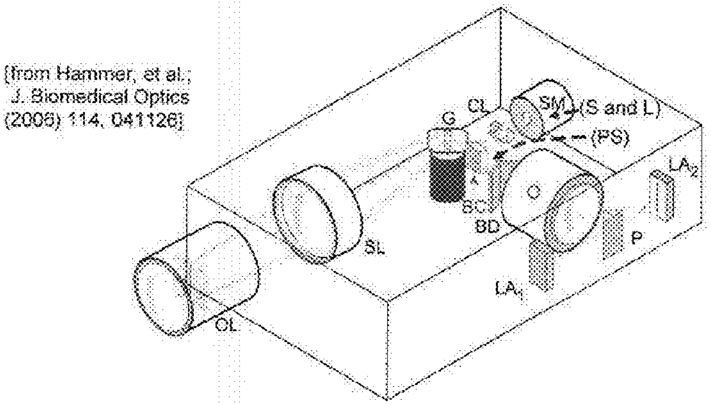
FIG. 51 illustrates an exemplary LSLO optical housing.

FIG. 51 illustrates an exemplary LSLO optical housing 701. The optical housing 701 may be provided with room to house the electronic driver boards for source module SM and galvanometer driven mirror G. The source module SM may contain driver electronics and multiple laser diode light sources S of differing wavelengths (e.g., 532, 670, 780, 830, and/or 905 nm) combined with dichroic beamsplitters and/or collimators or lenses L. The illumination light is collimated and spread in one dimension with a cylindrical lens CL and co-aligned to the return path with a beam-combining optic BC. The line is focused onto the retina with a scan lens SL and opthalmoscopic lens OL, and scanned with a galvanometer-driven mirror G. The back-scattered light from the retina is de-scanned by the galvanometer through the pupil stop PS and focused onto linear arrays LA1,2 with the detector objective O. The beam displacement optic BD separates and displaces left and right sub-apertures for stereo operation, if desired. The pupil may transferred to a conjugate between BC and G. The pupil may be split into three parts: (i) left sub-aperture and (ii) right sub-apertures for stereoscopic imaging, and (iii) BC placed in the center at the pupil conjugate to block corneal reflections from detection.

In this example the beam displacement optic or beam splitter BD consists of two identical windows fused at an angle of 37 deg. which function to displace the beam before the detector objective to achieve stereopsis, the angle of the windows producing a lateral separation between sub-apertures at the pupil. The separated sub-aperture beams are directed through detector objective O and pupil splitting optic P to a right and left pair of linear detectors LA1,2. Alternatively, BD The beam displacement optic may be omitted so that rays originating from the same structure will follow identical paths via the detector objective O to a single linear detector LA and produce no stereoscopic disparity.

Further description of LSLO operating principles and other examples of suitable components, optical parameters and aspects are described in U.S. Pat. No. 6,758,564, and in Hammer, et al.; "*Line-scanning laser opthalmoscope*"; J. Biomedical Optics (2006) 114, 041126, each of which publications are incorporated herein by reference.

Figure 52:
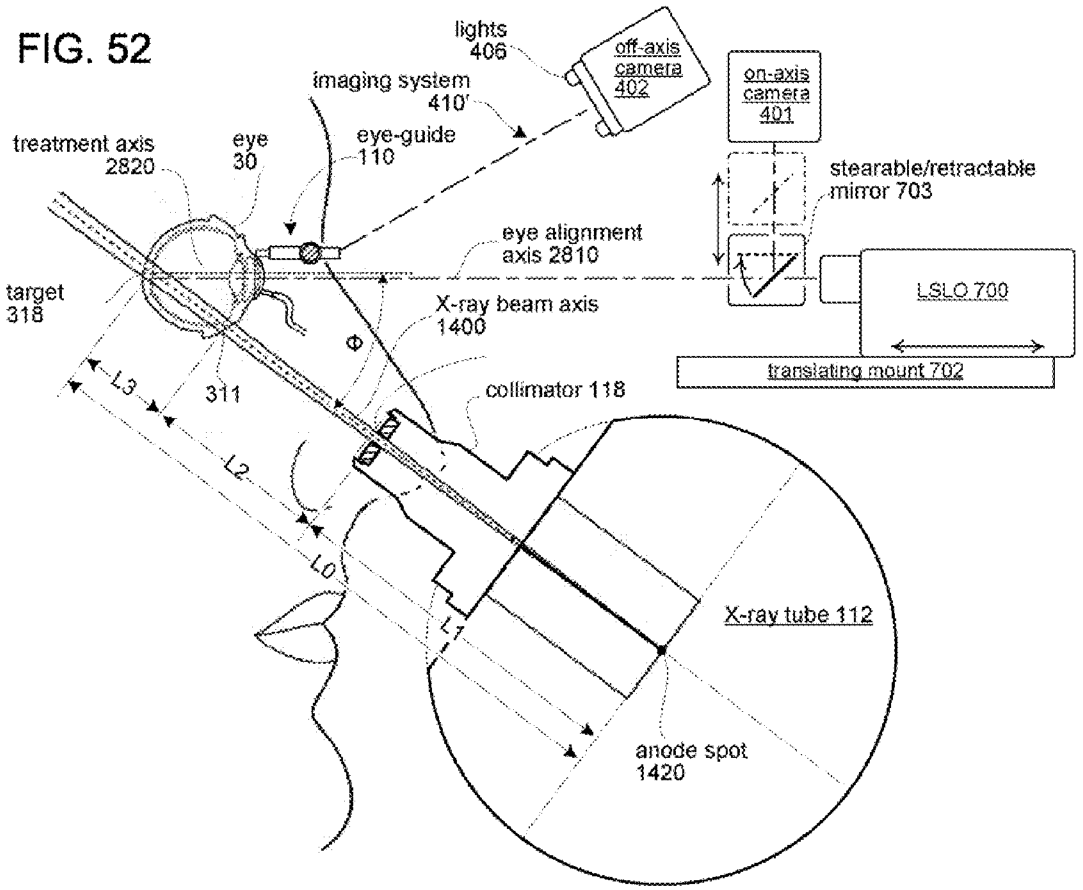
FIG. 52 illustrates an exemplary radiotherapy system having aspects of the invention having an imaging system including an retinal imaging instrument such as an LSLO.

FIG. 52 illustrates an exemplary radiotherapy system having aspects of the invention, generally similar to the embodiments shown in FIGS. 1-6, and having an imaging system 410' including an retinal imaging instrument, such as axially mounted LSLO 700. See description regarding FIGS. 3A and 3B for description of common elements. LSLO 700 may be supported by an mounting independent of the positioning system 115 of FIG. 1, or may be mounted to positioner 115, so as to be supported in a suitable imaging configuration. LSLO 700 may be adjusted by one or both of adjustable optics and an adjustable mounting so as so as to be supported in a suitable imaging configuration and to be compatible with eye tracking optics, as required.

Note that in the event that an axial tracking camera 401 is included, one or both of a translating mount 702 or a steerable/retractable mirror 703 may be included so as to allow each of camera 401 and LSLO 700 to access an unobstructed axial (system Z axis) path in turn. Alternatively, imaging system 410' may omit an axial tracking camera, such as where tracking is performed solely by off-axis cameras (e.g., including a stereoscopic camera pair). It should be understood that an alternative positioning system 115' may be included optimized to permit operation of a retinal imaging system and a tracking system conjointly, without departing from the spirit of the invention.

In one alternative, the actuators of positioning system 115' may be employed to provide 3-dimensional adjustment of the position of LSLO 700 for retinal image alignment. Alternatively or additionally, the mounting 702 may provide one or more degrees of freedom (automated and or manual) for adjustment of the position of LSLO 700, such as X-Y-Z translation and/or pitch and yaw angular adjustment.

In one operational method having aspects of the invention, LSLO 700 is configured and used to determine the retinal alignment with respect to the treatment axis 2820 prior to initiating treatment. For example, a retinal image (registered with the radiotherapy coordinate system) may be used to adjust the treatment axis 2820 to intersect a selected imaged anatomic feature of the patient's eye, such as the fovea (see step 2555 of FIG. 21A and FIG. 21D).

In another operational method having aspects of the invention, LSLO 700 is configured and used to capture one or a plurality of retinal images during the course of X-ray treatment. Such images may be used (e.g., via image recognition and processing methods similar to those described herein) to directly monitor retinal movement relative to X-ray treatment beams, leading to gating or corrective action as needed (see step 2565 of FIG. 21A).

In a further operational method having aspects of the invention, LSLO 700 is configured and used to plan a treatment, using adjustable parameters of X-ray source assembly 420 and positioner 115 (e.g., X-ray beam shape, diameter, dosage distribution, beam overlap, and the like) to tailor the treatment to a lesion of a particular shape or distribution, as determined by a retinal image (other modalities alternative or additional to LSLO may be included, such as OCT).

VIIC. Alternative Radiation Therapy Applications

The imaged-based movement and radiation dose tracking and mapping methods and devices such as described herein may be applied to the precision control of radiation therapy beams to other parts of a patient's body, in addition to the eye lesion treatment examples described in detail herein. In particular, in treatment system and method embodiments having aspects of the invention, a contact member having one or more fiducials may be engaged or attached to a surface of a portion of the patient's body adjacent to tissue to be treated. The body portion may then be accurately tracked by an imaging-system, permitting extrapolation of any body motion to the treatment target. A range of disease conditions may be treated in this fashion without departing from the spirit of the invention. Examples include radiation treatment delivered to targets of the brain, spine, a breast, musculoskeletal tissue, vasculature, abdominal or gastrointestinal lesions, both in humans and in animals. Reference is made to U.S. application Ser. No. 11/956,295 filed Dec. 13, 2007 which is incorporated by reference herein. In particular, see the description related to FIGS. 13-22 of that application.

Figure 53:
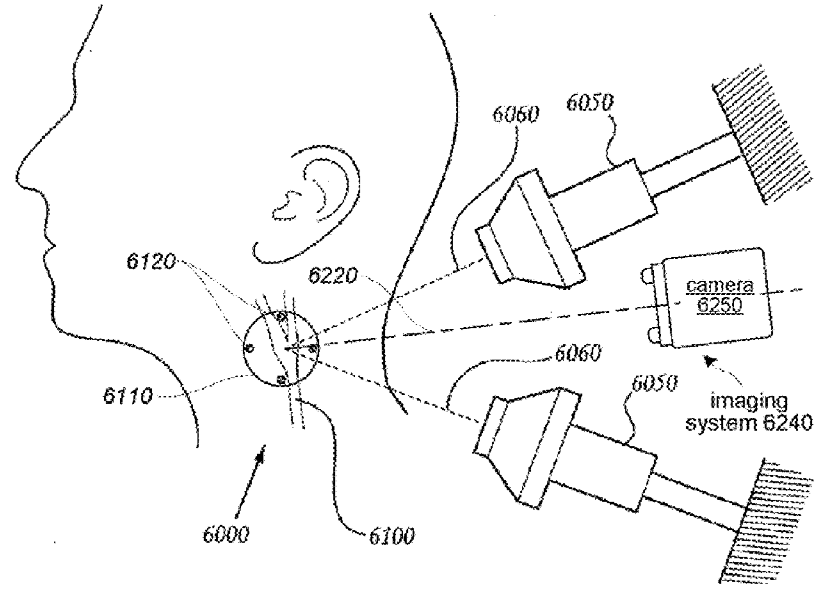
FIG. 53 illustrates an exemplary radiotherapy system having aspects of the invention treating a non-ocular target while tracking a contact member attached to the body.

FIG. 53 illustrates an exemplary radiotherapy system 6010 having aspects of the invention, generally similar to the embodiments shown in FIGS. 1-6, and configured for administering radiation therapy, such as by direction of a tightly-collimated orthovoltage X-ray beam through a body surface to a treatment target region 6000 lying within the body. Tracking of target motion and control of radiation emission or direction may be performed by methods generally similar to those described herein with respect to FIGS. 32-42, among other places.

In the example shown in FIG. 53, the treatment target is a region including vulnerable carotid lesions lying within a patient's neck. The goal of treatment may be prevention of restenosis or treatment of hyperplasia, or treatment of vulnerable atherosclerotic plaques present in the vessel. The radiotherapy may be administered in association with the placement of a stent or other vascular device. The radiotherapy can be combined with pharmaceutical therapy prior to or after the institution of radiotherapy, such as by administration of compounds describe herein, delivered locally or systemically to reach the treatment site. In some embodiments, the radiotherapy is delivered in one fraction of about 10 Gy to about 50 Gy and in some embodiments, the radiotherapy is delivered in doses of about 5 Gy to about 10 Gy in several fractions, which can be applied through different trajectories, as discussed in other embodiments.

Contact member 6110 is engaged with the surface of the neck, such as with a pressure sensitive adhesive, a clamping member or strap, or the like. One or more fiducial elements 6120 are mounted to the surface of member 6110, so as to be imageable be camera 6250 of imaging system 6240. FIG. 53 depicts x-ray delivery through skin overlying the peripheral vessels 6100 via one or more orthovoltage x-ray beams 6060 from radiotherapy devices 6050 to regions of peripheral vascular disease 6000.

Contact member 6110 may comprise a conformal or elastic material, or may comprise a rigid material. Alternatively, contact member 6110 may have a rigid upper portion attached to a conformal skin-contacting surface material. In other embodiments, contact member may be a disposable unit which is conformable in shape at the time of application to the skin, being composed to be hardened (e.g., via a curing resin or the like) in place to provide a rigid platform during treatment. The contact member 6110 may comprise a material easily penetrated by orthovoltage radiation, such as a layer of low-density polymer, or the like. The contact member 6110 may have radio-opaque elements or fiducials, permitting convenient location in X-ray imagery. The contact member 6110 may be shaped so as to expose portions of the skin at the point of X-ray beam entry.

Alignment and registration of the contact member 6110 with a coordinate system of treatment device 6050 may be performed with methods and devices such as are described with respect to FIGS. 3-4 and 17-25, such as by aligning member 6110 to a treatment axis 6220 by computer processing of images captured by camera 6250. The position of treatment target 6100 relative to contact member 6110 may be determined by a number of means, such as medical imagery, CT scans, ultrasound, and the like, so as to register the position of member 6110 to target 6100. Subsequent motion of the patient resulting in movement of contact member 6110 and target 6100 may be determined by tracking the motion of member 6110 by the methods described in detail herein, suitably adapted to the geometry/anatomy of the body portion being treated. Radiotherapy beam energy, beam width, and direction can be chosen in accordance with the tissue, disease, and time to treatment.

Example of Eye Tracking Without an Eye Contact Member.

Figure 54:
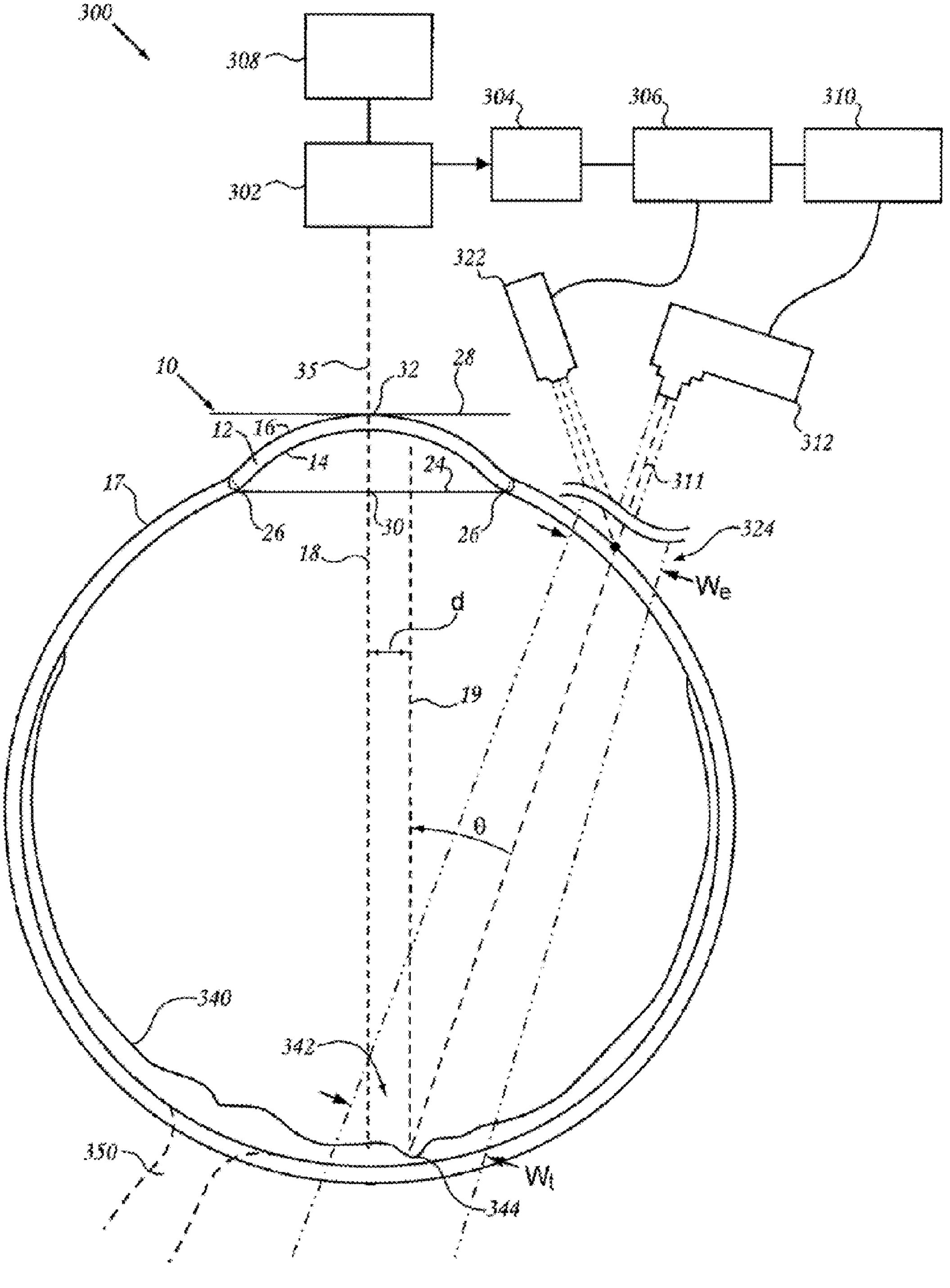
FIG. 54 illustrates an exemplary radiotherapy system having aspects of the invention, generally similar to the embodiments shown in FIGS. 1-6, but having an eye tracking system which employs cornea reflections for alignment.
Figure 55C:
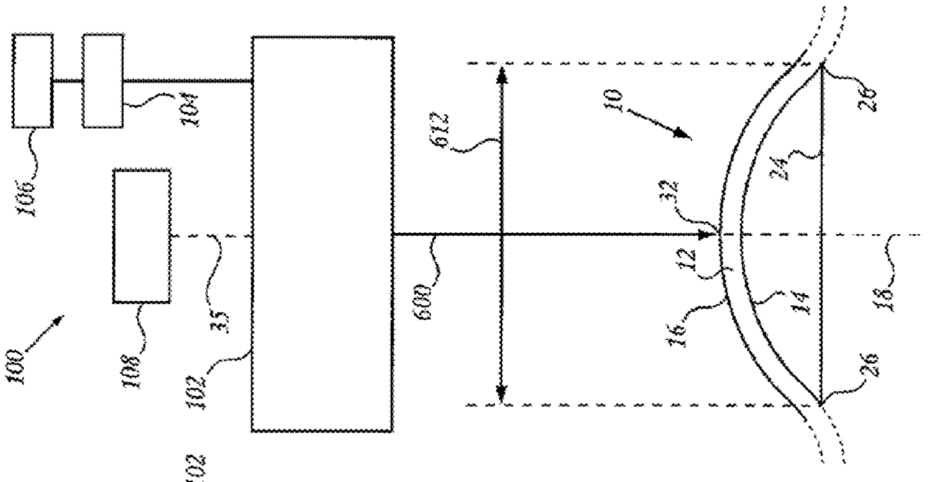
FIGS. 55A-C illustrate schematic side views of an anterior portion of an eye in three orientations with respect to an embodiment of an alignment system having aspects of the invention, depicting a method utilizing limbus sizing to define the reference axis.
Figure 55B:
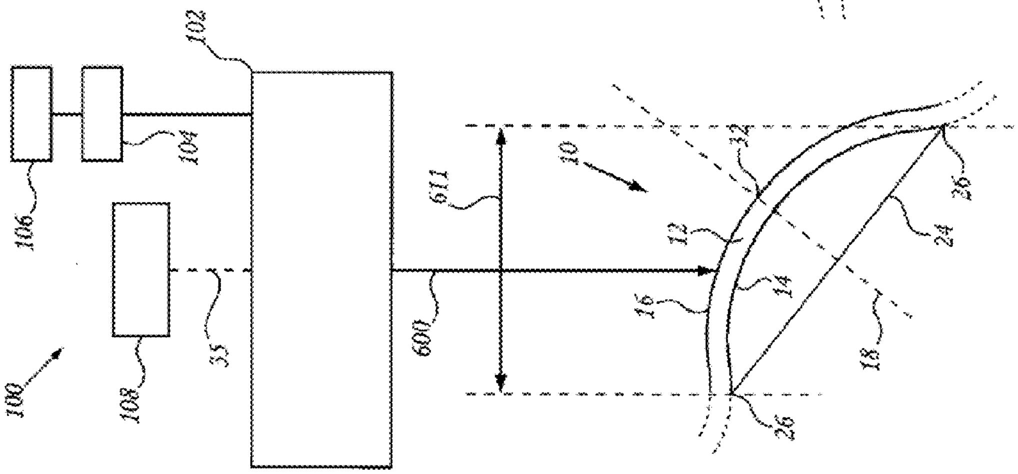
Figure 55A:
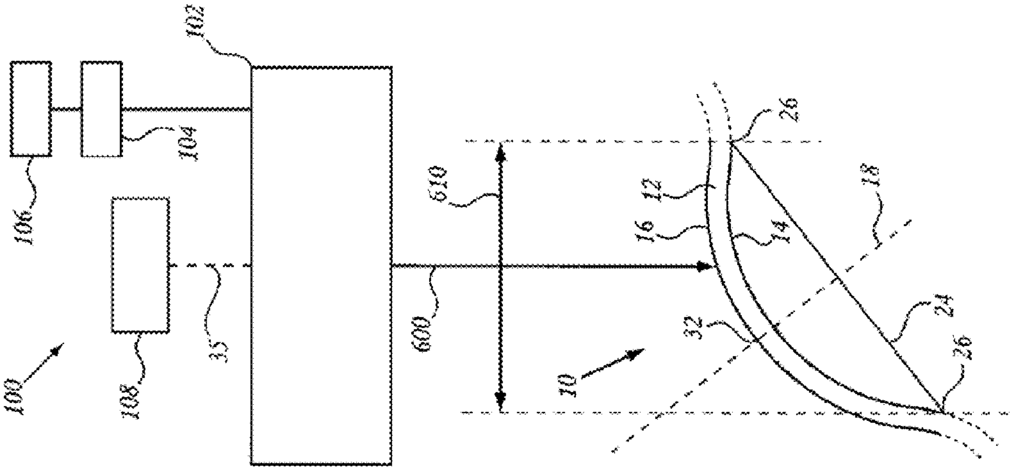
Figure 56:
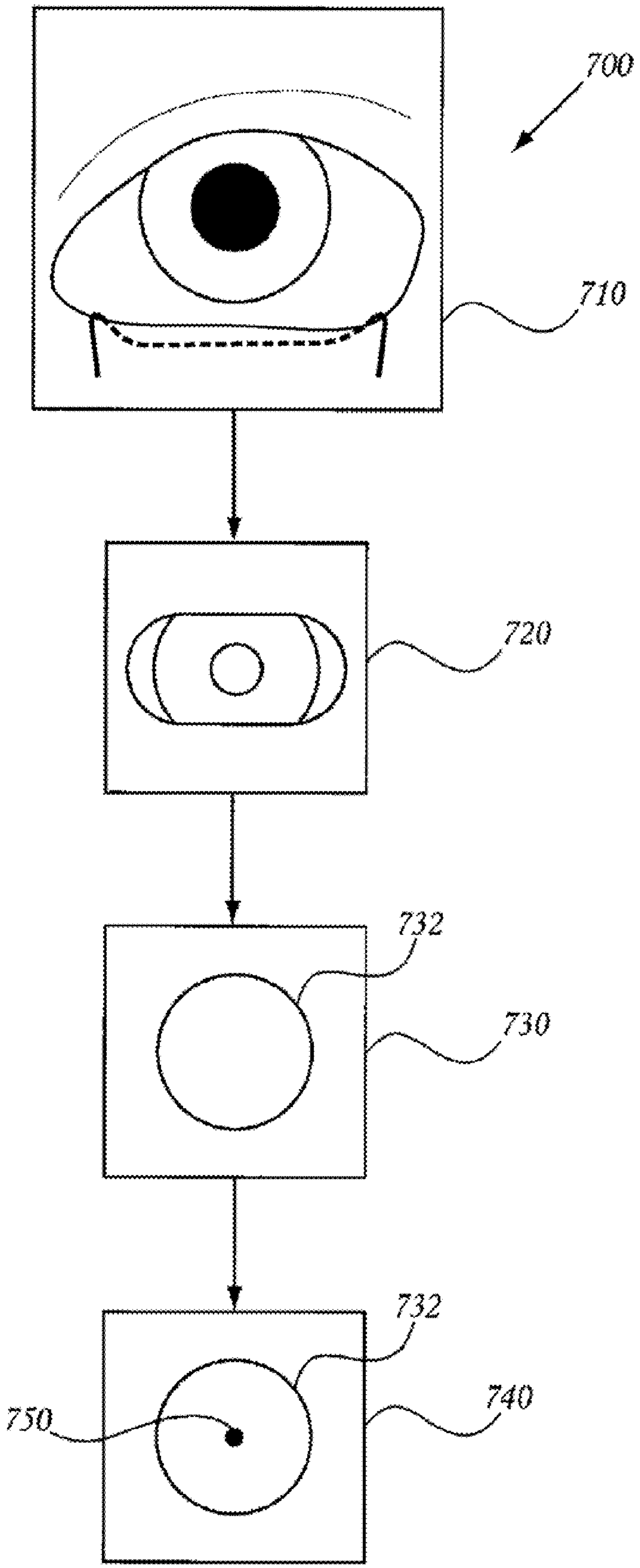
FIG. 56 is a diagram of an exemplary method having aspects of the invention, showing a sequence of the successive data processing steps used to identify the limbic boundary and limbic center.

FIGS. 54, 55 and 56 illustrate alternative exemplary radiotherapy system and method embodiments having aspects of the invention, generally similar to the embodiments shown in FIGS. 1-6, but having an eye tracking system which employs an eye-imaging system which is operable independently of an eye-contact member, and may be used without an eye-contact member. In addition to the examples described below, please see the examples, illustrations and description of co-invented priority application Ser. No. 12/103,534 filed Apr. 15, 2008, which is incorporated herein by reference.

Corneal Refection Alignment

FIG. 54 shows schematic view is shown of an alignment and treatment embodiment 300, including a cross-sectional view of a portion of the eye taken along the geometric axis. In the example shown, image generator 306 is coupled to a positioning device 310 used to position an ophthalmic treatment device 312, e.g., a radiotherapy device. The position of the geometric axis 18, properly located by the alignment system, can be used by positioning device 310 to direct ophthalmic treatment device 312 at a tissue target 318, which may or may not be positioned along axis 18. In this example, target 318 is positioned off-axis with respect to geometric axis 18.

System 300 includes an image capture device 302 positioned to image eye 10 along the geometric axis 18. Image capture device 302 provides video image data of eye 10 to a display 304. Coupled to display 304 is an image generator 306, such as a personal computer programmed with commercially-available computer aided design software, capable of generating and overlaying geometric images onto the image of eye 10 appearing on display 304. In operation, image generator 106 overlays an image on the image of eye 10 on display 304. The overlaid image is typically a geometric shape sized and positioned to coincide with an anatomical landmark appearing in the image of eye 10. The selected anatomical landmark should be one that remains unchanged in size, shape and position relative to the eye 10.

A preferred anatomical landmark is limbus 26, which is circular. Accordingly, as a first step, image generator 306 can be operated to position an image of a circle on the image of limbus 26. Image generator 306 can then locate the center 30 of limbus 26. Next, the first Purkinje reflex 32 is identified. Light from light source 308 travels along path 35, entering the eye 10 through the cornea 12 and is directed by the lens to the retina. A portion of the light is reflected at point 32 off the anterior surface of the cornea 16, identifying the first Purkinje reflex. Alignment of the limbus center 30 with the first Purkinje reflex 32 defines and allows accurate location of the geometric axis 18 as a reference axis with respect to the external coordinate system.

With the position of the geometric axis 18 properly located, the geometric axis 18 becomes an axis of reference, and can thereby be used by positioning device 310 to direct ophthalmic treatment device 312 toward the eye at a predetermined orientation with respect to from geometric axis 18 such that a therapeutic beam, such as a beam of collimated electromagnetic radiation 311, can be aimed at a predetermined coordinate of the eye 10 so as to enter the body surface (point 324 on the surface sclera 17) and propagate to impinge on a selected target tissue 318.

Note that FIG. 54 is a planar illustration of 3-dimensional eye anatomy, and in general beam axis 311 of device 312 need not intersect the geometric reference axis 18 (i.e., axes 18 and 311 may, but need not, lie within a plane). In general, the beam axis 311 may have a selected orientation with respect to geometric reference axis 18, such as a selected angle "θ" and offset "d" with respect to axis 18. The device 312 can in fact be angled to intersect any anterior-posterior line within the eye.

Once reference axis 18 is identified, treatment may be carried out by a device oriented with respect axis 18, for example where a treatment target lies along axis 18 (see description regarding FIG. 3B). Alternatively, a distinct axis 19 may be defined with respect to axis 18, for example by a shift of distance "d", so that axis 19 intersects treatment target 318 positioned off-axis with respect to axis 18. Axis 19 may be called the "treatment" axis. Based on straightforward geometry, the device 312 can now be positioned so that its beam axis 311 intersects treatment axis 19 at tissue target 318. Axis 18 may be used to define one or more correlated geometric axes in the external coordinate system, and to define one or more additional intersection points with respect to beam 311. Note for treatment targets lying on reference axis 18, offset "d" may be about zero, and for treatment delivered through or to the cornea, angle "θ" may approach zero.

As shown in FIG. 54, in one example of an orthovoltage X-ray treatment for macular degeneration, off-set d is selected to define a treatment axis 19 centered on the macula, angle θ is selected to provide intersection of beams 311 on the macular surface and surface entry point 324 in a region of the lower anterior sclera beyond the boundary of limbus 26. In this example, an X-ray beam source may positioned by positioning device 310 so as to project a collimated beam from a selected X-ray source distance so as to form a beam having a characteristic width at tissue entry "w". Note that although a treatment beam may be projected through an eye-lid or other tissue proximal to the eye, the eyelids (in this case the lower eyelid) may be conveniently retracted so as to expose an additional area of the anterior sclera 17.

Alignment by Limbus Sizing

FIGS. 55A-55C illustrate another embodiment having aspects of the invention, including a schematic side views of an anterior portion of an eye in three orientations with respect to an embodiment of an alignment system having aspects of the invention, depicting a method utilizing limbus sizing to define the reference axis. In this method utilizes limbus sizing to define the geometric axis. In this embodiment, as illustrated in FIGS. 55A-55C, a schematic side view of a portion of an eye 10 is shown. The alignment system and method in this embodiment of the invention is based on the detection of the maximal area of the limbus 26 of the subject's eye 10. The cornea 12 of eye 10 is characterized by an anterior surface 16 and a posterior surface 14 that are concentric with one another, the iris 24 extending outward to posterior surface 14 of cornea 12. The circle of intersection between iris 24 and interior surface 14 is an anatomical landmark known as the limbus 26. The limbus of an eye is readily imageable.

As discussed above, an "axis of interest" indentified as a reference axis for eye alignment method embodiments having aspects of the invention may advantageously be, but is not necessarily, the optical axis or the geometric axis of the eye. The geometric axis 18 in FIGS. 55A-55C, may be determined to be aligned with the external coordinate system of system 100 when axis 18 is coincident with the center of the limbus 26 when the area circumscribed by the boundary of the limbus is positioned to achieve its maximum apparent area with respect to camera 102. In the illustrated embodiment, camera 102 is positioned to image eye 10 along direction 600. Light from light source 108 travels along path 35, entering the eye 10 through the cornea 12 and is directed by the lens to the retina. Camera 102 provides video image data of eye 10 to display 104. Coupled to display 104 is an image generator 106. In operation, image generator 106 generates an image of the limbus 26 and displays it on display 104. Accordingly, as a first step, image generator 106 can be operated to generate a first image of limbus 26 when the eye is in a first position, as shown in FIG. 55A. Image generator 106 can then locate the boundary of limbus 26.

Next, the first area defined by the boundary of the limbus is determined. As shown, FIG. 55A depicts eye 10 angled such that the area 610 defined by the boundary of the limbus is less than maximal. The camera 102, or preferably the eye 10, is then positioned in a second position and image generator 106 is operated to generate a second image of limbus 26, as shown in FIG. 55B. Image generator 106 can then locate the boundary of limbus 26. Next, the second area 611 defined by the boundary of the limbus is determined. As shown, FIG. 55B depicts eye 10 angled such that the area 610 defined by the boundary of the limbus is less than maximal. This process is repeated until the maximum area defined by the limbus boundary is identified, as illustrated in FIG. 55C, where direction 600 is co-aligned with the reference axis 18. Detection of the maximum area 612 of limbus 26 signals the eye is in alignment with the system, and the reference axis 18 is defined.

Identification of the Limbic Boundary

FIG. 56 is a diagram of an exemplary method having aspects of the invention, showing a sequence of the successive data processing steps used to identify the limbic boundary and limbic center (in alternatively or complementary to the methods described herein with respect to FIGS. 21A-E).

As noted above, the limbic boundary is determined in the alignment methods described. Determination of the limbic boundary, and limbic center, can be accomplished in a variety of ways. An exemplary method for determining the center of the limbus is diagrammatically illustrated in FIG. 56, showing the sequence 700 of the successive data processing steps to identify the limbic boundary and limbic center. Input image 710 represents the relatively high-resolution eye image data that is applied. The first data processing step 720 is to average and reduce input image 710. This can be accomplished by convolving the data defining input image 710 with a low-pass Gaussian filter that serves to spatially average and thereby reduce high frequency noise. Since spatial averaging introduces redundancy in the spatial domain, the filtered image is next sub-sampled without any additional loss of information. The sub-sampled image serves as the basis for subsequent processing with the advantage that its smaller dimensions and lower resolution lead to fewer computational demands relative to the original, full size, input image 710.

The next data processing steps involved in localizing the limbus boundary, and center of the limbus, include the sequential location of various components of the limbic boundary. In sequence, step 730 locates the limbic (or outer) boundary 732 of the iris. The localization step can be performed in two sub-steps. The first sub-step includes an edge detection operation that is tuned to the expected configuration of high contrast image locations. This tuning is based on generic properties of the boundary component of interest (e.g., orientation) as well as on specific constrains that are provided by previously isolated boundary components. The second sub-step includes a scheme where the detected edge pixels vote to instantiate particular values for a parameterized model of the boundary component of interest.

In more detail, for the limbic boundary 732 of step 730, the image is filtered with a gradient-based edge detector that is tuned in orientation so as to favor near verticality. Thus, even with occluding eyelids, the left and right portions of the limbus should be clearly visible and oriented near the vertical, when the head is in an upright position. The limbic boundary is modeled as a circle parameterized by its two center coordinates, xc and yc, and its radius, r. The detected edge pixels are thinned and then histogrammed into a three-dimensional (xc, yc, r)-space, according to permissible (xc, yc, r) values for a given (x, y) image location. The (xc, yc, r) point with the maximal number of votes is taken to represent the limbic boundary. Finally, with the limbic boundary 732 isolated, the final processing step 740 includes locating the center 750 of the limbus.

The above-described approach to identifying the center of the limbus can be generalized in a number of ways. For example, image representations other than oriented gradient-based edge detection may be used for enhancing iris boundaries. Second, alternative parameterizations for the iris boundary may be employed. Finally, iris boundary localization may be performed without the initial steps of spatial averaging and subsampling.

From the foregoing, it can be seen how various objects and features of the invention are met. While certain aspects and embodiments of the disclosure have been described, these have been presented by way of example only, and are not intended to limit the scope of the disclosure. The methods and systems described herein may be embodied in a variety of other forms, and alternative components, arrangements, and data acquisition and processing devices may be included or substituted without departing from the spirit thereof. All publications and patents cited herein are expressly incorporated herein by reference for the purpose of describing and disclosing systems and methodologies which might be used in connection with the invention.

The invention claimed is:

1. A method of treating a lesion on or adjacent the retina of an eye of a patient with an external-beam radiation device, comprising:

(a) placing the patient's eye in alignment with a known system axis in an external three-dimensional coordinate system, and measuring the eye's axial length;

(b) from the known position of the system axis and from the measured axial length, determining the coordinates of the lesion to be treated in the external coordinate system;

(c) directing a collimated X-ray radiation beam along a known beam axis in the external coordinate system at the lesion to be treated;

(d) during said directing, tracking the position of the patient's eye with respect to the known system axis, thereby tracking the position of the lesion to be treated in the external coordinate system; and (e) based on the known beam axis of the collimated beam in the external coordinate system, and the instantaneous position of the lesion to be treated in the external coordinate system, as determined at least in part by the tracked position of the eye, calculating a total radiation equivalent received at the lesion to be treated during the treatment.

2. The method of claim 1, wherein:

step (b) further includes determining the coordinates of at least one radiation-sensitive structure in the external coordinate system;

step (d) further includes tracking the position of the at least one radiation-sensitive structure in the external coordinate system; and step (e) further includes, based on the instantaneous position of the at least one radiation-sensitive structure in the external coordinate system, calculating a total radiation equivalent received at the at least one radiation-sensitive structure during the treatment;

the method further comprising the step of (f) based on the calculated radiation equivalent from step (e), controlling the radiation beam to insure that the at least one radiation-sensitive structure does not receive more than a preselected radiation equivalent during the treatment.

3. The method of claim 2, wherein step (a) includes measuring the axial length of the patient's eye by ultrasound imaging, and step (b) includes scaling the measured axial length from step (a) to a standard human-eye model, and determining the coordinates of the lesion to be treated and the at least one radiation-sensitive structure from the eye model.

4. The method of claim 2, which further includes attaching an eye guide to the patient's eye, centered thereon so that a geometric axis of the eye corresponds approximately to an axis of the eye guide, and aligning an axis of the eye guide with the known system axis.

5. The method of claim 4, wherein step (b) includes using the measured optical length of the patient's eye to place the patient's eye in registry with an eye model, and using the coordinates of the lesion to be treated and the at least one radiation-sensitive structure in the model to determine the coordinates thereof in the external coordinate system.

6. The method of claim 5, wherein step (d) includes tracking the position of the eye guide axis with respect to the system axis, thereby tracking the positions of the lesion and radiation-sensitive structures in the external coordinate system.

7. The method of claim 6, wherein the eye model includes a virtual medium by which the attenuation of a radiation beam along a known path through the model can be determined; and step (e) includes determining the spatial accumulation of radiation received at the macular region of the patient's eye based the known intensity of the collimated beam, the instantaneous positions of the of the patient's eye, and the attenuation of the beam through the virtual medium along known pathways within the eye.

8. The method of claim 6, wherein step (e) includes mapping a spatial quantity indicative of a distribution of total radiation onto the eye model, based on the tracked position of the patient's eye during a period of directing a radiation beam at the retinal region of the patient's eye.

9. The method of claim 2, wherein the lesion to be treated is the macula, the at least one radiation-sensitive structure includes at least a portion of the optic nerve or optic disk of the eye, and step (e) includes calculating the total radiation equivalent received at the macula and at the optic disk during the treatment.

10. The method of claim 2, wherein step (f) of controlling the radiation beam includes controlling the radiation beam to do one or more of:

(i) achieve a desired dose of radiation at the lesion;

(ii) avoid exceeding a selected level of radiation dose at the radiation-sensitive structure; and (iii) avoid exceeding a selected threshold based on a spatial quantity, the threshold indicative of eye-motion-based departure of the beam axis from the selected target.

11. The method of claim 2, wherein step (e) of calculating total radiation equivalent received at the lesion to be treated and the at least one radiation-sensitive structure during the treatment; includes determining a time-increment vector summation of a parameter indicative of an eye-motion-based departure of the beam axis from the selected target lesion to be treated.

12. The method of claim 2, wherein step (e) of calculating total radiation equivalent received at the lesion to be treated and the at least one radiation-sensitive structure during the treatment includes modulating a pre-determined radiation distribution model representing predicted radiation dose distribution to be received by tissue of the patient from the collimated radiation beam in the absence of eye motion, the modulation based on tracked eye motion during treatment, so as to determine a radiation dose distribution accounting for actual eye motion during treatment.

13. The method of claim 2, wherein step (e) of calculating total radiation equivalent received at the lesion to be treated and the at least one radiation-sensitive structure during the treatment; further includes modulating a pre-determined radiation distribution model for a plurality of successive time increments during radiation treatment so as to determine a cumulative dose distribution during the course of treatment; and wherein step (f) includes (i) comparing the cumulative dose received by a selected non-target anatomical structure with a pre-determined dose threshold quantity to determine when the threshold has been exceeded and (ii) in the event that the threshold has been exceeded, controlling the radiation beam or beam axis to reduce or eliminate further radiation dose to the selected non-target anatomical structure.

14. The method of claim 13, wherein step (f) includes turning off the beam being directed onto the patient's eye when the position of the patient's macula, as tracked in step (d), relative to the axis of the beam, is greater than a predetermined threshold distance.

15. The method of claim 13, wherein step (f) includes directing the beam against the patient's macular region until the spatial accumulation of radiation mapped at the macula of the eye model reaches a predetermined dose level.

16. The method of claim 2, wherein step (e) of calculating total radiation equivalent received at the lesion to be treated and the at least one radiation-sensitive structure during the treatment; further includes sequentially performing the modulating a pre-determined radiation distribution model for a plurality of successive time increments during radiation treatment so as to determine a cumulative dose distribution during the course of treatment; and wherein step (f) includes (i) comparing the cumulative dose received by a selected anatomical target region with a pre-determined dose threshold quantity to determine when the threshold has been reached, and (ii) in the event that the threshold has been reached, controlling the radiation beam or beam axis to reduce or eliminate further radiation dose to the selected anatomical target region.

17. The method of claim 2, wherein the lesion is a macular lesion, and step (c) includes determining the position of the patient's macula in a treatment coordinate system from the known position of the eye and the coordinates of the macula in the external coordinate system, and determining a treatment axis in the external coordinate system that intersects the patient macula.

18. The method of claim 17, wherein step (c) includes directing a collimated X-ray beam along each of at least two different known treatment axes in the treatment coordinate system at a region of the macular region of the patient's retina.

19. The method of claim 18, wherein step (f) includes controlling the X-ray beam to deliver approximately equal doses of radiation at the patient's macula along each of the different known treatment axes.

20. The method of claim 1, wherein step (a) includes determining a patient-eye geometric axis that extends through the center of the limbus and contains the corneal reflection of the patient's eye, and aligning the geometric axis with the known system axis; and wherein step (d) includes tracking the angular deviation of the geometric axis of the eye with the known system axis.

21. A system for treating a target area in a patient with an irradiation beam, comprising:

(a) a tracking assembly for tracking the position of a patient body region containing the target area and at least one radiation-sensitive area with respect to a known reference axis in an external coordinate system;

(b) a X-ray beam source for directing an irradiation beam at the patient target area along a known treatment axis in the external coordinate system; and (c) a processor operatively connected to the tracking assembly and beam source, and configured to:

(i) determine, from the known position of body region in the external coordinate system, the coordinates of the target area to be treated and the coordinates of the at least one radiation-sensitive patient structure;

(ii) during a period when the irradiation beam is being directed along the treatment axis at the target area, and based on information received from the tracking assembly, track the positions of the target area to be treated and the at least one radiation-sensitive structure;

(iii) based on the known beam axis of the collimated beam in the external coordinate system, and the instantaneous positions of the target area to be treated and the at least one radiation-sensitive structure, calculate a total radiation equivalent received at the target area and at least one radiation-sensitive structure; and (iv) based on the calculated radiation equivalents from step (iii), control the irradiation beam to insure that the at least one radiation-sensitive structure does not receive more than a preselected radiation equivalent during the treatment.

22. The system of claim 21, wherein the tracking assembly includes (i) an imaging device for recording an image of a region of the patient's body that contains natural or fiducial landmarks that define a geometric axis of the imaged region and (ii) an image detector operably connected to the imaging device for converting the recorded image to a digital image made up of known-coordinate pixels, and the processor is operably connected to said detector for determining pixel coordinates of the geometric axis of the body region and step (ii) of the processor operation includes using the pixel coordinates of the geometric axis, relative to known pixel coordinates of the reference axis, to track the position of the patient body region relative to the reference axis.

23. The system of claim 21, for use in treating an ocular lesion, wherein the body region includes the patient eye, the target area includes the ocular lesion, the at least one radiation-sensitive structure includes the optic disc of the eye, the natural landmarks of the eye that define its geometric axis are the center of the limbus and a first corneal reflection, and the beam source produces a collimated x-ray beam.

24. The system of claim 21, for use in treating an ocular lesion, wherein the body region includes the patient eye, the target area includes the ocular lesion, the at least one radiation-sensitive structure includes the optic disc of the eye, and the natural landmarks of the eye that define its geometric axis are the center of the limbus and a first corneal reflection, which further includes an eye guide adapted to be placed on the patient's eye, centered thereon so that the geometric axis of the eye corresponds approximately to the axis of an eye guide, and a detector for determining the coordinates of the axis of the eye guide in the external coordinate system, and the processor is operably connected to said detector for determining the coordinates of the eye guide axis and step (ii) of the processor operation includes using the coordinates of the eye-guide axis, relative to the known coordinates of the reference axis, to track the position of the patient's eye relative to the reference axis.

25. The system of claim 21, wherein said tracking assembly is operable to capture a plurality of time-sequenced images of the body region and its landmarks during the treatment method, and said processor is operable to determine the coordinates of the body region geometric axis for each of the plurality of images, and in step (ii) to determine a time-dependent change in the coordinates of the target area to be treated and the at least one radiation-sensitive structure.

26. The system of claim 25, wherein the processor is operable to carry out, in step (iii) generating a map of total equivalent radiation covering the target area and the at least one radiation-sensitive area in the patient body region, and in step (iii), to determine from the total equivalent radiation map, the radiation equivalent received at any time during treatment by the target area and at least one radiation-sensitive area.

27. The system of claim 26, for use in treating an ocular lesion, wherein the body region includes the patient eye, the target area includes the ocular lesion, the at least one radiation-sensitive structure includes the optic disc of the eye, and the processor is operable, to carry out in step (iii) generating a map of total equivalent radiation covering the target area and the at least one radiation-sensitive area in the patient body region, and in step (iii), determining from the total equivalent radiation map, the radiation equivalent received at any time during treatment by the ocular lesion and the at least one radiation-sensitive area.

28. The system of claim 21, for use in treating an ocular lesion, wherein the body region includes the patient eye, the target area includes the ocular lesion, the at least one radiation-sensitive structure includes the optic disc of the eye, and said processor includes a model of the human eye by which the coordinates of the lesion to be treated and the at least one radiation-sensitive structure can be determined, when the patient's eye is superimposed on the eye model.

29. The system of claim 28, wherein the eye model in the processor includes a virtual medium by which the attenuation of a radiation beam along a known path through the model can be determined, and the processor is operable to determine from the known intensity of the beam and the length of the radiation path through the virtual medium within the eye model, the amount of radiation that is received by the retina in the eye model.

30. The system of claim 28, wherein said processor is operable to direct the beam against the patient's retinal region until the spatial accumulation of radiation mapped at the lesion of the eye model reaches a predetermined dose level.

31. The system of claim 21, for use in treating an ocular lesion, wherein the body region includes the patient eye, the target area includes the ocular lesion, the at least one radiation-sensitive structure includes the optic disc of the eye, wherein said processor is operable, by determining the position of the ocular lesion in the external coordinate system, to determine a treatment axis in a treatment coordinate system that intersects the lesion.

32. The system of claim 31, wherein said processor is operable to determine at least two different treatment axes in the treatment coordinate system, and to control the radiation beam to deliver approximately equal doses of radiation at the lesion along each of the different known axes.

33. The system of claim 32, wherein said processor is operable to turn off the beam being directed onto the patient's eye when the distance between the position of the patient's lesion, as determined in operation (c)(ii), and the intersection of the axis of the beam on the retina, is greater than a predetermined threshold distance.

34. Non-transitory machine-readable medium operable with an electronic computer, in monitoring the total radiation dose received at a target site during the course of treatment in which the target site is irradiated with a collimated x-radiation, to perform the steps comprising:

(a) defining, in an external coordinate system, coordinates for (i) a reference axis, (ii) a radiation-beam axis, and (iii) the target site which, when a body axis having a known relationship to the target site is aligned with the reference axis, places the radiation beam at the center of the target area, (b) receiving from a body tracking device, ongoing information during the course of radiation treatment on the position of the body axis with respect to the reference axis, (c) from the information received in step (b), and from the known intensity of the beam at the radiation beam, calculating the spatial distribution of radiation received in the region of the target site over the course of the treatment, and (d) using the spatial distribution of radiation calculated in step (c) to monitor the total radiation dose at the target site over the course of the treatment.

35. The medium of claim 34, wherein the treatment method is intended to treat an ocular lesion, the target area includes the ocular lesion, the body axis is the geometric axis of the eye, and information received from a body tracking device is in the form of ocular images from which the geometric axis of the eye can be determined.

36. The medium of claim 34, wherein the treatment method is intended to treat an ocular lesion, the target area includes the ocular lesion, the body axis is the geometric axis of the eye, and the eye is irradiated during the course of treatment by a collimated x-radiation beam directed at the target site along at least two different beam axes.

37. The medium of claim 36, wherein an eye guide is centered on the eye such that an eye guide axis corresponds approximately to the geometric axis of the eye, and the information received from a body tracking device is in the form of information on the position of the eye guide.

38. The medium of claim 34, wherein the target site is at a patient's eye, and wherein the medium is further operable, in step (a) to determine the coordinates, in the external coordinate system, of the optic disc of the patient's eye, based on a known spatial relationship between the lesion and the optic disc, and further operable in step (d) to use the spatial distribution of radiation calculated in step (c) to monitor the total radiation dose at the optic disc during the course of treatment.

39. Non-transitory machine-readable medium operable with an electronic computer, in controlling the treatment of an ocular lesion by exposing the lesion to a collimated x-radiation beam, to perform the steps comprising:

(a) using information received from an eye-tracking system to determine a geometric axis of the eye in an external coordinate system, (b) with the geometric axis of the eye placed in alignment with a reference axis, determining the coordinates of the lesion in an external coordinate system, (c) from the coordinates of the ocular lesion determined in step (b), determining a beam axis that intersects the lesion with the patient eye in an defined position with respect to the reference axis, and (d) controlling the position of an x-ray beam source to position the beam along the beam axis determined in step (c).

40. The medium of claim 39, wherein the information received from the eye tracking system is an ocular image from which the geometric axis can be determined by determining the center of the sclera and a corneal reflection from the ocular image.

41. The medium of claim 39, wherein an eye guide is centered on the eye such that an eye guide axis corresponds approximately to the geometric axis of the eye, and the information received from a body tracking device is in the form of information on the position of the eye guide.

42. The medium of claim 39, wherein step (c) includes determining two or more beam axes that intersect the lesion with the patient eye in a defined position with respect to the reference axis.

43. The medium of claim 42, wherein the computer is operably connected to a beam-source robotic device for positioning the beam along a selected beam axis, and step (d) includes acting on the robotic device to shift the beam axis during the course of treatment, from one beam axis to another determined in step (c).

44. A computer-executed method for use in an X-ray radiation treatment device including a computer processor and a body-part motion tracking device operably connected to the computer processor, the tracking device including a body-contact member configured to engage the surface of a body part of the patient which includes a radiation treatment target, and a camera configured to capture an electronic image of the body part, the processor effective to execute instructions to perform the steps comprising:

(a) determining an initial position and orientation of the body part, based on:

(i) determining the alignment of the contact member as engaged with the body so as to have a known orientation relative to an anatomical axis of the body part and a known position relative to the contacted body surface; and (ii) determining the alignment of the contact member as engaged with the body with the radiation treatment device so as to have a known initial position and orientation in a coordinate system of the radiation treatment device;

(b) determining an initial position of the treatment target in the coordinate system of the radiation treatment device, based on determining the relative position of the treatment target to the contact member;

(c) electronically capturing a plurality of time-sequenced images including the contact member while engaged with the body during the administration of radiation treatment;

(d) processing the images in the computer processor so as to determine one or both of an orientation and a position of the contact member in the coordinate system of the radiation treatment device at the time of capture of each image; and (e) determining for each image, from the orientation and/or position of the contact member at the time of capture of the image, the change from the initial orientation and/or position of the contact member in the coordinate system of the radiation treatment device; and (f) determining for each image, the change from the initial position of the treatment target in the coordinate system of the radiation treatment device, so as to track the sequential motion of the treatment target; and (g) controlling at least one aspect of the radiation treatment based on the tracking of the sequential motion of the treatment target.

45. The computer-executed method of claim 44, wherein the body part is an eye, wherein the treatment target includes a portion of the retina, and wherein the contact member includes a lens element contacting the surface of the eye.

46. The computer-executed method of claim 44, wherein the body part includes a treatment target is selected from the group consisting essentially of a portion of the brain, spine, a breast, musculoskeletal tissue, vasculature, abdominal and gastrointestinal lesions.

* * * * *